United States Patent
Anderson et al.

(10) Patent No.: US 7,528,242 B2
(45) Date of Patent: *May 5, 2009

(54) **METHODS AND COMPOSITIONS COMPRISING *RENILLA* GFP**

(75) Inventors: David Anderson, San Bruno, CA (US); Beau Peelle, Sommerville, MA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 272 days.

This patent is subject to a terminal disclaimer.

(21) Appl. No.: 11/178,146

(22) Filed: Jul. 8, 2005

(65) Prior Publication Data

US 2007/0298973 A1 Dec. 27, 2007

Related U.S. Application Data

(63) Continuation of application No. 10/133,973, filed on Apr. 24, 2002, now Pat. No. 7,090,976, and a continuation-in-part of application No. 09/710,058, filed on Nov. 10, 2000.

(60) Provisional application No. 60/290,287, filed on May 10, 2001, provisional application No. 60/164,592, filed on Nov. 10, 1999.

(51) Int. Cl.
   C07H 21/00 (2006.01)
   C07H 21/02 (2006.01)
   C07H 21/04 (2006.01)
   C12Q 1/68 (2006.01)
   C12P 21/06 (2006.01)
   C12P 21/04 (2006.01)
   C12N 9/00 (2006.01)
   C12N 15/00 (2006.01)

(52) U.S. Cl. ............ 536/23.1; 536/23.4; 536/23.7; 435/6; 435/69.1; 435/69.7; 435/183; 435/320.1

(58) Field of Classification Search ............ 435/6, 435/69.1, 69.7, 183, 320.1; 536/23.1, 23.4, 536/23.7
See application file for complete search history.

(56) References Cited

U.S. PATENT DOCUMENTS

| | | | |
|---|---|---|---|
| 5,798,441 A | 8/1998 | Cormier et al. | |
| 5,874,304 A | 2/1999 | Zolotukhin et al. | ......... 435/366 |
| 5,925,558 A | 7/1999 | Tsien et al. | |
| 5,958,713 A | 9/1999 | Thastrup et al. | |
| 5,976,796 A | 11/1999 | Szalay et al. | |
| 6,020,192 A | 2/2000 | Muzyczka et al. | |
| 6,025,192 A | 2/2000 | Beach et al. | |
| 6,025,485 A | 2/2000 | Kamb et al. | |
| 6,027,881 A | 2/2000 | Pavlakis et al. | |
| 6,054,321 A | 4/2000 | Tsien et al. | |
| 6,114,111 A | 9/2000 | Luo et al. | |
| 6,130,313 A | 10/2000 | Li et al. | |
| 6,150,176 A | 11/2000 | Tsien et al. | |
| 6,153,380 A | 11/2000 | Nolan et al. | |
| 6,172,188 B1 | 1/2001 | Thastrup et al. | ............. 530/350 |
| 6,180,343 B1 | 1/2001 | Anderson et al. | |
| 6,197,928 B1 | 3/2001 | Tsien et al. | |
| 6,232,107 B1 | 5/2001 | Bryan et al. | ................ 435/189 |
| 6,248,550 B1 | 6/2001 | Tsien et al. | |
| 6,255,071 B1 | 7/2001 | Beach et al. | |
| 6,265,548 B1 | 7/2001 | Pavlakis et al. | |
| 6,316,181 B1 | 11/2001 | Fillmore et al. | |
| 6,365,344 B1 | 4/2002 | Nolan et al. | |
| 6,455,247 B1 | 9/2002 | Nolan et al. | |
| 6,548,249 B1 | 4/2003 | Anderson et al. | |
| 6,562,617 B1 | 5/2003 | Anderson et al. | |
| 6,596,485 B2 | 7/2003 | Anderson et al. | |
| 7,090,976 B2 * | 8/2006 | Anderson et al. | ............. 435/6 |

FOREIGN PATENT DOCUMENTS

| | | |
|---|---|---|
| WO | WO 94/19478 | 9/1994 |
| WO | 95/07463 A1 | 3/1995 |
| WO | WO 97/11094 | 3/1997 |
| WO | 97/27212 A1 | 7/1997 |
| WO | 97/27213 A1 | 7/1997 |
| WO | WO 98/14605 | 4/1998 |
| WO | 99/49019 A3 | 9/1999 |
| WO | 99/54494 | 10/1999 |
| WO | 99/58663 | 11/1999 |
| WO | 01/34806 A3 | 5/2001 |
| WO | WO 01/32688 | 5/2001 |
| WO | 01/68824 A2 | 9/2001 |
| WO | WO 01/64843 | 9/2001 |
| WO | WO 02/057451 | 7/2002 |

OTHER PUBLICATIONS

U.S. Appl. No. 09/710,058, filed Nov. 2000, Anderson et al.*
Hanazono, Human Gene Ther. vol. 8: pp. 1313-1319 (1997).
Levy et al., Nature Biotech. vol. 14: pp. 610-614 (1996).
Cheng et al., Nature Biotech. vol. 14: pp. 606-609 (1996).
Borjigin, "Insertional mutagenesis as a probe of rhodopsin's topography, stability, and activity." JBC, (1994), 269: 14715-14722.
Chalfie, M. et al., "Green fluorescent protein as a marker for gene expression," Science, (1994), 263(5148): 802-5.
Day, R.N. et al., "Fluorescence resonance energy transfer microscopy of localized protein interactions in the living cell nucleus," Methods, (2001), 25(1): 4-18.
Doi et al., "Screening of conformationally constrained random polypeptide libraries," CMLS, (1998), 54(5):394-404.
Felts, K. et al., "Recombinant *Renilla Reniformis* GFP displays low toxicity," Strategies, (2000), 13: 85-87.
Foster, T. P. et al., "Expression of the enhanced green fluorescent protein by herpes simplex virus type 1 (HSV-1) as an in vitro marter for virus entry and replication," J Virol Methods, (1998), 75(2): 151-160.

(Continued)

*Primary Examiner*—Sue Liu
(74) *Attorney, Agent, or Firm*—Klarquist Sparkman, LLP

(57) ABSTRACT

The invention relates to methods and compositions utilizing *Renilla* green fluorescent proteins (rGFP), and *Ptilosarcus* green fluorescent proteins (pGFP). In particular, the invention relates to the use of *Renilla* GFP or *Ptilosarcus* GFP proteins as reporters for cell assays, particularly intracellular assays, including methods of screening libraries using rGFP or pGFP.

3 Claims, 12 Drawing Sheets

OTHER PUBLICATIONS

Geada, M.M. et al., "Movement of vaccinia virus intracellular enveloped virions with GFP tagged to the F13L envelope protein," J Gen Virol, (2001), 82(Pt 11): 2747-2760.

Hawley, R.G. et al., "Versatile retroviral vectors for potential use in gene therapy," Gene Ther, (1994), 1(2): 136-8.

Heim, R. et al., "Engineering green fluorescent protein for improved brightness, longer wavelengths and fluorescence resonance energy transfer." Curr Biol. (1996), 6(2).

Kinsella, T.M. et al., "Episomal vectors rapidly and stably produce high-titer recombinant retrovirus," Hum Gene Ther, (1996), 7(12): 1405-13.

Kitamura T. et al.,"Efficient screening of retroviral cDNA expression libraries," Proc Natl Acad Sci, (1995), 92(20): 9146-50.

Ladner, "Constrained peptides as binding entities," Trends Biotechnol, 1995),13(10):426-30.

Liu, H.S. et al., "Is green fluorescent protein toxic to theliving cells?" (1999), Biochem Biophys Res Commun, 260(3): 712-7.

Lorens, J.B. et al., "Retroviral delivery of peptide modulators of cellular functions," Mol Ther, (2000), 1(5): 438-447.

Mahajan, N.P. et al., "Bcl-2 and Bax interactions in mitochondria probed with green fluorescent protein and fluorescence resonance energy transfer," Nat Biotechnol, (1998), 16(6): 547-52.

Matz, M.V. et al., "Fluorescent proteins from nonbioluminescent *Anthozoa* species," Nat Biotechnol, (1999), 17(10): 969-73.

McConnel et al., "Tendamistat as a scaffold for conformationally constrained phage peptide libraries," J Mol Biol, (1995), 250(4): 460-70.

Miesenbock, G. et al., "Visualizing secretion and synaptic transmission with pH-sensitive green fluorescent proteins," Nature, (1998), 394(6689): 192-5.

Mitra, R.D. et al., "Fluorescence resonance energy transfer between blue-emitting and red-shifted excitation derivatives of the green fluorescent protein," Gene, (1996), 173(1 Spec No): 13-7.

Miyawaki, A. et al., "Monitoring protein conformations and interactions by fluorescence resonance energy transfer between mutants of green fluorescent protein," Methods Enzymol, (2000), 327: 472-500.

Miyawaki, A. et al., Fluorescent indicators for Ca2+based on green fluorescent proteins and calmodulin, Nature, (1997), 388(6645): 882-7.

Miyoshi, H. et al., "Development of a self-inactivating lentivirus vector," J Virol, (1998), 72(10): 8150-7.

Niwa, H. et al., "Chemical nature of the light emitter of the Aequorea green fluorescent protein," Proc Natl Acad Sci, (1996), 93(24): 13617-22.

Pear, W.S. et al., "Production of high-titer helper-free retroviruses by transient trasfection," Proc Natl Acad Sci, (1993), 90(18): 8392-6.

Rogers, B. et al., "New Mammalian Expression Vectors Employ Stable, High-Level Fluorescence Humanized Renilla GFP Reporter," Strategies, (2000), 13: 141-144.

Romoser, V.A. et al., "Detection in living cells of Ca2+-dependent changes in the fluorescence emission of an indicator composed o ftwo green fluorescent protein variants linked by a calmodulin-binding sequence. A new class of fluorescent indicators," J Biol Chem, (1997), 272(20): 13270-4.

Sakai, R. et al., "Design and characterization of a DNA-encoded, voltage-sensitive fluorescent protein," Eur J. Neurosci, (2001), 13(12): 2314-8.

Siegel, M.S. et al., "A genetically encoded optical probe of membrane voltage," Neuron, (1997), 19(4): 735-41.

Stauber, R.H. et al., "Development and applications of enhanced green fluorescent protein mutants," Biotechniques, (1998), 24(3): 462-6, 468-71.

Tsien, R.Y., "The green fluorescent protein," Annu Rev Biochem, (1998), 67: 509-44.

Ward, W.W. et al., "An energy transfer protein in coelenterate bioluminescence. Characterization of the *Renilla* green-fluorescent protein," J Biol Chem, (1979), 254(3): 781-8.

Yang, F. et al., "Highly efficient green fluorescent protein-based kinase substrates," Anal Biochem, (1999), 266(2): 167-73.

Zheng, C. et al., "Genomic integration and gene expression by a modified adenoviral vector," Nat Biotechnol, (2000), 18(2): 176-80.

Zolotukhin, S. et al., "A"humanized" green fluorescent protein cDNA adapted for high-level exression in mammalian cells," J Virol, (1996), 70(7): 4646-54.

Abedi, M.R. et al., "Green fluorescent protein as a scaffold for intracellular presentation of peptides," *Nucleic Acids Res* 26(2):623-30 (1998).

Aran, J.M. et al., "Construction and characterization of bicistronic retroviral vectors encoding the multidrug transporter and β-galactosidase or green fluorescent proten," *Cancer Gene Therapy* 5(4):195-206 (1998).

Ormo M, et al., "Crystal structure of the Aequorea victoria green fluorescent protein," *Science* 273:1392-5 (Sep. 1996).

Peelle, B., "Intracellular protein scaffold-mediated display of random peptide libraries for phenotypic screens in mammalian cells," *Chemistry & Biology* 8:521-534 (2001).

Peelle, B. et al. "Characterization and Use of green Fluorescent Proteins from *Renilla mulleri* and *Ptilosarcus guernyi* for the Human Cell Display Functional Peptides," *J Protein Chem* 20(6):507-19 (2001).

Phillips GN, "Structure and dynamics of green fluorescent protein," *Curr Opin Struct Biol*. 7(6):821-7 (Dec. 1997).

Yang F, et al., "The molecular structure of green fluorescent protein," *Nat Biotechnol*. 14(10):1246-51 (Oct. 1996).

Result 4 Database Alignment Search Seq. Id 15 of US Pat. No. 6,232,107, Jan. 16, 2003.

* cited by examiner

```
     1              15             30             45             60
ZFP5 ---MAQSKHGLTKEM TMDYRMEGCVDGHKF VITGEGIGYPFKGKQ --AINLCVVEGGPLP
ANEM ---MALSNKFIGDDM KMTYHMDGCVNGHYF TVKGEGNGKPYEGTQ TSTFKVTMANGGPLA
DSFP ---MSCSKSVIKEEM LIDLHLEGTFNGHYF EIKGKGKGQPNEGTN --TVTLEVTKGGPLP
FP48 IPKALTTMGVIKPDM KIKLKMEGNVNGHAF VIEGEGEGKPYDGTH --TLNLEVKEGAPLP
PTIL MNRNVLKNTGLKEIM SAKASVEGIVNNHVF SMEGFGKGNVLFGNQ --LMQIRVTKGGPLP
RENM MSKQILKNTCLQEVM SYKVNLEGIVNNHVF TMEGCGKGNILFGNQ --LVQIRVTKGAPLP
AEQV ---MSKGEELFTGVV PILVELDGDVNGQKF SVSGEGEGDATYGKL --TLKFICTTG-KLP
CONS ---M------I---M --K---GE-VNGH-F ---GEG-G-P--G-Q --T----VT-GGPLP 75             90            105   A        120
ZFP5 FAEDILSAAFNYGNR VFTEYPQ--DIVDYF KNSCPAGYTWDRSFL FEDGAVCICNADITV
ANEM FSFDILSTVFKYGNR CFTAYPT--SMPDYF KQAFPDGMSYERTFT YEDGG--VATASWEI
DSFP FGWHILCPQFQYGNK AFVHHPD--NIHDYL KLSFPEGYTWERSMH FEDGG--LCCITNDI
FP48 FSYDILSNAFQYGNR ALTKYPD--DIADYF KQSFPEGYSWERTMT FEDKG--IVKVKSDI
PTIL FAFDIVSIAFQYGNR TFTKYPD--DIADYF VQSFPAGFFYERNLR FEDGA--IVDIRSDI
RENM FAFDIVSPAFQYGNR TFTKYPN--DISDYF IQSFPAGFMYERTLR YEDGG--LVEIRSDI
AEQV VPWPTLVTTFSYGVQ CFSRYPDHMKQHDFF KSAMPEGYVQERTIF YKDDG--NYKTRAEV
CONS F--DILS-AFQYGNR -FTKTPD--DI-DYF KQSFP-GY--ERT-- FEDGG---------I

B          135             150           C165            180
ZFP5 SVEENCMYHESKFYG VNFPADG-PVMKKMT DNWEPSCEKIIPVPK QGILKGDVSMYLLLK
ANEM SLKGNCFEHKSTFHG VNFPADG-PVMAKKT TGWDPSFEKMTVCD- -GILKGDVTAFLMLQ
DSFP SLTGNCFYYDIKFTG LNFPPNG-PVVQKKT TGWEPSTERLYPRD- -GVLIGDIHHALTVE
FP48 SMEEDSFIYEIRFDG MNFPPNG-PVMQKKT LKWEPSTEIMYVRD- -GVLVGDISHSLLLE
PTIL SLEDDKFHYKVEYRG NGFPSNG-PVMQKAI LGMEPSFEVVYMNS- -GVLVGEVDLVYKLE
RENM NLIEDKFVYRVEYKG SNFPDDG-PVMQKTI LGIEPSFEAMYMNN- -GVLVGEVILVYKLN
AEQV KFEGDTLVNRIELKG IDFKEDGNILGHKME YNYNSHNVYIMADKQ KNGIKVNFKIRHNIE
CONS SLE-D-F-Y---F-G -NFP-DG-PVMQK-T -GWEPS-E--Y---- -GVL-GDV---L-L-

D         195        E     210            225F            240
ZFP5 DG-GRLRCQFDTVYK AKSVPRKMPDWHFIQ HKLTREDRSDAKNQK WHLTEHAIASG-SAL
ANEM GG-GNYRCQFHTSYK TK-KPVTMPPNHVVE HRIARTDLDKGGNS- VQLTEHAVAHITSVV
DSFP GG-GHYACDIKTVYR AKKAALKMPGYHYVD TKLVIWNNDKEFMK- VEEHEIAVARHHPFY
FP48 GG-GHYRCDFKSIYK AKK-VVKLPDYHFVD HRIEILNHDKDYNK- VTLYENAVARYSLLP
PTIL SG-NYYSCHMKTFYR SKGGVKEFPEYHFIH HRLEKTYVEEG--SF VEQHETAIAQLTTIG
RENM SG-KYYSCHMKTLMK SKGVVKEFPSYHFIQ HRLEKTYVEDG--GF VEQHETAIAQMTSIG
AEQV DGSVQLADHYQQNTP IGDGPVLLPDNHYLS TQSALSKDPNEKRDH MILLEFVTAAGITHG
CONS -G-G-Y-C--KT-Y- -K------P-YHF-- HRL------------ V-L-E-A-A------

ZFP5 P--------- 231
ANEM PF-------- 229
DSFP EPKKDK---- 232
FP48 SQA------- 231
PTIL KPLGSLHEWV 238
RENM KPLGSLHEWV 238
AEQV MDELYK---- 238
CONS ----------
```

FIG._1

```
ATGGGCAGCAAGCAGATCCTGAAGAACACCTGCCTGCAGGAGGTGATGAGCTACAAGGTG    (co)
ATG---AGTAAACAAATATTGAAGAACACTTGTTTACAAGAAGTAATGTCGTATAAAGTA    (wt)

AACCTGGAGGGCATCGTTAACAACCACGTGTTCACCATGGAGGGCTGCGGCAAGGGCAAC
AATCTGGAAGGAATTGTAAACAACCATGTTTTTACAATGGAGGGTTGCGGCAAAGGGAAT

ATCCTGTTCGGCAACCAATTGGTGCAGATCCGCGTGACCAAGGGCGCCCCCCTGCCCTTC
ATTTTATTCGGCAATCAACTGGTTCAGATTCGTGTCACGAAAGGGGCCCCACTGCCTTTT

GCCTTCGACATCGTGAGCCCCGCCTTCCAGTACGGCAACCGTACGTTCACCAAGTACCCC
GCATTTGATATTGTGTCACCAGCTTTTCAATATGGCAACCGTACTTTCACGAAATATCCG

AACGACATCAGCGACTACTTCATCCAGAGCTTCCCCGCCGGCTTCATGTACGAGCGCACC
AATGATATATCAGATTATTTTATACAATCATTTCCAGCAGGATTTATGTATGAACGAACA

CTGCGCTACGAGGACGGCGGCCTGGTGGAGATCCGCAGCGACATCAACCTGATCGAGGAC
TTACGTTACGAAGATGGCGGACTTGTTGAAATTCGTTCAGATATAAATTTAATAGAAGAC

AAGTTCGTGTACCGCGTGGAGTACAAGGGCAGCAACTTCCCCGACGACGGGCCCGTGATG
AAGTTCGTCTACAGAGTGGAATACAAAGGTAGTAACTTCCCAGATGATGGTCCCGTCATG

CAGAAGACCATCCTGGGCATCGAGCCCAGCTTCGAGGCCATGTACATGAACAACGGCGTG
CAGAAGACTATCTTAGGAATAGAGCCTTCATTTGAAGCCATGTACATGAATAATGGCGTC

CTGGTGGGCGAGGTGATCCTGGTGTACAAGCTTAACAGCGGCAAGTACTACAGCTGCCAC
TTGGTCGGCGAAGTAATTCTTGTCTATAAACTAAACTCTGGGAAATATTATTCATGTCAC

ATGAAGACCCTGATGAAGAGCAAGGGCGTGGTGAAGGAGTTCCCCAGCTACCACTTCATC
ATGAAAACATTAATGAAGTCGAAAGGTGTAGTAAAGGAGTTTCCTTCGTATCATTTTATT

CAGCACCGCCTCGAGAAGACCTACGTGGAGGACGGCGGCTTCGTGGAGCAGCACGAGACC
CAACATCGTTTGGAAAAGACTTACGTAGAAGACGGGGGGTTCGTTGAACAGCATGAGACT

GCCATCGCCCAGATGACCAGCATCGGCAAGCCCCTGGGATCCCTGCACGAGTGGGTG
GCTATTGCTCAAATGACATCTATAGGAAAACCACTAGGATCCTTACACGAATGGGTT
```

FIG._2

```
ATGGGCAACCGCAACGTGCTGAAGAACACCGGCCTGAAGGAGATCATGAGCGCCAAGGCC    (co)
ATG---AACCGCAACGTATTAAAGAACACTGGACTGAAAGAGATTATGTCGGCAAAAGCT    (wt)

AGCGTGGAGGGCATCGTGAACAACCACGTGTTCAGCATGGAGGGCTTCGGCAAGGGCAAC
AGCGTTGAAGGAATCGTGAACAATCACGTTTTTTCCATGGAAGGATTTGGAAAAGGCAAT

GTGCTGTTCGGCAACCAGCTGATGCAGATCCGCGTGACCAAGGGCGGCCCCCTGCCCTTC
GTATTATTTGGAAACCAATTGATGCAAATCCGGGTTACAAAGGGAGGTCCGTTGCCATTC

GCCTTCGACATCGTGAGCATCGCCTTCCAGTACGGCAACCGCACCTTCACCAAGTACCCC
GCTTTCGACATTGTTTCCATAGCTTTCCAATACGGGAATCGCACTTTCACGAAATACCCA

GACGACATCGCCGACTACTTCGTGCAGAGCTTCCCCGCCGGCTTCTTCTACGAGCGCAAC
GACGACATTGCGGACTACTTTGTTCAATCATTTCCGGCTGGATTTTTCTACGAAAGAAAT

CTGCGCTTCGAGGACGGCGCCATCGTGGACATCCGCAGCGACATCAGCCTGGAGGACGAC
CTACGCTTTGAAGATGGCGCCATTGTTGACATTCGTTCAGATATAAGTTTAGAAGATGAT

AAGTTCCACTACAAGGTGGAGTACCGCGGCAACGGCTTCCCCAGCAACGGCCCCGTGATG
AAGTTCCACTACAAAGTGGAGTATAGAGGCAACGGTTTCCCTAGTAACGGACCCGTGATG

CAGAAGGCCATCCTGGGCATGGAGCCCAGCTTCGAGGTGGTGTACATGAACAGCGGCGTG
CAAAAAGCCATCCTCGGCATGGAGCCATCGTTTGAGGTGGTCTACATGAACAGCGGCGTT

CTGGTGGGCGAGGTGGACCTGGTGTACAAGCTGGAGAGCGGCAACTACTACAGCTGCCAC
CTGGTGGGCGAAGTAGATCTCGTTTACAAACTCGAGTCAGGGAACTATTACTCGTGCCAC

ATGAAGACCTTCTACCGCAGCAAGGGCGGCGTGAAGGAGTTCCCCGAGTACCACTTCATC
ATGAAAACGTTTTACAGATCCAAAGGTGGAGTGAAAGAATTCCCGGAATATCACTTTATC

CACCACCGCCTGGAGAAGACCTACGTGGAGGAGGGCAGCTTCGTGGAGCAGCACGAGACC
CATCATCGTCTGGAGAAAACCTACGTGGAAGAAGGAAGCTTCGTGGAACAACACGAGACG

GCCATCGCCCAGCTGACCACCATCGGCAAGCCCCTGGGCAGCCTGCACGAGTGGGTG
GCCATTGCACAACTGACCACAATTGGAAAACCTCTGGGCTCCCTTCATGAATGGGTG
```

FIG._3

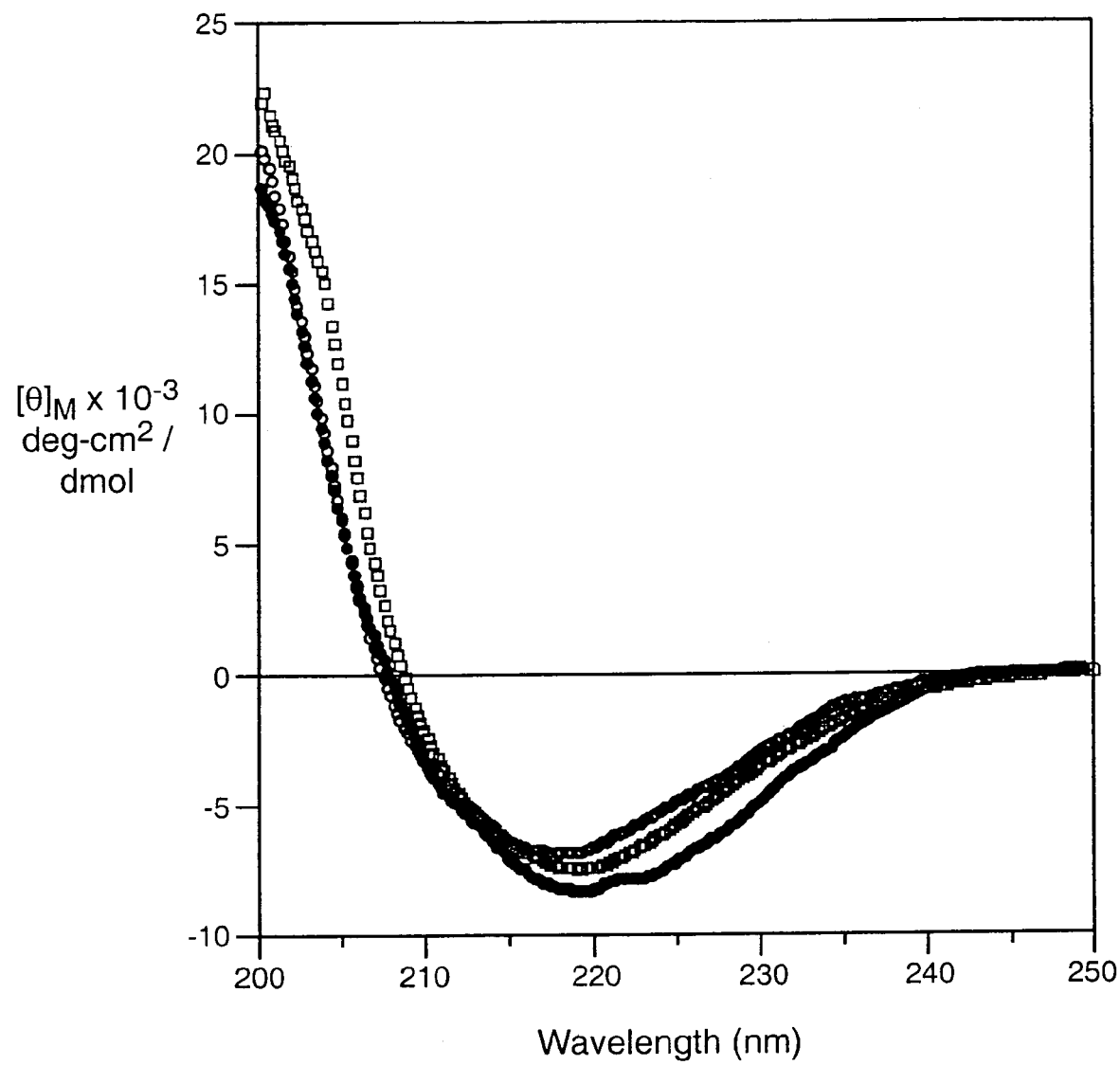
FIG._4

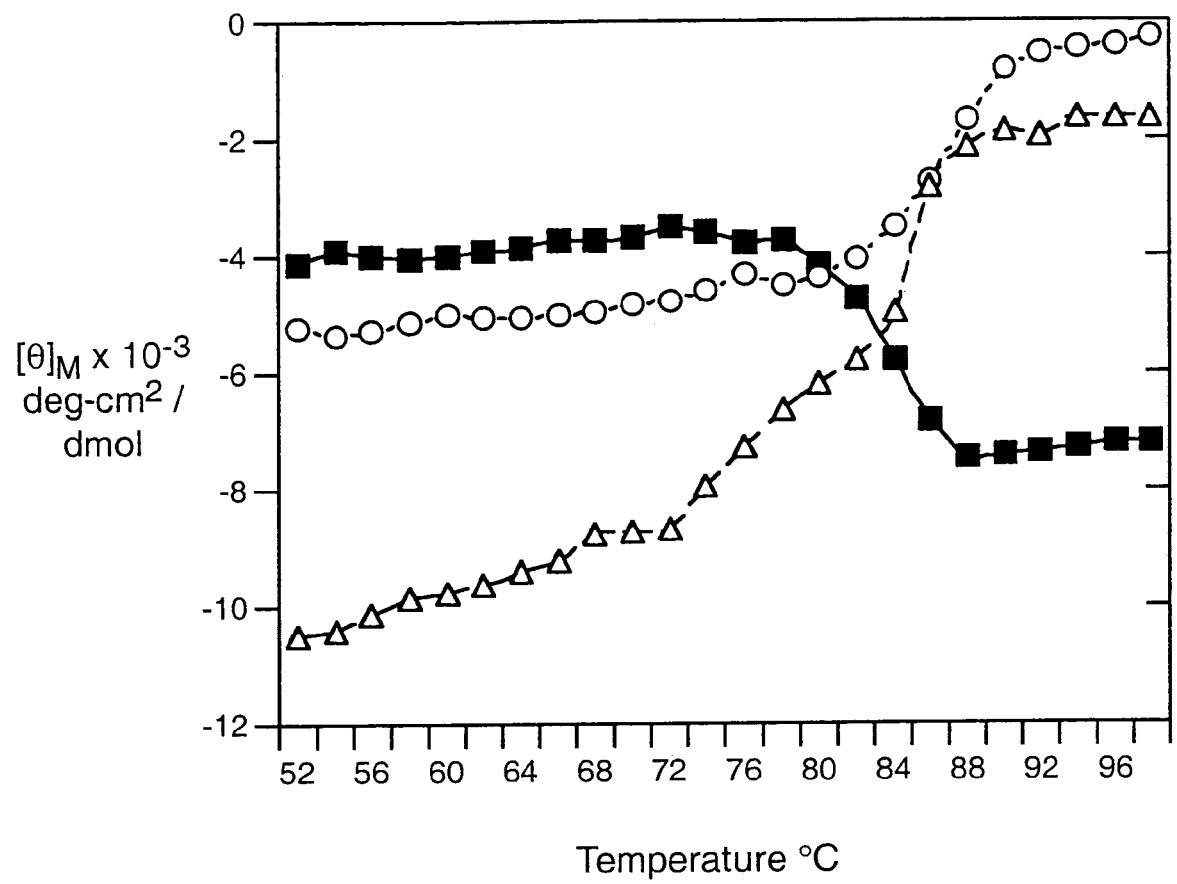
FIG._5

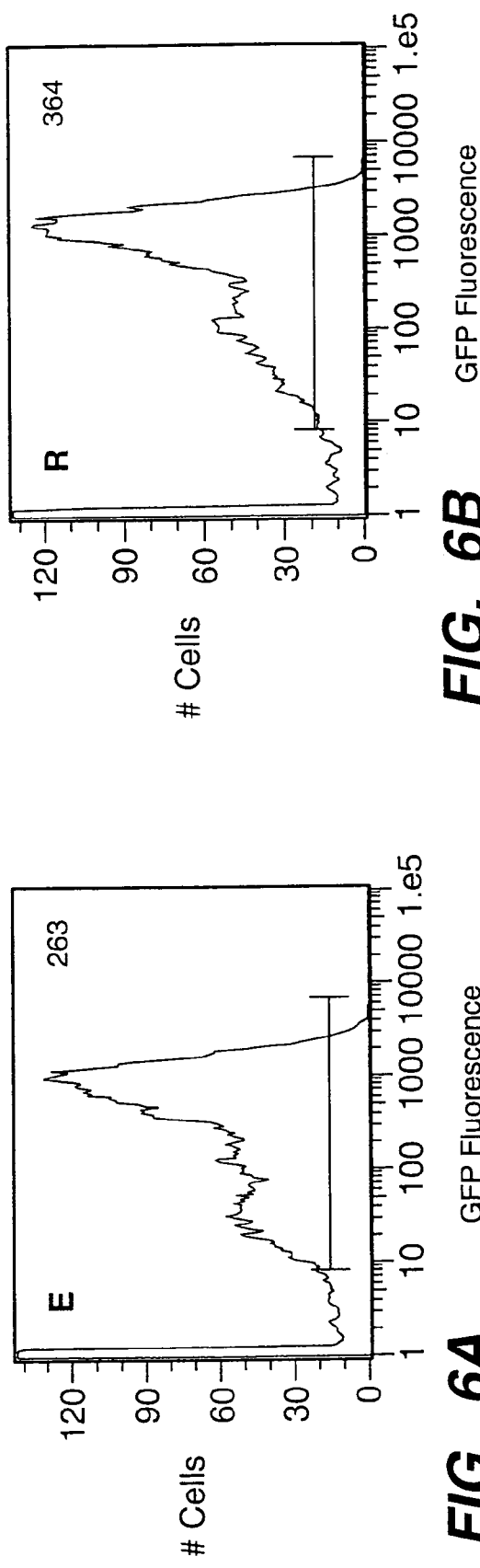
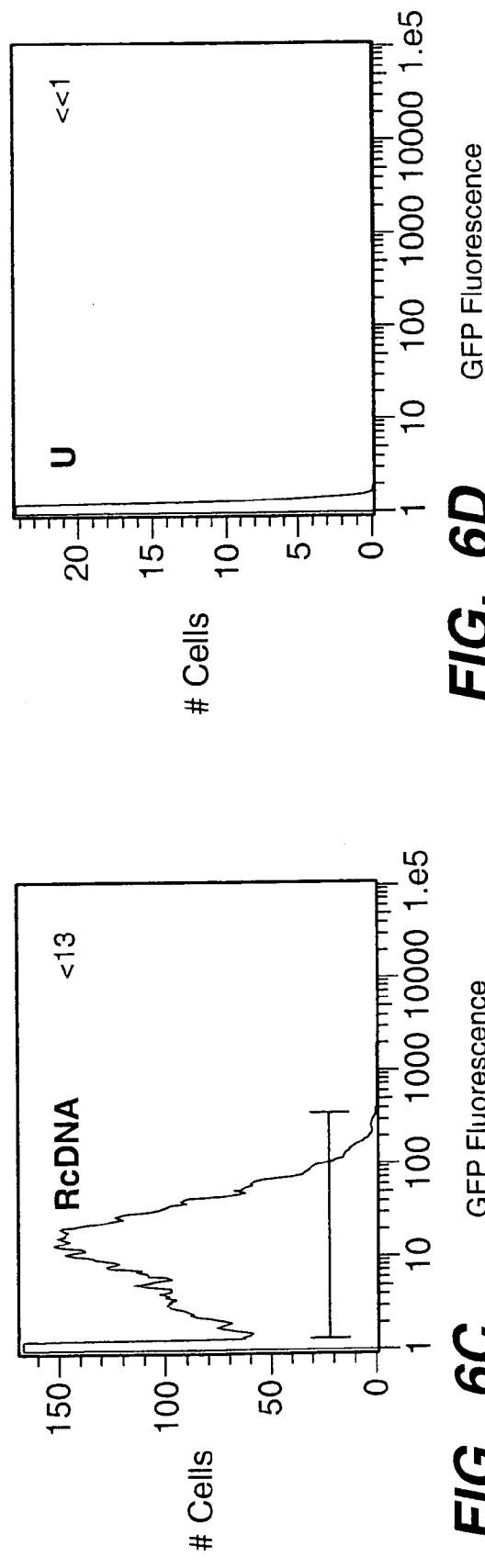
FIG._6A  FIG._6B  FIG._6C  FIG._6D

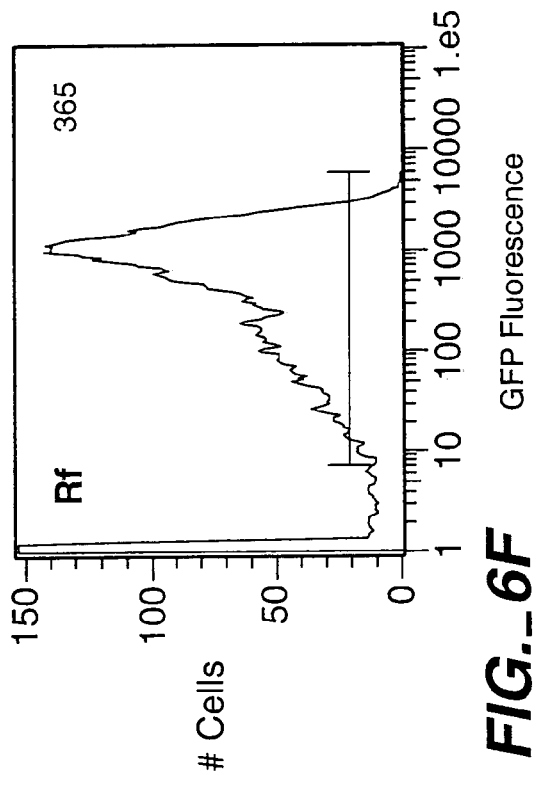
FIG._6E
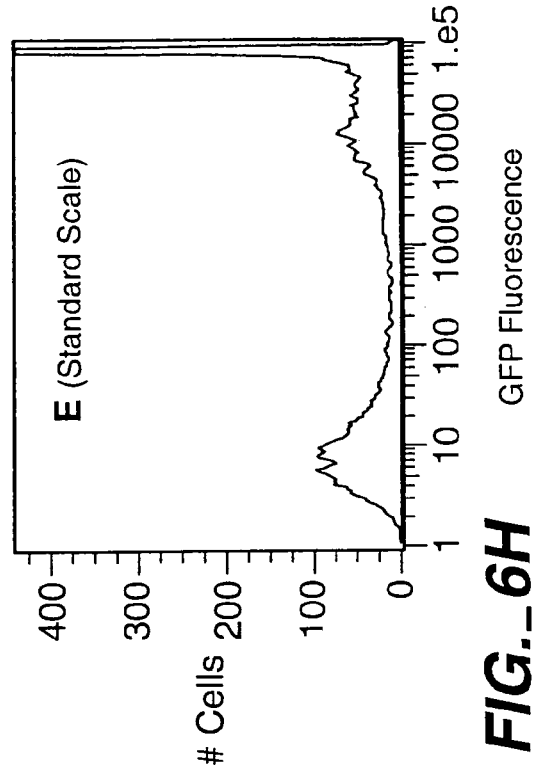
FIG._6F
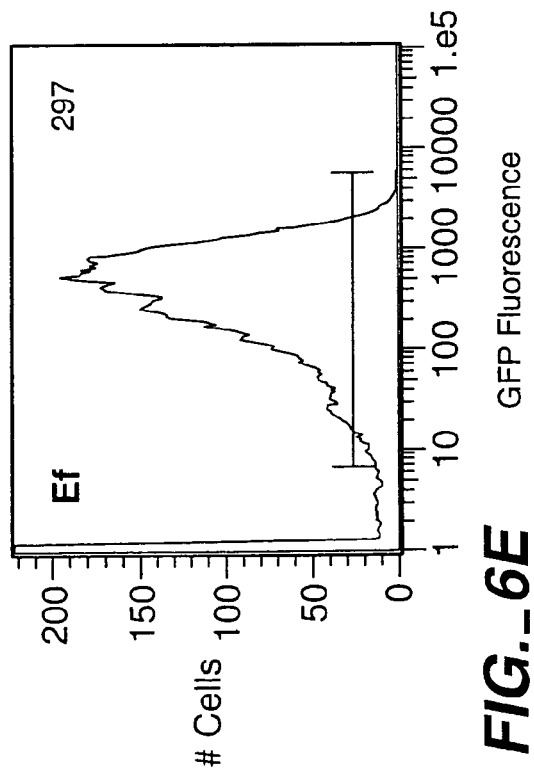
FIG._6G
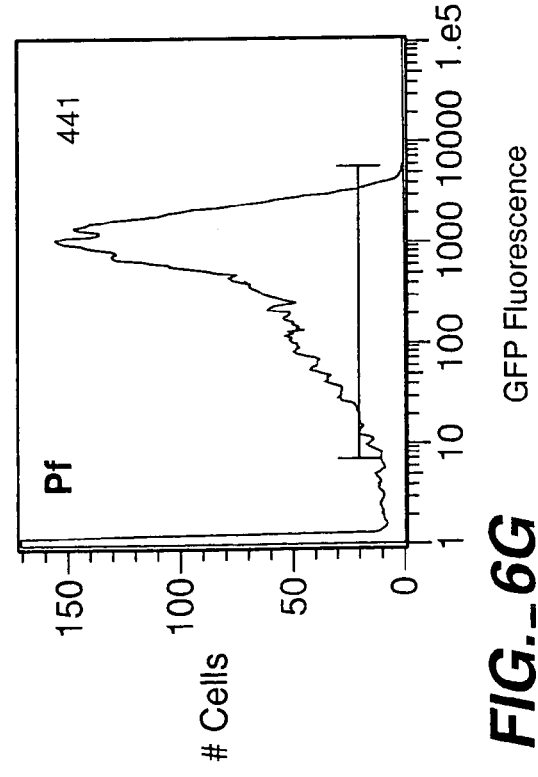
FIG._6H

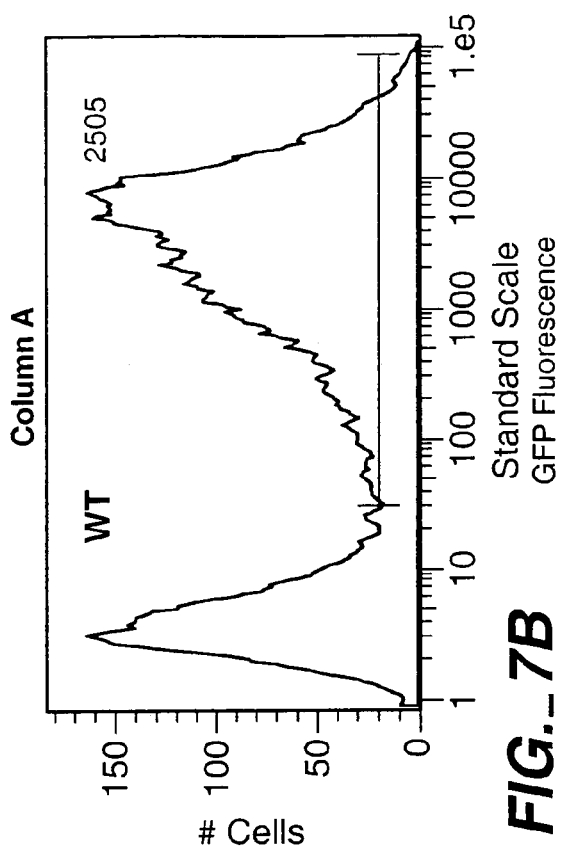
FIG._7A
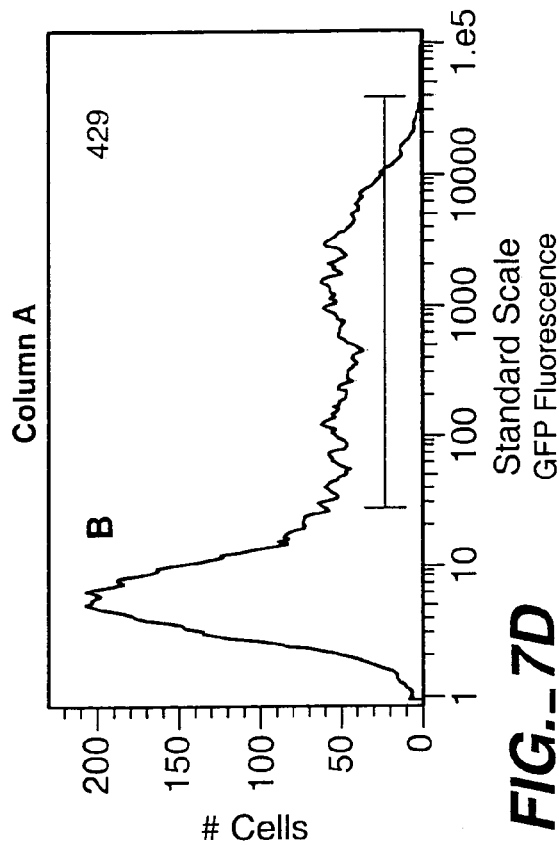
FIG._7B
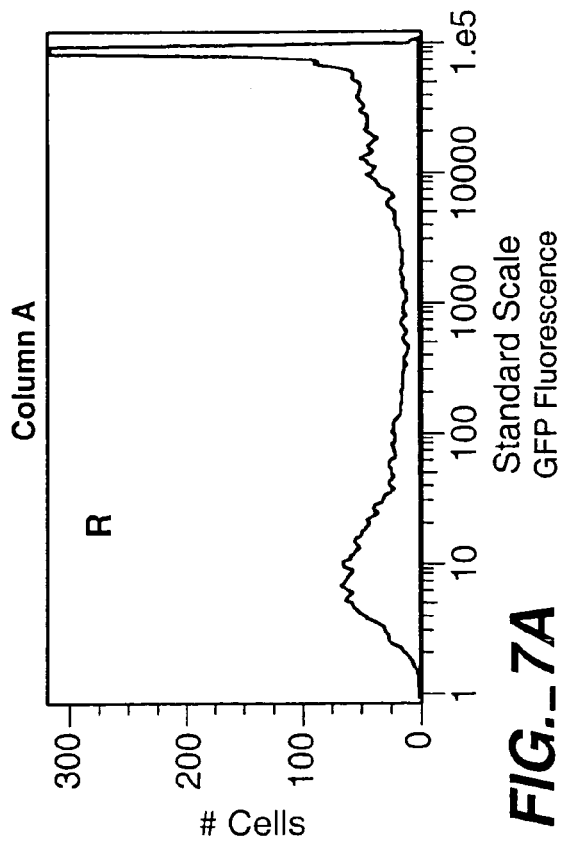
FIG._7C
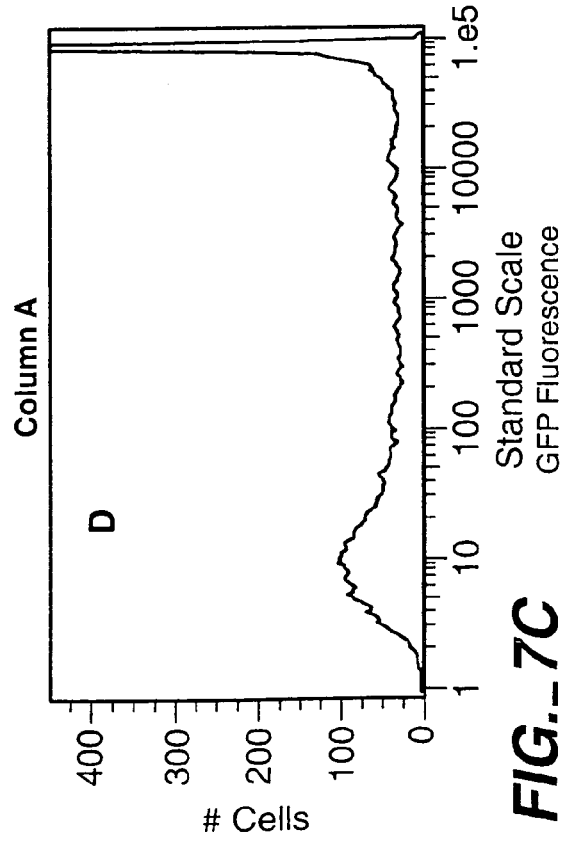
FIG._7D

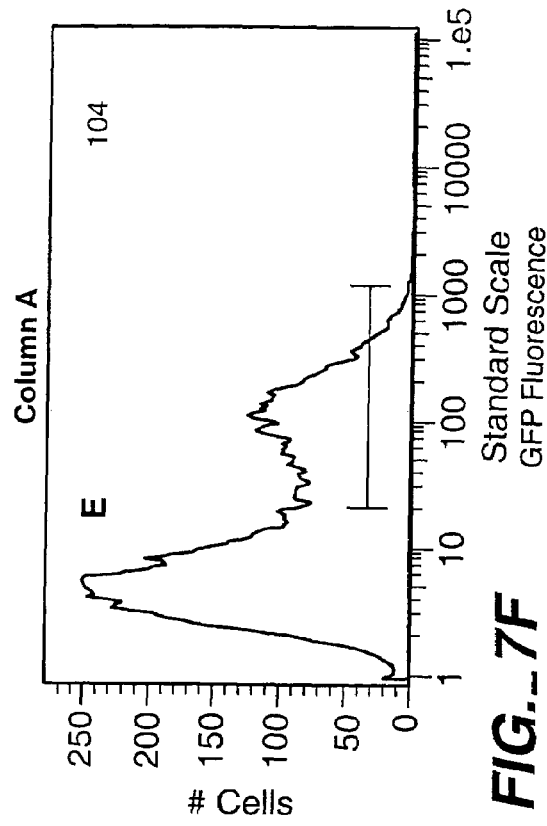
FIG._7E
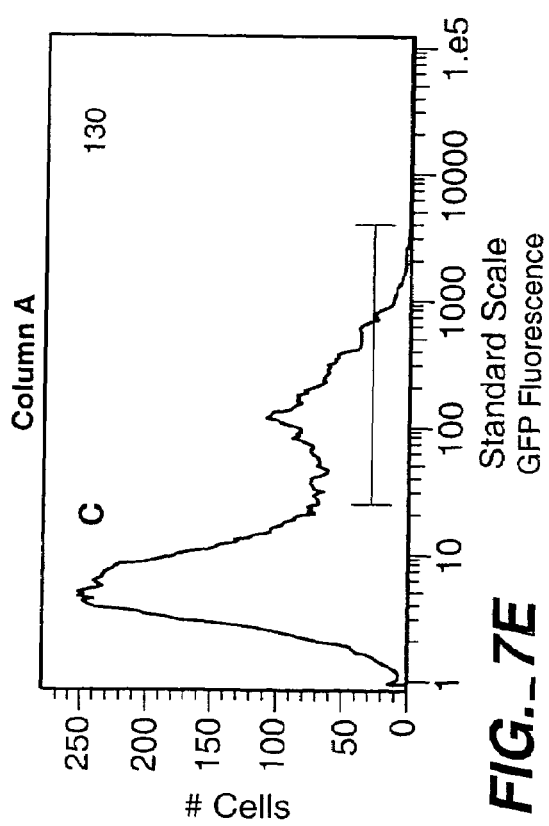
FIG._7F
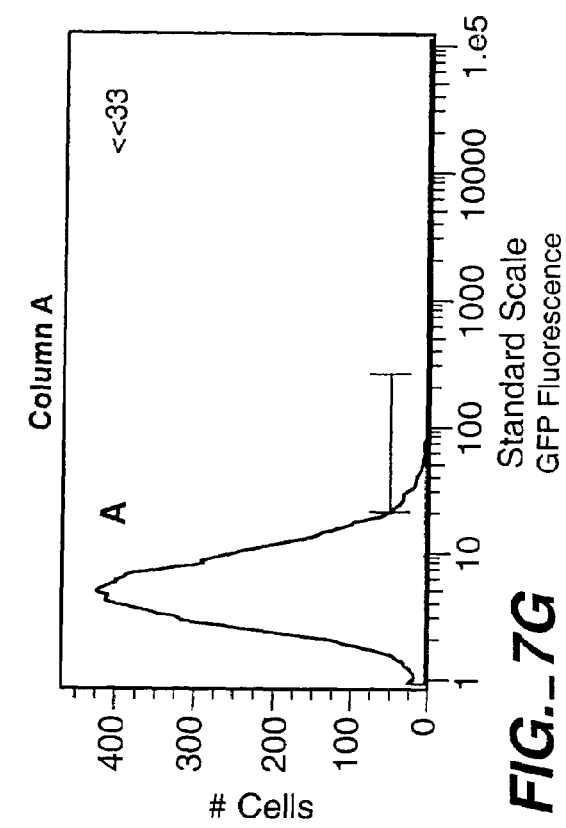
FIG._7G

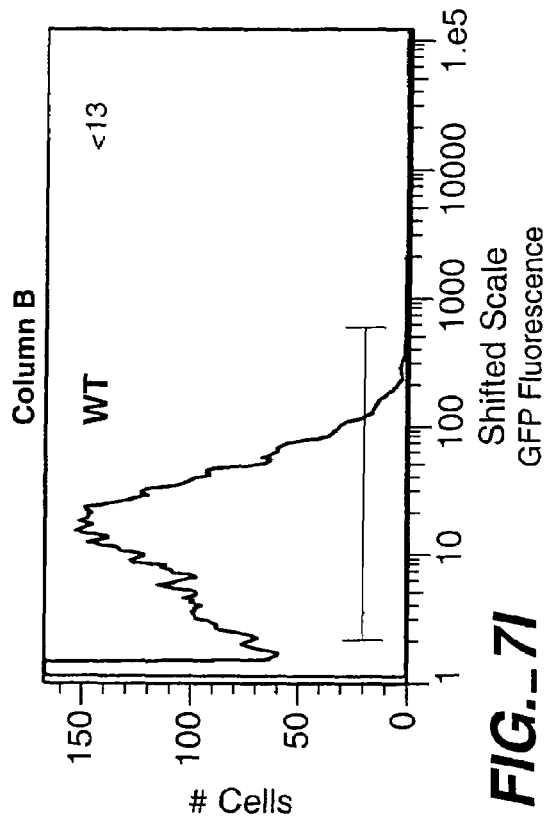
FIG._7H
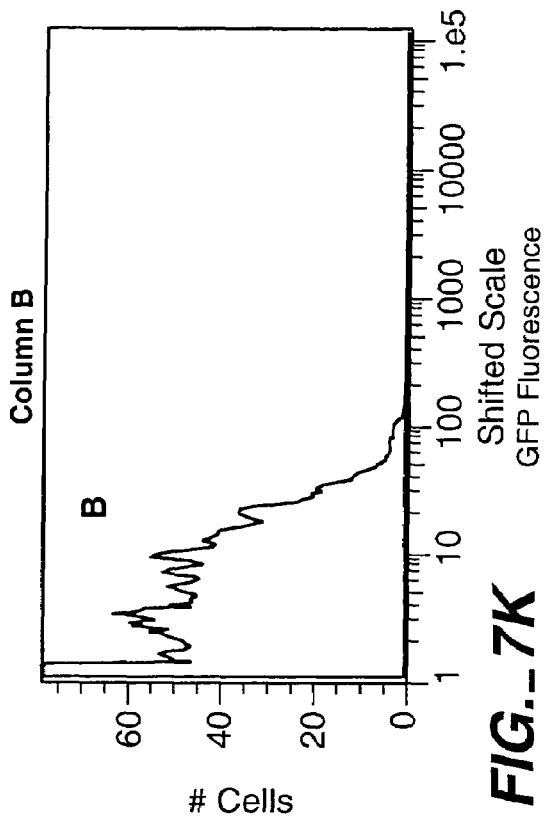
FIG._7I
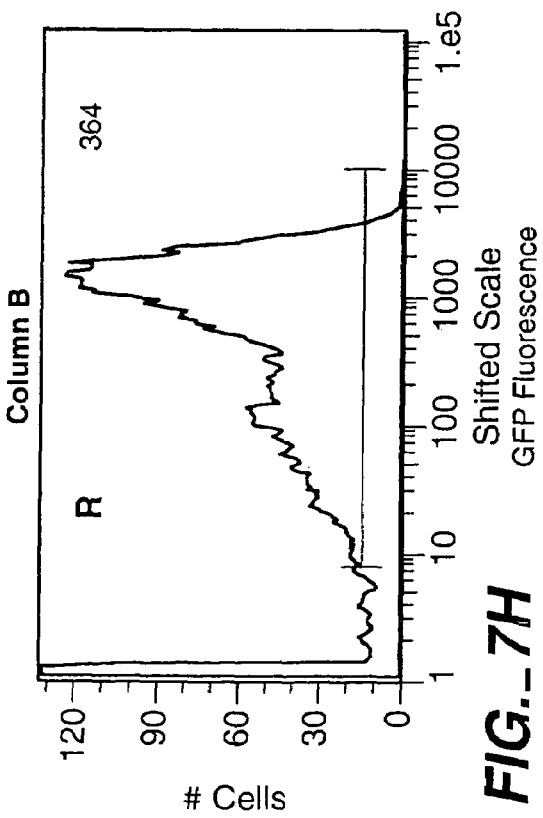
FIG._7J
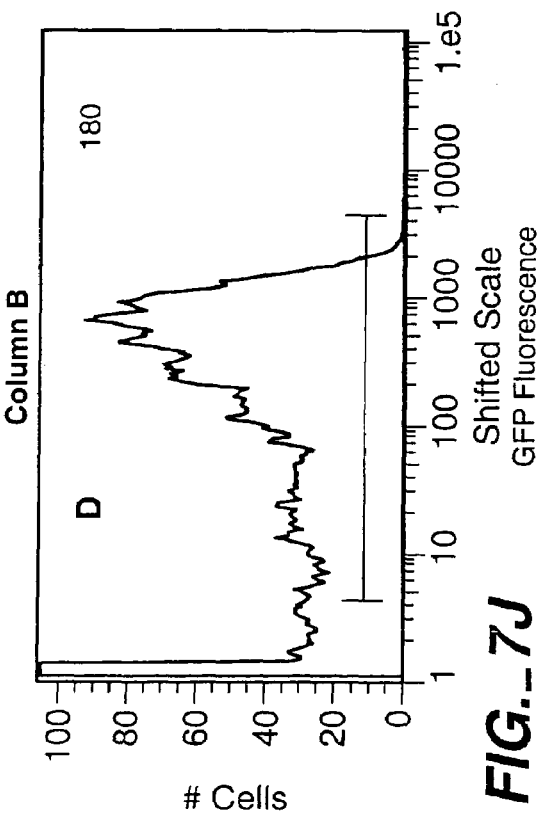
FIG._7K

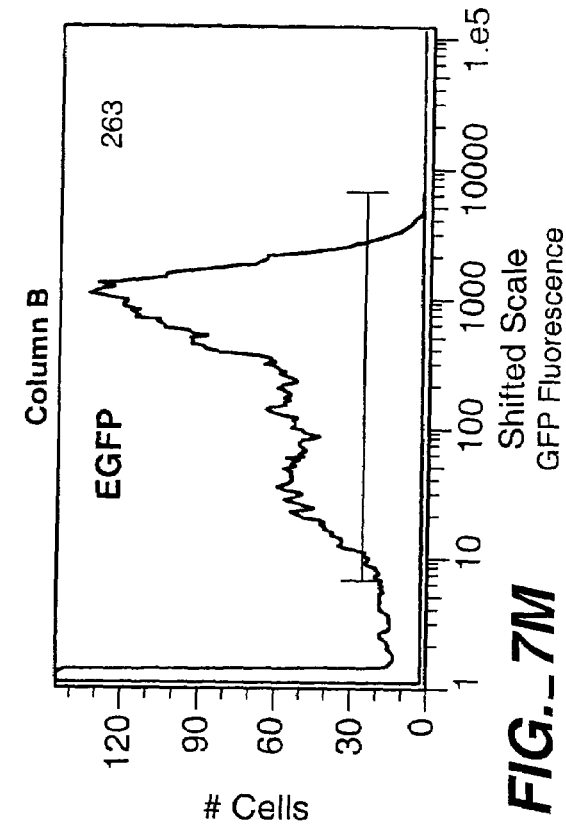
FIG._7M
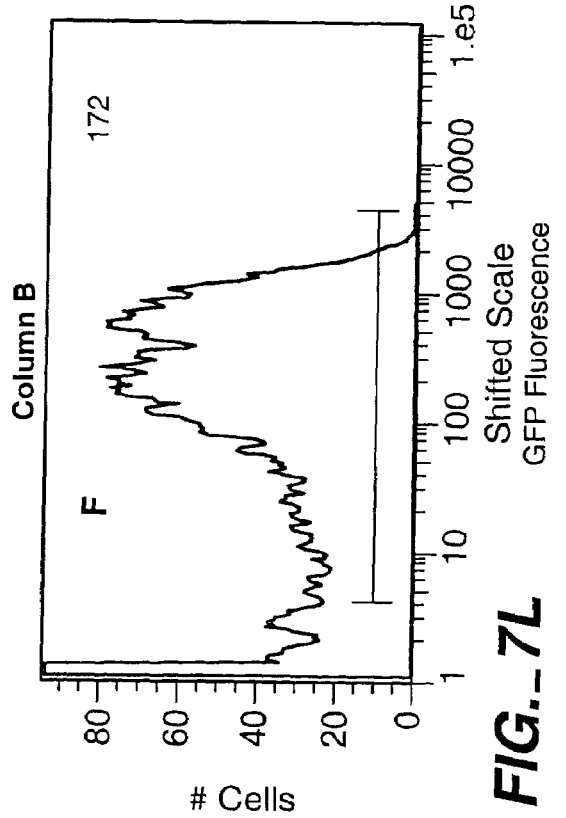
FIG._7L
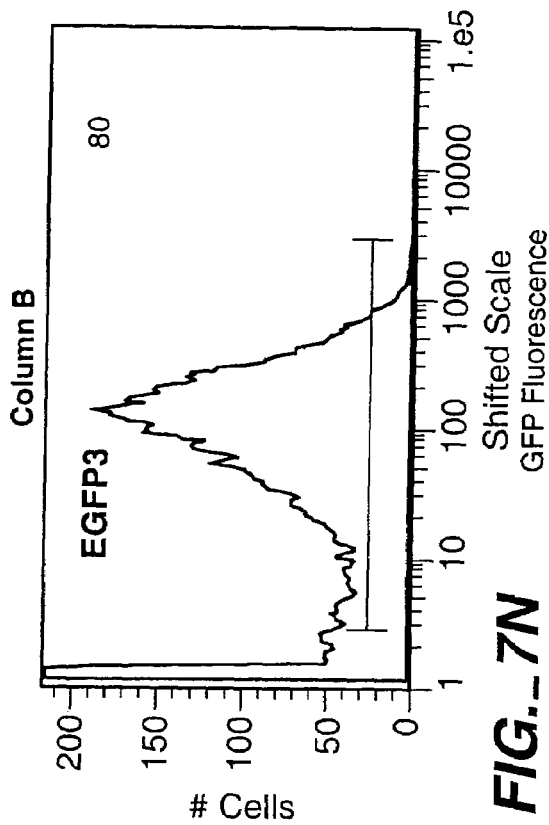
FIG._7N

FIG._8A
FIG._8C
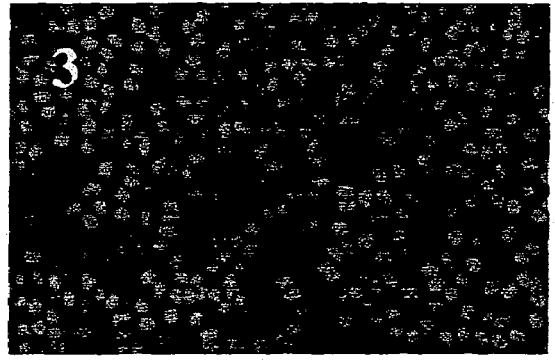
FIG._8B
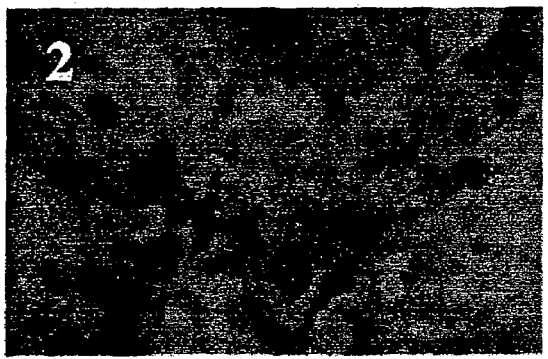
FIG._8D
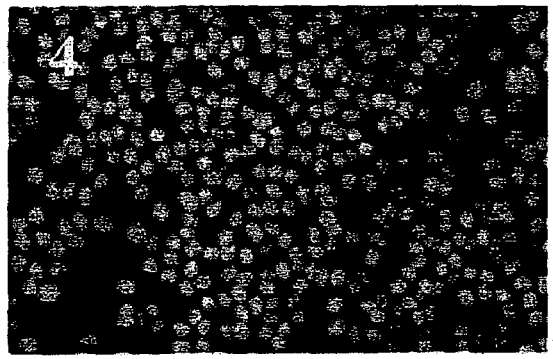
FIG._9
```
AHYAGYFADL-IH-I-T----
AHYAGYFASL-IH-V-T----
GYHADYYRQR-IH-V-T----
AYHADYYKQR-IH-V-M----
GYHADYYKQR-IH-V-M----
KQTLNFDLLK-AG-V-S----
KQLLNFDLLK-AG-V-S----
KQLLNFDLLK-AG-V-S----
KQLLNFDLLK-AG-V-S----
KQLLNFDLLK-AG-V-S----
KQMCNFDLLK-AG-V-S----
KQCTNFSLLK-AG-V-S----
KQCTNFSALK-AG-V-S----
EGATNFSLLK-AG-V-L----
XXXXXXXXXXLXXDXEXNPGP
```

METHODS AND COMPOSITIONS COMPRISING *RENILLA* GFP

CROSS-REFERENCE TO RELATED APPLICATIONS

This application is a continuation of U.S. application Ser. No. 10/133,973 (issued as U.S. Pat. No. 7,090,976), filed Apr. 24, 2002, which application claims the benefit of provisional application 60/290,287, filed May 10, 2001, and is a continuation-in-part of U.S. application Ser. No. 09/710,058, filed Nov. 10, 2000, which application claims the benefit of provisional application 60/164,592, filed on Nov. 10, 1999. The contents of these patent applications are incorporated by reference herein in their entirety for all purposes.

FIELD OF THE INVENTION

The invention relates to methods and compositions using *Renilla* green fluorescent proteins (rGFP) and *Ptilosarcus* green fluorescent proteins (pGFP). In particular, the invention relates to the use of rGFP or pGFP proteins as reporters for cell assays, particularly intracellular assays, including methods of screening libraries using rGFP and pGFP.

BACKGROUND OF THE INVENTION

The field of biomolecule screening for biologically and therapeutically relevant compounds is rapidly growing. Relevant biomolecules that have been the focus of such screenings include chemical libraries, nucleic acid libraries, and peptide libraries in search for molecules that either inhibit or augment the biological activity of identified target molecules. With particular regard to peptide libraries, the isolation of peptide inhibitors of targets and the identification of formal binding partners of targets has been a key focus. However, one particular problem with peptide libraries is the difficulty of assessing whether any particular peptide has been expressed, and at what level, prior to determining whether the peptide has a biological effect.

The green fluorescent protein from *Aequoria victoria* (hereinafter "aGFP") is a 238 amino acid protein displaying autofluorescent properties. The crystal structure of the protein and several point mutants has been solved (Ormo, M. et al. (1996) Science 273: 1392-95; Yang. F. et al. (1996) Nature Biotechnol. 14: 1246-51). The fluorophore, consisting of a modified tripeptide, is buried inside a relatively rigid β-can structure, where it is almost completely protected from solvent access. The protein fluorescence is sensitive to a number of point mutations (Phillips, G. N. (1997) Curr. Opin. Struct. Biol. 7: 821-27). Since any disruption of the structure allowing solvent access to the fluorophoric tripeptide results in fluorescence quenching, the fluorescence appears to be a sensitive indication of the preservation of the native structure of the protein.

Uses of GFP as a biological marker, such as gene expression, protein targeting, protein interactions, and biosensors, are well known. The extensively examined aGFP folds efficiently at or below room temperature, but fails to fold properly at higher temperatures. Aggregation of the protein appears to occur when overexpressed in certain organisms, resulting in weak fluorescence. In addition, the fluorescence of the native aGFP has a low quantum yield, which has prompted a search for variants of aGFP with improved stability and fluorescence properties. Although expression of aGFP is generally non-toxic to the cell in which it is expressed, there is some suggestion that aGFP is cytotoxic and may induce apoptosis in expressing cells (Liu, H. S. et al. (1999) Biochem. Biophys. Res. Commun. 260: 712-17). Finally, aGFP has been used as a scaffold for peptide display. However, some peptide insertions at the surface loops of aGFP result in low fluorescence, which suggests that aGFP may be sensitive to structural perturbations.

In view of the physical and biological properties of aGFP, other forms of GFPs are desirable with fluorescence and stability characteristics different from aGFP. Green fluorescent proteins have been cloned from *Renilla reniformis* (hereinafter "rrGFP"), *Renilla muelleri* (hereinafter "rmGFP"), and *Ptilosarcus gurneyi* (hereinafter "pGFP") (see WO 99/49019, hereby expressly incorporated by reference). The core chromophore sequence of the rGFP and pGFPs is different from aGFP, and the *Renilla* forms have fluorescence characteristics with higher molar absorbance coefficient and narrower absorption/emission spectra as compared to aGFP (Ward, W. W. et al. (1979) J. Biol. Chem. 254: 781-88). The lack of significant homology to aGFP suggests that *Renilla* and *Ptilosarcus* forms provide important alternatives to the extensively exploited aGFP. Accordingly, it is the object of the present invention to provide compositions and methods comprising rGFP and pGFP.

SUMMARY OF THE INVENTION

In accordance with the objects outlined above, the present invention provides retroviral vectors comprising a promoter and a rGFP and/or a pGFP nucleic acid. Additional nucleic acid vectors embodied by this invention comprise a first gene of interest, a separation site, and a second gene of interest, wherein the first or second gene of interest is a rGFP or pGFP gene. The separation site may be an IRES element, a Type 2A sequence, or a protease recognition sequence. The gene of interest may comprise reporter genes, selection genes, cDNAs, genomic DNAs, or random peptides.

In a preferred embodiment, the rmGFP or pGFP used in the vectors are codon optimized for expression. That is, the rmGFP or pGFP are variants containing the preferred codons used in the cells or organism in which the rmGFP or pGFP are to be expressed. In a preferred embodiment, the rmGFP or pGFP is codon optimized for expression in mammalian cells, most preferably in human cells.

In another preferred embodiment, the present invention provides for fusions of a gene of interest and a gene encoding rmGFP or pGFP. The gene of interest may comprise cDNA, genomic DNA, or a nucleic acid encoding a random peptide. In a preferred embodiment, the codons are optimized for expression as described above.

In a further preferred embodiment, the fusion nucleic acids comprise a library of fusion nucleic acids. That is, in one aspect, each member of the library may comprise a promoter, gene of interest, a separation sequence, and a second gene of interest, wherein the first or second gene of interest comprises a rGFP or pGPF. In another aspect, the library may comprise fusions of a gene of interest and a gene encoding codon optimized rmGFP or pGFP. The present invention also provides for cells and libraries of cells comprising either these types of fusion nucleic acids.

In a preferred embodiment, the present invention also provides for methods of screening for bioactive agents capable of altering a cell phenotype. The methods comprise contacting a cell or a plurality of cells comprising a fusion nucleic acid comprising a promoter and a codon optimized rmGFP or pGFP with at least one candidate agent, and screening the cells for an altered phenotype. Alternatively, the cells comprise a fusion nucleic acid comprising a promoter, rGFP or pGFP, a separation sequence, and a gene of interest.

In a preferred embodiment, the present invention provides a method of screening for bioactive agents capable of inhibiting or activating a promoter. The method of screening comprises first combining a candidate bioactive agent and a cell comprising a fusion nucleic acid comprising a promoter of interest and a nucleic acid encoding either rGFP or pGFP, then optionally inducing the promoter and detecting the presence of said rGFP or pGFP protein. In another aspect, the promoter is operably linked to a fusion nucleic acid comprising a rGFP or pGFP, a separation sequence, and a gene of interest. The gene of interest may comprise a reporter gene, a selection gene, or a nucleic acid encoding a dominant effect protein.

In a further preferred embodiment, the method comprises screening for agents inhibiting or activating an IL-4 inducible ε promoter. The method comprises first combining a candidate bioactive agent with a cell comprising a fusion nucleic acid comprising an IL-4 inducible ε promoter operably linked to the fusion nucleic acids described above; inducing said promoter with IL-4; and then detecting the presence of said rGFP or pGFP protein. The absence of said rGFP or pGFP protein indicates whether an agent inhibits the IL-4 inducible ε promoter.

The methods of screening for candidate agents altering a cell phenotype further comprises isolating the cell with the altered phenotype and identifying the candidate agent responsible for producing the altered phenotype.

DETAILED DESCRIPTION OF THE FIGURES

FIG. 1 SEQ ID NOS: 3-9 shows an alignment of amino acid sequences of anthozoan GFPs with the *Aequoria* sequence using ClustalW program. The *Renilla muelleri* (RENM) and *Ptilosarcus gurneyi* (PTIL) sequences (SEQ ID NOS: 7-8) are shown above the *Aequoria* GFP (AEQV) sequence (SEQ ID NO: 9) at the bottom. The italicized residues are the fluorescent tripeptide (chromophore). The sequences of the four Anthozoan GFPs that emit light between 483-506 nm are from Matz, M. et al. (1999) Nature Biotech. 17: 969-973: ANEM, *Anemonia majano* GFP (SEQ ID NO: 4); DSFP, *Discosoma striata* GFP; FP48 (SEQ ID NO: 5), *Clavularia* GFP (SEQ ID NO: 6); and ZFP5, *Zoanthus* GFP (SEQ ID NO: 3). The first 35 residues are removed from the amino terminus of FP48. A consensus residue (CONS) was listed if at least 4 of the 7 residues were identical. Residues comprising turns and loops between the β-strands in the *Aequoria* GFP based on visual analysis of *Aequoria* GFP crystal structure (Yang, et al. (1996) Nature Biotechnol. 14: 1246-51) are underlined. The two residues on either side of the site of the inserted 22 mer peptide in the *Renilla muelleri* sequence are listed in bold type and designated as loops A-F in bold. The corresponding replacement sites in *Aequoria* GFP that allow formation of a fluorescent protein (Peelle, B. et al. (2001) Chem. Biol. 8: 521-34) are also shown in bold.

FIG. 2 compares the nucleic acid sequence of wild type (SEQ ID NO: 10; wt; lower sequence) *Renilla muelleri* GFP and the variant sequence codon optimized (SEQ ID NO: 1; co; upper sequence) for expression in human cells. In the codon optimized variant, 9 of the 239 amino acids are not optimized for preferred human codons in order to introduce restriction sites into the coding sequences. The codon optimized sequence has a glycine inserted following the initiating methionine residue to provide further stability to the expressed rmGFP.

FIG. 3 compares the nucleic acid sequence of wild type (SEQ ID NO: 11; wt; lower sequence) *Ptilosarcus gurneyi* GFP and a variant sequence codon optimized (SEQ ID NO: 2; co; upper sequence) for expression in human cells. Similar to the codon optimized *Renilla muelleri* variant, the optimized *Ptilosarcus* GPF has 11 of the 239 amino acids not optimized for preferred human codons in order to introduce restriction sites into the coding sequences. As above, a glycine residue is inserted after the initiating methionine residue to provide stability to the expressed pGFP. FIG. 4 shows the circular dichroism (CD) spectra of *Aequoria victoria, Renilla muelleri*, and *Ptilosarcus gurneyi* GFPs. CD spectras are taken at pH 7.5 in 10 mM potassium phosphate buffer with 0.1 M potassium fluoride and measured from 200-250 nm: EGFP (open circles), *Renilla* (open grey squares) and *Ptilosarcus* (filled squares) GFPs. Deconvolution of these spectra indicates the secondary structure content of all three GFPs to be identical.

FIG. 5 shows the thermal denaturation curves for *Aequoria victoria, Renilla muelleri*, and *Ptilosarcus gurneyi* GFPs as measured by CD. The most stable protein was *Renilla* GFP (open circles) with a $T_m$ of 86.1° C. followed by EGFP (filled squares) with a $T_m$ of 83.7° C. and *Ptilosarcus* GFP (open triangles) with a $T_m$ of 80.5° C.

FIG. 6 gives the results of retroviral expression in human cells of human codon optimized *Renilla muelleri, Ptilosarcus gurneyi*, and *Aequoria victoria* GFPs. The retroviral constructs were introduced into Jurkat E cells and examined by flow cytometry. FACS plots of wild type (WT) and codon optimized *Renilla muelleri* GFP (R), *Aequoria victoria* GFP (E), and flag tagged versions of *Ptilosarcus* GFP (Pf), *Renilla* GFP (Rf) and *Aequoria* GFP (Ef) were obtained 4 days after infection. Both *Ptilosarcus* and *Renilla* GFPs have higher fluorescence intensities than *Aequoria* GFP. Uninfected cells are shown off scale due to shift of the dynamic range, ca. 2.6 log units to the left by FL1 compensation on the cytometer. Geometric mean fluorescence values are listed in the upper right corner for each population within the gated region underlined.

FIG. 7 gives FACS analysis of Jurkat E cell expression of *Renilla* GFP with a 22mer HA epitope tag inserted into positions A to F. Plots in column A are shown with a standard fluorescence scale. For plots in Column B, FL-1 channel compensation was used to shift the fluorescence detection range, ca. 2.6 log units, to the left to observe the high level of fluorescence. *Renilla* GFP is shown without insert (R), and with inserts in positions A, B, C, D, E, and F as labeled. *Aequoria* GFP is shown without an insert (EGFP) and with the same insert in its equivalent position D (EGFP3). The sites of insertion, A-F are shown underlined in FIG. 1. The constructs were retrovirally expressed in Jurkat E cells and analyzed by FACS 4 days post-infection. The GFP geometric mean fluorescence values from the gated regions are listed in the upper right of each plot. D, F, and EGFP3 retain 30-49% of their respective parent GFP fluorescence levels. B, C, and E had observable but much lower levels of fluorescence than the parent *Renilla* GFP. The position A insert has almost no measurable fluorescence above background.

FIG. 8 shows fluorescence micrographs of cells expressing fusion proteins comprising peptides inserted into sites D and F of *Renilla muelleri* GFP. The fusion proteins were retrovirally expressed in A549 cells. Expression of a fusion protein comprising a hemagglutinin epitope (HA) inserted into sites D and F is shown in panels 1 and 2, respectively. Fluorescence occurs throughout the cell. Expression of NLS-GFP fusion protein, derived from SV40, inserted into site D and F (panels 3 and 4, respectively), results in fluorescence only in the nucleus. The results show that displayed NLS peptide is functional when presented as a peptide inserted onto a GFP scaffold and that the GFP molecule retains its fluorescence.

FIG. 9 (SEQ ID NOS: 12-23) shows various Type 2A separation sequences useful in the present invention. These Type 2A sequences are found in aptho- and cardioviral genomes. The general sequence is XXXXXXXXXX-LXXDXEXNP<u>GP</u> (SEQ ID NO: 23), where X is any amino acid. Invariant amino acids are shown in bold. Failure of peptide bond formation occurs at the junction between the carboxy terminal glycine and proline (underlined). The 2A sequence also shows a number of residues with conserved amino acid substitutions.

DETAILED DESCRIPTION OF THE INVENTION

The present invention is directed to the use of *Renilla* green fluorescent protein (hereinafter "rGFP") in a variety of methods and compositions that exploit the autofluorescent properties of rGFP. These methods include, but are not limited to, the use of rGFP as a reporter molecule in cell screening assays, including intracellular assays; the use of rGFP as a scaffold protein for fusions with random peptide libraries; etc. Similarly, compositions of rGFP are provided, including constructs of rGFP such as fusion constructs that include rGFP as a reporter gene, retroviral constructs including rGFP and separation sequences, etc. Basically, the invention provides a number of novel uses for rGFP, similar to those outlined for aGFP in WO 95/07463, hereby incorporated by reference in its entirety. In addition, the invention is also directed to the use of *Ptilosarcus* green fluorescent protein, the amino acid sequence of which is shown in FIG. 1 (SEQ ID NO: 7) and is also depicted in WO 99/49019. It should be noted that while the discussion below is generally directed to rGFP, pGFP may be used as well.

In a preferred embodiment, the invention provides compositions including rGFP. By "*Renilla* green fluorescent protein" or "rGFP" herein is meant a protein that has significant homology, as defined herein, to the wild-type *Renilla reniformis* or *Renilla muelleri* protein of FIG. 1 (SEQ ID NO: 8), both of which are described in WO 99/49019, hereby incorporated by reference in its entirety.

In a preferred embodiment, the invention provides compositions including pGFP. By "*Ptilosarcus* green fluorescent protein" or "pGFP" herein is meant a protein that has significant homology, as defined herein, to the wild-type protein *Ptilosarcus* protein of FIG. 1 (SEQ ID NO: 7), as described in WO 99/49019, hereby incorporated by reference in its entirety.

A rGFP or pGFP protein of the present invention may be identified in several ways. "Protein" in this sense includes proteins, polypeptides, and peptides. A nucleic acid or rGFP protein is initially identified by substantial nucleic acid and/or amino acid sequence homology to the sequences shown in FIGS. 1 and 2 (SEQ ID NOS: 1, 3-10). Such homology can be based upon the overall nucleic acid or amino acid sequence. Similarly, a nucleic acid or pGFP protein is also initially identified by substantial nucleic acid and/or amino acid sequence homology to the sequences shown in FIGS. 1 and 3 (SEQ ID NOS: 2, 3-9, 11). And again, such homology can be based upon overall nucleic acid or amino acid sequence.

As used herein, a protein is a "rGFP protein" or "pGFP protein" if the overall homology of the protein sequence to the respective amino acid sequences shown in FIG. 1 is preferably greater than about 75%, more preferably greater than about 80%, even more preferably greater than about 85%, and most preferably greater than 90%. In some embodiments the homology will be as high as about 93 to 95 or 98%.

Homology in this context means sequence similarity or identity, with identity being preferred. This homology will be determined using standard techniques known in the art, including, but not limited to, the local homology algorithm of Smith and Waterman (1981) Adv. Appl. Math. 2:482; by the homology alignment algorithm of Needleman and Wunsch, (1970) J. Mol. Biol. 48:443; by the search for similarity method of Pearson and Lipman (1988) Proc. Natl. Acad. Sci. USA 85:2444; by computerized implementations of these algorithms (GAP, BESTFIT, FASTA, and TFASTA in the Wisconsin Genetics Software Package, Genetics Computer Group, 575 Science Drive, Madison, Wis.); or the Best Fit sequence program described by Devereux, J. et al. (1984) Nucleic Acids Res. 12: 387-95, preferably using the default settings, or by inspection.

In a preferred embodiment, similarity is calculated by FastDB based upon the following parameters: mismatch penalty of 1.0; gap size penalty of 0.33; and joining penalty of 30.0 ("Current methods in Comparison and Analysis", Macromolecule Sequencing and Synthesis, selected methods and Applications, pp. 127-149, Alan R. Liss, Inc., 1998). Another example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle (1987) J. Mol. Evol. 35: 351-60; the method is similar to that described by Higgins and Sharp (1989) CABIOS 5: 151-3. Useful PILEUP parameters include a default gap weight of 3.00, a default gap length weight of 0.10, and weighted end gaps.

An additional example of a useful algorithm is the BLAST algorithm, described in Altschul, S. F. et al. (1990) J. Mol. Biol. 215: 403-10 and Karlin, et al. (1993) Proc. Natl. Acad. Sci. USA 90: 5873-87. A particularly useful BLAST program is the WU-BLAST-2 program, which was obtained from Altschul et al. (1996) Methods Enzymol. 266:460-80; available on-line at blast.wustl/edu/blast/README.html. WU-BLAST-2 uses several search parameters, most of which are set to the default values. The adjustable parameters are set with the following values: overlap span=1, overlap fraction=0.125, and word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the rGFP or pGFP proteins (FIG. 1). A preferred method utilizes the BLASTN module of WU-BLAST-2 set to the default parameters, with overlap span and overlap fraction set to 1 and 0.125, respectively.

An additional useful algorithm is gapped BLAST as reported by Altschul, S. F. et al. (1997) Nucleic Acids Res. 25:3389-402. Gapped BLAST uses BLOSUM-62 substitution scores; threshold T parameter set to 9; the two-hit method to trigger ungapped extensions; charges gap lengths of k a cost of 10+k; $X_u$ set to 16; and $X_g$ set to 40 for database search stage and to 67 for the output stage of the algorithms. Gapped alignments are triggered by a score corresponding to ~22 bits.

The alignment may include the introduction of gaps in the sequences to be aligned (see FIG. 1). In addition, for sequences which contain either more or fewer amino acids than the protein sequences shown in FIG. 1, it is understood that the percentage of homology will be determined based on the number of homologous amino acids in relation to the total number of amino acids. Thus, for example, homology of sequences shorter than that shown in FIG. 1, as discussed below, will be determined using the number of amino acids in the shorter sequence.

The rGFP and pGFP proteins of the present invention may be shorter or longer than the amino acid sequences shown in FIG. 1. Thus, in a preferred embodiment, included within the definition of rGFP and pGFP proteins are portions or fragments of the sequences depicted herein. Portions or fragments of rGFP or pGFP proteins are considered rGFP or pGFP proteins if a) they share at least one antigenic epitope; b) have at least the indicated homology; c) preferably have rGFP or pGFP biological activity, e.g., including, but not limited to, autofluorescence; or d) fold into a stable structure that is similar to the wild-type rGFP or pGFP structure.

For example, rGFP or pGFP deletion mutants can be made. At the N-terminus, it is known that only the first amino acid of the aGFP protein may be deleted without loss of fluorescence. At the C-terminus of the aGFP, up to 7 residues can be deleted without loss of fluorescence (see Phillips, G. N. et al. (1997) Curr. Opin. Struct. Biol. 7: 821-27). This presumably applies to rGFP and pGFP as well.

In one embodiment, the rGFP or pGFP proteins are derivative or variant rGFP or pGFP proteins. That is, as outlined more fully below, the derivative rGFP or pGFP will contain at least one amino acid substitution, deletion or insertion, with amino acid substitutions being particularly preferred. The amino acid substitution, insertion or deletion may occur at any residue within the rGFP or pGFP protein. These variants ordinarily are prepared by site specific mutagenesis of nucleotides in the DNA encoding the GFP proteins, using cassette or PCR mutagenesis, DNA shuffling mutagenesis, or other techniques well known in the art, to produce DNA encoding the variant, and thereafter expressing the DNA in recombinant cells as is known in the art and outlined herein. However, variant rGFP or pGFP protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the rGFP or pGFP protein amino acid sequence. The variants typically exhibit the same qualitative biological activity as the naturally occurring analogue, although variants can also be selected which have modified characteristics; as will be more fully outlined below. That is, in a preferred embodiment, when non-wild-type rGFP or pGFP is used, the derivative preferably has at least 1% of wild-type fluorescence, with at least about 10% being preferred, at least about 50-60% being particularly preferred, and 95% to 98% to 100% being especially preferred. In general, what is important is that there is enough fluorescence to allow sorting and/or detection above background, for example when using a fluorescence-activated cell sorter (FACS) machine. However, in some embodiments, for example when fusion proteins with rGFP or pGFP are made, it is possible to detect the fusion proteins non-fluorescently using, for example, antibodies directed to either an epitope tag (i.e., purification sequence) or to the rGFP or pGFP itself. In this case, the rGFP or pGFP scaffold does not have to be fluorescent, if it can be shown that the rGFP or pGFP is folding correctly and/or reproducibly.

Thus, the rGFP or pGFP may be wild type or variants thereof. These variants fall into one or more of three classes: substitutional, insertional or deletional variants. These variants ordinarily are prepared by site specific mutagenesis of nucleotides in the DNA encoding the GFP, using cassette or PCR mutagenesis or other techniques well known in the art, to produce DNA encoding the variant, and thereafter expressing the DNA in recombinant cell culture as outlined herein. However, variant protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the rGFP or pGFP amino acid sequences. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed scaffold variants screened for the optimal combination of desired activity. Techniques for making substitution mutations at predetermined sites in DNA having a known sequence are well known, for example, M13 primer mutagenesis and PCR mutagenesis. Screening of the mutants is done using assays of scaffold protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the rGFP or pGFP protein are desired, substitutions are generally made in accordance with the following table:

TABLE I

| Original Residue | Exemplary Substitutions |
| --- | --- |
| Ala | Ser |
| Arg | Lys |
| Asn | Gln, (His) |
| Asp | Glu |
| Cys | Ser |
| Gln | Asn |
| Glu | Asp |
| Gly | Pro |
| His | Tyr, (Asn), (Gln) |
| Ile | Leu, Val |
| Leu | Ile, Val |
| Lys | Arg, (Gln), (Glu) |
| Met | Leu, Ile |
| Phe | Tyr, Trp, (Met), (Leu) |
| Ser | Thr |
| Thr | Ser |
| Trp | Tyr, Phe |
| Tyr | Trp, Phe |
| Val | Ile, Leu |

Less favored substitutions are given in parenthesis. Substantial changes in function or immunological identity are made by selecting substitutions that are less conservative than those shown in Table I. For example, substitutions may be made that more significantly affect the structure of the polypeptide backbone in the area of the alteration of the alpha-helical or beta-sheet structure, the charge or hydrophobicity of the molecule at the target site, or the bulk of the side chain. In general, the substitutions expected to produce the greatest changes, in the polypeptide's properties are those in which (a) a hydrophilic residue, e.g., seryl or threonyl, is substituted for (or by) a hydrophobic residue (e.g., leucyl, isoleucyl, phenylalanyl, valyl or alanyl); (b) a cysteine or proline is substituted for (or by) any other residue; (c) a residue having an electropositive side chain (e.g., lysyl, arginyl, or histidyl) is substituted for (or by) an electronegative residue (e.g., glutamyl or aspartyl); or (d) a residue having a bulky side chain (e.g., phenylalanine) is substituted for (or by) one not having a side chain (i.e., glycine).

As outlined above, the variants typically exhibit the same qualitative biological activity (i.e., fluorescence) although variants also are selected to modify the characteristics of the rGFP or pGFP protein as needed.

In a preferred embodiment, specific residues of rGFP or pGFP protein are substituted, resulting in proteins with modified characteristics. Such substitutions may occur at one or more residues, with 1-10 substitutions being preferred. Preferred characteristics to be modified include range of spectral emission, including shifts in excitation spectrum, emission spectrum, rate of folding, stability, solubility, expression levels, toxicity, sensitivity to halide ions, and emission intensity. As is known in the art, there are a number of aGFP variants with desirable properties, and these may be varied in the corresponding rGFP and pGFP amino acid residues.

In a preferred embodiment, residue 46 of rmGFP, pGFP, and residue 43 of rrGFP (corresponding to residue 43 of aGFP) is substituted with a Thr or Ala.

In a preferred embodiment, residue 68 of rm GFP, pGFP and residue 65 of rrGFP (corresponding to residue 64 of aGFP) is substituted with a Leu or Val.

In a preferred embodiment, residue 69 of rmGFP, pGFP, and residue 66 of rrGFP (corresponding to residue 65 of aGFP) is substituted with a Thr, Ile, Cys, Ser, Leu, Ala or Gly.

In a preferred embodiment, residue 70 rmGFP, pGFP, and residue 67 of rrGFP (corresponding to residue 66 of aGFP) is substituted with a His, Phe, or Trp.

In a preferred embodiment, residue 72 of rmGFP, pGFP, and residue 69 of rrGFP (corresponding to residue 68 of aGFP) is substituted with a Val or Leu.

In a preferred embodiment, residue 76 of rmGFP, pGFP, and residue 73 of rrGFP (corresponding to residue 72 of aGFP) is substituted with a Ser or Ala.

In a preferred embodiment, residue 101 of rmGFP, pGFP, and residue 98 of rrGFP (corresponding to residue 99 of aGFP) is substituted with a Phe or Ser.

In a preferred embodiment, residue 125 of rmGFP and pGFP, and residue 124 of rrGFP (corresponding to residue 123 of aGFP) is substituted with an Ile.

In a preferred embodiment, residue 147 rmGFP and pGFP, and residue 146 of rrGFP (corresponding to residue 145 of aGFP) is substituted with a Tyr, Phe or His.

In a preferred embodiment, residue 148 of rGFP and pGFP, and residue 147 of rrGFP (corresponding to residue 146 of aGFP) is substituted with an Asn or Ile.

In a preferred embodiment, residue 150 of rmGFP and pGFP, and residue 149 of rrGFP (corresponding to residue 148 of aGFP) is substituted with a H is or Arg.

In a preferred embodiment, residue 155 of rGFP and pGFP, and residue 154 of rrGFP (corresponding to residue 153 of aGFP) is substituted with a Thr or Ala.

In a preferred embodiment, residue 162 of rmGFP and pGFP, and residue 161 of rrGFP (corresponding to residue 163 of aGFP) is substituted with a Val or Ala.

In a preferred embodiment, residue 166 of rmGFP and pGFP, and residue 165 of rrGFP (corresponding to residue 167 of aGFP) is substituted with an Ile or Thr.

In a preferred embodiment, residue 200 of rmGFP and pGFP, residue 199 of rrGFP (corresponding to residue 202 of aGFP) is substituted with an Ser or Phe.

In a preferred embodiment, residue 201 of rmGFP and pGFP, and residue 200 of rrGFP (corresponding to residue 203 of aGFP) is substituted with an Ile, Thr, or Tyr.

In a preferred embodiment, residue 203 of rmGFP and pGFP, and residue 202 of rrGFP (corresponding to residue 205 of aGFP) is substituted with an Ser or Thr.

In a preferred embodiment, residue 210 of rmGFP and pGFP, and residue 209 of rrGFP (corresponding to residue 212 of aGFP) is substituted with an Asn or Val.

In a preferred embodiment, residue 218 of rmGFP and pGFP, and residue 216 of rrGFP (corresponding to residue 222 of aGFP) is substituted with a Gly or Ser.

In addition, rGFP or pGFP proteins can be made that are longer than the wild-type, for example, by the addition of epitope or purification tags, the addition of other fusion sequences, etc., as is more fully outlined below.

In another preferred embodiment, GFP variants as used herein include GFPs containing codons replaced with degenerate codons coding for the same amino acid. This arises from the degeneracy of the genetic code where the same amino acids are encoded by alternative codons. Replacing one codon with another degenerate codon changes the nucleotide sequence without changing the amino acid residue. An extremely large number of nucleic acids may be made, all of which encode the GFPs of the present invention. Thus, having identified a particular amino acid sequence, those skilled in the art could make any number of different nucleic acids, by simply modifying the sequence of one or more codons in a way which does not change the amino acid sequence of the protein. In this regard, the present invention has specifically contemplated each and every possible-variation of polynucleotides that could be made by selecting combinations based on the possible codon choices, and all such variations are to be considered specifically disclosed and equivalent to the sequences of FIG. 1. It also should be noted that codon optimization that results in one or small number of amino acid changes, particularly, conservative changes are also possible.

Changing the codons may be desirable for a variety of situations. For example, substitutions with a degenerate codon is useful when eliminating cryptic splice signals present in the coding regions of a gene, inserting restriction sites in the gene, distinguishing between one version of the same gene from another (e.g., by hybridization), creating alternative primers for amplification reactions, examining mutational bias in genes, changing chromosomal methylation patterns (e.g., for determining preferential parental transmission), and changing the expression levels of the gene of interest.

Accordingly, in a further preferred embodiment, the GFP variants are codon optimized for expression in a particular organism. By "codon optimized" herein is meant changes in the codons of the gene of interest to those preferentially used in a particular organism such that the gene is efficiently expressed in the organism. Although the genetic code is degenerate in that most amino acids are represented by several codons, called synonyms or synonymous codons, it is well known that codon usage by particular organisms is non-random and biased towards particular codon triplets. This codon usage bias may be higher in reference to a given gene, genes of common function or ancestral origin, highly expressed proteins versus low copy number proteins, and the aggregate protein coding regions of an organism's genome. Although codon bias may arise from nucleotide composition or mutational biases in different organisms, codon usage bias in bacteria and yeast correlates with the abundance of tRNA species in the cell. In general, codon bias is often associated with the level of gene expression. That is, certain codons are preferentially represented in the protein coding regions of highly expressed gene products. Thus, changing the codons to the preferred codons of a particular organism may allow higher level expression of the encoded protein in that organism. In this regard, the present invention relates to GFP variants whose codons are altered to the preferred codons of the organism in which the gene of interest is being expressed. In other words, codons are preferably selected to fit the host cell in which the protein is being produced. For example, preferred codons used in bacteria are used to express the gene in bacteria; preferred codons used in yeast are used for expression in yeast; and preferred codons used in mammals cells are used for expression in mammalian cells.

By "preferred", "optimal" or "favored" codons, or "high codon usage bias" or grammatical equivalents as used herein is meant codons used at higher frequency in the protein coding regions than other codons that code for the same amino acid. The preferred codons may be determined in relation to codon usage in a single gene, a set of genes of common function or origin, highly expressed genes, the codon frequency in the aggregate protein coding regions of the whole organism, codon frequency in the aggregate protein coding regions of related organisms, or combinations thereof.

In a preferred embodiment, preferred or favored codons are determined for genes of common function, while in a more preferred embodiment, preferred codons are determined for protein coding regions of the whole organism or related organisms. In a most preferred embodiment, codon usage in a representative number of highly expressed gene products of an organism or related organisms will provide the basis for determining the set of preferred codons. Thus, in one aspect, preferred codons are those codons whose frequency increases with the level of gene expression. Since gene expression may be restricted to specific cells or certain developmental time periods (e.g., embryonic and adult), whether a gene is highly expressed is measured in respect to the cells and the temporal periods when the gene is expressed.

In another aspect, preferred codons are further delineated with respect to the size of the protein coding regions examined. Studies of codon bias show a negative correlation between the size of the protein and codon usage (see Duret, L. et al. (1999) Proc. Natl. Acad. Sci. USA 96: 4482-87). For proteins of increasing length, there is a tendency for less codon usage bias while highly expressed proteins of decreasing length display increased codon usage bias. Thus, in a preferred embodiment, the size of proteins used for assessing preferred codons includes proteins of all lengths, while a more preferred embodiment uses protein lengths up to about 550 amino acids. In the most preferred embodiment, proteins lengths of up to about 335 amino acids are used.

A variety of methods are known for determining the codon frequency (e.g., codon usage, relative synonymous codon usage) and codon preference in specific organisms, including multivariate analysis, for example, using cluster analysis or correspondence analysis, and the effective number of codons used in a gene (see GCG CodonPreference, Genetics Computer Group Wisconsin Package; CodonW, John Peden, University of Nottingham; McInerney, J. O (1998) Bioinformatics 14: 372-73; Stenico, M. et al. (1994) Nucleic Acids Res. 222437-46; Wright, F. (1990) Gene 87: 23-29). Codon usage tables are available for a growing list of organisms (see for example, Wada, K. et al. (1992) Nucleic Acids Res. 20: 2111-2118; Nakamura, Y. et al. (2000) Nucleic Acids Res. 28: 292; Duret, et al. supra). The data source for obtaining codon usage may rely on any available nucleotide sequence capable of coding for a protein. These data sets include nucleic acid sequences actually known to encode expressed proteins (e.g., complete protein coding sequences-CDS), expressed sequence tags (ESTS), or predicted coding regions of genomic sequences (see for example, Mount, D. *Bioinformatics: Sequence and Genome Analysis*, Chapter 8, Cold Spring Harbor Laboratory Press, Cold Spring Harbor, N.Y., 2001; Uberbacher, E. C. (1996) Methods Enzymol. 266: 259-281; and Tiwari, S. et al. (1997) Comput. Appl. Biosci. 13 263-270). Accordingly, the present invention relates to codon optimization for enhancing expression of a gene in any host organism.

In a preferred embodiment, the nucleotide sequence of rGFP or pGFP are substituted with codons preferentially used in the organism in which the GFP is to be expressed. In identifying the codons for modification or replacement, the codons of rGFP or pGFP (or any other protein coding region) are compared to the codons favored or preferred in the organism of interest. This analysis identifies differences between the preferred set of codons and the codons actually used, and thus identifies nucleotides for substitutions. In a preferred embodiment, codons in rGFP or pGFP that are the least preferred codons in the subject organism are selected for substitution. Further substitutions are made for frequently occurring codons in rGFP or pGFP that are not the preferred codons. Although the frequently occurring codons may not comprise the least preferred codons, presence of numerous non-preferred or nonoptimal codons can limit efficient expression of the protein product.

When several preferred codons are available for the same amino acid, the choice of substitution can rely on other considerations such ease of constructing the variant, concerns for limiting introduction of mutations during propagation of the gene in the host organism (i.e., mutational bias), secondary structure of the mRNA that may affect expression levels, and concern for generating splice sites. Other considerations may take into account the intended uses of the codon optimized variants, such as insertion of restriction sites for generating fusion proteins. Thus, some deviations from strict adherence to preferred codons are permissible to accommodate restriction sites in the resulting gene for the purposes of constructing the variant, replacement of gene segments (e.g., to simplify insertion of mutated gene segments), and for creating fusion proteins, as described below.

In certain embodiments, all codons need not be replaced to optimize the codon usage of the GFP since the natural sequence will comprise the preferred codons and because use of preferred codons may not be required for all amino acid residues. In one aspect, about 10 to about 35% of the codons are replaced or changed. Additional changes may be introduced to maximize expression. Consequently, codon optimized GFP sequences may contain preferred codons at about 40%, 50%, 60%, 70%, 80%, or greater than 90% of codon positions of the full length coding region.

Preferred genes of interest are codon optimized for prokaryotes or eukaryotes. Prokaryotes may comprise, among others, bacteria, including *Bacillus* (for example, subtilis, anthracis), *Clostridia, Staphylococcus, Streptococcus, Neisseria, Erysipelothrix, Listeria, Nocardia, Salmonella, Shigella, Escherichia, Klebsiella, Enterobacter, Serratia,*

*Proteus, Morganella, Providencia, Yersinia, Haemophilus, Brucella, Francisella, Vibrio, Pseudomonas, Campylobacter, Clostridium, Actinomyces, Corynebacterium, Bacteroides, Mycobacterium* (for example, tuberculosis, leprae); spirochetes, including *Trepanoma, Borrelia, Leptospira,* and *Spirillum*; archebacteria, including *Methanobacterium, Thermoplasma, Thermophilus,* or other thermophiles (e.g., *Sulfolobus*), and *Halobacterium*; and cyanobacteria. Eukaryotes may comprise, among others, protists, including *Mastigophora, Sarcodina, Ciliophora,* and *Sporozoa* (trypanosoma); fungi, including *Saccharomyces, Schizosaccharomyces, Candida, Neurospora, Aspergillus, Ustilago, Penicillium,* and *Sordaria*; plants, including *Chlorophyta* and *Tracheophyta—Angiosperms* and *Spermopsida* (e.g., tobacco, *arabidopsis*, corn, rice, wheat, tomato, potato, etc.); worms, including nematoda (e.g., *Caenorhabditis, Trichinella, Trichuris*), platyhelminthes (e.g., *Diphyllobothrium, Clonorchis,* and *Dugesia* (e.g., planaria); insects, including *Drosophila, Manduca, Bombyx* etc.; amphibia (e.g., *Xenopus*, newts, salamanders etc.); fish (e.g., salmon, catfish, zebrafish, Xiphophorus, trout, goldfish, tilapia and medaka etc.); aves (e.g., turkey, chicken, duck, quail, and geese, etc.); mammalia, including rodentia (e.g., mice, rats, gerbils, hamsters, etc.), legomorpha (e.g., rabbits, hares), artiodactyla (e.g., cows, pigs, sheep, goats, etc.), canis (e.g., domestic dog), felis (e.g., domestic cat), and primates (e.g., monkeys, chimpanzees, and humans). Codon optimization for expression in bacteria, yeast, mammalian cells (e.g., rodents, primates, etc.), and in particular human cell types, are most preferred.

Codon preference in the coding regions of human genes is given in Table II. The table shows for each codon the relative frequency of each codon among synonymous codons. The most preferred codons are given in bold. Methionine and tryptophane have a value of 1 since these residues are encoded by a single codon. For certain amino acids, such as arg, four synonymous codons are used at similar frequencies.

the process for generating the synthetic gene. In this regard, use of polymerase chain reaction of the hybridized overlapping oligonucleotides allows facile generation of these synthetic genes.

In accordance with the present invention, exemplary codon optimized variants for expression in human cells is provided by SEQ ID NO:1 for *Renilla muelleri* GFP and SEQ ID NO: 2 for *Ptilosarcus gurneyi* GFP (FIGS. 2 and 3, respectively). In the codon optimized rmGFP, 9 of the 239 amino acids are not the preferred human codons in order to accommodate restriction sites used for constructing various rmGFP fusion proteins. For the codon optimized pGFP, 11 of the 239 amino acids are not the preferred codons for the same reasons given above. It will be understood, however, that the codon optimized sequences of the present invention are by no means limited to the representative sequence provided herein. In view of the preceding discussion, one of skill in the art will readily be able to prepare a number of different codon optimized GFP sequences for expression in a given organism, especially for expression in human cells, or other cells as outlined herein.

In a preferred embodiment, the rGFP or pGFP protein, including variants is fused to a protein of interest, including peptides as outlined herein. By "fused" or "operably linked" herein is meant that the peptide, as defined below, and the rGFP or pGFP protein are linked together. In a preferred embodiment, fusion nucleic acids are made such that fusion polypeptides, e.g. a single polypeptide, are made. In an alternative embodiment, fusion nucleic acids comprising separation sites (e.g., protease recognition sequences, 2A sequences, or IRES sequences) are made as further described below. In one preferred embodiment, the fusions disrupts the fluorescence characteristic of the rGFP or pGFP. That is, the fluorescence characteristics of the rGFP or pGFP is changed, including under different solution conditions (e.g, temperature, pH, ion concentration, halide concentration, membrane potential, etc.). In another preferred embodiment, the fusions

TABLE II

| TTT | phe F | 0.43 | TCT | ser S | 0.18 | TAT | tyr Y | 0.42 | TGT | cys C | 0.42 |
|---|---|---|---|---|---|---|---|---|---|---|---|
| TTC | phe F | 0.57 | TCC | ser S | 0.23 | TAC | tyr Y | 0.58 | TGC | cys C | 0.58 |
| TTA | leu L | 0.06 | TCA | ser S | 0.15 | TTA | och Z | — | TGA | opa Z | — |
| TTG | leu L | 0.12 | TCG | ser S | 0.06 | TAG | amb Z | — | TGG | trp W | 1.00 |
| CTT | leu L | 0.12 | CCT | pro P | 0.29 | CAT | his H | 0.41 | CGT | arg R | 0.09 |
| CTC | leu L | 0.20 | CCC | pro P | 0.33 | CAC | his H | 0.59 | CGC | arg R | 0.19 |
| CTA | leu L | 0.07 | CCA | pro P | 0.27 | CAA | gln Q | 0.27 | CGA | arg R | 0.10 |
| CTG | leu L | 0.43 | CCG | pro P | 0.11 | CAG | gln Q | 0.73 | CGG | arg R | 0.19 |
| ATT | ile I | 0.35 | ACT | thr T | 0.23 | AAT | asn N | 0.44 | AGT | ser S | 0.14 |
| ATC | ile I | 0.52 | ACC | thr T | 0.38 | AAC | asn N | 0.56 | AGC | ser S | 0.25 |
| ATA | ile I | 0.14 | ACA | thr T | 0.27 | AAA | lys K | 0.40 | AGA | arg R | 0.21 |
| ATG | met M | 1.00 | ACG | thr T | 0.12 | AAG | lys K | 0.60 | AGG | arg R | 0.22 |
| GTT | val V | 0.17 | GCT | ala A | 0.28 | GAT | asp D | 0.44 | GGT | gly G | 0.18 |
| GTC | val V | 0.25 | GCC | ala A | 0.40 | GAC | asp D | 0.56 | GGC | gly G | 0.33 |
| GTA | val V | 0.10 | GCA | ala A | 0.22 | GAA | glu E | 0.41 | GGA | gly G | 0.26 |
| GTG | val V | 0.48 | GCG | ala A | 0.10 | GAG | glu E | 0.59 | GGG | gly G | 0.23 |

The codon optimized GFPs are made in accordance with methods well known in the art. When the substitutions or replacements are not extensive, oligonucleotide directed mutagenesis or other localized mutagenesis techniques, such as replacing fragments of the gene with fragments containing the preferred codons, are used to optimize the codons. If codon optimization is extensive, the GFP gene may be a synthetic gene generated from overlapping oligonucleotides (Jayaraman, K. et al. (1991) Proc. Natl. Acad. Sci. USA 88: 4084-8; Stemmer, W. P. et al. (1995) Gene 164: 49-53). The oligonucleotides may or may not be ligated together during only minimally disrupts stability of rGFP or pGFP. That is, the rGFP or pGFP preferably retains its fluorescence, or maintains a $T_m$ (thermal melting temperature) of at least 42° C.

In a preferred embodiment, the present invention is also useful in marking viruses and cells and as reporters for cell proliferation, as further illustrated below. General expression or specific regulated expression of the fusion proteins marks the cell, either constitutively or at specific periods in development. These marked viruses and cells may be detected and tracked to determine their migration or proliferation in a organism or in response to specific biological signals, for example cytokines and chemokines. As further described below, these cells may be used in screens to identify candidate agents that alter the infectivity, migration or proliferation of these viruses or cells in response to the biological signals.

In a preferred embodiment, the fusions to rGFP or pGFP are used for tracking or localizing the protein to a particular subcellular location; quantitating gene expression; display of peptides; indicator of cellular reactions; markers for cell growth and proliferation, etc. The fusions may be made to any protein of interest encoded by any gene of interest. These include genomic DNA, cDNA, protein-interaction domains, targeting sequences (e.g., localization sequences), stability sequences, protein-modification sequences (e.g., phosphorylation, ADP ribosylation, lipidation, glycosylation, protease sites, etc.), random peptides, biosensor sequences, as further discussed below. The fusions may be made to the amino terminal, the carboxy terminal, or internally to the GFP sequence. When the fusions are internal to the rGFP or pGFP, they are preferably in the internal loops of the fluorescent proteins. In a preferred embodiment, the fusions do not affect the fluorescence, which allows direct detection of the fusion protein. In another aspect, detecting the fusion protein uses a label that binds the fusion protein, such as a labeled antibody directed against r- or pGFP or the fused gene of interest, in which case the fusion protein need not be fluorescent. As outlined below, the fusion polypeptide (or fusion polynucleotide encoding the fusion polypeptide) can comprise additional components, including multiple peptides at multiple loops, fusion partners, linkers, etc.

In a preferred embodiment, the fusion to rGFP or pGFP, preferably a codon optimized variant, are used to track and localize proteins intracellular or extracellularly. Fusion may be made to any protein of interest to examine cellular processing events of the subject protein. Proteins of interest include cytoskeletal proteins for tracking cell movement and cell structure; focal adhesion proteins involved in cell adherence; nuclear proteins for examining signals involved in nuclear transport; nuclear membrane proteins involved in nuclear membrane dissolution and reformation; cell organelle replication and structure; intracellular transport of proteins (e.g. targeting signals); development of structural polarity in cells (e.g., neuronal or epithelial cells); monitoring cell division processes; and the like. Many of these aforementioned process are abnormal in disease cells, such as cancer cells. These fusion proteins expressed in cells are useful for identifying candidate agents that affect these biological processes in particular cell types. Thus, screens may be conducted for agents that confer a phenotype similar to a disease cell or for agents that convert an abnormal cell, characterized by an abnormal cellular process, to a normal cell.

In another preferred embodiment, the fusions are made to protein-modification sequences. These sequences may be a sequence capable of being modified by any modification process. In a preferred embodiment, the modification sequence is a modified by another protein or enzyme. In one aspect, the modification sequence comprises a phosphorylation sequence (Yang, F. et al. (1996) Anal. Biochem. 266: 167-73). A variety of phosphorylation sequences are known (e.g., src homology domain SH2 and SH3) and recognized by kinases that attach phosphates to specific amino acids (e.g., serine, threonine, tyrosine, histidine) (see Kreegiopuu, A. et al. (1999) Nucleic Acids Res. 27: 237-39). The phosphorylation sequences are fused to GFP to allow correct presentation to the cognate kinases. Phosphorylation of the sequence may or may not affect the fluorescence properties of rGFP or pGFP. By "fluorescence properties" herein is meant any detectable change in the fluorescence characteristic of the GFP. This may involve the molar extinction coefficient at the appropriate excitation wavelength, fluorescence quantum yield, excitation and emission spectra, ratio of excitation amplitudes at two different wavelengths, ratio of emission amplitudes at two different wavelengths, excitation lifetime, and fluorescence quenching.

In one preferred embodiment, phosphorylation of the fusion proteins does not affect the fluorescence characteristic. In this context, the GFP provides a scaffold for efficient presentation of the sequence as a substrate for a kinase. The phosphorylation is detected by direct labeling with labeled nucleotide substrate (e.g., ATP) or reaction with antibodies specific for phosphorylated sequences. In another preferred embodiment, phosphorylation of the fusion protein changes the fluorescence characteristics of the fluorescent protein such that the change provides an indication of kinase activity (see U.S. Pat. No. 6,248,550, expressly incorporated by reference). Generally, the kinase substrate fusion protein displays distinguishable properties between the phosphorylated and unphosphorylated states. Measuring the change in fluorescent characteristic before and after contacting with the kinase provides a measure of kinase activity.

In another preferred embodiment, the translocation from one cellular location, or the ability to interact with a phosphoprotein binding domain, provides another measure of phosphorylation. It is well known that phosphorylation of specific sequences alters the interaction of the sequence with a cognate binding partner. Phosphorylation may prevent or enhance these interactions. Thus, phosphorylation is detectable by examining affinity of the binding partners to the fusion protein or by examining changes in intracellular location of the rGFP or pGFP fusion polypeptide (see for example, Durocher, D. et al. (2000) Mol. Cell 6:1169-82; Yaffe, M. B. et al. (2001) Structure 9: R33-8).

In another preferred embodiment, the phosphorylation substrates are candidate substrates comprising library of random peptides, a library of cDNA fragments, or a library of genomic nucleic acid fragments fused to rGFP or pGFP, as discussed below. In one aspect, the library of candidate substrates is expressed in a host cell, each of which expresses a different candidate substrate. A kinase is contacted with the fusion proteins, for example by transfecting the cells with a vector expressing the kinase or by treating the cells to a condition that induces kinase activity. Peptides affecting the GFP fluorescence properties or localization of rGFP or pGFP fusion protein substrate following treatment with kinase is identified. Sequences producing detectable changes are isolated and sequenced to determine the putative kinase sequences.

The general approach outlined above are applicable to a variety of other protein modification reactions. For example, adenosine diphosphate (ADP)-ribosyltransferases binds nicotinamide adenine dinucleotide (NAD), and catalyzes the transfer of the ADP-ribose moiety to an acceptor nucleophile, with cleavage of the glycosidic bond between N-1 of the nicotinamide and C-1 of the adjacent ribose. The modification may comprise a mono-ADP ribosylation or poly-ADP ribosylation, depending on the transferase enzyme (Koch-Nolte, F. (2001) J. Biotechnol. 92: 81-87). Bacterial toxins, such as pertussis toxin and cholera toxin, act by ADP ribosylating heterotrimeric GTP binding proteins that control intracellular signaling and vesicle trafficking. Poly-ADP ribosylation appears to play roles in DNA damage recovery, DNA replication, and viral integration. Thus, the present invention provides for fusion proteins comprising rGFP or pGFP and ADP ribosylation sites made in the same manner as that provided for phosphorylation sites. Mono and poly ADP ribosylated sequences include, among others, those present on heterotrimeric G proteins (Yamamoto, M. (1993) Oncogene 8: 1449-55; Finck-Barbancon, V. (1995) Biochemistry 34: 1070-75; and von Olleschik-Elbheim, L. (1997) Adv Exp Med Biol 419: 87-91), muscle protein desmin (Zhou, H., et al. (1996) Arch. Biochem. Biophys. 334: 214-222), poly-ADP ribosylase (Martinez, M. (1991) Biochem Biophys Res Commun. 181: 1412-8), and phosphorylase kinase (Okazaki, I. J. (1996) Adv. Pharmacol. 35: 247-80).

In another preferred embodiment, the fusion proteins comprise rGFP or pGFP fused to protease recognition sequences for detecting protease activity. Biological functions of proteases are well known in the art, including, but not limited to pathogenesis (e.g., polyprotein processing by HIV protease), cell death (e.g., caspases), cell adhesion (e.g., metalloproteases), and the like. In one aspect, protease recognitions sequences, as further described below, are fused to rGFP or pGFP, or variants thereof. Cleavage of the fusion protein changes the fluorescence characteristic, which provides a measure of protease activity. In one aspect, the cleavage site is inserted into the rGFP or pGFP. That is, the protease recognition sequence is inserted into the internal regions of GFP, preferably the surface loops.

In another preferred embodiment, the protease substrates may comprise fusion of rGFP or pGFP to rGFP or pGFP variants or other fluorescent proteins such that fluorescence resonance energy transfer (FRET) is possible between the two linked fluorescent molecules. Generally, fluorescence resonance energy transfer occurs between two dye molecules in which excitation is transferred from a donor molecule to an acceptor molecule without emission of a photon. Donor and acceptor molecules must be in close proximity (i.e., radial distance within approximately 10 nm of each other) and have their transition dipole orientations approximately parallel to each other. For excitation transfer from donor to acceptor to occur, the absorption spectrum of the acceptor must overlap the fluorescence emission spectrum of the donor. Suitable pairs of fluorescent molecules capable of undergoing FRET signal may include rGFP or pGFP with BFP (blue fluorescent protein, Heim, R. et al. (1996) Curr. Biol. 6: 178-82), rGFP or pGFP with BFP5 (Mitra, R. D. (1996) Gene 173: 13-17), rGFP or pGFP with cyan fluorescent protein (CFP), rGFP or pGFP with *Anemonia majano* fluorescent protein amFP486 (Matz, M. V. (1999) Nat. Biotechnology 17: 969-73), rGFP or pGFP with Discosoma striata dsFP 483 (Matz, supra), rGFP or pGFP with Clavularia cFP484 (Matz, supra), and the like. In these donor-acceptor pairs, the rGFP or pGFP functions as the acceptor. In principle, other donor-acceptor pairs are possible in which rGFP or pGFP serves as the donor to acceptor fluorescent protein variants having excitation and emission peaks of about 20 nm or more than the those of rGFP or pGFP. Examples of suitable acceptors include yellow fluorescent protein (i.e., class 4 GFPs, see Tsien, R. (1998) Ann. Rev. Biochem. 67: 509-44), Zoanthus zFP538 (Matz, supra), *Discosoma* drFP583 (Matz, supra), and the like. The protease recognition site is incorporated as part of the linker sequence connecting the donor and acceptor GFPs. Cleavage of the linker by proteases results in physical separation of the two fluorescent proteins, thus resulting in loss of FRET. A variety of protease and protease recognition sequence combinations may be used, as further described below. The reactions may occur in vitro by contacting the protease with a FRET protease substrate. In another aspect, the reactions are done in vivo by expressing the protease substrates in the cell and introducing vectors expressing the protease or inducing protease activity by appropriate treatment of the cells. In one preferred embodiment, the FRET protease substrate and/or protease are introduced into the cell by retroviral vectors.

Since FRET based reactions provide a basis for monitoring various biological processes, FRET using rGFP or pGFP or their variants as either the donor or acceptor is also applicable for examining various biological reactions. In one preferred embodiment, the FRET molecule comprising rGFP or pGFP, acting as either a donor or acceptor molecule, further comprises a sequence capable of binding an analyte or ligand which causes a change in the spatial orientation of the donor fluorescent protein and the acceptor fluorescent protein relative to one another (see U.S. Pat. No. 6,197,928, hereby expressly incorporated by reference). In one preferred embodiment, the ligand binding region is fused to the two fluorescent proteins without linkers. In another preferred embodiment, the ligand binding region is fused to the fluorescent proteins by linkers to provide proper spatial orientation between the donor and acceptor fluorescent proteins for FRET to occur and to permit binding of ligand to the binding sequence.

Various binding regions may be used with the present invention. These include calcium binding regions (Romoser, V. A. (1997) J. Biol. Chem. 272: 13270-74), protein interaction domains (e.g., phosphoprotein binding domain), receptors (e.g., Fas), and the like (see U.S. Pat. No. 6,197,928). Linkers may comprise glycines or serines or combinations thereof to prevent structural perturbations between the GFPs (e.g., to cause proper folding of the proteins) and the binding domains. Linker sequences are appropriately positioned to either cause an increase or a decrease in FRET upon binding of ligand to the binding sequence. In one aspect, various mutant forms of the binding domain may be made to maximize the range of ligand concentrations capable of being detected in vivo or in vitro by FRET. Fusing these fusion proteins to targeting sequences allows measuring the concentration of the analytes within particular subcellular compartments. In a preferred embodiment, the GFPs used for FRET and their corresponding binding regions and linker sequences are codon optimized to maximize expression within particular cells, especially mammalian cells. Codon optimization is employed because non-optimized forms may not produce sufficient changes in FRET signal to act as a FRET reporter molecule.

In another preferred embodiment, the FRET based reactions do not use a sequence that physically links the donor and acceptor pairs. That is, the donor and acceptor fluorescent fusion proteins exists separately. In this preferred embodiment, rGFP or pGFP fusions may be made to protein-interaction domains. Thus, a first fusion protein comprises a first protein interaction domain fused to rGFP or pGFP, or their variants. A second fusion protein comprises a second protein interaction domain, which is capable of interacting with the first protein interaction domain, fused to a fluorescent protein capable of undergoing FRET with rGFP or pGFP. Juxtaposition of the two fluorescent proteins through the protein interaction regions results in a FRET signal. In general, fused fluorescent proteins separated by a linker provide a positive control for a detectable FRET signal. Conversely, expression of each fluorescent protein fused to its cognate protein interaction domain provides a negative control for determining background signal and the relative signal intensities of the two fluorescent proteins. Cells expressing the fusion proteins may be examined in vivo, in vitro, or after fixation in a chemical fixative (e.g., formaldehyde, paraformaldehyde, glutaraldehyde). Generally, measuring the FRET ratio provides one basis for determining interaction between the two protein interaction domains (Miyawaki, A. et al. (2000)

Methods Enzymol. 327: 472-500). As further described below, the protein interaction domain comprises any sequence capable of interacting with other molecules, including other proteins, nucleic acids, lipids, carbohydrates, and the like. The interaction domains may be identical, in which case homomultimeric interactions may be examined, while in other cases, the interaction domains are different, in which case heteromultimeric interactions may be examined (Guo, C. et al. (1995) J. Biol Chem 270: 27562-68; Mahajan, N. P. (1998) Nat. Biotechnol. 16: 547-52; Ng, E. K. (2002) J. Cell Biochem. 84: 556-66; and Day, R. N. (2001) Methods 25: 4-18).

Since fluorescent proteins serve as useful reporters of cellular events, the present invention further relates to fusion proteins comprising rGFP or pGFP fused to various protein interaction domains whose interactions change depending on the physiological state of the cell. These fusion proteins serves as biosensors, as defined below. Protein interaction domains whose interactions with binding partners change with different cellular states are well known in the art. As illustrated below, pleckstrin domains bind specifically to PtdInsP$_2$, which is released from the membrane by action of phospholipases activated by signal transduction events. Phosphoprotein binding domains (e.g., SH2 domains) interact with specific phosphorylated peptide sequences as part of their mechanism of signal transduction. The voltage sensing domain of voltage sensitive ion channels (e.g. Shaker potassium channels) shifts within the membrane depending on the membrane potential, thus altering the solution environment of sequences adjacent to the voltage sensor (Siegel, M. S. (1997) Neuron 19: 735-41). In the present invention, rGFP, pGFP or variants thereof are fused to these sequences to generate fusion proteins whose cellular localization or fluorescence properties change depending on the physiological state of the cell. Determining changes in cellular localization may be done by fluorescence microscopy while changes in fluorescence may be examined by measuring the fluorescence characteristics at two different cellular states.

In another preferred embodiment, the fusion polypeptides comprise rGFP or pGFP fused to peptides or proteins encoded by cDNA or cDNA fragments. As used herein, cDNA is meant a DNA that is complementary to at least a portion of an RNA, preferably a messenger RNA, and is generally synthesized from an RNA preparation using reverse transcriptase. As further described below, the cDNA may be full length (i.e., complementary to the full length RNA) or a partial cDNA, which is less than the full length RNA. The cDNA may be a cDNA fragment, which is derived from a larger cDNA by methods described below. Methods for constructing cDNA libraries from RNA, especially mRNA, are well known in the art (see Ausubel, F. In Current Protocols in Molecular Biology, John Wiley & Sons, updated October 2001, Chapter 5, Construction of Recombinant DNA Libraries, particularly Section III, Preparation of Insert DNA from Messenger RNA, expressly incorporated by reference herein). In addition, two commonly used methods of producing cDNA are described in Okayama and Berg, Mol. (1982) Cell Biol. 2: 161-170 and Guber and Hoffman (1983) Gene 25: 263-269. In a preferred embodiment, the cDNAs are inserted into the carboxy or the amino terminal region of rGFP or pGFP. In another preferred embodiment, cDNA is inserted onto the internal regions of rGPF or pGFP. Preferably, the insertions do not affect the fluorescence of the rGFP or pGFP to allow monitoring of cDNA expression. Fusions to the amino terminal or internal regions of rGFP or pGFP permit identification of cDNAs that are in frame with respect to the GFP protein as indicated by the expression of fluorescent fusion proteins. Preferably, codon optimized rGFP or pGFP variants are used to maximize expression of the fusion polypeptides and to increase the fluorescence signal of expressed fusion nucleic acids.

As provided more fully below, cDNA may be generated from any number of organisms and cells types, including cDNAs generated from eukaryotic and prokaryotic cells, viruses, cells infected with viruses, pathogens, or from genetically altered cells. The cDNA may encode specific domains, such as signaling domains, protein-interaction domains, membrane binding domains, targeting domains, and the like. Furthermore, the cDNA may be frameshifted by adding or deleting nucleotides, which may result in an out of frame construct, such that a pseudorandom peptide or protein is encoded. In addition, the cDNAs and cDNA libraries contemplate various subtracted cDNA or enriched cDNA libraries (e.g., secreted or membrane proteins; see Kopczynski, C. C. (1998) Proc. Natl. Acad. Sci. USA 95: 9973-78). That is, a cDNA library may be a complete cDNA library from a cell, a partial library, an enriched library from one or more cell types, or a constructed library with certain cDNAs being removed to form a library.

In another preferred embodiment, the fusion polypeptides comprise rGFP or pGFP fused to proteins or peptides encoded by genomic DNA. As elaborated above for cDNA, the genomic DNA can be derived from any number of organisms or cells, including genomic DNA of eukaryotic or prokaryotic cells, or viruses. They may be from normal cells or cells defective in cellular processes, such as tumor suppression, cell cycle control, or cell surface adhesion. As more fully explained below, the genomic DNA may be from entire genomic constructs or fractionated constructs, including random or targeted fractionation.

In another preferred embodiment, the fusion polypeptides comprise rGFP or pGFP fused to random peptides. Generally, peptides ranging from about 4 amino acids in length to about 100 amino acids may be used, with peptides ranging from about 5 to about 50 being preferred, with from about 8 to about 30 being particularly preferred and from about 10 to about 25 being especially preferred. As more fully explained below, the peptides are fully randomized or they are biased in their randomization. In one preferred embodiment, the random peptide is linked to a fusion partner to structurally constrain the peptide and allow proper interaction with other molecules while in another preferred embodiment, the expressed random peptide is not linked to a fusion partner. Random peptides expressed as fusions with rGFP, pGFP, or variants thereof may be screened for its ability to produce an altered cellular phenotype.

For the fusion polypeptides of the present invention, the fusions are made in a variety of ways. In one preferred embodiment, the peptide is fused to the N-terminus of the rGFP or pGFP. The fusion can be direct, i.e., with no additional residues between the C-terminus of the peptide and the N-terminus of the rGFP or pGFP, or indirect; that is, intervening amino acids are used, such as one or more fusion partners, including a linker. In this embodiment, when the fusion are to peptides, such as random peptides or protein interaction domains, preferably a presentation structure is used to confer some conformational stability to the peptide. Particularly preferred embodiments include the use of dimerization sequences.

In one embodiment, N-terminal residues of the rGFP or pGFP are deleted, i.e., one or more amino acids of the rGFP or pGFP can be deleted and replaced with the protein or peptide of interest. However, as noted above, deletions of more than 7 amino acids may render the rGFP or pGFP less fluorescent, and thus larger deletions are generally not preferred. In a preferred embodiment, the fusion is made directly to the first amino acid of the rGFP or pGFP.

In a preferred embodiment, the peptide is fused to the C-terminus of the rGFP or pGFP. As above for N-terminal fusions, the fusion can be direct or indirect, and C-terminal residues may be deleted.

In a preferred embodiment, proteins, peptides and fusion partners are added to both the N- and the C-terminal regions of the rGFP or pGFP. As the N- and C-terminal region of rGFP and pGFP are putatively on the same "face" of the protein as is the case for aGFP, in spatial proximity (within 18 Å), it is possible to make a non-covalently "circular" rGFP or pGFP using the components of the invention. Thus, for example, the use of dimerization sequences can allow formation of a non-covalently cyclized protein. By attaching a first dimerization sequence to either the N- or C-terminus of rGFP or pGFP; and adding a peptide of interest and a second dimerization sequence to the other terminus, a large compact structure can be formed, with the protein or peptide displayed in a structure constrained by the dimerization sequences.

In a preferred embodiment, the protein or peptide of interest is fused to an internal position of the rGFP or pGFP; that is, the peptide is inserted at an internal position of the rGFP or pGFP. While the peptide can be inserted at virtually any position, preferred positions include insertion at the very tips of "loops" on the surface of the rGFP or pGFP, to minimize disruption of the rGFP and pGFP β-can protein structure. Thus, the rGFP or pGFP fusion polypeptide retains its ability to fluoresce, or maintain a $T_m$ of at least 42° C. under assay conditions.

In a preferred embodiment, the proteins, peptides or other fusion partner is inserted in rGFP and/or pGFP loops. That is, as outlined below, peptides or libraries of peptides can be inserted into (e.g., without replacing any residues) or replace external loops by the addition of the peptides or other fusion partners to replace one or more of the native residues. In a preferred embodiment, the loop comprises residues from about 51 to about 62 for rmGFP or pGFP, and residues from about 48 to about 58 for rrGFP. Similar preferred embodiments utilize replacements or insertions at positions from about 79 to about 84 of both rmGFP and pGFP (about 76 to about 81 for rrGFP); replacements or insertions at positions from about 101 to about 107 (about 99 to about 104 for rrGFP); replacements or insertions at positions from about 117 to about 120 (about 114 to about 117 for rrGFP); replacements or insertions at positions from about 130 to about 148 (about 127 to about 145 for rrGFP); replacements or insertions at positions from about 154 to about 160 (about 151 to about 157 for rrGFP); replacements or insertions at positions from about 170 to about 170-177 (about 167 to about 174 for rrGFP); replacements or insertions at positions from about 186 to about 197 (about 183 to about 194 for rrGFP); and replacements or insertions at positions from about 206 to about 213 (about 202 to about 211 for rrGFP). More preferably, the insertion or replacement will take place between residues 117-120 for rmGFP or pGFP (114-117 for rrGFP); 170-177 (167-174 for rrGFP); or 206-213 (202-211 for rrGFP). Most preferably the insertion will take place between residues 170-177 or 208-213 of rmGFP or pGFP and corresponding residues of rrGFP.

In a preferred embodiment, the peptide of interest is inserted, without any deletion of rGFP or pGFP residues. That is, the insertion point is between two amino acids in the loop, adding the new amino acids of the peptide and fusion partners, including linkers. Generally, when linkers are used, the linkers are directly fused to the rGFP or pGFP, with additional fusion partners, if present, being fused to the linkers and the peptides.

In a preferred embodiment, the peptide is inserted into the rGFP or pGFP, with one or more rGFP or pGFP residues being deleted; that is, the peptide (and fusion partners, including linkers) replaces one or more residues. In general, when linkers are used, the linkers are attached directly to the rGFP or pGFP. Thus, it is linker residues which replace the GFP residues, again generally at the tip of the loop. In general, when residues are replaced, from one to five residues of GFP are deleted, with deletions of one, two, three, four and five amino acids all possible. In another preferred embodiment, fusion polypeptides of the invention do not include linkers. When linkers are not used, the fusion polypeptides will be significantly more constrained because of the reduction in conformational freedom imposed by the GFP structure.

In a preferred embodiment, peptides (including fusion partners, if applicable) can be inserted into more than one loop of the scaffold, the amino terminal region, the carboxy terminal region, or combinations thereof. Thus, for example, adding peptides to two loops can increase the complexity of a random peptide library but still allow presentation of these loops on the same face of the protein. Similarly, it is possible to add peptides to one or more loops, and add other fusion partners to other loops, or amino terminal or carboxy terminal regions, for example targeting sequences, etc., to provide additional biological properties to the fusion polypeptide or to localize the peptide to subcellular or extracellular compartments where molecular interactions can take place.

Accordingly, in a preferred embodiment, the fusion polypeptides may further comprise fusion partners. By "fusion partner" herein is meant a sequence that is associated with the peptide that confers upon all members of the library in that class a common function or ability. Fusion partners can be heterologous (i.e., not native to the host cell), or synthetic (i.e., not native to any cell). Suitable fusion partners include, but are not limited to: a) presentation structures, as defined below, which provide the peptides in a conformationally restricted or stable form; b) targeting sequences, defined below, which allow the localization of the peptide into a subcellular or extracellular compartment; c) rescue sequences as defined below, which allow the purification or isolation of either the peptides or the nucleic acids encoding them; d) stability sequences, which affects stability or protection from degradation to the peptide or the nucleic acid encoding it, for example resistance to proteolytic degradation; e) linker sequences, which conformationally decouple the random peptide elements from the scaffold itself, which keep the peptide from interfering with scaffold folding; f) any protein of interest; or g) any combination of the above, as well as linker sequences as needed. Since particular fusion partners are active in certain organisms or cells while not active in others, those skilled in the art can choose the appropriate fusion partner for particular cells or organisms.

In a preferred embodiment, the fusion partner is itself a presentation structure. By "presentation structure" or grammatical equivalents herein is meant a sequence, which, when fused to peptides, causes the peptides to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with a target protein. This fact has been recognized in the combinatorial library generation systems using biologically generated short peptides in bacterial phage systems. A number of workers have constructed small domain molecules in which one might present peptide structures (e.g., randomized peptide sequences).

Thus, synthetic presentation structures, i.e. artificial polypeptides, are capable of presenting a peptide as a conformationally-restricted domain. Generally such presentation structures comprise a first portion joined to the N-terminal end of the peptide of interest, and a second portion joined to the C-terminal end of the peptide; that is, the peptide is inserted into the presentation structure, although variations may be made, as outlined below, in which elements of the presentation structure are included within the peptide sequence. To limit the background cellular effects of protein sequences that are not part of the expressed protein or peptide of interest, the presentation structures are selected or designed to have minimal biologically activity when expressed in the target cell.

Preferred presentation structures enhance interaction with binding partners by conformationally constraining the displayed peptide and maximizing accessibility to the peptide by presenting it on an exterior surface such as a loop. Accordingly, suitable presentation structures include, but are not limited to, dimerization sequences, minibody structures, loops on β-turns and coiled-coil stem structures in which residues not critical to structure are randomized, zinc-finger domains, cysteine-linked (disulfide) structures, transglutaminase linked structures, cyclic peptides, B-loop structures, helical barrels or 4-helix bundles, leucine zipper motifs, etc.

In a preferred embodiment, the presentation structure is a coiled-coil structure, allowing the presentation of a peptide, especially a random peptide, on an exterior loop (see Myszka et al. (1994) Biochem. 33: 2362-2373, hereby incorporated by reference). Using this system investigators, have isolated peptides capable of high affinity interaction with the appropriate target. In general, coiled-coil structures allow for between 6 to 20 randomized positions.

A preferred coiled-coil presentation structure is as follows: MGC<u>AALESEVSALESEVASLESEVAAL</u>GRGDMP <u>LAAVKSKLSAVKSKLASVKSKLAA</u>CGPP (SEQ ID NO: 24). The underlined regions represent a coiled-coil leucine zipper region defined previously (see Martin et al. (1994) EMBO J. 13:5303-09, incorporated by reference). The bolded GRGDMP region represents the loop structure and when appropriately replaced with peptides (i.e., peptides, generally depicted herein as (X)$_n$, where X is an amino acid residue and n is an integer of at least 5 or 6) can be of variable length. The replacement of the bolded region is facilitated by encoding restriction endonuclease sites in the underlined regions, which allows the direct incorporation of oligonucleotides encoding peptides of interest at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two peptide regions that are presented along a single face of the tertiary structure in the folded protein (see Bianchi et al. (1994) J. Mol. Biol. 236: 649-59, and references cited therein, all of which are incorporated by reference). Investigators have shown this minimal domain is stable in solution and have used phage selection systems in combinatorial libraries to select minibodies with displayed peptide sequences exhibiting high affinity, $K_d=10^{-7}$, for the pro-inflammatory cytokine IL-6.

A preferred minibody presentation structure is as follows: MGRNSQATSGFTFSHFYMEWVRGGEY-IAASRHKHNKYTTEYSASVKGRYIVS-RDTSQSILYLQKKKGPP (SEQ ID NO: 25). The bold, underlined regions are the regions which may be replaced with a peptide or randomized. The italicized phenylalanine must be invariant in the first peptide display region. The entire peptide is cloned in a three-oligonucleotide variation of the coiled-coil embodiment, thus allowing two different peptides of interest to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred ex vivo, for example when secretory targeting sequences are used. As will be appreciated by those in the art, any number of peptide sequences, with or without spacer or linking sequences, may be flanked with cysteine residues. In other embodiments, effective presentation structures may be generated by the peptides of interest themselves. For example, the random peptides may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the presentation sequence confers the ability to bind metal ions to confer secondary structure. Thus, for example, C2H2 zinc finger sequences are used; C2H2 sequences have two cysteines and two histidines placed such that a zinc ion is chelated. Zinc finger domains are known to occur independently in multiple zinc-finger peptides to form structurally independent, flexibly linked domains (see Nakaseko, Y. et al. (1992) J. Mol. Biol. 228: 619-36). A general consensus sequence is (5 amino acids)-C-(2 to 3 amino acids)-C-(4 to 12 amino acids)-H-(3 amino acids)-H-(5 amino acids) (SEQ ID NO: 26). A preferred example would be -FQCEEC- peptide of 3 to 20 amino acids-HIRSHTG- (SEQ ID NO: 27).

Similarly, CCHC boxes can be used that have a consensus sequence -C-(2 amino acids)-C-(4 to 20 amino acid peptide)-H-(4 amino acids)-C- (SEQ ID NO: 28) (see Bavoso, A. et al. (1998) Biochem. Biophys. Res. Commun. 242: 385-89, hereby incorporated by reference). Preferred examples include (1) -VKCFNC-4 to 20 amino acids-HTARNCR- (SEQ ID NO: 29), based on the nucleocapsid protein P2; (2) a sequence modified from that of the naturally occurring zinc-binding peptide of the Lasp-1 LIM domain (Hammarstrom, A. et al. (1996) Biochemistry 35: 12723-32); and (3) -MNPNCARCG-4 to 20 amino acid peptide-HKACF- (SEQ ID NO: 30), based on the NMR structural ensemble 1ZFP (Hammarstrom, A et al., supra).

In a preferred embodiment, the presentation structure includes two dimerization sequences, including self-binding peptides. A dimerization sequence allows the non-covalent association of two peptide sequences, which can be the same or different, with sufficient affinity to remain associated under normal physiological conditions. These sequences may be used in several ways. In a preferred embodiment, one terminus of the protein or peptide is joined to a first dimerization sequence and the other terminus is joined to a second dimerization sequence, which can be the same or different from the first sequence. This allows the formation of a loop upon association of the dimerizing sequences. Alternatively, the use of these sequences effectively allows small libraries of peptides (for example, $10^4$) to become large libraries if two peptides per cell are generated which then dimerize, to form an effective library of $10^8$ ($10^4 \times 10^4$). It also allows the formation of longer protein or peptide libraries, if needed, or more structurally complex peptide molecules. The dimers may be homo- or heterodimers.

Dimerization sequences may be a single sequence that self-aggregates, or two different sequences that associate. That is, nucleic acids are made encoding both a first peptide with dimerization sequence 1, and a second peptide with dimerization sequence 2, such that upon introduction into a cell and expression of the nucleic acid, dimerization sequence 1 associates with dimerization sequence 2 to form a new peptide structure. The use of dimerization sequences allows the noncovalent "constraint" of the displayed peptides; that is, if a dimerization sequence is used at each terminus of the peptide, the resulting structure can form a constrained structure. Furthermore, the use of dimerizing sequences fused to both the N- and C-terminus of the scaffold such as rGFP or pGFP forms a noncovalently constrained scaffold peptide library.

Suitable dimerization sequences will encompass a wide variety of sequences. Any number of protein-protein interaction sites are known. In addition, dimerization sequences may also be elucidated using standard methods such as the yeast two hybrid system, traditional biochemical affinity binding studies, or even using the present methods (see for example, WO 99/51625, hereby incorporated by reference in its entirety). Particularly preferred dimerization peptide sequences include, but are not limited to, -EFLIVKS- (SEQ ID NO: 31), EEFLIVKKS- (SEQ ID NO: 32), -FESIKLV- (SEQ ID NO: 33), and -VSIKFEL- (SEQ ID NO: 34). More preferred dimerization peptide sequences include EEEFLIVEEE (SEQ ID NO: 35) when used together with KKKFLIVKKK (SEQ ID NO: 36).

In a preferred embodiment, the fusion partner is a targeting sequence. As will be appreciated by those in the art, the localization of proteins within a cell is a simple method for increasing effective concentration within a defined compartment. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of increasing the protein concentration in a limited volume within a cell; that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be present in a specific compartment such that effectors (e.g., inhibitors) must be localized appropriately.

Thus, suitable targeting sequences include, but are not limited to, binding sequences capable of causing binding of the expression product to a predetermined molecule or class of molecules while retaining bioactivity of the expression product (for example by using enzyme inhibitor or substrate sequences to target a class of relevant enzymes); sequences signaling selective degradation, of itself or co-bound proteins; and signal sequences capable of constitutively localizing the peptides to a predetermined cellular locale, including a) subcellular locations such as the Golgi, endoplasmic reticulum, nucleus, nucleoli, nuclear membrane, mitochondria, chloroplast, secretory vesicles, lysosome, periplasmic space, cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (PKKKRKV (SEQ ID NO: 37), Kalderon, D. et al. (1984) Cell 39: 499-509); the human retinoic acid receptor-β nuclear localization signal (AR-RRRP (SEQ ID NO: 38)), NFκB p50 (EEVQRKRQKL (SEQ ID NO: 39), Ghosh, S. et al. (1990) Cell 62: 1019-29); NF-kB p65 (EEKRKRTYE (SEQ ID NO: 40), Nolan, G. et al. (1991) Cell 64: 961-99; and others (see for example, Boulikas, T. (1994) J. Cell. Biochem. 55: 32-58, hereby incorporated by reference) and double basic NLS's exemplified by that of the *Xenopus* (African clawed toad) protein, nucleoplasmin (AVKRPAATKKAGQAKKKKLD (SEQ ID NO: 41); Dingwall, C. et al. (1982) Cell, 30: 449-58 and Dingwall, S. et al. (1988) J. Cell Biol. 107: 641-49). Numerous localization studies have demonstrated that NLSs incorporated in synthetic peptides or grafted onto proteins not normally targeted to the cell nucleus cause these peptides and proteins to concentrate in the nucleus (see Dingwall S. et al. (1986) Ann. Rev. Cell Biol. 2: 367-90; Bonnerot, C. et al. (1987) Proc. Natl. Acad. Sci. USA 84: 6795-99; Galileo, and D. S. et al. (1990) Proc. Natl. Acad. Sci. USA 87: 458-62.)

Membrane-anchoring sequences are well known in the art and are based on the genetic geometry of mammalian transmembrane molecules. Peptides are inserted into the membrane via a signal sequence (designated herein as ssTM) and stably held in the membrane through a hydrophobic transmembrane domain (TM). The transmembrane proteins are positioned in the membrane such that the protein region encompassing the amino terminus relative to the transmembrane domain are extracellular and the region towards the carboxy terminal are intracellular. Of course, if the position of transmembrane domains is towards the amino end of the protein relative to the peptide of interest, the TM will serve to position the peptide intracellularly, which may be desirable in some embodiments. ssTMs and TMs are known for a wide variety of membrane bound proteins, and these sequences are used accordingly, either as pairs from a particular protein or with each component being taken from a different protein. Alternatively, the ssTM and TM sequences are synthetic and derived entirely from consensus sequences, thus serving as artificial delivery domains.

As will be appreciated by those in the art, membrane-anchoring sequences, including both ssTM and TM, are known for a wide variety of proteins and any of these are useful in the present invention. Particularly preferred membrane-anchoring sequences include, but are not limited to, those derived from CD8, ICAM-2, IL-8R, CD4 and LFA-1. Other useful ssTM and TM domains include sequences from: (a) class I integral membrane proteins, such as IL-2 receptor beta-chain (residues 1-26 are the signal sequence, 241-265 are the transmembrane residues; see Hatakeyama, M. et al. (1989) Science 244: 551-56 and von Heijne, G. et al. (1988) Eur. J. Biochem. 174: 671-78) and insulin receptor β chain (residues 1-27 are the signal domain, 957-959 are the transmembrane domain and 960-1382 are the cytoplasmic domain; see Hatakeyama, supra, and Ebina, Y. et al. (1985) Cell 40: 747-58); (b) class II integral membrane proteins, such as neutral endopeptidase (residues 29-51 are the transmembrane domain, 2-28 are the cytoplasmic domain; see Malfroy, B. et al. (1987) Biochem. Biophys. Res. Commun. 144: 59-66); (c) type III proteins such as human cytochrome P450 NF25 (Hatakeyama, supra); and (d) type IV proteins, such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1-32 in the case of CD8 (MASPLTRFLSLNLLLLGESILGSGEAK-PQAP (SEQ ID NO: 42), Nakauchi, H. et al. (1985) Proc. Natl. Acad. Sci. USA 82: 5126-30) and amino acids 1-21 in the case of ICAM-2 (MSSFGYRTLTVALFTLICCPG (SEQ ID NO: 43), Staunton, D. E. et al. (1989) Nature 339: 61-64). These leader sequences deliver the construct to the membrane while the hydrophobic transmembrane domains placed at the carboxy terminal region relative to the peptide of interest or peptide candidate agents serve to anchor the construct in the membrane. These transmembrane domains are encompassed by amino acids 145-195 from CD8 (PQRPEDCRPRGS-VKGTGLDFACDIYIWAPLAGICVALLLSLIITLICYHSR (SEQ ID NO: 44), Nakauchi, supra) and 224-256 from ICAM-2 (MVIIVTVVSVLLSLFVTSVLLCFIF-GQHLRQQR (SEQ ID NO: 45), Staunton, supra).

Alternatively, membrane anchoring sequences include the GPI anchor, which results in a covalent bond between the molecule and the lipid bilayer via a glycosyl-phosphatidylinositol bond. The GPI anchor sequence is exemplified by protein DAF, which comprises the sequence PNKGSGTTS-GTTRLLSGHTCFTLTGLLGTLVTMGLLT (SEQ ID NO: 46), with the bolded serine the site of the anchor; (see Homans, S. W. et al. (1988) Nature 333: 269-72 and Moran, P. et al. (1991) J. Biol. Chem. 266: 1250-57). Adding GPI anchor sites is accomplished by inserting the GPI sequence from Thy-1 in the carboxy terminal region relative the inserted peptide of interest or randomized peptide. Thus, the GPI anchor sequences replaces the transmembrane domain in these constructs.

Similarly, acylation signals for attachment of lipid moieties can also serve as membrane anchoring sequences (see Stickney, J. T. (2001) Methods Enzymol. 332: 64-77). It is known that the myristylation of c-src localizes the kinase to the plasma membrane. This property provides a simple and effective method of membrane localization given that the first 14 amino acids of the protein are solely responsible for this function: MGSSKSKPKDPSQR (SEQ ID NO: 47) (see Cross, F. R. et al. (1984) Mol. Cell. Biol. 4: 1834-42; Spencer, D. M. et al. (1993) Science 262:1019-24, both of which are hereby incorporated by reference) or MGQSLTTPLSL (SEQ ID NO: 48). The modification at the glycine residue (in bold) of the motif is effective in localizing reporter genes and can be used to anchor the zeta chain of the TCR. The myristylation signal motif is placed at the amino end relative to the variable region (or protein of interest) in order to localize the construct to the plasma membrane. Another lipid modification is isoprenoid attachment, which includes the 15 carbon farnesyl or the 20 carbon geranyl-geranyl group. The conserved sequence for isoprenoid attachment comprises CaaX motif with the cysteine residue as the lipid modified amino acid. The X residue determines the type of isoprenoid modification. The preferred isoprenoid is geranyl-geranyl when X is a leucine or phenylalanine (Farnsworth, C. C. et al. (1994) Proc. Natl. Acad. Sci. USA 91: 11963-67). Farnesyl is the preferred lipid for a broader range of X amino acids such as methionine, serine, glutamine and alanine. The "aa" in the isoprenoid attachment motif are generally aliphatic residues, although other residues are also functional. Farnesylation sequences include carboxy terminal SKDGKKKKKKSKT-KCVIM (SEQ ID NO: 49) of K-Ras4B. Other isoprenoid attachment motifs are found in the C termini of N and H-Ras GTPases (Aronheim, A. et al. (1994) Cell 78: 949-61). Attachment of farnesyl groups to various forms of GFP provides a useful marker for monitoring cell membrane morphology and cell sorting by FACS. Moreover, cells retain the farnesylated forms upon treating the cells with fixative while cytoplasmic forms of GFP may leach out of the cell.

In addition, localization to the cell membrane by lipid modification is also achieved by palmitoylation. Attachment of the palmitoyl group can be directed to either the amino or carboxy terminal region relative to the protein of interest. In addition, multiple palmitoyl residues or combinations of palmitoyl and isoprenoids are possible. Amino terminal additions of palmitoyl group may use the sequence MVCCMR-RTKQV (SEQ ID NO: 50) from Gap43 protein while carboxy terminal modifications are possible with CMSCKCV-LKKKKKK (SEQ ID NO: 51) from Ras mutant (modified amino acids in bold). Other palmitoylation sequences are found in G protein-coupled receptor kinase GRK6 sequence (LLQRLFSRQDCCGNCSDSEEELPTRL (SEQ ID NO: 52), Stoffel, R. H. et al. (1994) J. Biol. Chem. 269: 27791-94); rhodopsin (KQFRNCMLTSLCCGKNPLGD (SEQ ID NO: 53), Barnstable, C. J. et al. (1994) J. Mol. Neurosci. 5: 207-09); and the p21H-ras 1 protein (LNPPDESGPGCMSCK-CVLS (SEQ ID NO: 54), Capon, D. J. et al. (1983) Nature 302: 33-37). Use of the carboxy terminal sequence LNPP-DESGPGC(p)MSC(p)KC(f)VLS (SEQ ID NO: 55) of H-Ras (modified amino acids in bold; p is palmitoyl group and f is farnesyl group) allows attachment of both palmitoyl and farnesyl lipids.

In a preferred embodiment, the targeting sequence is a lysosomal targeting sequence, including, for example, a lysosomal degradation sequence such as Lamp-2 (KFERQ (SEQ ID NO: 56), Dice, J. F. (1992) Ann. N.Y. Acad. Sci. 674: 58-64); or lysosomal membrane sequences from Lamp-1 (MLIPIAGFFALAGLVLIVLIAYLIGRKRSHAGYQTI (SEQ ID NO: 57), Uthayakumar, S. et al. (1995) Cell. Mol. Biol. Res. 41: 405-20) or Lamp-2 (LVPIAVGAALAGVLIL-VLLAYFIGLKHHHAGYEQF (SEQ ID NO: 58), Konecki, D. S. et al. (1994) Biochem. Biophys. Res. Comm. 205: 1-5; where italicized residues comprise the transmembrane domains and underlined residues comprise the cytoplasmic targeting signal).

Alternatively, the targeting sequence may be a mitochondrial localization sequence, including mitochondrial matrix sequences (e.g., yeast alcohol dehydrogenase III; MLRTSS-LFTRRVQPSLFSRNILRLQST (SEQ ID NO: 59), Schatz, G. (1987) Eur. J. Biochem. 165: 1-6); mitochondrial inner membrane sequences (yeast cytochrome c oxidase subunit IV; MLSLRQSIRFFKPATRTLCSSRYLL (SEQ ID NO: 60), Schatz, supra); mitochondrial intermembrane space sequences (yeast cytochrome c1; MFSMLSKRWAQRTL-SKSFYSTATGAASKS-GKLTQKLVTAGVAAAGITASTLLYADSLTAEAMTA (SEQ ID NO: 61), Schatz, supra); or mitochondrial outer membrane sequences (yeast 70 kD outer membrane protein; MKSFITRNKTAILATVAATG-TAIGAYYYYNQLQQQQQRGKK (SEQ ID NO: 62), Schatz, supra).

The target sequences may also be endoplasmic reticulum sequences, including the sequences from calreticulin (KDEL (SEQ ID NO: 63), Pelham, H. R. (1992) Royal Society London Transactions B; 1-10) or adenovirus E3/19K protein (LYLSRRSFIDEKKMP (SEQ ID NO: 64), Jackson, M. R. et al. (1990) EMBO J. 9: 3153-62). Furthermore, targeting sequences also include peroxisome sequences (for example, the peroxisome matrix sequence of luciferase, SKL; Keller, G. A. et al. (1987) Proc. Natl. Acad. Sci. USA 4: 3264-68); or destruction sequences (cyclin B1, RTALGDIGN (SEQ ID NO: 65); Klotzbucher, A. et al. (1996) EMBO J. 1: 3053-64).

In a preferred embodiment, the targeting sequence is a secretory signal sequence capable of effecting the secretion of the peptide of interest or peptide candidate agent. There are a large number of known secretory signal sequences which direct secretion of the peptide into the extracellular space when placed at the amino end relative to the peptide of interest. Secretory signal sequences and their transferability to unrelated proteins are well known (see Silhavy, T. J. et al. (1985) Microbiol. Rev. 49: 398-418). Secretion of the peptide is particularly useful for generating peptides capable of binding to the surface of, or affecting the physiology of target cells other than the host cell, e.g., the cell infected with the retrovirus. In a preferred approach, a fusion product is configured to contain, in series, secretion signal peptide-presentation structure-randomized peptide region or protein of interest-presentation structure. In this manner, target cells grown in the vicinity of cells expressing the library of peptides are exposed to the secreted peptide. Target cells exhibiting a physiological change in response to the presence of the secreted peptide (i.e., by the peptide binding to a surface receptor or by being internalized and binding to intracellular targets) and the peptide secreting cells are localized by any of a variety of selection schemes and the structure of the peptide effector identified. Exemplary effects include that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO: 66), Villinger, F. et al. (1995) J. Immunol. 155: 3946-54), growth hormone (MATGSRTSLLLAFGLLCLPWLQEGSA FPT (SEQ ID NO: 67), Roskam, W. G. et al. (1979) Nucleic Acids Res. 7: 305-20); preproinsulin (MALWMRLLPLLA-LLALWGPDPAAAFVN (SEQ ID NO: 68), Bell, G. I. et al. (1980) Nature 284: 26-32); and influenza HA protein (MKAKLLVLLYAFVAGDQI (SEQ ID NO: 69), Sekikawa, K. et al. (1983) Proc. Natl. Acad. Sci. USA 80: 3563-67), with cleavage occurring between the nonunderlined-underlined junction. A particularly preferred secretory signal sequence is the signal leader sequence from the secreted cytokine IL-4, MGLTSQLLPPLFFLLACAGNFVHG (SEQ ID NO: 70), which comprises the first 24 amino acids of IL-4.

In a preferred embodiment, the fusion partner is a rescue sequence. A rescue sequence is a sequence which may be used to purify or isolate either the peptide of interest or the candidate agent or the nucleic acid encoding it. Thus, for example, peptide rescue sequences include purification sequences such as the $His_6$ tag for use with $Ni^{+2}$ affinity columns and epitope tags useful for detection, immunoprecipitation, or FACS (fluorescence-activated cell sorting). Suitable epitope tags include myc (for use with the commercially available 9E10 antibody), the BSP biotinylation target sequence of the bacterial enzyme BirA, flu tags, lacZ, GST, and Strep tag I and II.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence that affects the stability of the peptide of interest or candidate bioactive agent. In one aspect, the stability sequence confers stability to the peptide of interest or candidate bioactive agent. For example, peptides may be stabilized by the incorporation of glycines after the initiating methionine (MG or MGG), for protection of the peptide to ubiquitination as per Varshavsky's N-End Rule, thus conferring increased half-life in the cell (see Varshavsky, A. (1996) Proc. Natl. Acad. Sci. USA 93: 12142-49). Similarly, adding two prolines at the C-terminus makes peptides that are largely resistant to carboxypeptidase action. The presence of two glycines prior to the prolines impart both flexibility and prevent structure perturbing events in the di-proline from propagating into the peptide structure. Thus, preferred stability sequences are $MG(X)_n GGPP$ (SEQ ID NO: 71), where X is any amino acid and n is an integer of at least four.

In another aspect, the stability sequence decreases the stability of the peptide of interest or candidate bioactive agent. Sequences, such as PEST sequences (i.e., polypeptide sequences enriched in proline (P), glutamic acid (E), serine (S) and threonine (T); see Rechsteiner, M. (1996) Trends Biochem. Sci. 21: 267-71) and destruction boxes. (Glotzer, M. (1991) Nature 349: 132-38) destabilize proteins by targeting proteins for degradation. For example, fusion of PEST sequences to GFP reporter protein decreases the half-life of GFP, thus providing an indicator of dynamic cellular processes, including, but not limited to, regulated protein degradation, reporter for transcriptional activity, and cell cycle status (Mateus, C. et al. (2000) Yeast 16: 1313-23; Li. X. (1998) J. Biol. Chem. 273: 34970-75). Numerous PEST sequences useful for targeting peptides for degradation are known. These include amino acids 422-461 of ornithine decarboxylase (Corish, P. (1999) Protein Eng. 12: 1035-40; Li, X, et al., U.S. Pat. No. 6,130,313) and the C terminal sequences of IκBα (Lin, R. (1996) Mol. Cell. Biol. 16: 1401-09). Destruction boxes found in cell cycle proteins, for example cyclin B1, can also reduce the half-life of fusion proteins but in a cell cycle dependent manner (Corish, P., supra).

The fusion partners may be placed anywhere (i.e., N-terminal, C-terminal, internal loops) in the structure as the biology and activity permits. In addition, while the discussion has been directed to the fusion of fusion partners to the peptide or protein of interest of the fusion polypeptide, it is also possible to fuse one or more of these fusion partners to the rGFP or pGFP portion of the fusion polypeptide. Thus, for example, the rGFP or pGFP may contain a targeting sequence (either N-terminal region, C-terminal region, or internal region, as described above) at one location, and a rescue sequence in the same place or a different place on the molecule. Thus, any combination of fusion partners, peptides of interest, and rGFP or pGFP proteins may be made.

In a preferred embodiment, the fusion partner includes a linker or spacer sequence. Linker sequences between various targeting sequences, for example, membrane targeting sequences, and the other components of the constructs, such as the randomized peptides, may be desirable to allow the peptides to interact with potential targets unhindered. For example, useful linkers include glycine polymers $(G)_n$, glycine-serine polymers (including, for example, $(GS)_n$, $(GSGGS)_n$ (SEQ ID NO: 72) and $(GGGS)_n$ (SEQ ID NO: 73), where n is an integer of at least one), glycine-alanine polymers, alanine-serine polymers, and other flexible linkers, such as the tether for the shaker potassium channel, and a large variety of other flexible linkers, as will be appreciated by those in the art. Glycine and glycine-serine polymers are preferred since both of these amino acids are relatively unstructured, and therefore may be able to serve as a neutral tether between components. Glycine polymers are the most preferred as glycine accesses significantly more phi-psi space than even alanine, and is much less restricted than residues with longer side chains (see Scheraga, H. A. (1992) Rev. Computational Chem. III 73-142). Secondly, serine is hydrophilic and therefore able to solubilize what could be a globular glycine chain. Third, similar chains have been shown to be effective in joining subunits of recombinant proteins such as single chain antibodies.

In a preferred embodiment, the peptide is connected to the rGFP or pGFP via linkers. That is, while one embodiment utilizes the direct linkage of the peptide of interest to the rGFP or pGFP, or of the peptide and any fusion partners to the rGFP or pGFP protein, a preferred embodiment utilizes linkers at one or both ends of the peptide. That is, when attached either to the N- or C-terminus, one linker may be used. When the peptide of interest is inserted in an internal position, as is generally outlined above, preferred embodiments utilize at least one linker and preferably two, one at each terminus of the peptide. Linkers are generally preferred for conformationally decoupling any insertion sequence (i.e., the peptide) from the scaffold structure itself, to minimize local distortions in the scaffold structure that can either destabilize folding intermediates, or allow access to GFPs' buried tripeptide fluorophore, which decreases (or eliminates) rGFP or pGFP fluorescence due to exposure to exogenous collisional fluorescence quenchers (see Phillips, G. N. (1997) Curr. Opin Struct. Biol. 7: 821-27, hereby incorporated by reference in its entirety).

Accordingly, as outlined below, when the peptides are inserted into internal positions in the rGFP or pGFP protein, preferred embodiments utilize linkers, and preferably (Gly)n linkers, where n is 1 or more, with n being two, three, four, five and six, although linkers of 7-10 or more amino acids are also possible. Generally in this embodiment, no amino acids with β-carbons are used in the linkers.

In addition, the fusion partners, including presentation structures, may be modified, randomized, and/or mutated to alter the presentation orientation of the randomized expression product. For example, determinants at the base of the loop may be modified to slightly modify the internal loop peptide tertiary structure, to properly display the protein or peptide of interest.

In a preferred embodiment, combinations of fusion partners are used. Thus, for example, any number of combinations of peptides of interest, presentation structures, targeting sequences, rescue sequences, and stability sequences may be used, with or without linker sequences. As will be appreciated by those in the art, using a base vector that contains a cloning site for inserting various peptides, a person skilled in the art can cassette in various fusion partners. In addition, as discussed herein, it is possible to have more than one peptide of interest in a construct, either together to form a new surface or to bring two other molecules together. Similarly, as described below, it is possible to have peptides inserted at two or more different loops of the rGFP or pGFP protein, preferably but not required to be on the same "face" of the GFP protein.

In view of the foregoing, the present invention further relates to fusion nucleic acids for encoding and expressing the proteins described above. By "fusion nucleic acid" herein is meant a plurality of nucleic acid components that are joined together, either directly or indirectly. As will be appreciated by those in the art, in some embodiments the sequences described herein may be DNA, for example when extrachromosomal plasmids are used, or RNA when retroviral vectors are used. In some embodiments, the sequences are directly linked together without any linking sequences while in other embodiments linkers such as restriction endonuclease cloning sites, linkers encoding flexible amino acids, such as glycine or serine linkers such as known in the art, are used, as discussed above. In addition, the fusion nucleic acids may further comprise substitutions to codon optimize the nucleic acid for expression of the encoded proteins in a particular target organism.

To facilitate the generation of fusion polypeptides comprising rGFP or pGFP, the present invention further provides for rGFP or pGFP fusion nucleic acids with multiple cloning site (MCS) inserted into the rGFP or pGFP nucleic acid sequences at about the amino terminal region, the carboxy terminal region, or at least one loop as outlined above, or combinations thereof. The presence of an MCS facilitates generation of fusion constructs, including cDNA, genomic DNA, and random peptide fusion libraries. When the MCS site is at the amino terminal region, the MCS may contain its own translation initiation sequence to regulate translation of inserted nucleic acids lacking its own translation initiation sites (e.g., random peptide sequences). Alternatively, when the MCS is present downstream of the initiating amino acid (i.e., methionine) near the amino terminal region, or at the carboxy terminal or internal loops of rGFP or pGFP, the translation initiation sequences of rGFP or pGFP are generally used.

In the present invention, the fusion nucleic acids further comprise expression vectors for expressing the proteins of the present invention. The expression vectors may be either self-replicating extrachromosomal vectors or vectors which integrate into a host genome. Generally, these expression vectors include control sequences operably linked to the nucleic acid encoding the protein. The term "control sequences" refers to DNA sequences necessary for the expression of an operably linked coding sequence in a particular host organism. Thus, control sequences include sequences required for transcription and translation of the nucleic acids, which are selected in reference to the target organism used for expressing the proteins. For example, for prokaryotes, the sequences include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. In the present context, operably linked means that the control sequences, such as transcription and translation regulatory sequences, are positioned relative to the coding sequence in such a manner that expression of the encoded protein occurs. For example, a promoter or enhancer is operably linked to a coding sequence if it affects the transcription of the sequence; or a ribosome binding site is operably linked to a coding sequence if it is positioned so as to facilitate translation. Where the fusion nucleic acid encodes a fusion protein, for example a protein linked to a secretory leader sequence, the DNA for the secretory leader is operably linked to DNA for a polypeptide if it is expressed in a manner resulting in secretion of the polypeptide.

In general, the transcriptional and translational regulatory sequences may include, but are not limited to, promoter sequences, enhancer or transcriptional activator sequences, ribosomal binding sites, CAP sequences, transcriptional start and stop sequences, and translational start and stop sequences. In a preferred embodiment, the regulatory sequences include a promoter and transcriptional start and stop sequences.

Promoter sequences, are either constitutive or inducible promoters. By "promoter" herein is meant nucleic acid sequences capable of initiating transcription of the fusion nucleic acid or portions thereof. Promoters may be constitutive wherein the transcription level is constant and unaffected by modulators of promoter activity. Promoter may be inducible in that promoter activity is capable of being increased or decreased, for example as measured by the presence or quantitation of transcripts or translation products (see Walter, W. et al. (1996) J. Mol. Med. 74: 379-92). Promoters may also be cell specific wherein the promoter is active only in particular cell types. Thus, promoter as defined herein includes sequences required for initiating and regulating the transcription level and transcription in specific cell types. Furthermore, the promoters may be either naturally occurring promoters, hybrid promoters which combine elements of more than one promoter, or synthetic promoters based on consensus sequence of known promoters.

The fusion nucleic acid comprising the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating into the host chromosomal elements, the expression vector may contain sequences necessary for the integration process. The integration sequences used will depend on the integration mechanism. For homologous recombination, a sequence homologous to specific regions of a host cell genome is incorporated into the fusion nucleic, as is well known in the art. Preferably two homologous sequences flank the expression construct or the region to be inserted into the genome. By selecting the appropriate homologous sequence, the vector may be directed to specific regions of the host cell genome. Alternatively, integration is directed by inclusion of sequences necessary for site specific recombination. A variety of site specific recombination systems are known. The cre-lox system comprises the Cre recombinase of bacteriophage P1, which catalyzes recombination between short 34 basepair lox-P sites. Presence of lox-P sites on two different DNAs results in recombination between the two lox-P sites, thus generating a single recombinant containing two lox-P sites flanking the integrated DNA (see for example, Fukushige, S. et al. (1992) Proc. Natl. Acad. Sci. USA 89: 7905-09). Cre-lox recombinations can function in any cell system containing lox-P sites and Cre recombinase. Insertion of lox-P sites into the genome of organisms and expression of Cre allows for recombination events in bacterial, yeast, plant, and mammalian cells (Sauer, B. (1996) Nucleic Acids Res. 24: 4608-13; Araki, K. et al. (1997) Nucleic Acids Res. 25: 868-72; and Vergunst, A. C. (1998) Plant Mol. Biol. 38: 393-406; U.S. Pat. No 4,959,317).

Other systems applicable for integrating the expression vectors include, but are not limited to, the flp recombinase system (see for example, U.S. Pat. No. 6,140,129), the λ integrase system, bacteriophage phage Mu, transposon systems (e.g., γδ), retroviral vectors, and the like. As some of the integration mechanisms function only in certain organisms, the appropriate integration system is selected according to the cells in which the expression vectors are used, as is well known in the art.

In another preferred embodiment, the site-specific recombination sites are not used for integration but for deletion or rearrangement of nucleic acid sequences on the fusion nucleic acid. Suitable site specific recombination sequences include cre-lox and flp. Rearrangements may occur for fusion nucleic acids present extrachromosomally or for fusion nucleic acids integrated into the host chromosome. Generally, the site-specific recombination sequences flank the nucleic acid sequences selected for deletion or rearrangement. That is, a first site-specific sequence is present 5' and a second site specific sequence is present 3' of the sequence to be deleted or rearranged. Thus, the sites may flank promoter or promoter controlling elements, genes of interest, splicing sequences, translational controlling elements, or combinations thereof. Whether the site specific recombination sequences lead to deletion or rearrangement generally depend on the orientation of the recombination sites. Placement of flp or loxP sites in head-to-head orientation (i.e., inverted repeat) results in inversion of the interlying DNA while placement in head-to-tail orientation (i.e., direct repeat) results in excision of the interlying DNA. These features may be useful in several situations, for example, when it is desirable to activate expression of the rGFP or pGFP fusion polypeptide in specific cells, tissues, or at specific periods, especially at specific times in cellular development. To achieve this effect, a rGFP or pGFP fusion nucleic acid, flanked by loxP or flp sites placed in inverse repeat orientation, is linked in a reverse orientation relative to a promoter such that transcription results in generation of an antisense strand rather than the sense strand of the fusion nucleic acid encoding the fusion polypeptide, thus resulting in absence of rGFP or pGFP protein. To properly express rGFP or pGFP protein in these cells, the recombinase is expressed in these cells, either by transfection or by inducing expression of an endogenous copy of the recombinase, which results in inversion of the rGFP or pGFP relative to the promoter. This rearrangement places the gene in proper orientation for synthesis of the sense strand that leads to expression of the protein.

In a preferred embodiment, the expression vector also contains a selectable marker gene to allow the selection of transformed host cells. Generally, the selection will confer a detectable phenotype that provides a way of differentiating between cells that express and do not express the selection gene. Selection genes are well known in the art and will vary with the host cell used, as further described below.

In accordance with the foregoing, a variety of expression vectors are used to express the nucleic acids encoding the proteins of the present invention. As used herein, the term "vector" includes plasmids, cosmids, artificial chromosomes, viruses, and the like. In one preferred embodiment, the expression vectors are bacterial expression vectors including vectors for *Bacillus subtilis*, *E. coli*, *Haemophilus*, *Streptococcus cremoris*, and *Streptococcus lividans*, among others. These vectors are well known in the art. A suitable bacterial promoter is any nucleic acid sequence capable of binding bacterial RNA polymerase and initiating the downstream (3') transcription of the coding sequence of the fusion protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage (e.g., pL) may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli*, the ribosome binding site is the Shine-Delgarno (SD) sequence and includes an initiation codon and a sequence 3-9 nucleotides in length located 3-11 nucleotides upstream of the initiation codon.

The expression vector may also include a signal peptide sequence that provides for secretion of the fusion protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors and introduced in bacterial host cells, using techniques well known in the art (e.g., calcium chloride treatment, electroporation, etc.).

In another preferred embodiment, the expression vectors are used to express the proteins in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*. Preferred promoter sequences for expression in yeast include the inducible GAL promoters (e.g., GAL 1, GAL 4, GAL 10. etc.), the promoters from alcohol dehydrogenase (ADH or ADC1), enolase, glucokinase, glucose-6-phosphate isomerase, glyceraldehyde-3-phosphate-dehydrogenase, hexokinase, phosphofructokinase, 3-phosphoglycerate mutase, pyruvate kinase, fructose bisphosphate, acid phosphatase gene, tryptophase synthase (TRP5) and copper inducible CUP1 promoter. Any plasmid containing a yeast compatible promoter, an origin of replication, and termination sequences is suitable.

Yeast selectable markers include genes complementing mutations ADE2, HIS4, LEU2, TRP1, URA3, and genes conferring resistance to tunicamycin (ALG7 gene), G418 (neomycin phosphotransferase gene), growth in presence of copper ions (metallothionein CUP1 gene), resistance to fluoroacetate, (fluoroacetate dehalogenase), or resistance to formaldehyde (formaldehyde dehydrogenase).

In another preferred embodiment, the expression vectors are used for expression in plants. Plant expression vectors are well known in the art. Vectors are known for expressing genes in *Arabidopsis thaliana*, tobacco, carrot, and maize and rice cells. Suitable promoters for use in plants include those of plant or viral origin, including, but not limited to CaMV 35S promoter (active in both monocots and dicots, Chapman, S. et al. (1992) Plant J. 2, 549-557) nopoline promoter, mannopine synthase promoter, soybean or *Arabidopsis thaliana* heat shock promoters, tobacco mosaic virus promoter (Takmatsu, et al. (1987) EMBO J. 6: 307), AT2S promoters of *Arabidopsis thaliana* (i.e., PAT2S1, PATS2, PATS3 etc.). In another preferred embodiments, the promoters are tissue specific promoters active in specific plant tissues or cell types (e.g., roots, leaves, shoot meristem etc.), which are well known in the art. Alternatively, the expression vectors comprise recombinant plasmid expression vectors based on Ti plasmids or root inducing plasmids.

In another aspect, regulatory sequences include "enhancers" to regulate expression. Preferably these are of plant, bacterial (e.g. *Agrobacterium*), viral origin which are specific to plants. The enhancers may act at either the transcriptional or translational level. The fusion nucleic acids may also comprise one or more introns, preferably of plant origin, to increase the efficiency of expression of the fusion nucleic acid. For example, insertion of an intron into the 5' untranslated sequence of a gene (e.g., between site of transcription initiation and translation initiation) leads to increased stability of the messenger RNA. The intron is preferably, though not necessarily, the first intron.

Optionally, a selectable marker gene is used with the expression vectors. The marker may be a drug resistance gene, a herbicide resistance gene, or any other selectable marker that can be used for selecting cells containing the vector. Suitable plant markers include adenosine deaminase, dihydrofolate reductase, hygromycin transferase, bar gene (Lohar, D. P. (2001) J. Exp. Bot. 52: 1697-702), green fluorescent proteins (including rGFP and pGFPs of the present invention), amino-glycoside 3'-O-phosphotransferase II (i.e., kanamycin, neomycin, and G418 resistance).

In addition, the plant expression vectors may comprise plant specific targeting sequences in addition to the targeting sequences described above. In one aspect, the sequences are chloroplast or mitochondrial targeting sequences. An example of a chloroplast targeting signals is the small subunit of ribulose 1,5 diphosphate of *Pisum sativum*. For a mitochondrial targeting sequence, an example is: the precursor of the beta subunit of mitochondrial ATPase F1 of *Nicotiana plumbaginifolia*. In another aspect, the targeting signal comprises a vacuolar targeting sequences or "propeptide". These sequences target the proteins to vacuoles of aqueous tissues, including leaves or protein bodies of storage tissues (Neuhaus, J. M et al. (1991) Proc. Natl. Acad. Sci. USA 88: 10362-66; and Sebastiani, F. L. et al. (1991) Eur. J. Biochem. 199: 441-50).

In another preferred embodiment, the expression vectors are used to express the proteins and nucleic acids of the present invention in insects and insect cells. In one preferred embodiment, fusion proteins are produced in insect cells. Expression vectors for the transformation of insect cells, and in particular, baculovirus vectors used to create recombinant baculoviruses for expressing foreign genes, are well known in the art (see for example, O'Reilly, D. R. et al. "Baculovirus Expression Vectors: A Laboratory Manual," W.H. Freeman & Co, New York, 1992). By "baculovirus" or "nuclear polyhedrosis viruses" as used herein is meant expression systems using viruses classified under the family of baculoviridae, preferably subgroup A. In preferred embodiments, these include systems specific for *Bombyx, Autographica*, and *Spodoptera* (see for example, U.S. Pat. No. 5,194,376). Other expression systems include Amsacta moorei entomopoxvirus (AmEPV), *Aedes aegypti* desonucleosis (Aedes DNV, U.S. Pat. No. 5,849,523), and *Galleria mellonella* densovirus (GmDNV, Tal, et al. (1993) Arch. Insect Biochem. Physiol. 22: 345-356). In another preferred embodiment, expression vectors comprise fusion nucleic acids that integrate into the host chromosome. This may be achieved by homologous recombination, particularly modified homologous recombination techniques when the insect cells or insect do not readily undergo homologous recombination (see Rong, Y. S. (2000) Science 288: 2013-18); site directed recombination (e.g., cre-lox); and transposon mediated integration (e.g., P-element transposition elements).

Promoters suitable for controlling expression in insects include *Autographa californica* nuclear polyhydrosis virus polyhedrin promoter, heat shock promoter (e.g., hsp 70), tubulin promoter, p10 promoter, Aedes DNV viral p7 and p61 promoters. In one preferred embodiment, the promoter allows expression at an early stage in viral infection and/or allows expression in substantially all tissues of an insect. In another preferred embodiment, the promoter is a cell specific and developmental stage specific promoter, many of which are well known in the art. As used herein, developmental specific promoters are promoters that are active at only certain stages in insect development, for example, embryonic, larval, pupal, and adult stages. An example of a developmental stage specific promoter is the ecdysone regulated promoters that are active during molting and larval/pupal stages because of increases in the steroid hormone ecdysone during these developmental periods. Cell specific promoters include promoters active in the nervous system (e.g., ELAV), imaginal discs, gut, malphigian tubules, antennae (e.g., odor binding protein gene promoter), etc.

Although mammalian targeting sequences function in insect cells, targeting sequences derived from insect genes are preferred under some circumstances, for example to efficiently express secreted or membrane bound proteins in insect cells. Signal sequence include *Manduca sexta* AKH signal peptide sequence, *Drosophila* cuticle protein signal peptides (e.g., CP1, CP2, CP3 and CP4, U.S. Pat. No. 5,278, 050), and honey bee mellitin excretion peptide (MKFLVD-VALVFMVVYISYIYA) (SEQ ID NO: 74).

In a preferred embodiment, the expression vectors are used for expression in animals, especially mammals. A variety of expression vectors are known for expressing proteins in animal cells, including fusion nucleic acids existing extrachromosomally, as integrants in the host chromosome, or as viral nucleic acids. Viral vectors may be based on adenoviral, lentiviral, alphaviral, poxvirus (vaccinia virus), or retroviral vectors. In a preferred embodiment, the viral expression vector system is a retroviral vector, such as is generally described in PCT/US97/01019 and PCT/US97/01048, both of which are hereby expressly incorporated by reference.

By "retroviral vectors" herein is meant vectors used to introduce into appropriate hosts the nucleic acids of the present invention in the form of a RNA viral particle. A variety of retroviral vectors are known in the art. Preferred retroviral vectors include a vector based on the murine stem cell virus (MSCV) (Hawley, R. G. et al. (1994) Gene Ther. 1: 136-38) and a modified MFG virus (Riviere, I. et al. (1995) Proc. Natl. Acad. Sci. USA 92: 6733-37), and pBABE (see PCT US97/01019). In addition, particularly well suited retroviral transfection systems for generating retroviral vectors are described in Mann et al., supra; Pear, W. S. et al. (1993) Proc. Natl. Acad. Sci. USA 90: 8392-96; Kitamura, T. et al. (1995) Proc. Natl. Acad. Sci. USA 92: 9146-50; Kinsella, T. M. et al. (1996) Hum. Gene Ther. 7: 1405-13; Hofmann, A. et al. (1996) Proc. Natl. Acad. Sci. USA 93: 5185-90; Choate, K. A. et al. (1996) Hum. Gene Ther. 7: 2247-53; WO 94/19478; PCT US97/01019, and references cited therein, all of which are incorporated by reference. Other suitable retroviral vectors include, among others, LRCX retroviral vector set; pSIR retroviral vector; pLEGFP-NI retroviral vector, pLAPSN retroviral vector; pLXIN retroviral vector; pLXSN retroviral vector; all of which are commercially available (e.g., Clontech, Palo Alto, Calif.). Generally, the retroviral vectors described above are used to express the nucleic acids of the present invention in proliferating cells. When target cells are non-proliferating (e.g., brain cells), useful viral vectors are derived from lentiviruses (Miyoshi, H. et al. (1998) J. Virol. 72: 8150-57), adenoviruses (Zheng, C. et al. (2000) Nat. Biotechnol. 18: 176-80) or alphaviruses (Ehrengruber, M. U. (1999) Proc. Natl. Acad. Sci. USA 96: 7041-46). In addition, the retroviral vectors may incorporate the self-inactivating (SIN) feature of 3' LTR enhancer/promoter to inactivate viral promoters upon integration, which allows use of other promoters for regulating expression of the fusion nucleic acid. It is possible to configure these SIN retroviral vectors to permit inducible expression of retroviral inserts after integration of a single vector into a target cell (Hofmann, et al. (1996) Proc. Natl. Acad. Sci. USA 93: 5185).

The mammalian vectors may include inducible and constitutive promoters for expressing the genes of interest encoding the polypeptides of the present invention. A mammalian promoter will have a transcription initiating region, generally located 5' to the start of the coding region, and a TATA box, present at about 25-30 basepairs upstream of the transcription initiation site. The promoter will also contain upstream regulatory elements that control the rate and initiation of transcription, including CAAT and GC box, enhancer sequences, and repressor/silencer sequences (see for example, Chang B D (1996) Gene 183: 137-42). These promoter controlling elements may act directionally, requiring placement upstream of the promoter region, or act non-directionally. These aforementioned transcriptional control sequences may be provided from non-viral or viral sources. Commonly used promoters and enhancers are from viral sources since the viral genes have a broad host range and produce high expression rates. Viral promoters, including upstream controlling sequences, may be from polyoma virus, adenovirus 2, simian virus 40 (early and late promoters), herpes simplex virus (e.g., HSV thymidine kinase promoter), human cytomegalovirus promoter (CMV), and mouse mammary tumor virus (MMTV-LTR) promoter. A variety of non-viral promoters with constitutive, inducible, cell specific, or developmental stage specific activities are also well known in the art (e.g., β-globin promoter, mammalian heat shock promoter, metallothionein, ubiquitin C promoters, EF-1 alpha promoters, etc.). Cell specific promoters, which are well known in the art, include promoters active in specific cells including, but not limited to brain, olfactory bulb, thyroid, lung, muscle, pancreas, liver, lung, heart, breast, prostate, kidney, etc. Promoters and promoter controlling elements are chosen based on the desired level of promoter activity and the cell type in which the proteins of the present invention are to be expressed.

Generally, the mammalian vectors also include selectable marker genes. Suitable marker genes include reporter or selection genes as further described below. Selection genes include, but are not limited to neomycin, blastocidin, bleomycin, puromycin, hygromycin, and multiple drug resistance (MDR) genes. Suitable reporter genes include fluorescent proteins (e.g., green fluorescent proteins, luciferases) enzymatic markers (e.g., b-galactosidase, glucouronidase, alkaline phosphatase etc.), and surface proteins (e.g., CD8).

Additional sequences in the expression vectors include splice sites for proper expression, polyadenylation signals, 5' CAP sequence, transcription termination sequences, and the like. Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation. Examples of transcription terminator and polyadenylation signals include those derived from SV40.

Other sequences may include centromere sequences for generating human artificial chromosomes (HACs) for delivering larger fragments of DNA than can be contained and expressed in a plasmid or viral vector. HACs of 6 to 10 M bp are constructed and delivered via conventional delivery methods (liposomes, polycationic amino polymers, or vesicles) for therapeutic purposes. The choice and design of an appropriate vector is within the ability and discretion of one of ordinary skill in the art.

In a further preferred embodiment, the fusion nucleic acids of the present invention may comprise a first gene of interest, a separation sequence, and a second gene of interest. In a preferred embodiment, at least one of the gene of interest is a rGFP or pGFP or their variants, or a rGFP or pGFP fusion polypeptide described above. By "gene of interest" herein is meant any nucleic acid sequence capable of encoding a "protein of interest" or a "protein," as defined below. However, in some embodiments, the "gene of interest" encompasses a nucleic acid sequence element that does not encode a protein. These elements may include, but are not limited to, promoter/enhancer elements, chromatin organizing sequences, ribosome binding sequences, mRNA splicing sequences, multiple cloning sites, etc.

In a preferred embodiment, the gene of interest is a reporter gene. By "reporter gene" or "selection gene" or grammatical equivalents herein is meant a gene that by its presence in a cell (i.e., upon expression) allows the cell to be distinguished from a cell that does not contain the reporter gene. Reporter genes can be classified into several different types, including detection genes, survival genes, death genes, cell cycle genes, cellular biosensors, proteins producing a dominant cellular phenotype, and conditional gene products. In the present invention, expression of the protein product causes the effect distinguishing between cells expressing the reporter gene and those that do not. As is more fully outlined below, additional components, such as substrates, ligands, etc., may be additionally added to allow selection or sorting on the basis of the reporter gene.

In a preferred embodiment, the first and second gene of interest encode the same rGFP or pGFP. These constructs allow increased expression of the GFP molecule or GFP fusion polypeptide since two copies of the same gene are expressed in a single transcriptional event. The presence of a separation sequence allows the synthesis of separate fluorescent proteins, thus obviating any detrimental effect that might arise from fusing two reporter proteins to each other. Synthesizing high levels of encoded protein is desirable when needed to produce a cellular phenotype, for example when expressing a random peptide fused to rGFP or pGFP. Similarly, for example when screening for promoter regulators, signal amplification may be accomplished by expressing two identical rGFP or pGFP reporter genes.

In another preferred embodiment, the gene of interest comprises a reporter gene distinguishable from rGFP or pGFP. Expressing two distinguishable, separate reporter proteins allows targeting of individual reporter proteins to distinct cellular locations, provides increased discrimination of cells expressing the fusion nucleic acid, and affords a basis for monitoring expression of the other reporter gene.

In a preferred embodiment, the distinguishable reporter gene comprises a protein that can be used as a direct label, for example a detection gene for sorting the cells or for cell enrichment by FACS. In this embodiment, the protein product of the reporter gene itself can serve to distinguish cells that are expressing the reporter gene. In one aspect, suitable reporter genes include distinguishable wildtype and variant forms of *Renilla reniformis* GFP, *Ptilosarcus gurneyi* GFP, and *Renilla muelleri* GFP. In another aspect, the reporter gene comprises other fluorescent proteins, such as *Aequoria victoria* GFP (Chalfie, M. et al. (1994) Science 263: 802-05), EGFP; Clontech—Genbank Accession Number U55762), blue fluorescent protein (BFP; Quantum Biotechnologies, Inc. 1801 de Maisonneuve Blvd. West, 8th Floor, Montreal (Quebec) Canada H3H 1J9; Stauber, R. H. (1998) Biotechniques 24: 462-71; Heim, R. et al. (1996) Curr. Biol. 6: 178-82), enhanced yellow fluorescent protein (EYFP; 1. Clontech Laboratories, Inc., 1020 East Meadow Circle, Palo Alto, Calif. 94303), *Anemonia majano* fluorescent protein (amFP486, Matz, M. V. (1999) Nat. Biotech. 17: 969-73), *Zoanthus* fluorescent proteins (zFP506, zFP538; Matz, supra), *Discosoma* fluorescent protein (dsFP483, drFP583; Matz, supra), and *Clavularia* fluorescent protein (cFP484; Matz, supra). Other suitable reporter genes include, among others, luciferases (for example, firefly, Kennedy, H. J. et al. (1999) J. Biol. Chem. 274: 13281-91; *Renilla reniformis*, Lorenz, W. W. (1996) J Biolumin. Chemilumin. 11: 31-37; *Renilla muelleri*, U.S. Pat. No. 6,232,107), β-galactosidase (Nolan, G. et al. (1988) Proc. Natl. Acad. Sci. USA 85: 2603-07), β-glucouronidase (Jefferson, R. A. et al. (1987) EMBO J. 6: 3901-07; Gallager, S., "GUS Protocols: Using the GUS Gene as a reporter of gene expression," Academic Press, Inc., 1992), horseradish peroxidase, alkaline phosphatase, and SEAP (i.e., the secreted form of human placental alkaline phosphatase; Cullen, B. R. et al. (1992) Methods Enzymol. 216: 362-68).

In another embodiment, the reporter gene encodes a protein that will bind a label that can be used as the basis of the cell enrichment (sorting); that is, the reporter gene serves as an indirect label or detection gene. In a preferred embodiment, the reporter gene encodes a cell-surface protein. For example, the reporter gene may be any cell-surface protein not normally expressed on the surface of the cell, such that secondary binding agents serve to distinguish cells that contain the reporter gene from those that do not. Alternatively, albeit non-preferably, reporters comprising normally expressed cell-surface proteins could be used, and differences between cells containing the reporter construct and those without could be determined. Thus, secondary binding agents bind to the reporter protein. These secondary binding agents are preferably labeled, for example with fluors, and can be antibodies, haptens, etc. For example, fluorescently labeled antibodies to the reporter gene can be used as the label. Similarly, membrane-tethered streptavidin could serve as a reporter gene, and fluorescently-labeled biotin could be used as the label, i.e., the secondary binding agent. Alternatively, the secondary binding agents need not be labeled as long as the secondary binding agent can be used to distinguish the cells containing the construct; for example, the secondary binding agents may be used in a column, and the cells passed through, such that the expression of the reporter gene results in the cell being bound to the column, and a lack of the reporter gene (i.e. inhibition), results in the cells not being retained on the column. Other suitable reporter proteins/secondary labels include, but are not limited to, antigens and antibodies, enzymes and substrates (or inhibitors), etc.

In a preferred embodiment, the reporter gene comprises a survival gene that serves to provide a nucleic acid without which the cell cannot survive, such as drug resistance genes. In this embodiment, expressing the survival gene allows selection of cells expressing the fusion nucleic acid by identifying cells that survive, for example in presence of a selection compound. Examples of drug resistance genes include, but are not limited to, puromycin resistance (puromycin-N-acetyl-transferase) (de la Luna, S. et al. (1992) Methods Enzymol. 216: 376-85), G418 neomycin resistance gene, hygromycin resistance gene (hph), and blasticidine resistance genes (bsr, brs, and BSD; Pere-Gonzalez, et al. (1990) Gene, 86: 129-34; Izumi, M. et al. (1991) Exp. Cell Res. 197: 229-33; Itaya, M. et al. (1990) J. Biochem. 107: 799-801; Kimura, M. et al. (1994) Mol. Gen. Genet. 242:121-29). In addition, generally applicable survival genes are the family of ATP-binding cassette transporters, including multiple drug resistance gene (MDR1) (see Kane, S. E. et. al. (1988) Mol. Cell. Biol. 8: 3316-21 and Choi, K. H. et al. (1988) Cell 53: 519-29), multi-drug resistance associated proteins (MRP) (Bera, T. K. et al. (2001) Mol. Med. 7: 509-16), and breast cancer associated protein (BCRP or MXR) (Tan, B. et al. (2000) Curr. Opin. Oncol. 12: 450-58). When expressed in cells, these selectable transporter genes can confer resistance to a variety of toxic reagents, especially anti-cancer drugs (i.e., methotrexate, colchicine, tamoxifen, mitoxanthrone, and doxorubicin). As will be appreciated by those skilled in the art, the choice of the selection/survival gene will depend on the host cell type used.

In a preferred embodiment, the reporter gene comprises a death gene that causes the cells to die when expressed. Death genes fall into two basic categories: death genes that encode death proteins requiring a death ligand to kill the cells, and death genes that encode death proteins that kill cells as a result of high expression within the cell and do not require the addition of any death ligand. Preferred are cell death mechanisms that require a two-step process: the expression of the death gene and induction of the death phenotype with a signal or ligand such that the cells may be grown expressing the death gene, and then induced to die. A number of death genes/ligand pairs are known, including, but not limited to, the Fas receptor and Fas ligand (Schneider, P. et al. (1997) J. Biol. Chem. 272: 18827-33; Gonzalez-Cuadrado, S. et al. (1997) Kidney Int. 51: 1739-46; Muruve, D. A. et al. (1997) Hum. Gene Ther. 8: 955-63); p450 and cyclophosphamide (Chen, L. et al. (1997) Cancer Res. 57: 4830-37); thymidine kinase and gancyclovir (Stone, R. (1992) Science 256: 1513); and tumor necrosis factor (TNF) receptor and TNF.

When death genes requiring ligands are used, preferred embodiments use chimeric death genes (i.e, chimeric death receptor genes). Chimeric death receptors may comprise the extracellular domain of a ligand-activated multimerizing receptor and the endogenous cytoplasmic domain of a death receptor gene, such as Fas or TNF. This avoids endogenous activation of the death gene. Thus, in one embodiment, substituting the extracellular portion of a death receptor, such as Fas, with the extracellular portion of another ligand activated multimerizing receptor provides a basis for using a completely different signal to activate cell death. Suitable ligand-activated dimerizing receptors include, but are not limited to, the CD8 receptor, erythropoietin receptor, thrombopoietin receptor, growth hormone receptor, Fas receptor, platelet derived growth hormone receptor, epidermal growth factor receptor, leptin receptor, and various interleukin receptors (e.g., IL-1, IL-2, IL-3, IL-4, IL-5, IL-6, IL-7, IL-8, IL-9, IL-11, IL-12, IL-13, IL-15, and IL-17). When particular receptors are employed to modulate promoter activity, these receptors (e.g., IL-4 when examining IL-4 induced promoter activity) are not preferred for use as a chimeric death gene receptor.

In a preferred embodiment, the chimeric cell death receptor genes are chimeric Fas receptors. The exact combination will depend on the cell type used and the receptors normally produced by these cells. For illustration, when the cells are human cells, a non-human extracellular domain and a human cytosolic domain are preferred to prevent endogenous induction of the death gene. Thus, when human cells are used, a preferred chimeric receptor gene may comprise a murine extracellular Fas receptor domain and a human cytosolic domain, such that the endogenous human Fas ligand will not activate the murine receptor domain. Alternatively, human extracellular domains may be used when the cells do not endogenously produce the cognate ligand. For example, human EPO extracellular domain may be used when cells do not endogenously produce EPO (Kawaguchi, Y. et al. (1997) Cancer Lett. 116: 53-59; Takebayashi, H. et al. (1996) Cancer Res. 56: 4164; Rudert, F. et al. (1994) Biochem Biophys Res Commun. 204: 1102-10; Takahashi, T. et al. (1996) J. Biol. Chem. 271: 17555-60). In another aspect, the extracellular domains are combinations of different extracellular domains that form functional receptors (Mares, et al. (1992) Growth Factors, 6: 93-101; Seedorf, K. et al. (1991) J. Biol. Chem. 266: 12424-31; Heidaran, M. A. et al. (1990) J. Biol. Chem. 265: 18741-44; Okuda, K. et al. (1997) J. Clin. Invest. 100: 1708-15; Anders, R. A. et al. (1996) J. Biol. Chem. 271: 21758-66; Krishnan, K. et al. (1996) Oncogene, 13: 125-33; Ohashi, et al. (1994) Proc. Natl. Acad. Sci. USA, 91: 158-62; and Amara, J. F. et al. (1997) Proc. Natl. Acad. Sci. USA 94: 10618-23. In general, the chimeric death gene receptors have a transmembrane domain. As will be appreciated by those skilled in the art, the transmembrane domain from any of the receptors can be used, although it is preferable to use the transmembrane domain associated with the chosen cytosolic domain to preserve the interaction of the transmembrane domain with other endogenous signaling proteins (Declercq, W. et al. (1995) Cytokine 7: 701-09).

Alternatively, the death genes are "one step" death genes, which need not require a ligand and death results from high expression of the gene. These death genes kill a cell without requiring a ligand or secondary signal. In one aspect, cell death is induced by the overexpression of a number of programmed cell death (PCD) proteins known to cause cell death, including, but not limited to, caspases, bax, TRADD, FADD, SCK, MEK, etc.

In another aspect, one step death genes also include toxins that cause cell death, or impair cell survival or cell function when expressed by a cell. These toxins generally do not require addition of a ligand to produce toxicity. An example of a suitable toxin is *campylobacter* toxin CDT (Lara-Tejero, M. (2000) Science, 290: 354-57). Expression of CdtB subunit, which has homology to nucleases, causes cell cycle arrest and ultimately cell death. Another toxin, the diptheria toxin (and similar *Pseudomonas* exotoxin), functions by ADP ribosylating the ef-2 (elongation factor 2) molecule in the cell and preventing translation. Expression of the diptheria toxin A subunit induces cell death in cells expressing the toxin fragment. Other useful toxins include cholera toxin and pertussis toxin (catalytic subunit-A ADP ribosylates G proteins that regulate adenylate cyclase), pierisin from cabbage butterflys (induces apoptosis in mammalian cells; Watanabe, M. (1999) Proc. Natl. Acad. Sci. USA 96: 10608-13), phospholipase snake venom toxins (Diaz, C. et al. (2001) Arch. Biochem. Biophys. 391: 56-64), ribosome inactivating toxins (i.e. ricin A chain, Gluck, A. et al. (1992) J. Mol. Biol. 226: 411-24; and nigrin, Munoz, R. et al. (2001) Cancer Lett. 167: 163-69), and pore forming toxins (hemolysin and leukocidin). When the target cells are neuronal cells, neuronal specific toxins may be used to inhibit specific neuronal functions. These include bacterial toxins such as botulinum toxin and tetanus toxin, which are proteases that act on synaptic vesicle associated proteins (i.e., synaptobrevin) to prevent neurotransmitter release (see Binz, T. et al. (1994) J. Biol. Chem. 269: 9153-58; Lacy, D. B. et al. (1998) Curr. Opin. Struct. Biol. 8: 778-84).

Another preferred embodiment of a gene of interest is a cell cycle gene, that is, a gene that causes alterations in the cell cycle. For example, Cdk interacting protein p21 (see Harper, J. W. et al. (1993) Cell 75: 805-16), which inhibits cyclin dependent kinases, does not cause cell death but causes cell-cycle arrest. Thus, expressing p21 allows selecting for regulators of promoter activity or regulators of p21 activity based on detecting cells that grow out much more quickly due to low p21 activity, either through inhibiting promoter activity or inactivation of p21 protein activity. As will be appreciated by those in the art, it is also possible to configure the system to select cells based on their inability to grow out due to increased p21 activity. Similar mitotic inhibitors include p27, p57, p16, p15, p18 and p19, p19 ARF (or its human homolog p14 ARF). Other cell cycle proteins useful for altering cell cycle include cyclins (Cln), cyclin dependent kinases (Cdk), cell cycle checkpoint proteins (i.e., Rad17, p53), Cks1 p9, Cdc phosphatases (i.e., Cdc 25), etc.

In yet another preferred embodiment, the gene of interest encodes a cellular biosensor. In these fusion nucleic acids, at least one of the genes of interest may encode a rGFP or pGFP fusion polypeptide, which is itself a cellular biosensor, or the cellular biosensor may be expressed in addition to the rGFP or pGFP (or rGFP or pGFP fusion protein). By a "cellular biosensor" herein is meant a gene product that when expressed within a cell can provide information about a particular cellular state. Biosensor proteins allow rapid determination of changing cellular conditions, for example $Ca^{+2}$ levels in the cell, pH within cellular organelles, and membrane potentials (see Miesenbock, G. et al. (1998) Nature 394: 192-95; U.S. Pat. No. 6,150,176). An example of an intracellular biosensor is Aequorin, which emits light upon binding to $Ca^{+2}$ ions. The intensity of light emitted depends on the $Ca^{+2}$ concentration, thus allowing measurement of transient calcium concentrations within the cell. When directed to particular cellular organelles by fusion partners, as more fully described below, the light emitted by Aequorin provides information about $Ca^{+2}$ concentrations within the particular organelle. Other intracellular biosensors are chimeric GFP molecules engineered for fluorescence resonance energy transfer (FRET) upon binding of an analyte, such as $Ca^{+2}$ (U.S. Pat. No. 6,197,928; Miyawaki, A. et al. (1997) Nature 388: 882-87). For example, cameleon comprises a blue or cyan mutant of GFP, calmodulin, CaM binding domain of myosin light chain kinase, and a green or yellow GFP. Upon binding of $Ca^{+2}$ by the CaM domain, FRET occurs between the two GFPs because of a structural change in the chimera. Thus, FRET intensity is dependent on the $Ca^{+2}$ levels within the cell or organelle (Kerr, R. et al. Neuron (2000) 26: 583-94). Other examples of intracellular biosensors include sensors for detecting changes in cell membrane potential (Siegel, M. et al. (1997) Neuron 19: 735-41; Sakai, R. (2001) Eur. J. Neurosci. 13: 2314-18), monitoring exocytosis (Miesenbrock, G. et al. (1997) Proc. Natl. Acad. Sci. USA 94: 3402-07), and measuring intracellular/organellar ATP concentrations via luciferase protein (Kennedy, H. J. et al. (1999) J. Biol. Chem. 274: 13281-91). These biosensors find use in monitoring the effects of various cellular effectors, for example pharmacological agents that modulate ion channel activity, neurotransmitter release, ion fluxes within the cell, and changes in ATP metabolism.

Other intracellular biosensors comprise detectable gene products with sequences that are responsive to changes in intracellular signals. These sequences include peptide sequences acting as substrates for protein kinases, peptides with binding regions for second messengers, and protein interaction sequences sensitive to intracellular signaling events (see for example, U.S. Pat. No. 5,958,713 and U.S. Pat. No. 5,925,558). For example, a fusion protein construct comprising a GFP and a protein kinase recognition site allows detecting intracellular protein kinase activity by measuring changes in GFP fluorescence arising from phosphorylation of the fusion construct. Alternatively, the GFP is fused to a protein interaction domain whose interaction with cellular components are altered by cellular signaling events. For example, it is well known that inositol-triphosphate (InsP3) induces release of $Ca^{+2}$ from intracellular stores into the cytoplasm, which results in activation of a kinases responsible for regulating various cellular responses. The precursor to InsP3 is phosphatidyl-inositol-4,5-bisphosphate ($PtdInsP_2$), which is localized in the plasma membrane and cleaved by phospholipase C (PLC) following activation of an appropriate receptor. Many signaling enzymes are sequestered in the plasma membrane through pleckstrin homology domains that bind specifically to $PtdInsP_2$. Following cleavage of $PtdInsP_2$, the signaling proteins translocate from the plasma membrane into the cytosol where they activate various cellular pathways. Thus, a reporter molecule such as GFP fused to a pleckstrin domain will act as a intracellular sensor for phospholipase C activation (see Haugh, J. M. et al. (2000) J. Cell. Biol. 15: 1269-80; Jacobs, A. R. et al. (2001) J. Biol. Chem. 276: 40795-802; and Wang, D. S. et al. (1996) Biochem. Biophys. Res. Commun. 225: 420-26). Other similar constructs are useful for monitoring activation of other signaling cascades and are applicable as assays in screens for candidate agents that inhibit or activate particular signaling pathways.

Since protein interaction domains, such as the described pleckstrin homology domain, are important mediators of cellular responses and biochemical processes, other preferred genes of interest are proteins containing protein-interaction domains. By "protein-interaction domain" herein is meant a polypeptide region that interacts with other biomolecules, including other proteins, nucleic acids, lipids, etc. These protein domains frequently act to provide regions that induce formation of specific multiprotein complexes for recruiting and confining proteins to appropriate cellular locations or affect specificity of interaction with targets ligands, such as protein kinases and their substrates. Thus, many of these protein domains are found in signaling proteins. Protein-interaction domains comprise modules or micro-domains ranging about 20-150 amino acids that can be expressed in isolation and bind to their physiological partners. Many different interaction domains are known, most of which fall into classes related by sequence or ligand binding properties. Accordingly, the genes of interest comprising interaction domains may comprise proteins that are members of these classes of protein domains and their relevant binding partners. These domains include, among others, SH2 domains (src homology domain 2), SH3 domain (src homology domain 3), PTB domain (phosphotyrosine binding domain), FHA domain (forkedhead associated domain), WW domain, 14-3-3 domain, pleckstrin homology domain, C1 domain, C2 domain, FYVE domain (Fab-1, YGL023, Vps27, and EEA1), death domain, death effector domain, caspase recruitment domain, Bcl-2 homology domain, bromo domain, chromatin organization modifier domain, F box domain, hect domain, ring domain ($Zn^{+2}$ finger binding domain), PDZ domain (PSD-95, discs large, and zona occludens domain), sterile a motif domain, ankyrin domain, arm domain (armadillo repeat motif), WD 40 domain and EF-hand (calretinin), PUB domain (Suzuki T. et al. (2001) Biochem. Biophys. Res. Commun. 287: 1083-87), nucleotide binding domain, Y Box binding domain, H.G. domain, all of which are well known in the art.

Since protein interactions domains are pervasive in cellular signal transduction cascades and other cellular processes, such as cell cycle regulation and protein degradation, expression of single proteins or multiple proteins with interaction domains acting in specific signaling or regulatory pathway may provide a basis for inactivating, activating, or modulating such pathways in normal and diseased cells. In another aspect, the preferred embodiments comprise binding partners of these interactions domains, which are well known to those skilled in the art or are identifiable by well known methods (i.e. yeast two hybrid technique, co-precipitation of immune complexes, etc.).

Included within the protein-interaction domains are transcriptional activation domains capable of activating transcription when fused to an appropriate DNA binding domain. Transcriptional activation domains are well known in the art. These include activator domains from GAL4 (amino acids 1-147; Fields, S. et al. (1989) Nature 340: 245-46; Gill, G. et al. (1990) Proc. Natl. Acad. Sci. USA 87: 2127-31), GCN4 (Hope, I. A. et al. (1986) Cell 46: 885-94), ARD1 (Thukral, S. K. et al. (1989) Mol. Cell. Biol. 9: 2360-69), human estrogen receptor (Kumar, V. et al. (1987) Cell 51: 941-51), VP16 (Triezenberg, S. J. et al. (1988) Genes Dev. 2: 718-29), Sp1 (Courey, A. J. (1988) Cell 55: 887-98), AP-2 (Williams, T. et al. (1991) Genes Dev. 5: 670-82), and NF-kB p65 subunit and related Rel proteins (Moore, P. A. et al. (1993) Mol. Cell. Biol. 13: 1666-74). DNA binding domains include, among others, leucine zipper domain, homeo box domain, $Zn^{+2}$ finger domain, paired domain, LIM domain, ETS domain, and T Box domain.

Since the genes of interest may comprise DNA binding domains and transcriptional activation domains, other genes of interest useful for expression in the present invention are transcription factors. Preferred transcription factors are those producing a cellular phenotype when expressed within a particular cell type. Transcription factors as defined herein include both transcriptional activator or inhibitors. As not all cells will respond to expression of a particular transcription factor, those skilled in the art can choose appropriate cell strains in which expression of a transcription factor results in dominant or altered phenotypes as described below.

In another aspect, the transcription factor regulates expression of a different promoter of interest on an expression vector that does not encode the transcription factor. This arrangement requires introducing into a single cell a plurality or multiple vectors, as described below, one of which expresses the transcription factor regulating the different promoter of interest. Expression of the transcription factor is made inducible or the transcription factor itself is an inducible transcription factor, thus allowing further regulation of the different promoter of interest.

In an alternative embodiment, the transcription factor encoded by the gene of interest regulates the promoter on the expression vector encoding the transcription factor. Thus, these constructs are autoregulatory for expression of the fusion nucleic acid (Hofmann, A. (1996) Proc. Natl. Acad. Sci. USA 93: 5185-90). Accordingly, if the transcription factor inhibits the promoter activity on the expression vector, continued synthesis of transcription factor restricts expression of the fusion nucleic acid. On the other hand, if the transcription factor activates transcription, synthesis is elevated because of continued synthesis of the transcriptional activator. Consequently, by use of separation sequences to express a plurality of genes of interest, one of which encodes the transcription factor, the retroviral vector autoregulates expression of the genes of interest. To enhance autoregulation, the transcription factor is an inducible transcription factor, for example a tetracycline or steroid inducible transcription factor (e.g., RU-486 or ecdysone inducible, see White J H (1997) Adv. Pharmacol. 40: 339-67). Incorporation of an inducible transcription factor in a retroviral vector as a single autoregulatory cassette eliminates the need for additional vectors for regulating the promoter activity. Moreover, this system results in rapid, uniform expression of the gene(s) of interest.

In another preferred embodiment, the gene of interest encodes a protein whose expression has a dominant effect on the cell (i.e., produces an altered cellular phenotype). By "dominant effect" herein is meant that the protein or peptide produces an effect upon the cell in which it is expressed, or on another cell not expressing the dominant effect protein, and is detected by the methods described below. The dominant effect may act directly on the cell to produce the phenotype or act indirectly on a second molecule, which leads to a specific phenotype. Dominant effect is produced by introducing into cells small molecule effectors, expressing a single protein, or by expressing multiple proteins acting in combination (e.g., proteins acting synergistically on a cellular pathway or a multisubunit protein effector). As is well known in the art, expression of a variety of genes of interest may produce a dominant effect. Expressed proteins may be mutant proteins that are constitutive for a biological activity (Segouffin-Cariou, C. et al. (2000) J. Biol. Chem. 275: 3568-76; Luo et al. (1997) Mol. Cell. Biol. 17: 1562-71) or are inactive forms that sequester or inhibit activity of normal binding partners (Bossu, P. (2000) Oncogene, 19: 2147-54; Mochizuki, H. (2001) Proc. Natl. Acad. Sci. USA 98: 10918-23). The inactive forms as defined herein include expression of small modular protein-interaction regions or other domains that bind to binding partners in the cell (see for example, Gilchrist, A. et al. (1999) J. Biol. Chem. 274: 6610-16). Dominant effects are also produced by overexpression of normal cellular proteins, expression of proteins not normally expressed in a particular cell type, or expression of normally functioning proteins in cells lacking functional proteins due to mutations or deletions (Takihara, Y. et al. (2000) Carcinogenesis 21: 2073-77; Kaplan, J. B. (1994) Oncol. Res. 6: 611-15). Random peptides or biased random peptides introduced into cells can also produce dominant effects. An exemplary effect of a dominant effect by a peptide is random peptides which bind to Src SH3 domain resulting in increased Src activity. This activation is due to the peptides' antagonistic effect on negative regulation of Src (see Sparks, A. B. et al. (1994) J Biol Chem. 269: 23853-56).

As defined herein, dominant effect is not restricted to the effect on the cell expressing the protein. A dominant effect may be on a cell contacting the expressing cell or by secretion of the protein encoded by the gene of interest into the cellular medium. Proteins with dominant effect on other cells are conveniently directed to the plasma membrane or secretion by incorporating appropriate secretion and/or membrane localization signals. These membrane bound or secreted dominant effector proteins may comprise cytokines and chemokines, growth factors, toxins (e.g., neurotoxins), extracellular proteases (e.g., metalloproteases), cell surface receptor ligands (e.g., sevenless type receptor ligands), adhesion proteins (e.g., L1, cadherins, integrins, laminin), etc.

In an alternative embodiment, the gene of interest encodes a conditional gene product. By "conditional gene" product herein is meant a gene product whose activity is only apparent under certain conditions, for example at particular ranges of temperature. Other factors that conditionally affect activity of a protein include, but are not limited to, ion concentration, pH, and light (see Hager, A. (1996) Planta 198: 294-99; Pavelka J. (2001) Bioelectromagnetics 22: 371-83). A conditional gene product produces a specific cellular phenotype under a restrictive condition. In contrast, the conditional gene product does not produce a specific phenotype under permissive conditions. Methods for making or isolating conditional gene products are well known (see for example White, D. W. et al. (1993) J. Virol. 67:6876-81; Parini, M. C. (1999) Chem. Biol. 6: 679-87).

As is appreciated by those skilled in the art, conditional gene products are useful in examining genes that are detrimental to a cell's survival or in examining cellular biochemical and regulatory pathways in which the gene product functions. For those gene products that affect cell survival, use of conditional gene products allow survival of the cells under permissive conditions, but results in lethality or detriment at the restrictive condition. This feature allows screens at the restrictive condition for candidate agents, such as proteins and small molecules that may directly or indirectly suppress the effect of a conditional gene product but permit maintenance and growth of cells under permissive conditions. In addition, conditional gene products are also useful in screens for regulators of cell physiology when the conditional gene product is a participant in a cellular regulatory pathway. At the restrictive condition, the conditional gene product ceases to function or becomes activated, resulting in an altered cell phenotype due to dysregulation of the regulatory pathway. Candidate agents are then screened for their ability to activate or inhibit downstream pathways to bypass the disrupted regulatory point. Conditional gene products are well known in the art and include, among others, proteins such as dynamin involved in endocytic pathway (Damke, H. et al. (1995) Methods Enzymol. 257: 209-20), p53 involved in tumor suppression (Pochampally, R. et al. (2000) Biochem. Biophys. Res. Comm. 279: 1001-10 and Buckbinder, L. et al. (1994) Proc. Natl. Acad. Sci. USA 91: 10640-44), Vac1 involved in vesicle sorting, proteins involved in viral pathogenesis (SV40 Large T Antigen; Robinson C. C. (1980). J. Virol. 35: 246-48), and gene products involved in regulating the cell cycle, such as ubiquitin conjugating enzyme CDC 34 (Ellison, K. S. et al. (1991) J. Biol. Chem. 266: 24116-20).

In another preferred embodiment, the gene of interest comprises a multiple cloning site (MCS). This allows cassetting in of various genes of interest into the expression vectors. In one preferred embodiment, the MCS lacks nucleotide sequences capable of functioning as a translation initiation site, which allows cloning a gene of interest containing its own translation initiation sequences. Alternatively, the MCS comprises a peptide or protein coding region with its own translation initiation sequence for expressing proteins or peptides lacking a translation initiation sequence. In addition, other nucleic acid sequences that increase expression of the first gene of interest (e.g., Gly or GlyGly following the initiating methionine residue) may be included in the multiple cloning site. The coding region may also comprise an indicator gene, such as lacZ, to permit identification of inserts by insertional inactivation of lacZ. In these constructs, use of a promoter controlling element capable of being active in both eukaryotes and prokaryotes will allow detecting lacZ in prokaryotes during the cloning process (see Wirtz, E. et al. (1995) Science 268: 1179-83). In either case, a separation sequence chosen from a protease based, IRES based, of Type 2A based sequence, is operably linked to the multiple cloning site. When at least one of the genes of interest comprises rGFP or pGFP, expression of the fluorescent proteins allows monitoring expression of a gene of interest cloned into the MCS.

In yet another preferred embodiment, the gene of interest comprises candidate bioactive agents comprising candidate nucleic acids, as described below. Thus, a gene of interest may comprise candidate bioactive agents in the form of cDNAs, cDNA fragments, genomic DNA fragments, and nucleic acids encoding random or biased random peptides, as described below. Expression of fusion nucleic acids where the gene of interest is a candidate agent allows selection of cells expressing the candidate agent based on expression of the rGFP or pGFP.

In the present invention, there is no particular order of the first gene of interest and the second gene of interest. When at least one of the genes of interest is rGFP or pGFP, a preferred embodiment may have a gene of interest upstream of the GFP. Another preferred embodiment may have the GFP upstream and the gene of interest downstream. By "upstream" and "downstream" herein is meant the proximity to the point of transcription initiation, which is generally localized 5' to the coding sequence of the fusion nucleic acid. Thus, in a preferred embodiment, the upstream position is more proximal to the transcription initiation site than the downstream position.

As will be appreciated by those skilled in the art, the positioning of the gene of interest relative to the GFP is determined by the person skilled in the art. Factors to consider include the need for detecting expression of a gene of interest or optimizing the synthesis of a protein of interest. In the embodiments described above, the GFP gene may be placed downstream of the gene of interest so that expression of the GFP will be a faithful indication of expression of the gene of interest. This will depend on the types of separation sites chosen by the person skilled in the art. When protease cleavage or Type 2A separation sequences are incorporated into the fusion nucleic acid, a GFP or other reporter gene situated downstream of the gene of interest will generally provide direct information on expression of the gene of interest. In the case of IRES sequences, however, detecting expression of the GFP or reporter gene to monitor expression of an upstream gene of interest is less direct since separate translation initiations occur for the first genes of interest and the second gene of interest, generally resulting in lower amount of the second protein being made. In some cases, the ratio of expression of first and second proteins can be as high as 10:1.

The order of the gene of interest on the fusion nucleic acid and the choice of separation sequence is also important when the relative amounts gene of interest are at issue. For example, use of IRES sequences may result in lower amounts of downstream gene product as compared to upstream GFP gene because of differing translation initiation rates. Relative levels of translation initiation is easily determined by comparing expression of upstream gene of interest versus downstream gene of interest. Where controlling expression levels are important, the person skilled in the art will order the gene product needed at higher levels upstream of the downstream gene product when IRES separation sequences are used. Alternatively, multiple copies of IRES sequences are adaptable to increase expression of the downstream gene. On the other hand, use of protease or Type 2A separation sequences will lessen the need for ordering the gene of interest on the fusion nucleic acid since these separation sequences tend to produce equal levels of upstream and downstream gene product.

As will be appreciated by those skilled in the art, various combinations of genes of interest may be used in the fusion nucleic acids of the present invention. In a preferred embodiment, at least one of the genes of interest comprises a rGFP or pGFP gene, or its variants. In one aspect, the rGFP or pGFP protein functions as a reporter protein for monitoring expression of the gene of interest. For example, if the gene of interest is a nucleic acid encoding a dominant effect protein, a candidate agent comprising cDNA, or a candidate nucleic acid encoding a random peptide, expression of rGFP or pGFP provides a basis for selecting cells expressing the gene of interest and for monitoring their expression levels. In another aspect, expression of the rGFP or pGFP along with a gene of interest comprising another reporter or selection gene allows for increased discrimination for selecting cells expressing the fusion nucleic acid. This increased selectivity is desirable when measuring promoter activity, for example when screening for candidate agents affecting promoter activity.

In another preferred, at least one of the genes of interest comprises a fusion nucleic acid encoding a rGFP or pGFP fusion protein. In one aspect, the rGFP or pGFP is fused to a cDNA, genomic DNA, or nucleic acid encoding a random peptide. That is, the rGFP or pGFP fusion protein comprises candidate agents, as described below. In these constructs, a gene of interest may comprise a distinguishable reporter gene to monitor expression of the rGFP or pGFP fusion protein. In another aspect, the gene of interest may comprise a dominant effect protein, a cell cycle gene, or a conditional gene product that produces a specific cellular phenotype. This allows identification of candidate agents expressed by at least one of the gene of interest (i.e., the rGFP or pGFP fused to cDNA, genomic DNA or random peptides) that alters the cellular phenotype produced by another gene of interest. In another aspect, the gene of interest may comprise a cellular biosensor, which allows analysis of cell physiological events induced by expression of a separate rGFP or pGFP fusion protein.

When the vectors are used to express separate protein products encoded by the genes of interest, the fusion nucleic acids further comprise separation sequences. By a "separation sequence" or "separation site" or grammatical equivalents as used herein is meant a sequence that results in protein products not linked by a peptide bond. Separation may occur at the RNA or protein level. By being separate does not preclude the possibility that the protein products of the first gene of interest and the second gene of interest interact either non-covalently or covalently following their synthesis. Thus, the separate protein products may interact through hydrophobic domains, protein-interaction domains, common bound ligands, or through formation of disulfide linkages between the proteins.

Various types of separation sequences may be employed. In one preferred embodiment, the separation sequence encodes a recognition site for a protease. A protease recognizing the site cleaves the translated protein product into two or more proteins. Preferred protease cleavage sites and cognate proteases include, but are not limited to, prosequences of retroviral proteases including human immunodeficiency virus protease, and sequences recognized and cleaved by trypsin (EP 578472), Takasuga, A. et al. (1992) J. Biochem. 112: 652-57), proteases encoded by Picornaviruses (Ryan, M. D. et al. (1997) J. Gen. Virol. 78: 699-723), factor $X_a$ (Gardella, T. J. et al. (1990) J. Biol. Chem. 265: 15854-59; WO 9006370), collagenase (J03280893; WO 9006370; Tajima, S. et al. (1991) J. Ferment. Bioeng. 72: 362), clostripain (EP 578472), subtilisin (including mutant H64A subtilisin, Forsberg, G. et al. (1991) J. Protein Chem. 10: 517-26), chymosin, yeast KEX2 protease (Bourbonnais, Y. et al. (1988) J. Bio. Chem. 263: 15342-47), thrombin (Forsberg et al., supra; Abath, F. G. et al. (1991) BioTechniques 10: 178), *Staphylococcus aureus* V8 protease or similar endoproteinase-Glu-C to cleave after Glu residues (EP 578472; Ishizaki, J. et al. (1992) Appl. Microbiol. Biotechnol. 36: 483-86), cleavage by NIa proteinase of tobacco etch virus (Parks, T. D. et al. (1994) Anal. Biochem. 216: 413-17), endoproteinase-Lys-C (U.S. Pat. No. 4,414,332) and endoproteinase-Asp-N, *Neisseria* type 2 IgA protease (Pohlner, J. et al. (1992) Biotechnology 10: 799-804), soluble yeast endoproteinase yscF (EP 467839), chymotrypsin (Altman, J. D. et al. (1991) Protein Eng. 4: 593-600), enteropeptidase (WO 9006370), lysostaphin, a polyglycine specific endoproteinase (EP 316748), the family of caspases (i.e., caspase 1, caspase 2, caspase 3, etc.), and metalloproteases.

The present invention also contemplates protease recognition sites identified from a genomic DNA, cDNA, or random nucleic acid libraries (see for example, O'Boyle, D. R. et al. (1997) Virology 236: 338-47). For example, the fusion nucleic acids of the present invention may comprise a separation site which is a randomizing region for the display of candidate protease recognition sites. The first and second gene of interest encode reporters molecules useful for detecting protease activity, such as rGFP or pGFP capable of undergoing FRET with other fluorescent proteins via linkage through a candidate recognition site (see Mitra, R. D. et al. (1996) Gene; 173: 13-7). Proteases are expressed or introduced into cells expressing these fusion nucleic acids. Random peptide sequences acting as substrates for the particular protease result in separate GFP proteins when acted on by a protease, thus producing a loss of FRET signal. By identifying classes of protease recognition sites, optimal or novel protease recognition sequences may be determined.

In addition to their use in producing separate proteins of interest, the protease cleavage sites and the cognate proteases are also useful in screening for candidate agents that enhance or inhibit protease activity. Since many proteases are crucial to pathogenesis of organisms or cellular regulation, for example the HIV or caspase proteases, the ability to express reporter or selection proteins linked by a protease cleavage site allows screens for therapeutic agents directed against a particular protease.

Another preferred embodiment of separation sequences are internal ribosome entry sites (IRES). By "internal ribosome entry sites", "internal ribosome binding sites", or "IRES elements", or grammatical equivalents herein is meant sequences that allow CAP independent initiation of translation (Kim, D. G. et al. (1992) Mol. Cell. Biol. 12: 3636-43; McBratney, S. et al. (1993) Curr. Opin. Cell Biol. 5: 961-65). IRES sequences appear to act by recruiting 40S ribosomal subunit to the mRNA in the absence of translation initiation factors required for normal CAP dependent translation initiation. IRES sequences are heterogenous in nucleotide sequence, RNA structure, and factor requirements for ribosome binding. They are frequently located on the untranslated leader regions of RNA viruses, such as the Picornaviruses. The viral sequences range from about 450-500 nucleotides in length, although IRES sequences may also be shorter or longer (Adam, M. A. et al. (1991) J. Virol. 65: 4985-90; Borman, A. M. et. al. (1997) Nucleic Acids Res. 25: 925-32; Hellen, C. U. et al. (1995) Curr. Top. Microbiol. Immunol. 203: 31-63; Mountford, P. S. et al. (1995) Trends Genet. 11: 179-84). Embodiments of viral IRES separation sites are the Type I IRES sequences present in entero- and rhinoviruses and Type II sequences of cardioviruses and apthoviruses (i.e. encephalomyocarditis virus; see Elroy-Stein, O. et al. (1989) Proc. Natl. Acad. Sci. USA 86: 6126-30; Alexander, L. et al. (1994) Proc. Natl. Acad. Sci. USA 91: 1406-10). Other viral IRES sequences are found in hepatitis A viruses (Brown, E. A. et al. (1994) J. Virol. 68: 1066-74), avian reticuloendotheliosis virus (Lopez-Lastra, M. et al. (1997) Hum. Gene Ther. 8: 1855-65), Moloney murine leukemia virus (Vagner, S. et al. (1995) J. Biol. Chem. 270: 20376-83), short IRES segments of hepatitis C virus (Urabe, M. et al. (1997) Gene 200: 157-62), and DNA viruses (i.e. Karposi's sarcoma-associated virus, Bieleski, L. et al. (2001) J. Virol. 75: 1864-69).

Additionally, preferred embodiments of IRES sequences are non-viral IRES elements found in a variety of organisms including yeast, insects, birds and mammals. Like the viral IRES sequences, cellular IRES sequences are heterogeneous in sequence and secondary structure. Cellular IRES sequences, however, may comprise shorter nucleic acid sequences as compared to viral IRES elements (Oh, S. K. et al. (1992) Genes Dev. 6: 1643-53; Chappell, S. A. et al. (2000) 97: 1536-41). Specific IRES sequences include, but are not limited to, those involved in expression of immunoglobulin heavy chain binding protein, transcription factors, protein kinases, protein phosphatases, eIF4G (see Johannes, G. et al. (1999) Proc. Natl. Acad. Sci. USA 96: 13118-23; Johannes, G. et al. (1998) RNA 4: 1500-13), vascular endothelial growth factor (Huez, I. et al. (1989) Mol. Cell. Biol. 18: 6178-90), c-myc (Stoneley, M. et al. (2000) Nucleic Acids Res. 28: 687-94), apoptotic protein Apaf-1 (Coldwell, M. J. et al. (2000) Oncogene 19: 899-905), DAP-5 (Henis-Korenblit, S. et al. (2000) Mol. Cell. Bio. 20: 496-506), connexin (Werner, R. (2000) IUBMB Life 50: 173-76), Notch-2 (Lauring, S. A. et al. (2000) Mol. Cell. 6: 939-45), and fibroblast growth factor (Creancier, L. et al. (2000) J. Cell. Biol. 150: 275-81). As some IRES sequences act or function efficiently in particular cell types, the person skilled in the art will choose IRES elements with relevance to particular cells being used to express the fusion nucleic acid. Moreover, multiple IRES sequences in various combinations, either homomultimeric or heteromultimeric arrangements constructed as tandem repeats or connected via linkers, are useful for increasing efficiency of translation initiation of the genes of interest. The combinations of IRES elements comprise at least 2 to 10 or more copies or combinations of IRES sequences, depending on the efficiency of initiation desired.

In addition to their use as separation sequences, IRES elements serve as targets for therapeutic agents since IRES sequences mediate expression of proteins involved in viral pathogenesis or cellular disease states. Thus, the present invention is applicable in screens for candidate agents that inhibit IRES mediated translation initiation events. In these constructs, the rGFP or pGFP may serve as a reporter of IRES mediated translation or may comprise the candidate agent being screened (e.g, when expressed as a fusion protein with cDNAs or random peptides).

Another preferred embodiment of IRES elements are sequences in nucleic acid or random nucleic acid libraries that function as IRES elements. Screens for these IRES type sequences can employ fusion nucleic acids containing bicistronically arranged genes of interest encoding reporter genes or selection genes, or combinations thereof. Genomic, cDNA, or random nucleic acid sequences are inserted between the two reporter or selection genes. After introducing the nucleic acid construct into cells, for example by retroviral delivery, the cells are screened for expression of the downstream gene mediated by functional IRES sequences. Selection is based on expression of selection gene or reporter gene (e.g., FACS analysis for expression of a downstream rGFP or pGFP gene). The upstream gene of interest serves to permit monitoring expression of the fusion nucleic acid. The length of the nucleic acids screened is preferably 6 to 100 nucleotides, although longer nucleic acids may be used.

The present invention further contemplates use of enhancers of IRES mediated translation initiation. IRES initiated translation may be enhanced by any number of methods. Cellular expression of virally encoded proteases, which cleaves eIF4F to remove CAP-binding activity from the 40S ribosome complexes, may be employed to increase preference for IRES translation initiation events. These proteases are found in some Picornaviruses and can be expressed in a cell by introducing the viral protease gene by transfection or retroviral delivery (Roberts, L. O. (1998) RNA 4: 520-29). Other enhancers adaptable for use with IRES elements include cis-acting elements, such as 3' untranslated region of hepatitis C virus (Ito, T. et al. (1998) J. Virol. 72: 8789-96) and polyA segments (Bergamini, G. et al. (2000) RNA 6: 1781-90), which may be included as part of the fusion nucleic acid of the present invention. In addition, preferential use of cellular IRES sequences may occur when CAP dependent mechanisms are impaired, for example by dephosphorylation of 4E-BP, proteolytic cleavage of eIF4G, or when cells are placed under stress by g-irradiation, amino acid starvation, or hypoxia. Thus, in addition to the methods described above, IRES enhancing procedures include activation or introduction of 4E-BP targeted phosphatases or proteases of eIF4G. Alternatively, the cells are subjected to stress conditions described above. Other trans-acting IRES enhancers include heterogeneous nuclear ribonucleoprotein (hnRNP) (Kaminski, A. et al. (1998) RNA 4: 626-38), PTB hnRNP E2/PCBP2 (Walter, B. L. et al. (1999) RNA 5: 1570-85), La autoantigen (Meerovitch, K. et al. (1993) J. Virol. 67: 3798-07), unr (Hunt, S. L. et al. (1999) Genes Dev. 13: 437-48), ITAF45/Mpp1 (Pilipenko, E. V. et al. (2000) Genes Dev. 14: 2028-45), DAP5/NAT1/p97 (Henis-Korenblit, S. et al. (2000) Mol. Cell. Biol. 20: 496-506), and nucleolih (Izumi, R. E. et al. (2001) Virus Res. 76: 17-29). These factors may be introduced into a cell either alone or in combination. Accordingly, various combinations of IRES elements and enhancing factors are used to effect a separation reaction.

In another preferred embodiment, the separation sites are Type 2A separation sequences. By "Type 2A" sequences herein is meant nucleic acid sequences that when translated inhibit formation of peptide linkages. Type 2A sequences are distinguished from IRES sequences in that 2A sequences do not involve CAP independent translation initiation. Without being bound by theory, Type 2A sequences appear to act by disrupting peptide bond formation between the nascent polypeptide chain and the incoming activated tRNA$^{PRO}$ (Donnelly, M. L. et al. (2001) J. Gen. Virol 82: 1013-25). Although the peptide bond fails to form, the ribosome continues to translate the remainder of the RNA to produce separate peptides unlinked at the carboxy terminus of the 2A peptide region. An advantage of Type 2A separation sequences is that near stoichiometric amounts of first protein of interest and second protein of interest are made as compared to IRES elements. Moreover, Type 2A sequences do not appear to require additional factors, such as proteases that are required to effect separation when using protease recognition sites.

Preferred Type 2A separation sequences are those found in cardioviral and apthoviral genomes. These sequences are approximately 21 amino acids long and have the general sequence XXXXXXXXXXLXXDXEXNPGP (SEQ ID NO: 23), where X is any amino acid. Disruption of peptide bond formation occurs between the underlined carboxy terminal glycine (G) and proline (P). These 2A sequences are found in the apthovirus Foot and Mouth Disease Virus (FMDV), cardiovirus Theiler's murine encephalomyelitis virus (TME), and encephalomycarditis virus (EMC). Various viral Type 2A sequences are shown in FIG. 9 (SEQ ID NOS: 12-23). The 2A sequences function in a wide range of eukaryotic expression systems, thus allowing their use in a variety of cells and organisms. Accordingly, inserting these 2A separation sequences in between the nucleic acids encoding the first gene of interest and second gene of interest, as more fully explained below, will lead to expression of separate protein products of the first gene of interest and the second gene of interest.

In another embodiment, the present invention contemplates mutated versions or variants of Type 2A sequences. By "mutated" or "variant" or grammatical equivalents herein is meant deletions, insertions, transitions, transversions of nucleic acid sequences that exhibit the same qualitative separating activity as displayed by the naturally occurring analogue, although preferred mutants or variants have higher efficient separating activity and efficient translation of the downstream gene of interest. Mutant variants include changes in nucleic acid sequence that do not change the corresponding 2A amino acid sequence, but incorporate frequently used codons (i.e., codon optimized) to allow efficient translation of the 2A region (see Zolotukin, S. et al. (1996) J. Virol. 70: 4646-54). In another aspect, the mutant variants are changes in nucleic acid sequence that change the corresponding 2A amino acid sequence. Thus, one embodiment of a variant 2A sequences are short deletions of the 21 amino acid 2A sequence that retains separating activity. The deletion may comprise removal of about 3 to 6 amino acids at the amino terminus of the 2A region. In another embodiment, Type 2A sequences are mutated by methods well known in the art, such as chemical mutagenesis, oligonucleotide directed mutagenesis, and error prone replication. Mutants with altered separating activity are readily identified by examining expression of the fusion nucleic acids of the present invention. Assaying for production of a separate downstream gene product, such as a reporter protein or a selection protein, allows for identifying sequences having separating activity. Another method for identifying variants may use a FRET based assay using linked GFP molecules, as described above. Insertion of variant 2A sequences in place of or adjacent to the gly-ser linker region, or other suitable regions linking the GFPs, will allow detection of functional 2A separation sequences by identifying constructs that produce separated GFP molecules, as measured by loss of FRET signal. Sequences having no or reduced separating activity will retain higher levels of FRET signal due to physical linkage of the GFP molecules. This strategy will permit high throughput analysis of variants and allows selecting of sequences having high efficiency Type 2A separating activity.

In yet another embodiment, Type 2A separation sequences include homologs present in other nucleic acids, including nucleic acids of other viruses, bacteria, yeast, and multicellular organisms such as worms, insects, birds, and mammals. Homology in this context means sequence similarity or identity. A variety of sequence based alignment methodologies, which are well known to those skilled in the art, are useful in identifying homologous sequences. These include, but not limited to, the local homology algorithm of Smith, F. and Waterman, M. S. (1981) Adv. Appl. Math. 2: 482-89, homology alignment algorithm of Peason, W. R. and Lipman, D. J. (1988) Proc. Natl. Acad. Sci. USA 85: 2444-48, Basic Local Alignment Search Tool (BLAST) described by Altschul, S. F. et al. (1990) J. Mol. Biol. 215: 403-10, or the Best Fit program described by Devereau, J. et al. (1984) Nucleic Acids. Res. 12: 387-95, and the FastA and TFASTA alignment programs, preferably using default settings or by inspection.

In one preferred embodiment, similarity or identity for any nucleic acid or protein outlined herein is calculated by Fast alignment algorithms based upon the following parameters: mismatch penalty of 1.0; gap size penalty of 0.33, joining penalty of 30 (see "Current Methods in Comparison and Analysis" in Macromolecule Sequencing and Synthesis: Selected Methods and Applications, p. 127-149, Alan R. Liss, Inc., 1998). Another example of a useful algorithm is PILEUP. PILEUP creates multiple sequence alignment from a group of related sequences using progressive, pairwise alignments. It can also plot a tree showing the clustering relationships used to create the alignment. PILEUP uses a simplification of the progressive alignment method of Feng, D. F. and Doolittle, R. F. (1987) J. Mol. Evol. 25, 351-60, which is similar to the method described by Higgins, D. G. and Sharp, P. M. (1989) CABIOS 5: 151-3. Useful parameters include a default gap weight of 3.00, a default gap length weight of 0.10, and weighted end gaps.

Another example of a useful algorithm is the family of BLAST alignment tools initial described by Altschul et al. (see also Karlin, S. et al. (1993) Proc. Natl. Acad. Sci. USA 90: 5873-87). A particularly useful BLAST program is WU-BLAST-2 program described in Altschul, S. F. et al. (1996) Methods Enzymol. 266: 460-80. WU-BLAST uses several search parameters, most of which are set to default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the longer sequence in the aligned region. The "longer" sequence is one having the most actual residues in the aligned region (gaps introduced by WU-BLAST-2 to maximize the alignment score are ignored).

In a similar manner, "percent (%) nucleic acid sequence identity" with respect to the coding sequence of the polypeptide described herein is defined as the percentage of the nucleotide residues in a candidate sequence that are identical with the nucleotide residues in the coding sequence of the Type 2A regions. A preferred method utilizes the BLASTN module of WU-BLAST-2 set to the default parameters, with overlap span and overlap fraction set to 1 and 0.125, respectively.

An additional useful algorithm is gapped BLAST as reported by Altschul, S. F. et al. (1997) Nucleic Acids Res. 25: 3389-402. Gapped BLAST uses BLOSSOM-62 substitution scores; threshold parameter set to 9; the two-hit method to trigger ungapped extensions; charges gap lengths of k at cost of 10+k; Xu set to 16, and Xg set to 40 for database search stage and to 67 for the output stage of the algorithms. Gapped alignments are triggered by a score corresponding to −22 bits.

The alignment may include the introduction of gaps in the sequence to be aligned. In addition, for sequence which contain either more or fewer amino acids that the Type 2A sequences in FIG. 3, it is understood that the percentage of the homology will be determined based on the number of homologous amino acids in relation to the total number of amino acids. Thus, Type 2A sequences may be shorter or longer than the amino acid sequence shown in FIG. 3.

Another embodiment of Type 2A separating sequences are those sequences present in libraries of nucleic acids, including genomic DNA or cDNA that have Type 2A separating activity. By Type 2A separating activity herein is meant a nucleic acid which encodes a amino acid sequence that exhibits similar separating activity as the naturally occurring Type 2A sequences. Segments of nucleic acids are inserted between the first gene of interest and second gene of interest in the fusion nucleic acids of the present invention and examined for separating activity as described above. The preferred lengths to be tested are nucleic acids encoding peptides 5 to 50 amino acids or larger, with a more preferred range of peptides 10-30 amino acids long.

Embodiments of Type 2A sequence also encompass random nucleic acid libraries encoding peptides that have Type 2A separating activity. In these embodiments, the separation site represents a randomizing region where random or biased random nucleic acids encoding random or biased random peptides are inserted between the first gene of interest and second gene of interest. The preferred lengths of the random nucleic acids are nucleic acids encoding peptides 5 to 50 amino acids, with a more preferred range of peptides 10-30 amino acids. Random peptides having separating activity are identified using the above described assays. Identification of functional separation sequences will permit additional searches for related sequences having Type 2A like separating activity, either through homology searches, mutagenesis screens, or by use of biased random peptide sequences. Sequences with separating activity can then be used to express separate proteins of interest according to the present invention.

In a preferred embodiment, the genes of interest are linked to a fusion partner to form a fusion polypeptide as described above. In a preferred embodiment, combinations of fusion partners are used, with or without linkers.

As will be appreciated by those skilled in the art, the fusion nucleic acids of the present invention are not limited to a fusion nucleic acid comprising only a promoter, first gene of interest, separation sequence, and a second gene of interest. Any number of separation sequences and genes of interest may be used in the fusion nucleic acid. Additional separation sequences may be chosen from protease based, IRES based, or Type 2A based separating sequences and added to the fusion nucleic acids along with additional genes of interest. Consequently, a preferred embodiment further comprises a plurality of separating sequences and genes of interest. Thus, in one aspect, the fusion nucleic acids comprises a second separating sequence and a third gene of interest, and may further comprise a third separating sequence and a fourth gene of interest. As will be appreciated by those skilled in the art, by inserting additional separating sequences and additional genes of interest, any number of proteins encoded by the genes of interest may be separately expressed. Additional separating sequences and genes of interest may be desired in screening methods where the first and second gene of interest encode reporter proteins whose activities are affected by a third gene of interest or where expression of more than two genes of interest is necessary to produce a cellular phenotype.

The nucleic acids and the fusion nucleic acids described herein can be prepared using standard recombinant DNA techniques described in, for example, Sambrook, J. et al., Molecular Cloning: A Laboratory Manual, 2nd edition, Cold Spring Harbor Press, Cold Spring Harbor, N.Y., 1989, and Ausubel, F. et al., Current Protocols in Molecular Biology, Greene Publishing Associates and John Wiley & Sons, New York, N.Y., 1994. Generally, the expression vectors also contain the required regulatory or control sequences (e.g., promoters and promoter controlling elements, translation initiation and termination sequences, polyadenylation sequences, splicing signals, etc.), cloning and subcloning sites, reporter/selection or marker genes for identifying cells containing the fusion nucleic acid, and priming regions for sequencing, polymerase chain reaction, or library synthesis, and the like. As described above, these nucleic acid sequences are operably linked such that the resulting fusion nucleic acids are placed in a functional relationship with each other. That is, the components described are placed in a relationship permitting them to function is their intended manner.

When the fusion nucleic acids contain separation sequences, constructing the fusion nucleic acid will depend in part on the separation sequence employed. The separation sequence is operably linked to the first gene of interest and second gene of interest such that the fusion nucleic acid is capable of producing separate protein products of interest. Thus, in a preferred embodiment, the separation sequence is placed in between the first gene of interest and the second gene of interest. As will be appreciated by those skilled in the art, use of separation sequences based on protease recognition or Type 2A sequences requires that the fusion nucleic acid comprising the first gene of interest, separation sequence, and second gene of interest be in frame. By "in frame" herein is meant that the fusion nucleic acid encodes a continuous single polypeptide comprising the protein encoded by the first gene of interest, protein encoded by the separation sequence, and protein encoded by the second gene of interest. Standard recombinant DNA techniques may be used for placing the components of the fusion nucleic acid to encode a contiguous single polypeptide. Linkers may be added to the separation sequence to facilitate the separation reactions or limit structural interference of the separation sequence on the genes of interest. Preferred linkers are $(Gly)_n$ linkers, where n is 1 or more, with n being two, three, four, five or six, although linkers to 7-10 or more amino acids are possible.

As is appreciated by those skilled in the art, use of IRES sequences does not require the first gene of interest, separation sequence, and second gene of interest to be in frame since IRES sequences function as internal translation initiation sites. Accordingly, fusion nucleic acids using IRES elements have the genes of interest arranged in a cistronic structure. That is, transcription of the fusion nucleic acid produces a cistronic mRNA that encodes both first gene of interest and second gene of interest with the IRES element controlling translation initiation of the downstream gene of interest. Alternatively, separate IRES sequences may control the upstream and downstream gene of interest.

Nucleic acids for making libraries of the fusion nucleic acids comprising genomic DNA or cDNA as described herein are made by methods well known in the art. The libraries may also be directed to specific set of encoded protein sequences, such as protein interaction domains. These may be synthesized using standard oligonucleotide synthesis methods, by using libraries of cloned nucleic acids, or use of multiplex PCR of nucleic acids encoding the desired polypeptide domains.

When the nucleic acids comprise libraries of random nucleic acids sequences or random encoded peptides, these nucleic acids are preferably synthesized using known oligonucleotide synthesis techniques. These techniques include synthetic methods well known in the art and include, among others, phosphoramidite, phosphoramidate, and phosphonate chemistries (see Eckstein, Oligonucleotide and Analogues: A Practical Approach, IRL Press, Oxford University Press, 1991). Synthesis is controlled such that nucleic acids are totally random or biased random, as more fully described below.

Cells and cellular libraries comprising the fusion nucleic acids of the present invention are generated by introducing the fusion nucleic acids into a plurality of cells. By a "plurality of cells" herein is meant at least two cells, with at least $10^3$ being preferred, at least about $10^6$ being particularly preferred, and at least about $10^8$ and $10^9$ being especially preferred. This plurality of cells may comprise a cellular library, wherein generally each cell within the library contains a member of the library, for example different random nucleic acids, cDNAs or cDNA fragments, genomic DNA, and combinations thereof. As will be appreciated by those skilled in the art, some cells within the library may not contain a member of the library, and some may contain more than one. When methods other than retroviral infection are used to introduce the fusion nucleic acids into a plurality of cells, the distribution of candidate nucleic acids within the individual members of the cellular library may vary widely, as it is generally difficult to control the number of nucleic acids which are introduced into a cells, such as electroporation or transfection.

The fusion nucleic acids are introduced into cells for expressing the fusion polypeptides and for screening, as is more fully described below. By "introduced into" or grammatical equivalents herein is meant that the nucleic acids enter the cells in a manner suitable for subsequent expression of the nucleic acid. The method of introduction is largely dictated by the targeted cell type. Exemplary methods include $CaPO_4$ precipitation, dextran sulfate transfection, liposome fusion, Lipofectin®, electroporation, biolistic particle bombardment, microinjection, viral infection, etc. The person skilled in the art can choose the appropriate method of introduction based on the cells and the form of the nucleic acid being introduced. As many pharmaceutically important screens require human or model mammalian cell targets, retroviral vectors capable of transfecting such targets are preferred.

In a preferred embodiment, the preferred vectors are retroviral vectors. Preferred retroviral vectors include a vector based on the murine stem cell virus (MSCV) (see Hawley, R. G. et al. (1994) Gene Ther. 1: 136-38) and a modified MFG virus (Riviere, I. et al. (1995) Genetics 92: 6733-37), and pBABE. Other suitable vector include, among others, LRCX retroviral vector set; pSIR retroviral vector; pLEGFP-NI retroviral vector, pLAPSN retroviral vector; pLXIN retroviral vector; pLXSN retroviral vector; all of which are commercially available (e.g., Clontech, Palo Alto, Calif.). When target cells are non-proliferating (e.g., brain cells), useful viral vectors are derived from lentiviruses (Miyoshi, H. et al. (1998) J. Virol. 72: 8150-57), adenoviruses (Zheng, C. et al. (2000) Nat. Biotechnol. 18: 176-80) or alphaviruses (Ehrengruber, M. U. (1999) Proc. Natl. Acad. Sci. USA 96: 7041-46).

Preferably, the fusion nucleic acids and the library of fusion nucleic acids or candidate agents are first cloned into a viral shuttle vector to produce a library of plasmids. A typical shuttle vector is pLNCX (Clontech, Palo Alto, Calif.). The resulting plasmid library can be amplified in *E. coli.*, purified, and introduced into retroviral packaging cell lines. Suitable retroviral packaging cell lines include, but are not limited to the Bing and BOSC23 cells lines (WO 94/19478; Soneoka, Y. et al. (1985) Nucleic Acids Res. 23: 628-33; Finer, M. H. et al. (1994) Blood 83: 43-50); Phoenix packaging lines such as PhiNX-ampho; 292T+gag pol and retrovirus envelope; PA 317; and other cell lines outlined in Markowitz, D. et al. (1998) Virology 167: 400-06 (see also Markowitz, D. et al. (1998) J. Virol. 63: 1120-24; Li, K. J. et al. (1996) Proc. Natl. Acad. Sci. USA 93: 11658-63; and Kinsella, T. M. et al. (1996) Hum. Gene Ther. 7: 1405-13).

In a preferred embodiment, viruses are made by transient transfection of the cell lines referenced above. The resulting viruses can either be used directly or be used to infect another retroviral cell line for expansion of the library.

In a preferred embodiment, the library of virus particles is used to transfect packaging cell lines disclosed herein to produce a primary viral library. By "primary viral" library" herein is meant a library of virus particles comprising the fusion nucleic acids of the present invention. The production of the primary library is preferably done under conditions known in the art to reduce clone bias. The resulting primary viral library can be titred and stored, used directly to infect a target host cell line, or be used to infect another retroviral producer cell for "expansion" of the library.

Concentration of virus may be done as follows. Generally, retroviruses are titred by applying retrovirus containing supernatant onto indicator cells, such as NIH3T3 cells, and then measuring the percentage of cells expressing phenotypic consequences of infection. The concentration of virus is determined by multiplying the percentage of cells infected by the dilution factor involved, and taking into account the number of target cells available to obtain relative titre. If the retrovirus contains a reporter gene, such as lacZ, then infection, integration, and expression of the recombinant virus is measured by histological staining for lacZ expression or by flow cytometry (i.e., FACS analysis). In general, retroviral titres generated from even the best of the producer cells do not exceed $10^7$ per ml unless concentrated, for example by centrifugation and ultrafiltration. However, flow-through transduction methods can provide up to a ten-fold higher infectivity by infecting cells on a porous membrane and allowing retrovirus supernatant to flow past the cells. This provides the capability of generating retroviral titres higher than those achieved by concentration (see Chuck, A. S. (1996) Hum. Gene Ther. 7: 743-50).

To obtain the secondary viral library, host cells are preferably infected with a multiplicity of infection (MOI) of 10. By "secondary viral library" herein is meant a library of retroviral particles expressing the claimed fusion nucleic acids and candidate agents described herein.

As will be appreciated by those in the art, the viral libraries described above are used to produce the cellular libraries of the present invention. As will be appreciated by those in the art, the types of cells used in the present invention can vary widely. Basically any mammalian cells may be used, including preferred cell types from mouse, rat, primate, and human cells. As is more fully described below, cell types implicated in a wide variety of disease conditions are particularly useful, so long as a suitable screen may be designed to allow the selection of cells that exhibit an altered phenotype as a consequence of treating the cells with candidate agents. As will be appreciated by those in the art, modifications of the system by pseudotyping allows all eukaryotic cells to be used, preferably in higher eukaryotes (Morgan, R. A. et al. (1993) J. Virol. 67: 4712-21; Yang, Y. et al. (1995) Hum. Gene Ther. 6: 1203-13).

The fusion nucleic acids are introduced into a host cell and treated under the appropriate conditions to induce or cause expression of the fusion protein. As described above, various expression vectors may be made for introducing the fusion nucleic acids into a variety of organisms, including prokaryotic and eukaryotic. Appropriate host cells include bacteria, archebacteria, yeast, fungi, worms, plants, insect cells, and animal cells, including fish and mammalian cells. For example, bacterial host cells include *Bacillus subtilis, Escherichia coli, Streptococcus cremoris, Streptococcus lividans, Haemophilus influenza* etc. Yeast cells include *Saccharomyces cerevisiae, Candida albicans, Candida maltosa, Hansenula polymorpha, Kluyveromyces fragilis, Kluyveromyces lactis, Pichia guillerimondi, Schizosaccharomyces pombe,* and *Yarrowia lipolytica*. Appropriate insect cells include Lepidoptera cell lines, such as *Spodoptera frugiperda* (e.g. Sf9) or *Trichoplusia ni*. However, those skilled in the art will recognize the applicability of other insect cell system, such as the silkworm *Bombyx mori, Drosophila* cells (Schneider 2, KC, BG2-C6, and Shi), *A. albopictus, A.*

*aegypti, Choristoneura fumiferana, Heliothis virescens; Heliothis zea, Orgyia, pseudotsugata, Lymantria dispar, Plutella xylostella, Malacostoma disstria, Pieris rapae, Mamestra configurata*, and *Hyladphora cecropia*. In another preferred embodiment, live insects are used to express the proteins of the present invention. Larvae are the preferred form for expressing the desired product, including the larvae of *Manduca sexta, Bombyx mori, Drosophila*, and the like, which are susceptible to infection by recombinant insect viruses.

In a preferred embodiment, the fusion nucleic acids are expressed in mammalian cells. Basically, any mammalian cells may be used, with mouse, rat, primate and human cells being particularly preferred, as will be appreciated by those in the art. When retroviral vectors are used, preferred are mammalian cells in which the library of retroviral vectors are made.

In a preferred embodiment, cell types implicated in a wide variety of disease conditions are particularly useful when screens, as described below, are designed for selecting cells that exhibit an altered phenotype as a consequence of expression of the gene of interest, for example a random peptide, within the cell. Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. (see the ATCC cell line catalog, hereby expressly incorporated by reference).

To provide those skilled in the art the tools to use the present invention, the nucleic acids and cells of the present invention are assembled into kits. The components included in the kits may comprise the fusion nucleic acids (e.g., expression vectors or libraries), enzymatic reagents for making the fusion nucleic acid constructs, cells for packaging and amplification of viruses, and reagents for transfection and transduction into target cells. Alternatively, the kits contain libraries of fusion nucleic acids capable of being introduced into cells and/or contain cells already stably expressing the fusion nucleic acids (e.g., via integration of the retroviruses into the cellular chromosome).

In the present invention, the fusion nucleic acids and cells comprising the fusion nucleic acids of the present invention find use in screens for candidate agents producing an altered cellular phenotype. By "candidate agent" or "candidate small molecules" or "candidate expression products" herein is meant an agent or expression product which may be tested for the ability to alter the phenotype of a cell.

Candidate bioactive agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl, or carboxyl group, preferably at least two of them functional chemical groups. The candidate agents often comprise cyclical carbon or heterocyclic structures, and/or aromatic or polyaromatic structures substituted with one or more of the above functional groups. Candidate agents are also found among biomolecules including peptides, saccharides, fatty acids, steroids, purines, pyrimidines, and their derivatives, structural analogs or combinations thereof. Particularly preferred are proteins, candidate drugs, and other small molecules.

Candidate agents are obtained from a wide variety of sources, including libraries of synthetic or natural compounds. For example, numerous means are available for random and directed synthesis of a wide variety of organic compounds and biomolecules, including expression of randomized oligonucleotides (see for example, Gallop, M. A. et al. (1994) J. Med. Chem. 37:1233-51; Gordon, E. M. et al. (1994) J. Med. Chem. 37:1385-401; Thompson, L. A. et al. (1996) Chem. Rev. 96: 555-600; Balkenhol, F. et al. (1996) Angew. Chem. Int. Ed. 35: 2288-337; and Gordon, E. M. et al. (1996) Acc. Chem. Res. 29: 444-54). Alternatively, libraries of natural compounds in the form of bacterial, fungal, plant, and animal extracts are available or readily produced. Additionally, natural or synthetically produced libraries and compounds are readily modified through conventional chemical, physical, and biochemical means. Known pharmacological agents may be subjected to directed or random chemical modifications such as acylation, alkylation, esterification, and amidification to produce structural analogs.

The candidate agent can be pesticides, insecticides or environmental toxins; a chemical (including solvents, polymers, organic molecules, etc); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including prokaryotic and eukaryotic (including pathogenic cells), including mammalian tumor cells); viruses (including retroviruses, herpes viruses, adenoviruses, lentiviruses, etc.); and spores (e.g., fungal, bacterial etc.).

In a preferred embodiment of candidate agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus, "amino acid" or "peptide residue" as used herein means both naturally occurring and synthetic amino acids. For example, homo-phenylalanine, citrulline, and norleucine are considered amino acids for the purposes of the invention. "Amino acids" also includes imino residues such as proline and hydroxyproline. The side chains may be either the (R) or (S) configuration. In the preferred embodiment, the amino acids are in the (S) or L configuration. If non-naturally occurring side chains are used, non-amino acid substituents may be used, for example to prevent or retard in-vivo degradations. Proteins including non-naturally occurring amino acids may be synthesized or in some cases, made by recombinant techniques (see van Hest, J. C. et al. (1998) FEBS Lett. 428: 68-70 and Tang et al. (1999) Abstr. Pap. Am. Chem. S218: U138-U138 Part 2, both of which are expressly incorporated by reference herein).

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way, libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

Candidate agents may encompass a variety of peptidic agents. These include, but are not limited to, (1) immunoglobulins, particularly IgEs, IgGs, and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and diisopyramide), bronchodilators (theophylline), antibiotics (chloramphenicol, sulfonamides), antidepressants, immunosuppressants, abused drugs (amphetamine, methamphetamine, cannabinoids, cocaine and opiates) and antibodies to any number of viruses (including orthomyxoviruses, (e.g. influenza virus), paramyxoviruses (e.g. respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus; Vibrio*, e.g. *V. cholerae; Escherichia*, e.g. Enterotoxigenic *E. coli, Shigella*, e.g. *S. dysenteriae; Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae; Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis; Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphatase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cortisol, estradiol, follicle stimulating hormone (FSH), thyroid-stimulating hormone (TSH), luteinizing hormone (LH), progesterone, testosterone; and (4) other proteins (including α-fetoprotein, carcinoembryonic antigen CEA.

In a preferred embodiment, the candidate bioactive agents are peptides of from about 5 to about 30 amino acids, with from about 5 to about 20 amino acids being preferred, and from about 7 to about 15 being particularly preferred. These peptides may be digests of naturally occurring proteins, as described above, or random peptides or "biased" random peptides, and peptide analogs either chemically synthesized or encoded by candidate nucleic acids. By "randomized" or grammatical equivalents herein is meant that each nucleic acid and peptide consists of essentially random nucleotides and amino acids, respectively. Generally, since these random peptides (or nucleic acids, discussed below) are chemically synthesized, they may incorporate any amino acid or nucleotide at any position. The synthetic process can be designed to generate randomized proteins or nucleic acids to allow the formation of all or most of the possible combinations over the length of the sequence, thus forming a library of randomized candidate bioactive proteinaceous agents.

In one preferred embodiment, the library is fully randomized, with no sequence preference or constants at any position. In another preferred embodiment, the library is biased. That is, some positions within the sequence are either held constant or are selected from a limited number of possibilities. For example, in a preferred embodiment, the nucleotides or amino acid residues are randomized within a defined class, for example hydrophobic amino acids, hydrophilic residues, sterically biased (either small or large) residues, or are amino acid residues for crosslinking (i.e. cysteines) or phosphorylation sites (i.e. serines, threonines, tyrosines, or histidines).

In a preferred embodiment, the bias is toward peptides or nucleic acids that interact with known classes of molecules. For example, it is known that much of intracellular signaling is carried out by short regions of polypeptide interacting with other polypeptide regions of other proteins, such as the interaction domains described above. Another example of interaction domain is a short region from the HIV-1 envelope cytoplasmic domain that has been previously shown to block the action of cellular calmodulin. Regions of the Fas cytoplasmic domain, which shows homology to the mastoparn toxin from Wasps, can be limited to a short peptide region with death inducing apoptotic or G protein inducing functions. Magainin, a natural peptide derived from *Xenopus*, can have potent anti-tumor and anti-microbial activity. Short peptide fragments of a protein kinase C isozyme (β-PKC) have been shown to block nuclear translocation of PKC in *Xenopus* oocytes following stimulation. In addition, short SH-3 target proteins have been used as pseudosubstrates for specific binding to SH-3 proteins. This is of course a short list of available peptides with biological activity, as the literature is dense in this area. Thus, there is much precedent for the potential of small peptides to have activity on intracellular signaling cascades. In addition, agonists and antagonists of any number of molecules may be used as the basis of biased randomization of candidate bioactive agents as well.

Thus, a number of molecules or protein domains are suitable as starting points for generating biased candidate agents. A large number of small molecule domains are known that confer common function, structure or affinity. These include protein-protein interaction domains and nucleic acid interaction domains described above. As is appreciated by those in the art, while variations of these protein-protein or protein-nucleic acid domains may have weak amino acid homology, the variants may have strong structural homology.

In another preferred embodiment, the candidate agents are nucleic acids. By "nucleic acid" or "oligonucleotide" or grammatical equivalents herein is meant at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, S. L. et al. (1993) Tetrahedron 49: 1925-63 and references therein; Letsinger, R. L. et al. (1970) J. Org. Chem. 35: 3800-03; Sprinzl, M. et al. (1977) Eur. J. Biochem. 81: 579-89; Letsinger, R. L. et al. (1986) Nucleic Acids Res. 14: 3487-99; Sawai et al. (1984) Chem. Lett. 805; Letsinger, R. L. et al. (1988) J. Am. Chem. Soc. 110: 4470; and Pauwels et al. (1986) Chemica Scripta 26:141-49), phosphorothioate (Mag, M. et al. (1991) Nucleic Acids Res. 19: 1437-41; and U.S. Pat. No. 5,644,048), phosphorodithioate (Briu et al. (1989) J. Am. Chem. Soc. 111: 2321), O-methylphosphoroamidite linkages (see Eckstein, Oligonucleotides and Analogues: A Practical Approach, Oxford University Press, 1991), and peptide nucleic acid backbones and linkages (Egholm, M. (1992) Am. Chem. Soc. 114: 1895-97; Meier et al. (1992) Chem. Int. Ed. Engl. 31:1008; Egholm, M (1993) Nature 365: 566-68; Carlsson, C. et al. (1996) Nature 380: 207, all of which are incorporated by reference). Other analog nucleic acids include those with positive backbones (Dempcy, R. O. et al. (1995) Proc. Natl. Acad. Sci. USA 92: 6097-101); non-ionic backbones (U.S. Pat. Nos. 5,386,023, 5,637,684, 5,602,240, 5,216,141 and 4,469,863; Kiedrowshi et al. (1991) Angew. Chem. Intl. Ed. English 30: 423; Letsinger, R. L. et al. (1988) J. Am. Chem. Soc. 110: 4470; Letsinger, R. L. et al. (1994) Nucleoside & Nucleotide 13: 1597; Chapters 2 and 3, ASC Symposium Series 580, "Carbohydrate Modifications in Antisense Research", Ed. Y. S. Sanghui and P. Dan Cook; Mesmaeker et al. (1994) Bioorganic & Medicinal Chem. Lett. 4: 395; Jeffs et al. (1994) J. Biomolecular NMR 34: 17; (1996) Tetrahedron Lett. 37: 743) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al. (1995) Chem. Soc. Rev. 169-76). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties, such as labels, or to increase the stability and half-life of such molecules in physiological environments.

In addition, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or hybrid, where the nucleic acid contains any combination of deoxyribo- and ribonucleotides, and any combination of bases, including uracil, adenine, thymine, cytosine, guanine, xanthine hypoxanthine, isocytosine, isoguanine, etc., although generally occurring bases are preferred.

In a preferred embodiment, the candidate nucleic acids comprise cDNAs, including cDNA libraries, or fragments of cDNAs. The cDNAs can be derived from any number of different cells and include cDNAs generated from eucaryotic and procaryotic cells, viruses, cells infected with viruses or other pathogens, genetically altered cells, cells with defective cellular processes, etc. Preferred embodiments include cDNAs made from different individuals, such as different patients, particularly human patients. The cDNAs may be complete libraries or partial libraries. Furthermore, the candidate nucleic acids can be derived from a single cDNA source or multiple sources; that is, cDNA from multiple cell types or multiple individuals or multiple pathogens can be combined in a screen. In other aspects, the cDNA may encode specific domains, such as signaling domains, protein interaction domains, membrane binding domains, targeting domains, etc. The cDNAs may utilize entire cDNA constructs or fractionated constructs, including random or targeted fractionation. Suitable fractionation techniques include enzymatic (i.e., DNase I, restriction nucleases, etc.), chemical, or mechanical fractionation (i.e., sonicated or sheared). Also useful for the present invention are cDNA libraries enriched for a specific class of proteins, such as type I membrane proteins (Tashiro, K. et al. (1993) Science 261: 600-03) and membrane proteins (Kopczynski, C. C. (1998) Proc. Natl. Acad. Sci. USA 95: 9973-78). Additionally, subtracted cDNA libraries in which genes preferentially or exclusively expressed in particular cells, tissues, or developmental phases are enriched. Methods for making subtracted cDNA libraries are well known in the art (see Diatchenko, L. et al. (1999) Methods Enzymol. 303: 349-80; von Stein, O. D. et al. (1997) Nucleic Acids Res. 13: 2598-602: Carcinci, P. (2000) Genome Res. 10: 1431-32). Accordingly, a cDNA library may be a complete cDNA library from a cell, a partial library, an enriched library from one or more cell types, or a constructed library with certain cDNAs being removed to from a library.

In another preferred embodiment, the candidate nucleic acids comprise genomic nucleic acids, including organellar nucleic acids. As elaborated above for cDNAs, the genomic nucleic acids may be derived from any number of different cells, including genomic nucleic acids of eukaryotes, prokaryotes, or viruses. They may be from normal cells or cells defective in cellular processes, such as tumor suppression, cell cycle control, or cell surface adhesion. Moreover, the genomic nucleic acids may be obtained from cells infected with pathogenic organisms, for example cells infected with viruses or bacteria. The genomic nucleic acids comprise entire genomic nucleic acid constructs or fractionated constructs, including random or targeted fractionation as described above. Generally, for genomic nucleic acids and cDNAs, the candidate nucleic acids may range from nucleic acids lengths capable of encoding proteins of twenty to thousands of amino acid residues, with from about 50-1000 being preferred and from about 100-500 being especially preferred. In addition, candidate agents comprising cDNA or genomic nucleic acids may also be subsequently mutated using known techniques (e.g., exposure to mutagens, error prone PCR, error prone transcription, combinatorial splicing (e.g., cre-lox recombination) to generate novel nucleic acid sequences (or protein sequences). In this way libraries of procaryotic and eukaryotic nucleic acids may be made for screening in the systems described herein. Particularly preferred in the embodiments are libraries of bacterial, fungal, viral and mammalian nucleic acids, with the latter being preferred, and human nucleic acids being especially preferred.

In another preferred embodiment, the candidate nucleic acids comprise libraries of random nucleic acids. Generally, the random nucleic acids are fully randomized or they are biased in their randomization, e.g., in nucleotide/residue frequency generally or per position. As defined above, by "randomized" or grammatical equivalents herein is meant that each nucleic acid consists essentially of random nucleotides. Since the candidate nucleic acids are chemically synthesized, they may incorporate any nucleotide at any position. In the expressed random nucleic acid, at least 10, preferably at least 12, more preferably at least 15, most preferably at least 21 nucleotide positions need to be randomized. The candidate nucleic acids may also comprise nucleic acid analogs as described above.

For candidate nucleic acids encoding peptides, the candidate nucleic acids generally contain cloning sites which are placed to allow in-frame expression of the randomized peptides, and any fusion partners, if present, such as presentation structures and the GFPs of the present invention. For example, when presentation structures are used, the presentation structure will generally contain the initiating ATG as part of the parent vector. For candidate agents comprising RNAs, in addition to chemically synthesized RNA nucleic acids, the candidate nucleic acids may be expressed from vectors, including retroviral vectors. Thus, when the RNAs are expressed, vectors expressing the candidate nucleic acids are generally constructed with an internal promoter (i.e., CMV promoter), tRNA promoter, cell specific promoter, or hybrid promoters designed for immediate and appropriate expression of the RNA structure at the initiation site of RNA synthesis. For retroviral vectors, the RNA may be expressed anti-sense to the direction of retroviral synthesis and is terminated as known, for example with an orientation specific terminator sequences. Interference from native viral promoter initiated transcription may be minimized in the target cell by using the SIN vectors described herein.

When the nucleic acids are expressed in the cells, they may or may not encode a protein as described herein. Thus, included within candidate nucleic acids of the present invention are RNAs capable of producing an altered phenotype. Thus, in one aspect, the nucleic acid may be an antisense nucleic acid directed towards a complementary target nucleic acid. As is well known in the art, antisense nucleic acids find use in suppressing or affecting expression of various genes of pathogenic organisms or expression of cellular genes. These include suppression of oncogenes to affect the proliferative properties of transformed cells (Martiat, P. et al. (1993) Blood 81: 502-09; Daniel, R. (1995) Oncogene 10: 1607-14; and Niemeyer, C. C. (1998) Cell Death Differ. 5: 440-49), modulate cell cycle (Skotz, M. et al. (1995) Cancer Res. 55: 5493-98), inhibit proteins involved in cardiovascular disease states (Wang, H. (1999) Circ. Res. 85: 614-22) and inhibit viral pathogenesis (Lo, K. M. et al. (1992) Virology 190: 176-83; and Chatterjee S. et al (1992) Science 258: 1485-88).

In another preferred embodiment, the candidate nucleic acids are nucleic acids capable of catalyzing cleavage of target nucleic acids in a sequence specific manner, preferably in the form of ribozymes. Ribozymes include among others hammerhead ribozymes, hairpin ribozymes, and hepatitis delta virus ribozymes (Tuschl, T. (1995) Curr. Opin. Struct. Biol. 5: 296-302; Usman N. (1996) Curr Opin Struct Biol 6: 527-33; Chowrira B. M. et al. (1991) Biochemistry 30: 8518-22; and Perrotta A. T. et al. (1992) Biochemistry 3: 16-21). As with antisense nucleic acids, nucleic acids catalyzing cleavage of target nucleic acids may be directed to a variety of expressed nucleic acids, including those from pathogenic organisms or cellular genes (see for example, Jackson, W. H. et al. (1998) Biochem. Biophys. Res. Commun. 245: 81-84).

Another preferred embodiment of candidate nucleic acids are double stranded RNA capable of inducing RNA interference or RNAi (Bosher, J. M. et al. (2000) Nat. Cell Biol. 2: E31-36). Introducing double stranded RNA can trigger specific degradation of homologous RNA sequences, generally within the region of identity of the dsRNA (Zamore, P. D. et. al. (1997) Cell 101: 25-33). This provides a basis for silencing expression of genes, thus permitting a method for altering the phenotype of cells. The dsRNA may comprise synthetic RNA made either by known chemical synthetic methods or by in vitro transcription of nucleic acid templates carrying promoters (e.g., T7 or SP6 promoters). Alternatively, the dsRNAs are expressed in vivo, preferably by use of palindromic fusion nucleic acids, that allow facile formation of dsRNA (e.g., in the form of a hairpin) when expressed in the cell.

In a preferred embodiment, a library of candidate bioactive agents are used. These include libraries of small molecules, nucleic acids, peptides, cDNAs, genomic nucleic acids, etc. In a preferred embodiment, for candidate agents comprising random nucleic acids and peptides, the library should provide a sufficiently structurally diverse population of randomized expression products to effect a probabilistically sufficient range to provide one or more peptide products which has the desired properties, such as binding to protein interaction domains or producing a desired cellular response. Accordingly, a library must be large enough so that at least one of its members will have a structure that gives it affinity for some molecule, protein or other factor whose activity is involved in some cellular response, such as signal transduction. Although it is difficult to gauge the required absolute size of an interaction library, nature provides a hint with the immune response: a diversity of $10^7$-$10^8$ different antibodies provides at least one combination with sufficient affinity to interact with most potential antigens faced by an organism. Published in vitro selection techniques have also shown that a library size of about $10^7$ to $10^8$ is sufficient to find structures with affinity for the target. A library of all combinations of a peptide 7-20 amino acids in length, such as proposed here for expression in retroviruses, has the potential to code for $20^7$ ($10^9$) to $20^{20}$. Thus with libraries of $10^7$ to $10^8$ per ml of retroviral particles, the present methods allow a "working" subset of a theoretically complete interaction library for 7 amino acids, a subset of shapes for the $20^{20}$ library. Thus, in a preferred embodiment, at least $10^6$, preferably at least $10^7$, more preferably at least $10^8$ and most preferably at least $10^8$ different expression products are simultaneously analyzed in the subject methods. Preferred methods maximize library size and diversity.

The candidate bioactive agents are combined or added to a cell or population of cells or plurality of cells. By "population of cells" or "plurality of cells" herein is meant at least two cells, with at least about $10^5$ being preferred, at least about $10^6$ being particularly preferred, and at least about $10^7$, $10^8$, and $10^9$ being especially preferred.

The candidate agents and the cells are combined. As will be appreciated by those in the art, this may be accomplished in any number of ways, including adding the candidate agents to the surface of the cells, to the media containing the cells, or to a surface on which the cells grow or contact; or adding the agents into the cells, for example by using vector that will introduce agents into the cells, especially when the agents are nucleic acids or proteins.

In a preferred embodiment, the candidate agents are either nucleic acids or proteins that are introduced into the cells to screen for candidate agents capable of altering the phenotype of a cell. By "introduced into" or grammatical equivalents herein is meant that the nucleic acids enter the cells in a manner suitable for subsequent expression of the nucleic acid or protein. The method of introduction is largely dictated by the targeted cell type. Known methods include $CaPO_4$ transfection, DEAE dextran transfection, liposome fusion, Lipofectin®, electroporation, viral infection, biolistic particle bombardment, etc. The candidate nucleic acids may exist either transiently or stably in the cytoplasm or stably integrate into the genome of the host cell (i.e., by retroviral integration, homologous recombination). When mammalian cells are used, retroviral vectors capable of transfecting such targets are preferred.

In a preferred embodiment, the candidate bioactive agents are either nucleic acids or proteins (proteins in this context includes proteins, oligopeptides, and peptides) that are expressed in the host cells using vectors, including viral vectors. The choice of the vector will depend on the cell type. For example, when cells are replicating mammalian cells, retroviral vectors are used. When the cells are non-replicating mammalian cells, for example when arrested in one of the growth phases, viral vectors capable of infecting non-dividing cells, including lentiviral and adenoviral vectors, are used to express the nucleic acids and proteins.

In a preferred embodiment, the candidate bioactive agents are either nucleic acids or proteins that are introduced into the host cells using retroviral vectors, as is generally outlined in PCT US 97/01019 and PCT US97/01048, both of which are expressly incorporated by reference. Generally, a library is generated using a retroviral vector backbone; standard oligonucleotide synthesis is done to generate either the candidate agent or nucleic acid encoding a protein, for example a random peptide, using techniques well known in the art. After generating the nucleic acid library, the library is cloned into a first primer, which serves as a cassette for insertion into the retroviral construct. The first primer generally contains additional elements, including for example, the required regulatory sequences (e.g. translation, transcription, promoters, etc.) fusion partners, restriction endonuclease sites, stop codons, regions of complementarity for second strand priming.

A second primer is then added, which generally consists of some or all of the complementarity region to prime the first primer and optional sequences necessary to a second unique restriction site for purposes of subcloning. Extension with DNA polymerase results in double stranded oligonucleotides, which are then cleaved with appropriate restriction endonucleases and subcloned into the target retroviral vectors.

Any number of suitable retroviral vectors may be used. In one aspect, preferred vectors include those based on murine stem cell virus (MSCV) (Hawley, et al. (1994) Gene Therapy 1: 136), a modified MFG virus (Reivere et al. (1995) Genetics 92: 6733), pBABE, and others described above. Well suited retroviral transfection systems are described in Mann et al., supra; Pear et al. (1993) Proc. Natl. Acad. Sci. USA 90: 8392-96; Kitamura, et al. Human Gene Ther. 7: 1405-1413; Hofmann, et al Proc. Natl Acad. Sci. USA 93: 5185-90; Choate et (1996) Human Gene Ther 7: 2247; WO 94/19478; PCT US97/01019, and references cited therein, all of which are incorporated by reference.

The vectors used to introduce candidate agents may include inducible and constitutive promoters for the expression of the candidate agents, as described above. For example, there are situations wherein it is necessary to induce peptide expression only during certain phases of the selection process, such as during particular periods of the cell cycle. As described above, a large number of constitutive and inducible promoters are well known, and may be used to regulate expression of the candidate agents.

In a preferred embodiment, the bioactive candidate agents comprising nucleic acids and proteins are linked to a fusion partner, as described above. In one aspect, combinations of fusion partners are used. Any number of combinations of presentation structures, targeting sequences, rescue sequences, and stability sequences may be used with or without linker sequences. Thus, candidate agents, which include these components, may be used to generate a library of fragments, each containing a different candidate nucleotide sequence (e.g., random nucleic acid, cDNA, genomic DNA etc.) that may encode a different peptide sequence.

In a preferred embodiment, when the candidate agent is introduced to the cells using expression vectors, the candidate peptide agent is linked to a detectable molecule, and the methods of the invention include at least one expression assay. Thus, the detectable molecule may comprise reporter and selection genes as described herein. In one preferred embodiment, the detectable molecule is distinguishable from that expressed by the fusion nucleic acid expressing a gene of interest. An expression assay is an assay that allows the determination of whether a candidate bioactive agent has been expressed, i.e., whether a candidate peptide agent is present in the cell. Thus, by linking the expression of a candidate agent to the expression of a detectable molecule such as a label, the presence or absence of the candidate peptide agent may be determined. Accordingly, in this embodiment, the candidate agent is operably linked to a detectable molecule. Generally, this is done by creating a fusion nucleic acid. The fusion nucleic acid comprises a first nucleic acid expressing the candidate bioactive agent (which can include fusion partners, as outlined above), and a second nucleic acid expressing a detectable molecule. In a preferred embodiment, the fusion nucleic acid encodes a fusion polypeptide comprising the candidate agent and the detectable molecule. In another preferred embodiment, the fusion nucleic acid may use one promoter for the first nucleic and a second promoter for the second nucleic acid to produce separate nucleic acids comprising a candidate nucleic acid, which may or may not encode a protein, and the detectable molecule. In yet another preferred embodiment, the fusion nucleic acid may use separation sequences described herein to express separate candidate bioactive agent and detectable molecule. The terms "first" and "second" are not meant to confer an orientation of the sequences with respect to 5'-3' orientation of the fusion nucleic acid. For example, assuming a 5'-3' orientation of the fusion sequence, the first nucleic acid may be located either 5' to the second nucleic acid, or 3' to the second nucleic acid. Preferred detectable molecules in this embodiment include, but are not limited to, various fluorescent proteins and their variants, including *A. victoria* GFP, *Renilla muelleri* GFP, *Renilla reniformis* GFP, *Ptilosarcus gurneyi* GFP, YFP, BFP, RFP, *Anemonia majano* fluorescent proteins, *Zoanthus* fluorescent proteins, *Discosoma striata* fluorescent proteins, and *Clavularia* fluorescent proteins.

Thus, in one preferred embodiment, the vectors used to introduce candidate agents comprises a promoter operably linked to fusion nucleic acids encoding fusion polypeptides comprising rGFP or pGFP, including fusions with random nucleic acids (i.e., for expressing random peptides), cDNAs, and genomic DNA fragments. Fusions to rGFP or pGFP provide a way of monitoring expression of the candidate agent, tracking and localization of the candidate agent, and sorting cells expressing the candidate agents. In another aspect, a preferred embodiment comprises a vector comprising a promoter, a first gene of interest, a separation sequence, and second gene of interest comprising rGFP or pGFP. The gene of interest expresses the candidate agent while the GFP reporter allows monitoring its expression. Expressing separate candidate agent and reporter reduces any interference with activity of the candidate agent by fusing to a reporter protein. If the candidate agent comprises a rGFP or pGFP fusion protein, the second gene of interest may comprise a reporter distinguishable from rGPF or pGPF fusion protein.

In general, the candidate agents are added to the cells, either extracellularly or intracellularly, as outlined above, under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high throughput screening. Typically between 0.1 and 24 hour will be sufficient. Excess reagent is generally removed or washed away.

A variety of other reagents may be included in the assays. These include reagents like salts, neutral proteins, e.g., albumin, detergents, synthetic polymers (polyethylene glycol, dextran sulfate), ionic agents, etc., which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for detection. Washing or rinsing the cells will be done as will be appreciated by those in the art at different times, and may include the use of filtration and centrifugation. When second labeling moieties (also referred to herein as "secondary labels") are used, they are preferably added after excess non-bound target molecules are removed, in order to reduce non-specific binding. However, under some circumstances, all the components may be added simultaneously.

As will be appreciated by those in the art, the type of cells used in the present invention can vary widely. Basically, the screen may use any cell in which the fusion nucleic acids of the present invention can be introduced and expressed. These include bacterial, fungal, plant, insect, and mammalian cells. In a preferred embodiment, when the cells are mammalian cells, particularly preferred cells are mouse, rat, primate and human cells. When the candidate agents are in the form of retroviral vectors, the screen may use any mammalian cells in which a library of retroviral vectors comprising the fusion nucleic acids of the present invention are made. In addition, modifications of retroviral system by pseudotyping allows nearly all mammalian cell types to be used (see Morgan, R. A. et al. (1993) J. Virol. 67: 4712-21; Yang, Y. et al. (1995) Hum. Gene Ther. 6: 1203-13).

As is more fully described below, a screen is set up such that the cells exhibit a selectable phenotype in the presence of a candidate agent. For mammalian cells, cell types implicated in a wide variety of disease conditions are particularly useful, so long as a suitable screen may be designed to allow the selection of cells that exhibit an altered phenotype as a consequence of the presence of a candidate bioactive agent within the cell. Accordingly, suitable cell types include, but are not limited to, tumor cells of all types (particularly melanoma, myeloid leukemia, carcinomas of the lung, breast, ovaries, colon, kidney, prostate, pancreas, and testes), cardiomyocytes, endothelial cells, epithelial cells, lymphocytes (T-cells and B-cells), mast cells, eosinophils, vascular intimal cells, hepatocytes, leukocytes including mononuclear leukocytes, stem cells such as hemopoietic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, etc. See the ATCC cell line catalog, hereby expressly incorporated by reference.

In one embodiment, the cells may be genetically engineered, that is, contain exogenous nucleic acids, for example to contain target molecules.

In a preferred embodiment, a first plurality of cells is screened. That is, the cells into which the candidate nucleic acids are introduced are screened for an altered phenotype. Thus, in this embodiment, the effect of the bioactive candidate agent is seen in the same cells in which it is made; i.e., an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the retroviral molecular library, e.g., a different candidate nucleic acid, although as will be appreciated by those in the art, some cells within the library may not contain a retrovirus, and some may contain more than one. When methods other than retroviral infection are used to introduce the candidate nucleic acids into a plurality of cells, the distribution of candidate nucleic acids within the individual cell members of the cellular library may vary widely, as it is generally difficult to control the number of nucleic acids which enter a cell during electroporation, transfection, etc.

In a preferred embodiment, the candidate nucleic acids are introduced into a first plurality of cells, and the effect of the candidate bioactive agents is screened in a second or third plurality of cells, different from the first plurality of cells, i.e., generally a different cell type. That is, the effect of the bioactive agents is due to an extracellular effect on a second cell, i.e., an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" as used herein is a functional contact, and includes both direct and indirect. In this embodiment, the first plurality of cells may or may not be screened.

If necessary, the cells are treated to conditions suitable for the expression of the candidate nucleic acids, for example when inducible promoters are used, to produce the candidate expression products, either translation or transcription. Expression of the candidate agents results in functional contact of the candidate agent and the cell. Thus, in a preferred embodiment, the methods of the present invention comprise introducing candidate nucleic acids into a plurality of cells, a cellular library. The plurality of cells is then screened, as is more fully outlined below, for a cell exhibiting an altered phenotype. The altered phenotype is due to the presence of a candidate bioactive agent.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to, gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e., half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptibility, latency, adhesion, and uptake of viruses and bacterial pathogens; etc. By "capable of altering the phenotype" herein is meant that the candidate agent can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example, microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the randomized nucleic acid was introduced; in other embodiments, the altered phenotype is detected in a second cell which is responding to some molecular signal from the first cell.

In a preferred embodiment, once a cell with an altered phenotype is detected, the cell is isolated from the plurality which do not have altered phenotypes. Isolation of the altered cell may be done in any number of ways, as is known in the art, and will in some instances depend on the assay or screen. Suitable isolation techniques include, but are not limited to, FACS; lysis selection using complement; cell cloning; scanning by Fluoroimager, expression of a "survival" protein; induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes; etc.

In a preferred embodiment, the candidate nucleic acid and/or bioactive agent is isolated from the positive cell. In one aspect, primers complementary to DNA regions common to the expression constructs, or to specific components of the library such as a rescue sequence, defined above, are used to "rescue" the unique random sequence. Alternatively, the bioactive candidate agent is isolated using a rescue sequence. For example, rescue sequences comprising epitope tags or purification sequences may be used to pull out the bioactive candidate agent using immunoprecipitation or affinity columns. In some instances, as is outlined below, this may also pull out the primary target molecule if there is a sufficiently strong binding interaction between the bioactive agent and the target molecule. Alternatively, the peptide may be detected using mass spectroscopy.

Once rescued, the sequence of the candidate agent and/or bioactive nucleic acid is determined. This information can then be used in a number of ways.

In a preferred embodiment, the candidate agent is resynthesized and reintroduced into the target cells to verify the effect. For mammalian cells, this may be done using retroviruses, or alternatively using fusions to the HIV-1 Tat protein, and analogs and related proteins, which allows very high uptake into target cells (see for example, Fawell, S. et al. (1994) Proc. Natl. Acad. Sci. USA 91: 664-68; Frankel, A. D. et al. (1988) Cell 55: 1189-93; Savion, N. et al. (1981) J. Biol. Chem. 256: 1149-54; Derossi, D. et al. (1994) J. Biol. Chem. 269:10444-50; and Baldin, V. et al. (1990) EMBO J. 9: 1511-17, all of which are incorporated by reference).

In a preferred embodiment, the sequence of a candidate agent is used to generate more candidate bioactive agents. For example, the sequence of the candidate agent may be the basis of a second round of (e.g., biased) randomization, to develop other candidate agents with increased or altered activities. Alternatively, the second round of randomization may change the affinity of the candidate agent. Furthermore, it may be desirable to put the identified random region of the candidate agent into other presentation structures, or to alter the sequence of the constant region of the presentation structure, to alter the conformation/shape of the candidate agent. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the candidate agent or the candidate nucleic acid encoding it is used to identify target molecules. As will be appreciated by those in the art, there may be primary target molecules, to which the candidate agent binds or acts upon directly, and there may be secondary target molecules, which are part of the signaling pathway affected by the bioactive agent; these might be termed "validated targets".

In a preferred embodiment, the bioactive agent is used to pull out target molecules. For example, as outlined herein, if the target molecules are proteins, the use of epitope tags or purification sequences can allow the purification of primary target molecules via biochemical means (e.g., co-immunoprecipitation, affinity columns, etc.). Alternatively, the peptide, when expressed in bacteria and purified, can be used as a probe against a bacterial cDNA expression library made from mRNA of the target cell type. Alternatively, peptides can be used as "bait" in either yeast or mammalian two or three hybrid systems. Such interaction cloning approaches have been very useful in isolating DNA-binding proteins and other interacting protein components. The peptide(s) can be combined with other pharmacologic activators to study the epistatic relationships of signal transduction pathways in question. It is also possible to synthetically prepare labeled peptide candidate agent and use it to screen a cDNA library expressed in bacteriophage for those expressed cDNAs which bind the peptide. Furthermore, it is also possible that one could use cDNA cloning via retroviral libraries to "complement" the effect induced by the peptide. In such a strategy, the peptide would be required to be stoichiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

Once primary target molecules have been identified, secondary target molecules may be identified in the same manner, using the primary target as the "bait". In this manner, signaling pathways may be elucidated. Similarly, bioactive agents specific for secondary target molecules may also be discovered to identify a number of bioactive agents acting on a single pathway, for example for when developing combination therapies.

The methods of the present invention may be useful for screening a large number of cell types under a wide variety of conditions. Generally, the host cells are cells that are involved in disease states, and they are tested or screened under conditions that normally result in undesirable consequences on the cells. When a suitable bioactive candidate agent is found, the undesirable effect may be reduced or eliminated. Alternatively, normally desirable consequences may be reduced or eliminated, with an eye towards elucidating the cellular mechanisms associated with the disease state or signaling pathway.

In view of all the foregoing, the compositions and methods described herein are useful in a variety of applications. In one preferred embodiment, the compositions of the present invention are useful as reporters for gene expression. In these applications, the compositions may be operably linked to the promoter elements to provide a measure of gene expression. When used with separation sequences as a downstream gene of interest, the rGFP or pGFP provides a basis for monitoring levels of expression of the upstream gene of interest.

In another preferred embodiment, the compositions of the present invention are useful for tracking and localizing proteins. In these embodiments, proteins or peptides are fused to rGFP or pGPF, which serves as reporters for monitoring localization of proteins to subcellular compartments; assessing intracellular trafficking of proteins; or examining protein-protein interactions, protein-nucleic acid interactions, and protein interactions with other molecules.

Since protein-interaction domains serve as a basis for many cellular processes and cell signaling events, preferred embodiments of the present invention further comprise substrates for enzymatic reactions, such as proteases, kinases and phosphatase, and further serve as intracellular biosensors that provide information about the physiological state of the cell.

In other preferred embodiments, the compositions of the present invention are useful as candidate agents in the form of random nucleic acids, cDNAs, cDNA fragments or genomic DNA fragments fused to rGFP or pGFP gene. These GFP fusions provide a basis for monitoring expression and localization of the candidate agent, and importantly serves as a scaffold for constraining the peptide for presentation in an biologically active form. In addition, the GFP moiety is useful as a rescue sequence and for pulling out cellular targets of the candidate agents.

In these embodiment, the methods outlined herein are used to screen for modulators of cellular phenotypes. Cellular phenotypes that may be assayed include, but are not limited to, cell apoptosis, cell cycle, exocytosis, cytokine secretion, cell adhesion, signal transduction, protein interaction, etc. As will be appreciated by those in the art, any number of cellular assays that rely on rGFP or pGFP and their variants can be developed.

In one preferred embodiment, the rGFP or pGFP can be used to evaluate, test and screen promoters. Thus, in this embodiment, the present invention provides compositions comprising a promoter of interest and a gene encoding a rGFP or pGFP. Alternatively, the compositions comprise a promoter operably linked to a gene of interest, a separation sequence, and a gene encoding rGFP or pGFP. Preferably, the promoter is not the native rGFP or pGFP promoter.

In a preferred embodiment, the fusion nucleic acids are used to screen for modulators of promoter activity. By "modulation" of promoter activity herein is meant increase or decrease in transcription of the fusion nucleic acid regulated by the promoter of interest. Various promoters of different organisms are amenable to analysis, including promoters of bacterial, yeast, worm, insect, plant, and mammalian cells. In mammalian cells, examples of relevant promoters are IL-4 inducible ε promoter, IgH promoter, NF-kβ regulated promoters, APC/β-catenin regulated promoters, myc regulated promoters, cell specific promoters (peripheral nervous system, central nervous system, kidney, skin, bone, lung, heart, liver, bladder, ovary, testes, colon, etc.), cytokine regulated promoters, stress regulated promoters (e.g., heat shock), circadian rhythm regulated promoters, and promoters regulating HIV viral gene expression and cell cycle genes. Preferred are promoters that regulate expression of signal transduction proteins, cell cycle regulatory proteins, oncogenes, or promoters which are themselves regulated by signal transduction pathways, cell cycle regulators, or other aspects of cell regulatory networks.

Candidate agents are contacted with the cells comprising the fusion nucleic acid and examined for effects on reporter gene expression (see for example, WO 99/58663, hereby expressly incorporated by reference). If the promoter is inducible, promoter is induced with appropriate stimulus or effector. Alternatively, the promoter is induced prior to addition of the candidate bioactive agents, or simultaneously. For example, for the IL-4 inducible ε promoter, addition of cytokine IL-4 or IL-13 to the cells (e.g., IL-4 of not less than 5 units/ml and at a preferred concentration of 200 units/ml) can induce transcription of the ε promoter. Screening of candidate agents affecting inducible expression of the reporter will allow identification of cellular targets involved in signal transduction events mediated by the cytokine.

To provide a more stringent selection for promoter regulators, the fusion nucleic may comprise a promoter, a rGFP or pGFP, a separation sequence, and a reporter/selection gene distinguishable from rGFP or pGFP. The GFP allows selection of cells expressing the fluorescent protein while the reporter/selection gene allows an additional basis for selecting cells. In one aspect, the reporter/selection gene may be a death gene that provides a nucleic acid that encodes a protein causing cell death. It is preferable that cell death require a two step process: expression of the death gene and induction of death phenotype by a signal or ligand. This two step process is desirable when the promoter being analyzed is constitutively active. For example, if the selection gene is a thymidine kinase (TK), the cells can be selected based on killing by gancyclovir since TK activity is needed for gancyclovir toxicity. Alternatively, the selection gene may encode the heparin binding epidermal growth factor (HBEGF) protein and the killing initiated by adding diptheria toxin. Thus, candidate agents that repress promoter activity are readily identified by selecting for cells that are resistant to cell death and lacking in GFP expression. The presence of a separation sequence, such as Type 2A, allows expression of both reporter and selection genes from a single transcript, thus providing a sensitive indicator of promoter activity. Verification of the presence of the death gene is preferred to keep the levels of false positives low; that is, cells that survive the screen should be due to the presence of an inhibitor of the promoter rather than a lack of the death gene.

In another preferred embodiment, inducible promoter may be linked to "one step" death genes (e.g., diptheria toxin A fragment). In this embodiment, the inducible promoter is leaky such that some small amount of death gene and the reporter protein (e.g., rGFP or pGFP) is expressed. The low level of reporter gene expression allows selection of cells containing the death gene to avoid false positives. To these cells, candidate agents are contacted and promoter induced to express the death gene. Selection of surviving cells enriches for those cells that contain agents inhibiting the promoter.

For examining promoters regulated by specific signal transduction pathways, cells capable of transducing the signal are used. For example, for IL-4 inducible ε promoter system, any cells that express an IL-4 receptor that transduces the IL-4 signal to the nucleus and alters transcription can be used. Suitable cells include, but are not limited to, human cells and cell lines that show IL-4/13 inducible production of germline ε transcripts, including, but not limited to, DND39 (see Watanabe, supra), MC-116, (Kumar, et al. (1990) Eur. Cytokine Netw. 1: 109), CA46 (Wang, et al. (1996) J. Natl. Cancer. Inst. 88: 956). As is noted herein, the ability of MC-116 and CA-46 cells to produce germline ε transcripts upon IL-4/13 induction was not known prior to the present invention. Thus, preferred embodiments provide for MC-116 and/or CA-46 cells comprising recombinant nucleic acid reporter constructs as outlined herein.

In another preferred embodiment, the fusion construct comprises an endogenous promoter and an exogenous rGFP or pGFP gene. By "endogenous" in this context means present within the host cell. In this regard, an exogenous rGFP, pGFP, or variants thereof is incorporated into the genome such that the reporter gene is under the control of the endogenous promoter. These constructions are desirable for examining and modulating the full range of endogenous regulation, particularly promoter control elements (e.g., enhancers, inhibitory elements, etc.) other than promoter fragment.

Generating the endogenous-exogenous fusion construct may proceed in any number of ways depending on the organism used. In one preferred embodiment, homologous recombination mechanisms present in different organisms provides the basis for inserting the exogenous reporter gene to form the fusion construct. That is, gene "knock-in" constructions are made, whereby an exogenous rGFP or pGFP gene as outlined herein is added, via homologous recombination, to the genome, such that the reporter gene is under the control of the endogenous promoter. Homologous recombination methods are well known in the art (see Westphal, et al. (1997) Current Biology 7: R530-R533 and references cited therein; Rothstein, R. (1991) Methods Enzymol. 194: 281-301; Kaur, R. (1997) Nucleic Acids Res. 251080-81; and Miller, J. H., In Short Course in Bacterial Genetics: A Laboratory Manual and Handbook for *Escherichia coli*. and Related Bacteria, Cold Spring Harbor Laboratory Press, Cold Spring Harbor, N.Y., 1992). These homologous recombination driven methods may use recA or recA type proteins to enhance the recombination process (see PCT US93/03868, hereby incorporated by reference).

In another preferred embodiment, the selection of the "knock ins" are done by FACS on the basis of incorporation of the rGFP or pGFP gene. Thus, in one aspect, a first homologous recombination event places a rGFP or pGFP gene into at least one allele of the cell genome. When the promoter is the IL-4 inducible promoter, a cell type that exhibits IL-4 inducible production of at least germline ε transcripts is preferred so that the cells may be tested by IL-4 inducible reporter gene expression. That is, transformed cells are selected by FACS for reporter gene expression upon treatment with IL-4. Suitable cells include, but are not limited to, human cells and cell lines that show IL-4/13 inducible production of germline ε transcripts. Preferably, once a first endogenous promoter has been combined with an exogenous reporter construct, a second homologous recombination event may be done, preferably using a second reporter gene different from the first, to target the other allele of the cell genome, and tested as above. Generally, IL-4 induction of the rGFP or pGFP genes will indicate the correct placement of the genes, which can be confirmed via sequencing such as PCR sequencing, or by Southern blot hybridization. In addition, preferred embodiments utilize pre-screening steps to remove "leaky" cells, i.e., those showing constitutive expression of the rGFP or pGFP gene.

In another preferred embodiment, endogenous exogenous fusion constructs are made via site specific recombination. In these embodiments, the site specific recombination sequence, such as loxP, is inserted into the desired site(s), preferably by homologous recombination, although random insertions are possible with other vectors depending on cell type being used (e.g., phage Mu, retroviral vectors). Following generation of cells containing the site specific sites, a vector comprising the rGFP or pGFP and an appropriately placed loxP site is introduced into the cell. Expressing the cre recombinase allows recombination between the loxP sites on the two separate nucleic acids, thus resulting in insertion of the vector into the chromosomally located loxP site.

As above, these cells are induced with the appropriate inducer if the endogenous promoter of interest is inducible and then contacted with candidate agents. When the cells comprise fusion nucleic acids expressing candidate agents comprising rGFP or pGFP fusion proteins, or candidate agents expressed from a fusion nucleic acid comprising a first gene of interest, a separation sequence, and a second gene of interest comprising a rGFP or pGFP, a reporter gene distinguishable from the rGFP or pGFP proteins is used to monitor promoter modulation. This strategy allows simultaneous monitoring of the expression of the candidate agent and the promoter.

In another preferred embodiment, the fusion nucleic acids comprising rGFP or pGFP and a weak promoter, or no promoter, are inserted into a host chromosome to scan for promoter elements on the host chromosome. In a preferred embodiment, this may be done conveniently by using a viral backbone for constructing the fusion nucleic acids. For example, in bacteria, the phage Mu systems allow random insertions into the host chromosome while in mammalian cells, retroviral viral vectors provide a suitable vehicle for inserting the fusion nucleic acids into the host chromosome. When retroviral vectors are used, SIN type vectors lacking viral promoters are preferred so that the reporter gene is transcribed or activated from endogenous promoters or promoter regulatory elements upon insertion of the viral DNA into the host chromosome. Expression of rGFP or pGFP indicates insertion near an endogenous promoter. Identifying cells expressing the reporter gene upon treatment with inducers allow identification of promoters regulated by the inducing agent. Cells comprising these insertions are contacted with candidate agents, for example, by expressing candidate nucleic acid or proteins in the cells. Those agents modulating promoter activity are identified based on expression of the rGFP or pGFP reporter.

In the endogenous-exogenous fusion constructs described above, the exogenous fusion nucleic acid used to monitor promoter activity may comprise a rGFP or pGFP, or a fusion nucleic acid comprising a first gene of interest, a separation sequence, and a second gene of interest comprising a rGFP or pGFP. The latter construct allows identifying cells based on expression of two reporter/selection genes if the first gene of interest encodes reporter gene distinguishable from rGFP or pGFP.

In addition, in a preferred embodiment, the fusion nucleic acids of the present invention may also contain site specific recombination sites for deleting or rearranging the fusion nucleic acids when introduced into a cell. As described above, these sequences may comprise loxP or flp sites flanking the nucleic acid segment to be rearranged. As is well known in the art, the sites are placed in an appropriate orientation so that either deletion or rearrangement (i.e., inversion) will occur upon contact of the sequences with a site specific recombinase. In a preferred embodiment, the site specific sequences flank the rGFP or pGFP gene or flank the fusion nucleic acid comprising a first gene of interest, a separation sequence, and a second gene of interest comprising rGFP or pGFP. Thus, deletion or rearrangement results in removal or rearrangement that prevents operable linkage of the promoter to the fusion nucleic acid to be expressed. In another preferred embodiment, the site specific sequences are orientated such that rearrangement results in operable linkage of the promoter on the expression vector or the endogenous promoter when rearrangement is induced by the recombinase. This may be desirable when examining promoters active at specific stages in cell development or in examining cell lineage.

In a preferred embodiment, the fusion nucleic acids of the present invention are used to identify candidate agents that alter a cellular phenotype. In these embodiments, the fusion nucleic acids of the present invention provide a way, among others, for detecting or monitoring a cellular phenotype, inducing a phenotype being examined, and measuring synthesis of a gene of interest, such as candidate agents to be screened.

Accordingly, in one preferred embodiment, the fusion nucleic acids of the present invention find use in screens for cells with altered exocytosis. By "alteration" or "modulation" in relation to exocytosis is meant a decrease or increase in amount or frequency of exocytosis in one cell compared to another cell, or in the same cell under different conditions. Often mediated by specialized cells, exocytosis is vital for a variety of cellular processes, including neurotransmitter release by neurons, hormone release by adrenal chromaffin cells (e.g., adrenaline) and pancreatic β-cells (e.g., insulin), and histamine release by B-cells.

Disorders involving exocytosis are numerous. For example, inflammatory immune response mediated by mast cells leads to a variety of disorders, including asthma and allergies. Therapy for allergy remains limited to blocking mediators released by mast cells (e.g., antihistamines) and non-specific anti-inflammatory agents, such as steroids and mast cell stabilizers. These treatments are only marginally effective in alleviating the symptoms of allergy. To identify cellular targets for drug design or candidate effectors of exocytosis, the fusion nucleic acids expressing GFP fusion proteins (e.g., fused to random peptides) or expressing gene of interest comprising candidate agents may be introduced into appropriate cells, for example mast cells, and selected for modulation of exocytosis by assaying for changes in cellular exocytosis properties under various conditions. For example, the cells may be examined in the presence or absence of physiological signals, such as $Ca^{+2}$, ionophores, hormones, antibodies, peptides, drugs, antigens, cytokines, growth factors, membrane potentials, cell-cell contacts, and the like. In other aspects, the measurements are taken under the same conditions for different cells. These cells are stimulated with appropriate inducer if exocytosis is triggered by an inducing signal. Alternatively, cells with an conditional mutation for exocytosis events are used in screens for candidate agents affecting exocytosis regulators.

In one preferred embodiment, the cells used for screening may be engineered to be defective in exocytosis. For example, cells may be transformed with a fusion nucleic acid expressing a conditional gene product whose expression under restrictive conditions produces an exocytosis defect. Alternatively, the fusion nucleic acid may express a dominant effect protein affecting exocytosis. Examples of these types of genes of interest are dynamin and Ese1, proteins involved in endocytosis but which indirectly affect exocytosis. Expression of temperature sensitive conditional mutants of dynamin or Ese1 in cells can induce endocytosis and exocytosis defects (Damke, H. et al. (1995) J. Cell Biol. 131: 69-80; Damke, H. et al. (1994) J. Cell Biol. 127: 915-934; Sengar, A. S. (1999) EMBO J. 18: 1159-1171). Thus, in a preferred embodiment, the cell may comprise a fusion nucleic acid containing a conditional dynamin gene, a separation sequence, and reporter gene comprising rGFP or pGFP. Expression of dynamin gene under restrictive condition disrupts endocytosis, thus resulting in deficiency in exocytosis. Candidate agents are screened under the restrictive condition for activation of exocytosis. When candidate agents comprise GFP fusion proteins (e.g., random peptide or cDNA GFP fusions), or are expressed as a first gene of interest, a separation sequence, and a second gene of interest comprising rGFP or pGFP, the reporter gene chosen is distinguishable from the expressed GFP.

Assays for changes in exocytosis may comprise sorting cells in a fluorescence cell sorter (FACS) by measuring alterations of various exocytosis indicators, such as light scattering, fluorescent dye uptake, fluorescent dye release, granule release; targeting and quantity of granule specific proteins (see for example, WO 99/54494); and capacitance measurements. Use of combinations of indicators reduces background and increases specificity of the sorting assay.

Exocytosis assays based on changes in light scattering properties, including use of forward and side scatter properties of the cells, are indicative of size, shape, and granule content of the cell. Multiparamter FACS selections based on light scattering properties of cells are well known in the art (see Paretti, M. et al. (1990) J. Pharmacol. Methods 23: 187-94; Hide, I. et al. (1993) J. Cell Biol. 123: 585-93).

Assays based on uptake of fluorescent dyes reflect the coupling of exocytosis and endocytosis. In these assays, the endocytosis levels indirectly reflect exocytosis levels since the cell attempts to maintain cell volume and membrane integrity as the amount of cell membrane rapidly changes when secretory vesicles fuse with the cell membrane. Preferred fluorescent dyes include styryl dyes, such as FM1-43, FM4-64, FM14-68, FM2-10, FM4-84, FM1-84, FM14-27, FM14-29, FM3-25, FM3-14, FM5-55, RH414, FM6-55, FM10-75, FM1-81, FM949, FM4-95, FM4-59, FM9-40, and combinations thereof. Styryl dyes such as FM1-43 are only weakly fluorescent in water but highly fluorescent when associated with a membrane such that dye uptake by endocytosis is readily discernable (Betz, et al. (1996) Current Opinion in Neurobiology 6: 365-371; Molecular Probes, Inc., Eugene, Oreg., "Handbook of Fluorescent Probes and Research Chemicals", 6th Edition, 1996, particularly, Chapter 17, and more particularly, Section 2 of Chapter 17, hereby incorporated herein by reference). Useful solution dye concentration is about 25 to 1000-5000 nM, with from about 50 to about 1000 nM being preferred, and from about 50 to 250 being particularly preferred.

Exocytosis assays based on fluorescent dye release rely on release of dye that is taken up passively or actively endocytosed by the cell. Release of dyes taken up by a cell results in decreased cellular fluorescence and presence of the dye in the cellular medium, thus providing two basis for measuring dye release. For example, styryl dye taken up into cells by endocytosis is released into the cellular media by exocytosis, resulting in decreased cellular fluorescence and presence of the dye in the medium. Another dye release assay uses low pH dyes, such as acridine orange, LYSOTRACKER™ red, LYSOTRACKER™ green, and LYSOTRACKER™ blue (Molecular Probes, supra), which stains exocytic granules when dye is internalized by the cell.

Alternatively, the exocytosis assay relies on release of molecules contained in the granule. In one aspect, these may be proteins or detectable biomolecules, especially enzymes such as proteases and glyocosidases, released as part of the exocytic process. Many enzymes are inactive within the granule because of low pH in the vesicle but become activated when exposed to the extracellular media at physiological pH. Preferred granule enzymes include but are not limited to chymase, tryptase, arylsulfatase A, β-hexosaminidase, β-D-galactosidase, and the like. Enzyme activities are measurable using chromogenic or fluorogenic substrates. The generation of a signal via cleavage of a chromogenic or fluorogenic substrate is related to the amount of enzyme present, and thus a measure of exocytosis. If the exocytosis is inducible, an inducing signal is used.

The fluorogenic substrate may be a substrate that precipates upon action by the enzyme. For example, substrate for glucouronidase, such as ELF-97 glucuronide, precipitate through action of released enzyme. Other precipitating substrates are well known in the art and commercially available (see for example, Molecular Probes, supra, particularly Chapter 10, more particularly Section 2 or Chapter 10, and referenced related chapters). When the granule specific proteins comprises biological mediators released during exocytosis, such as serotonin, histamine, heparin, hormones, etc., these granule proteins may be identified using specific antibodies.

Preferential staining of exocytic granules when vesicles fuse with the cell membrane provides an additional assay for measuring exocytosis. Annexin V, which binds phospholipid phosphatidyl serine in a divalent ion dependent manner, specifically binds to exocytic granules present on the cell surface but fails to bind internally localized exocytic granules. This property of Annexin provides a basis for determining exocytosis by the level of Annexin bound to cells. Cells show an increase in Annexin binding in proportion to the time and intensity of the exocytic response. Annexin is detectable directly by use of fluorescently labeled Annexin derivatives (e.g., FITC, TRITC, AMCA, APC, or Cy-5 fluorescent labels), or indirectly by use of Annexin modified with a primary label (e.g., biotin), which is detected using a labeled secondary agent that binds to the primary label (e.g., fluorescently labeled avidin). In general, changes of 25% from baseline are preferred, with at least about 50% being more preferred, at least about 100% being particularly preferred and at least about 500% being especially preferred. Baseline as used herein means the amount of Annexin binding as compared to binding under a second state or different cell.

Alternatively, in a preferred embodiment the exocytosis indicators are engineered into the cells. For example, recombinant proteins comprising fusion proteins of a granule specific, or a secreted protein, and a reporter molecule are expressed in a cell by transforming or transfecting the cells with a fusion nucleic acid encoding the fusion protein. This is generally done as is known in the art, and will depend on the cell type. Generally, for mammalian cells, retroviral vectors, including those of the present invention, are preferred for delivery of the fusion nucleic acid. Preferred reporter molecules include, but are not limited to, *Aequoria victoria* GFP, *Renilla muelleri* GFP, *Renilla reniformis* GFP, *Renilla ptilosarcus*, GFP, BFP, YFP, and enzymes including luciferases (e.g., *Renilla*, firefly etc.) and β-galactosidases. Presence of the granule protein-reporter fusion construct on the cell surface or presence of secreted protein-reporter fusion construct in the medium indicates the level of exocytosis in the cells. In one preferred embodiment, cells are transformed with vectors expressing a fusion protein comprising a granule specific protein, such as synaptobrevin (VAMP) or synaptotagmin, fused to a GFP reporter molecule. The cells are monitored for localization of the fusion protein to the cell membrane. By incorporating a separation sequence and a second gene of interest comprising a distinguishable reporter or selection gene, cells expressing the fusion protein are readily selected. Moreover, the second gene of interest provides an internal standard to measure level of fusion protein content in the cell. Candidate agents, for example candidate nucleic acids and candidate peptides, introduced into these transformed cells are tested for their ability to affect distribution of the fusion protein. Alternatively, the fusion protein is detected, directly or indirectly, using an antibody.

In another preferred embodiment, the methods are used to examine cell cycle regulation. Complicated regulatory pathways control cell cycle progression. These regulatory molecules include, among others, cellular receptors, cyclins, cyclin dependent kinases, cyclin dependent kinase inhibitors, cell division cycle phosphatases (CDC), ubiquitin ligases and ubiquitin mediated proteases, tumor suppressor proteins (e.g., cell cycle checkpoint regulators), and transcription factors. Cell cycle regulation is implicated in tumor formation and immune system regulation. The compositions of the present invention are used to identify candidate agents producing an altered cell cycle phenotype, such as activation or suppression of cell cycle checkpoint. In one aspect, the candidate agents are fusion nucleic acids expressing candidate peptides fused to rGFP or pGFP. These candidate agents are introduced into cells in the form of vectors, preferably retroviral vectors when mammalian cells are used. In another aspect, the candidate agents are nucleic acids, peptides, cDNAs, and genomic DNAs expressed as a gene of interest. When these candidate agents comprise peptides and proteins, the fusion nucleic acid may further comprise a separation sequence and a rGFP or pGFP to produce separate proteins and to monitor expression of the candidate agent.

In another preferred embodiment, the fusion nucleic acids of the present invention is used to express cell cycle regulators or express mutants of cell cycle regulatory proteins which produce a cell cycle phenotype in the cells. In one aspect, the fusion nucleic acids may comprise a gene of interest comprising a cell cycle regulator, which induces a cell cycle phenotype when expressed. A separation sequence and a reporter gene, such a rGFP or pGFP allows monitoring expression of the gene of interest. When the candidate agent comprises rGFP or pGFP fusion proteins or when the candidate agent is expressed from a fusion nucleic acid comprising a first gene of interest, a separation sequence, and a second gene of interest comprising rGFP or pGFP, a distinguishable reporter gene (e.g., blue fluorescent protein) is used to monitor expression of the cell cycle regulator. Candidate agents are then introduced into the cells to identify those agents altering the induced cell cycle phenotype.

The cell cycle may be examined by a variety of methods well known to those skilled in the art (see for example, US 2001/0003042, which is expressly incorporated by reference). The assays permit determining whether cell cycle arrest occurs at a particular cell cycle stage (i.e., cell proliferation assays) and at a specific cell stage (i.e., cell phase assays). By measuring or assaying one or more of these parameters, it is possible to detect alterations in cell cycle regulation and also alteration of different steps of the cell cycle regulatory pathway. By "alteration" and "modulation" as used herein can include both increases and decreases in the cellular parameter being measured. In a preferred embodiment, the alteration results in a change in the cell cycle of a cell, i.e., proliferating cell arrests in any one of the phases, or an arrested cell moves out of its arrested phase to progress into cell cycle as compared to another cell or the same cell under different conditions. Alternatively, the progress of a cell through any particular phase may be altered; that is, there may be an acceleration or delay in the time for the cell to move through a particular growth phase.

In a preferred embodiment a proliferation assay is used. By "proliferation assay" herein is meant an assay that allows determining whether a cell population is proliferating, i.e., replicating or not replicating. In one preferred embodiment, the proliferation assay is a dye exclusion assay. A dye exclusion assay relies on uptake of dye by cells and subsequent dilution of the dye by succeeding rounds of cell division. Generally, the introduction of dye may be done in several ways. Either the dye cannot passively enter the cells (e.g., dye is charged), and the cells are induced to take up the dye. Alternatively, the dye passively enters the cells and is subsequently modified to limit diffusion out of the cells. For example, Molecular Probes CellTracker dyes comprise chloromethyl derivatives of fluorescent compounds that freely diffuse into cells and are subsequently modified by glutathione S-transferase, which renders the dyes membrane impermeant. Suitable inclusion dyes include, but are not limited to, CellTracker dyes including, but not limited to Cell-Tracker Yellow-Green, CellTracker Green, CellTracker Orange, PKH26 (Sigma), and others well known in the art (see Molecular Probes Handbook, supra).

In another preferred embodiment, the proliferation assay is an antimetabolite assay. In general, antimetabolite assays are most useful when agents causing cell cycle arrest at G1 or G2 resting phase is desired. In an antimetabolite assay, the use of a toxic metabolite that will kill dividing cells will result in survival of only those cells that are not dividing. Suitable antimetabolites include, but are not limited to, standard chemotherapeutic agents such as methotrexate, cisplatin, taxol, hydroxyurea, and nucleotide analogs (e.g., AraC). In addition, antimetabolite assays may include the use of genes that cause cell death upon expression.

The concentration at which the antimetabolite is added will depend on the toxicity of the particular antimetabolite, and will be determined as is known in the art. The antimetabolite is added and the cells are generally incubated for some period of time; again, the exact period of time will depend on the characteristics and identity of the antimetabolite as well as the cell cycle time of the particular cell population. Generally, the incubation time is sufficient for at least one cell division. In a preferred embodiment, at least one proliferation assay is done, with more than one being preferred.

In another preferred embodiment, either after or simultaneously with one or more of the proliferation assays outlined above, at least one cell phase assay is done. By "cell phase" assay herein is meant an assay that determines at which cell phase cell cycle arrest takes place, i.e., M, G1, S, or G2.

In one preferred embodiment, the cell phase assay is a DNA binding assay. When inside the cell, the dye binds to DNA, generally by intercalation, although in some cases, the dyes can be either major or minor groove binding compounds. Thus, the amount of dye is directly correlated to the amount of DNA in the cell, which varies with cell phase; G2 and M phase cells have twice the DNA content of G1 phase cells, and S phase cells have an intermediate amount. Suitable DNA binding dyes include, but are not limited to, Hoechst 33342 and 33258, acridine orange, 7AAD, LDS, 751, DAPI, and SYTO 16 (see Molecular Probes Handbook, supra, Chapters 8 and 16 in particular).

In general, the DNA binding dyes are added in concentrations ranging from about 1 µg/ml to about 5 µg/ml. The dyes are added to the cells and allowed to incubate for some period of time; the length of time will depend in part on the dye chosen. In one embodiment, measurements are taken immediately after addition of the dye. The cells are then sorted as outlined below, to create populations of cells that contain different amounts of dye, and thus different amounts of DNA; in this way, cells that are replicating are separated from those that are not. As will be appreciated by those in the art, in some cases, for example when screening for anti-proliferation agents, cells with the least fluorescence (and thus a single copy of the genome) can be separated from those that are replicating since the replicating cells contain more than a single genome of DNA. Alterations are determined by measuring the fluorescence at either different time points or in different cell populations, and comparing the determinations to one another or to standards.

In a preferred embodiment, the cell phase assay is a cyclin destruction assay. In this embodiment, prior to screening, and generally prior to the introduction of a candidate bioactive agent, a fusion nucleic acid is introduced to the cells. The fusion nucleic acid expresses a fusion protein comprising a cyclin destruction box and a detectable molecule. "Cyclin destruction boxes" are known in the art and are sequences that cause destruction via the ubiquitination pathway of destruction box containing proteins during particular cell phases. That is, for example, G1 cyclins may be stable during G1 phase but degraded during S phase due to the presence of a G1 cyclin destruction box. Thus, by linking a cyclin destruction box to a detectable molecule, for example green fluorescent protein, the presence or absence of the detectable molecule can serve to identify the cell phase of the cell population. In a preferred embodiment, multiple boxes are used, preferably each fused to distinguishable fluorescent proteins, such that detection of the cell phase can occur.

A number of cyclin destruction boxes are known in the art. For example, cyclin A has a destruction box comprising the sequence RTVLGVIGD (SEQ ID NO: 75) while the destruction box of cyclin B1 comprises the sequence RTALGDIGN (SEQ ID NO: 65) (Glotzer et al. (1991) Nature 349: 132-138. Other destruction boxes are known as well: YMTVSI-IDRFMQDSCVPKKMLQLVGVT (SEQ ID NO: 76) (rat cyclin B); KFRLLQETMYMTVSIIDRFMQNSCVPKK (SEQ ID NO: 77); RAILIDWLIQVQMKFRLLQET-MYMTVS (SEQ ID NO: 78) (mouse cyclin B1); DRFLQAQLVCRKKLQVVGITALLLASK (SEQ ID NO: 79) (mouse cyclin B2); and MSVLRGKLQLVGTAAMLL (SEQ ID NO: 80) (mouse cyclin A2). These cyclin destruction boxes are operably linked to nucleic acid encoding a detectable molecule to generate fusion proteins, as described above.

In a preferred embodiment, the cell cycle analysis further comprises a cell viability assay to ensure that a lack of cellular change is due to experimental conditions. Various suitable viability assays include, but are not limited to, light scattering, viability dye staining, and exclusion dye staining.

In a preferred embodiment, the viability assay is a light scattering assay, which is well known in the art. Cells have particular forward and side (90 degree) scatter properties representing the size, shape and granule content of the cells. Briefly, the scatter properties are affected by two parameters: side scatter of DNA condensation in dead and dying cells and the forward scatter affected by the state of membrane blebbing. Changes in the intensity of light scattering or the cell refractive index indicate alterations in viability. In a preferred embodiment, evaluating a live cell population of a particular cell type provides characteristic forward and side scatter properties for comparison to other cell populations.

In another preferred embodiment, the viability assay uses a viability dye. These dyes stain dead or dying cells but not growing cells. For example, Annexin V displays divalent ion dependent binding to the phospholipid phosphatidylserine, whose presence on the cell surface is an early signal of apoptosis. Other suitable viability dyes include, but are not limited to, ethidium homodimer-1, DEAD Red, propidium iodide, SYTOX Green, etc., and others known in the art (see Molecular Probes, supra "Apoptosis Assay," pg 285, and Chapter 16, hereby incorporated by reference). Preferably, the viability dye concentration used is about 100 ng/ul to about 500 ng/ml, and more preferably, from about 500 ng/ml to about 1 ug/ml, most preferably about 500 ng/ml to about 1 ug/ml, and from about 1 ug/ml to about 5 ug/ml being particularly preferred. In a preferred embodiment, the dye is directly labeled. For example, Annexin may be labeled with a fluorophore such as fluorescein isothiocyanate (FITC), Alexa dyes, TRITC, AMCA, APC, tri-color Cy-5, and others known in the art. In an alternative preferred embodiment, the viability dye is labeled with a first label (e.g., hapten or biotin), and a secondary fluorescent label is used to detect the first label.

In another preferred embodiment, the viability assay is a dye exclusion assay. Exclusion dyes rely on exclusion of the dye from living cells but entry into permeable dead or dying cells. Generally, the exclusion dyes bind to DNA and fluoresces but fluoresces poorly when not bound to DNA. Alternatively, exclusion dyes are detected using a secondary label. Preferred exclusion dyes include, but are not limited to ethidium bromide, ethidium bromide homodimer-1, propidium iodide, SYTOX Green, calcein AM, BBCECF AM, fluoresceine diacetate, TOTO, and TO-PRO (see Molecular Probes, supra) and others known in the art. These dyes are added to cells at a concentration of about 100 ng/ml to about 500 ng/ml, more preferably, about 500 ng/ml to about 1 ug/ml, and most preferably, from about 0.1 ug/ml to about 5 ug/ml, with about 0.5 ug/ml being particularly preferred. In addition, other cell viability assays are used, including assays that measures extracellular (e.g., proteases) or intracellular (e.g., mitochondrial enzymes) enzymes of live and dead cells.

In a preferred embodiment, at least one cell viability assay is run, with at least two different cell viability assays being preferred. When only one viability assay is run, a preferred embodiment uses light scattering assays (both forward and side scatter). When two viability assays are run, preferred embodiments use light scattering and dye exclusion or light scattering and viability dye staining. In some cases, all three assays are used.

Thus, in a preferred embodiment, cell cycle assays comprise sorting cells in a FACS by assaying several different cellular parameters, including, but not limited to, cell viability, cell proliferation, cell phase, and appropriate combinations thereof. The results from one or more of the assays are compared to cells not exposed to the candidate bioactive agent.

In the present invention, assays for other cellular assays are combined with the cell cycle assay. These include cellular parameters of cell shape, redox state, DNA content, nucleic acid sequence, chromatin structure, RNA content, total protein, antigens, lipids, surface proteins, intracellular receptors, oxidative metabolism, DNA synthesis, degradation, intracellular pH, etc. In a preferred embodiment, each of these measurements is determined simultaneously or sequentially using FACS (i.e., multiparameter FACS). By using more than one parameter to detect the cell cycle, background is reduced and specificity is increased. In one aspect, the cells are sorted at high speeds, for example greater than about 5,000 sorting events/s, with greater than about 10,000 sorting events/s being preferred, and greater than about 25,000 sorting events/s being particularly preferred, with speeds of greater than about 50,000 to 100,000 being especially preferred.

In another preferred embodiment, the present methods are useful in cancer applications. The ability to rapidly and specifically kill tumor cells is a cornerstone of cancer chemotherapy. In general, using the methods of the present invention, the fusion nucleic acids of the present invention can be introduced into any tumor cell, primary or cultured, to identify bioactive agents that can induce apoptosis, cell death, loss of cell division, or deceased cell growth. The methods of the present invention can be combined with other cancer therapeutics (e.g., drugs or radiation) to sensitize the cells, and thus induce rapid and specific apoptosis, cell death or decreased growth after exposure to secondary agent. Similarly, the present invention may be used in conjunction with known cancer therapeutics to screen for agonists to make the therapeutic treatments more effective or less toxic. This is particularly preferred when the chemotherapeutic agent is difficult or expensive to produce, such as taxol.

In a preferred embodiment, the present invention is used to identify candidate agents that alter the transformed phenotype of cancer cells. It is well known that oncogenes such as v-Abl, v-Src, v-Ras, and others induce a transformed phenotype leading to abnormal cell growth when transfected into certain cell types. Loss of growth control is also a major problem associated with metastasis of transformed cells. Thus, in a preferred embodiment, susceptible, non-transformed cells can be transformed with these oncogenes, and then candidate agents introduced into these cells to select for bioactive agents which reverse or correct the transformed state.

One of the identifying features of oncogenic transformation is a loss of contact inhibition and the ability to grow in soft-agar. This characteristic provides one method for identifying candidate agents that alter the transformed phenotype of tumor cells. In this assay, transforming viruses are constructed containing v-Abl, v-Src, or v-Ras, a separation sequence, and a puromycin selection gene. Following introduction of the viral constructs into NIH3T3 cells, the cells are subjected to puromycin selection. The NIH 3T3 cells hypertransform and detach from the plate, which allows their removal by washing with fresh medium. This feature can serve as a basis for a screen since cells that express a bioactive agent altering this phenotype will remain attached to the plate and form colonies.

Similarly, the growth and/or spread of certain tumor cell types is enhanced by stimulatory responses from growth factors and cytokines (e.g., PDGF, EGF, Heregulin, and others), which bind to receptors on the surfaces of specific tumors. In a preferred embodiment, the present invention is used to identify candidate agents capable of blocking the ability of growth factors or cytokines to stimulate the tumor cell. This screen comprises introducing the fusion nucleic acids expressing candidate agents followed by selecting for agents that block the binding, signaling, phenotypic and/or functional responses to these tumor cells to the subject growth factor or cytokine.

Similarly, the spread of cancer cells by tumor cell invasion or metastasis presents a significant problem in success of cancer therapies. The ability to restrict or inhibit the migration of specific tumor cells would provide a significant advance in the therapy of cancer. Tumor cells known to have high metastatic potential can have candidate agents introduced into them, and agents selected that inhibit migrative or invasive activity of the tumor cells. The present invention provides compositions for following the migration of cells, for example by expressing rGFP or pGFP in cells and examining invasive activity. Alternatively, the rGFP or pGFP fusion proteins are used to monitor cellular components involved in cell migration, such as cellular actin or focal adhesion proteins. Candidates agents may be introduced into these cells to identify agents that affect the invasive or metastatic properties of the tumor cells. These and other particular applications of inhibition of metastatic phenotype could allow specific inhibition of metastasis. This may include, for example, candidate agents that upregulate metastasis suppressor gene NM23, which codes for a dinucleoside diphosphate kinase. Peptides that counteract oncogenes, such s v-Mos, v-Raf, a-Raf, v-Src, v-Fes, and v-FMS, or inhibit the release or activity of matrix metalloproteinases would also act as anti-metastatic agents.

In a preferred embodiment, the present invention finds use in immunologic and inflammatory applications. Selective regulation of T lymphocytes is a desired goal for modulating immune mediated diseases. Thus, candidate agents of the present invention can be introduced into specific T-cell subsets (TH1, TH2, CD4+, CD8+, etc.) and examined for characteristic responses, for example cytokine generation, cytotoxicity, proliferation, and others. Agents can be selected that increase or decrease the known T-cell physiologic response. For monitoring these responses, the present invention may also be used as markers of physiologic response, for example by fusing rGFP or pGFP operably fused to promoters of cytokines that are regulated as part of the immune response. Candidate agents that affect regulation of the cytokine promoters can be screened on basis of expression of rGFP or pGFP. These approaches will be useful in any number of conditions, including: 1) autoimmune disease states where inducing tolerant state is desirable; 2) allergic diseases where decreasing the stimulation of IgE producing cells is desirable (e.g., blocking release from T-cell subsets of specific B-cell stimulating cytokines that induce switch to IgE production); 3) transplantation of organs where it is desirable to induce selective immunosuppression or prolong functioning of the transplanted organ; 4) in lymphoproliferative states for inhibiting growth or to sensitize a specific T-cell tumor to chemotherapy and/or radiation; 5) in tumor surveillance for inhibiting the elimination of cytotoxic T-cells via Fas ligand bearing tumor cells; and 6) in T-cell mediated autoimmune or inflammatory diseases such a rheumatoid arthritis, multiple sclerosis, inflammatory bowel disease, myasthenia gravis, systemic lupus erythematosus, early onset diabetes, etc.

In a preferred embodiment, the present invention is applicable in selective modulation of B-cell response. Activation of B-cells initiates various facets of humoral immunity, including immunoglobulin synthesis and antigen presentation by B-cells. Activation is mediated by engagement of the B-cell receptor (BCR), for example by binding of anti-IgM F(ab') fragments. Activation induces several signal transduction pathways leading to various B cell responses, including apoptosis, expression of cell surface marker CD69, and modulation of IgH promoter activity. Thus, in a preferred embodiment, candidate agents comprising the fusion nucleic acids of the present invention are introduced into appropriate B-cell lines, such as Ramos Human B-cell lines, M12.4, etc., to identify candidate agents affecting the signaling pathways activated by B-cell receptor engagement. The assay may comprise determining the level of CD69 cell surface marker (e.g., by fluorescently labeled anti-CD69 antibody and FACS selection of cells expressing high levels of CD69) or inhibition of apoptotic pathway (i.e., inhibition of cell death) following receptor activation. In one aspect, the candidate agents may be fusion nucleic acids expressing candidate peptides fused to rGFP or pGFP. These candidate agents are introduced into cells in the form of vectors, preferably retroviral vectors when mammalian cells are used. In another aspect, the candidate agents are nucleic acids, peptides, cDNAs, and genomic DNAs expressed as a gene of interest using the fusion nucleic acids described herein.

In another aspect, the present invention finds use as indicators of B-cell receptor mediated signal transduction. An IgH promoter may be operably linked to a rGFP or pGFP, which allows monitoring of BCR activation by providing a measure of IgH promoter activity. For example, the promoter reporter construct may comprise a fusion nucleic acid comprising a first gene of interest comprising a HBEGF, a Type 2A separation sequence, and a second gene of interest comprising rGFP or pGFP fused to a PEST sequence. Candidate agents are introduced into cells carrying this construct to identify agents that activate or suppress BCR mediated signal transduction, as reflected in changes in IgH promoter activity. Cells that survive exposure to diptheria toxin and/or have low levels of GFP expression will have low IgH promoter activity. Expression of the candidate agents may be under the control of an inducible promoter, such as tetP, thus limiting any detrimental effect of constitutively expressing candidate agents.

In a preferred embodiment, the present invention is used in infectious disease applications. Viral pathogens can produce chronic or acute infections leading to severe, disabling health effects, and death. Pathogenic viruses, such as human immunodeficiency virus, cytomegalovirus, leukemia virus, hepatitis virus, herpes virus, among others, are epidemic throughout the world. There is a need for understanding the infection process and identifying agents affecting propagation of the virus. In a preferred embodiment, the present invention is used to follow and track virus infection of cells. This is done in a number of ways. In one aspect, rGPF or pGFP are fused to a protein synthesized by the pathogenic organism. For viruses, fusions may be made to viral capsid or envelope proteins since these proteins can tolerate substantial modifications and still be incorporated into the viral particle. The fusions allow monitoring of infected cells, tracking of synthesized viral particle in the cell, and determining the presence of viral particles extruded from the cell. Other viral structural proteins suitable for fusions include the tegument proteins, which forms a structure generally located between the capsid and the envelope. Alternatively, the fusion nucleic acid comprising rGFP or pGPF gene is inserted into the viral genome, for example by homologous recombination, such that expression is driven by a viral promoter. Viral infection of cells results in expression of the reporter molecule, thus allowing monitoring of the infection process.

Analogously, cell lines are constructed in which a viral promoter is operably linked to a fusion nucleic acid comprising rGFP or pGFP. Upon infection of the cell by a virus, the viral promoter is activated resulting in fluorescent reporter gene expression. Consequently, expression of the GFP provides a measure of viral infection. A variety of viral promoters may be used. These may include immediate early gene promoter of many viruses or the viral promoters present on the long terminal repeats of pathogenic retroviruses (e.g., HIV). Cellular promoters modulated by viral infection may also be used.

The modified viruses and cells containing the described fusion nucleic acids are then used to identify candidate agents capable of affecting the infection process, for example, agents capable of inhibiting viral synthesis. Candidate agents are contacted with the cells and infected with the modified viruses. Candidate agents that lower the amount of virus produced or affect the promoters regulated by the infection process can be identified. When the candidate agents are the part of a fusion nucleic acid comprising rGFP or pGFP, the reporter gene selected for tracking and examining the infection process is a reporter distinguishable from rGFP or pGFP.

Many cellular pathogens are known to exist intracellularly. For example, mycobacteria, *rickettsia, salmonella, pneumocystis, yersinia, leishmania, Trypanosoma cruzi*, and the like can persist and replicate within cells such as macrophages and lymphocytes. In a manner similar to tagging pathogenic viruses described above, the fusion nucleic acids comprising rGFP or pGFP are used to mark or tag the pathogenic organism. As with viruses, marking or tagging these non-viral entities may be done in a number of ways. In one aspect, a fusion nucleic acid comprising a promoter active within the organism, such as a promoter that regulates expression of a protein required for infection, is operably linked to fusion nucleic acids comprising rGFP or pGFP. These constructs are inserted into the organism by various methods, for example by homologous recombination. Alternatively, the expression vectors may be maintained extrachromosomally by expression of a selection gene followed by treatment of the organism under selection conditions.

These marked or tagged organisms are used to infect appropriate cells or host organisms. The infection process may be tracked by monitoring expression of the reporter gene. Cells harboring the marked pathogens are readily identified. Candidate agents are contacted with these cells to identify agents that affect the infection process. Bioactive candidate agents may be selected for their ability to eliminate or kill the intracellular organisms, similar to the antibiotic peptide maganin. Other assays include selecting for agents that prevent initial infection, confer resistance to infection of the host cell, inhibit replication of the pathogen, or increase susceptibility of infected cells for destruction by host defense mechanisms (e.g, immune response).

For example, some viruses use cellular receptors and receptor complexes to bind and enter cells. For instance, HIV binds CD4 complexes, coroviruses bind CD13, and measles virus binds CD44 receptors to infect cells. It is desirable to identify agents that block viral infection in cells permissive for viral infection. In a specific example, it is known that entry of HIV-1 into cells requires CD4 and a co-receptor, which can be one of several seven transmembrane G-protein coupled receptors. In the case of macrophages, the co-receptor required for HIV infection is CCR-5. Individuals homozygous for a mutant allele of CCR-5 are resistant to HIV infection, and natural ligands of CCR-5, for example, CC chemokines RANTES, MIP1a and MIP1b can confer $CD8^+$ mediated resistance to HIV infection. Thus, agents that inhibit interaction between the CD4/CC5 receptor complex and HIV are desirable. In a preferred embodiment, the agents are inserted into the membrane and displayed extracellularly. In one aspect, a library of candidate peptides may comprise an epitope tagged, glycine-serine tethered peptides, which is a library of cyclized peptides of the general sequence CXXXXXXXXXXC or C—$(X)_n$—C, where C is cysteine and X is any amino acid. Cells expressing the CD4/CCR-5 complex are contacted with a library of the candidate peptide, and infected with the viruses described above. Cells that are not infected with viruses are identified by FACs and the candidate agent conferring resistance to infection identified. These agents are then further assayed for their ability to inhibit viral infection.

In another preferred embodiment, the present invention is used to find candidate agents affecting separation sequences used in various biological processes, including, but not limited to, cell death, viral pathogenesis, expression of cellular genes resulting in cell disease states, processing of cellular proteins, mechanism of action of bacterial toxins (e.g., botulinum toxin), and the like. In one aspect, when the separation sequences are protease recognition sequences, the fusion nucleic acids of the present invention are used to express substrates to detect protease activity, as described above. The substrates comprise fusions of protease recognition sequences to rGFP or pGFP. In another embodiment, the protease substrates are based on rGFP or pGFP linked to another fluorescent protein via a protease recognition sequence to generate substrates capable of undergoing FRET. Preferably, the substrates are codon optimized for the organism in which the substrates are expressed to maximize the signal. The protease site sequences include, among others, those recognized by caspase proteases; viral proteases involved in polyprotein processing, for example the HIV protease; proteases of bacterial toxins (e.g, botulinum toxin); proteases that process cellular proteins, especially those related to disease states (e.g., secretase processing of β-amyloid and Notch proteins; cathepsins, etc.); proteases regulating cell adhesion (e.g., metalloproteases associated with extracellular matrix); proteases involved in blood coagulation, inflammation and wound healing; tumor cell associated proteases; and the like. Preferably, the protease substrates are codon optimized for efficient expression in the subject organism.

In a preferred embodiment, the present invention finds applications in drug resistance or drug toxicity mechanism. Development of drug resistance in a variety of cell types limits the effectiveness of drug therapies. For example, multi drug resistance in tumor cells leads to selection of drug resistant tumor cells, which lead to relapse, morbidity, and increased mortality in cancer patients. Thus, in a preferred embodiment, fusion nucleic acids expressing candidate agents are introduced into drug resistant cells, either primary or cultured. Agents are identified that confer drug sensitivity when cells are exposed to a drug or combinations of drugs. Cells may be selected based on onset of apoptosis, changes in membrane permeability, release of intracellular ions, and release of fluorescent markers. Cells in which multi-drug resistance involves transporters can be preloaded with fluorescent transporter substrates, and selection carried out for candidate agents which block normal efflux of fluorescent drugs from these cells. Screening of candidate agents affecting drug resistance is well suited for poorly characterized mechanisms of resistance. Identifying candidate agents that increase susceptibility of these cells to drugs may provide a basis for identifying the cellular targets and for rational design of peptide inhibitors of drug resistance pathways.

In another aspect, the present invention is used to identify cellular targets that regulate synthesis of drug resistance proteins at the transcriptional or translational levels. In a preferred embodiment, promoters of drug resistance proteins, such as multi-drug resistance transporters, are operably linked to fusion nucleic acids comprising rGFP or pGFP. Candidate agents, such as a library of small molecules, random peptides, cDNAs, or genomic DNAs, are introduced into cells and screened for their ability to regulate drug resistance protein gene transcription. Candidate agents that activate or inhibit transcription are identified and used to design other inhibitors or identify the cellular targets of the candidate agents.

In another preferred embodiment, the fusion nucleic acids of the present invention are used to confer a drug resistance phenotype in cells by expressing drug resistance proteins, for example multi-drug resistance transporters (e.g., P-glycoproteins). The drug resistance protein may be expressed from a fusion nucleic acid comprising a first gene of interest, a separation sequence, and a second gene of interest where at least one of the genes of interest is the drug resistance gene and the other gene of interest is a reporter gene, such as rGFP or pGFP for monitoring expression. Cells expressing these fusion nucleic acids are contacted with candidate agents and screened for their ability to reduce drug resistance (i.e., increase drug sensitivity).

In a preferred embodiment, the present invention is useful in identifying candidate agents that bind specific cells, tissues and organs. Cells expressing libraries of candidate agents comprising rGFP or pGFP are contacted with cells or introduced into an organism. Candidate agents that bind to specific cells are selected. These bioactive candidate agents are useful for targeting coupled antibodies, enzymes, drugs, imaging agents, and the like to particular cells or organs.

In a preferred embodiment, the present invention provides compositions and methods utilizing rGFP and/or pGFP and a chip device comprising integrated photodetectors at individual loci. The method may be practiced with any suitable chip device that includes an electronic circuit capable of reading the sensed signal generated by each photodetector and generating output data signals therefrom. The output data signals are indicative of the light emitted, due to the presence of rGFP or pGFP, at the various loci. As will be appreciated by those in the art, any assay that evaluates binding interactions can utilize the present invention. Examples of binding interactions include proteins interaction domains, receptors and ligands, drugs and drug targets, enzymes and inhibitors, nucleic acid sequences and nucleic acid binding proteins, and binding of candidate agents, for example when expressed on a cell surface, to any binding partners above.

It is understood by the skilled artisan that the steps for constructing the fusion nucleic acids, retroviral libraries, and transformed cells can be varied according to the options provided herein. It is also understood, however, that the methods and examples in no way limit the true scope of the invention. Those skilled in the art may modify according to the skill in the art.

The following examples serve to more fully describe the manner of using the above-described invention, as well as to set forth the best modes contemplated for carrying our various aspects of the invention. It is under stood that these examples in no way serve to limit the true scope of the present invention, but rather are presented for illustrative purposes. All references cited herein are incorporated by reference in their entirety.

EXAMPLES

Example 1

Vector Construction and Expression in Mammalian Cells

Retroviral constructs were based on a pCGFP vector that carries a composite CMV promoter fused to the transcriptional start site of the MMLV R-U5 region of the LTR, an extended packaging sequence, deletion of the MMLV gag start ATG, and a multiple cloning region encoding EGFP, an *Aequoria Victoria* GFP variant codon optimized for expression in human cells (Clontech, Palo Alto, Calif.) and a Kozak consensus start, described in Kozak (1986) Cell 44: 283-292. The vector used to express flag tagged EGFP, pEf, is identical to pCGFP but has additional restriction sites in the open reading frame of EGFP (resulting in 8 non-human optimized codons) and a Flag tag fused to the C-terminus of EGFP with the linker EEAAKA.

pR and pP are retroviral expression vectors comprising *Renilla muelleri* and *Ptilosarcus gurneyi* GFPs (containing 9 and 11 non-optimized codons, respectively, to introduce restriction sites). Each has a Kozak consensus start and backbone vector sequence identical to that of pCGFP and pEf. These vectors were made by annealing and ligating 20 synthetic oligonucleotides (10 forward, 10 reverse for each GFP gene) creating a dsDNA fragment for each sequence. These fragments were PCR amplified with respective primers:

```
R forward, 5'-
                                     (SEQ ID NO: 82)
GATCATAGAATTCGCCACCATGGGCAGCAAGCAGATCCTGAAGAACACCT
GCCTG;

P forward, 5'-
                                     (SEQ ID NO: 83)
GATCATAGAATTCGCCACCATGGGCAACCGCAACGTGCTGAAGAACACCG
GCCTG;

R and P reverse, 5'-
                                     (SEQ ID NO: 84)
ATGATCGCGGCCGCTACACCCACTCGTGCAGGGATCCCAGGGGCTTGCCG
ATG;
``` and cloned into the EcoRI/NotI restriction sites of pEf (replacing the Ef coding region). C-terminal Flag tags were added to these GFPs through BamHI/NotI sites using annealed primers with sticky overhangs:

```
Forward, 5'-
                                     (SEQ ID NO: 85)
GATCCCTGCACGAGTGGGTGGAGGAGGCCGCCAAGGCCGACTACAAGGAC
GACGACGACAAGTAGGCCCGTGAGGCCCTAAGC;

Reverse, 5'-
                                     (SEQ ID NO: 86)
GGCCGCTTAGGGCCTCACGGGCCTACTTGTCGTCGTCCTTGTAGTCGGCC
TTGGCGGCCTCCTCCACCCACTCGTGCAGG;
``` creating Rf and Pf. pRcDNA was made by removing the *R. muelleri* cDNA gene from pET-34 Native *Renilla muelleri* GFP (Prolume Ltd., Pittsburgh, Pa.) by PCR amplification with primers:

```
Forward, 5'-
                                     (SEQ ID NO: 87)
   GATCATGAATTCGCCATGAGTAAACAAATATTGAAGAACACT;

Reverse, 5'-
                                     (SEQ ID NO: 88)
   TAGATCGCGGCCGCTTAAACCCATTCGTGTAAGGATCCTAGTGG;
``` and cloning into the EcoRI/NotI sites of pEf. Vectors containing codon optimized *R. muelleri* GFP with a linker-HA tag-linker sequence inserted into each position A-F were created by the PCR sew technique of two fragments using primers shown above R forward and R reverse). The two fragments for A-F were made by PCR amplification of the 5' section of R with respective primers: R forward, shown above;

```
A reverse, 5'-
                                     (SEQ ID NO: 89)
CTGGCGTAGTCGGGCACGTCGTAGGGGTAGCCACCGCCCTGGCCCTCGTA
GCGCAGGGTGCGCTCGTAC;

B reverse, 5'-
                                     (SEQ ID NO: 90)
CTGGCGTAGTCGGGCACGTCGTAGGGGTAGCCACCGCCCTGGCCCTCGAT
CAGGTTGATGTCGCTGCGG;

C reverse, 5'-
```

-continued

D reverse, 5'-
(SEQ ID NO: 91)
CTGGCGTAGTCGGGCACGTCGTAGGGGTAGCCACCGCCCTGGCCGTTCAT
GTACATGGCCTCGAAGCTG;

D reverse, 5'-
(SEQ ID NO: 92)
CTGGCGTAGTCGGGCACGTCGTAGGGGTAGCCACCGCCCTGGCCGTTAAG
CTTGTACACAGGATCACC;

E reverse, 5'-
(SEQ ID NO: 93)
CTGGCGTAGTCGGGACGTCGTAGGGGTAGCCACCGAAATGGAAGAAATTG
CTCTTCATCAGGGTCTTC;

F reverse, 5'-
(SEQ ID NO: 94)
CTGGCGTAGTCGGGCACGTCGTAGGGGTAGCCACCGCCCTGGCCGCCGCC
GTCCTCCACGTAGGTCTTC;

and the 3' section of R with respective primers:

A forward, 5'-
(SEQ ID NO: 95)
CCTACGACGTGCCCGACTACGCCAGCCTGGGCCAGCAGGTGGAGGCGACG
GCGGCCTGGTGGAGATCCGCA;

B forward, 5'-
(SEQ ID NO: 96)
CCTACGACGTGCCCGACTAGCCAGCCTGGGCCAAGCAGGTGGAGGCGACA
AGTTCGTGTACCGCGTGGAGT;

C forward, 5'-
(SEQ ID NO: 97)
CCTACGACGTGCCCGACTACGCCAGCCTGGGCCAAGCAGGTGGAGGCAAC
GGCGTGCTGGTGGGCGAGGTGA;

D forward, 5'-
(SEQ ID NO: 98)
CCTACGACGTGCCCGACTACGCCAGCCTGGGCCAAGCAGGTGGAGGCAGC
GGCAAGTACTACAGCTGCCACA;

E forward, 5'-
(SEQ ID NO: 99)
CCTACGACGTGCCCGACTACGCCAGCCTGGGCCAAGCAGGTGGAGGCGTG
GTGAAGGAGTTCCCCAGCTACC;

F forward, 5'-
(SEQ ID NO: 100)
CCTACGACGTGCCCGACTACGCCAGCCTGGGCCAAGCAGGTGGAGGCTTC
GTGGAGCAGCACGAGACCGCCA.

The PCR sewed fragments were put into the EcoRI/NotI sites of pEf.

The bacterial expression vector for purification of Ptilosarcus GFP was created by PCR amplification of pP with primers:

forward, 5'-
(SEQ ID NO: 101)
AGATCATAGATCTATGGGCAACCGCAACGTGCTGAAGAACACCGGCCTG;

P reverse, shown above.

Digestion of the fragment with BglII/NotI and ligation into the BamHI/NotI restriction sites of pGEX6P-1 (Pharmacia Biotech, Piscataway, N.J.). The vector containing R. muelleri GFP with C10G and C35E mutations (observed to aid in the folding of the protein in bacteria) was created by PCR sewing together a fragment created by annealing and extending primers:

forward, 5'-
(SEQ ID NO: 102)
AGATCATAGATCTGAATTCATGGGCAGCAAGCAGATCCTGAAGAACACCG
GCCTGCAGGAGGTGATGAGCTACAAGGTGACCTGGAGG;

reverse, 5'-
(SEQ ID NO: 103)
GCCAACAGGATGTTGCCCTTGCCCTCGCCCTCCATGGTGAACACGTGGTT
GTTAACGATGCCCTCCAGGTTCACCTTGTAGCTCATCAC;

R reverse, shown above.

The sewed product was digested BglII/NotI and ligated into the BamHI/NotI sites of pGEX6P-1.

Cells and Retrovirus Transduction

Phoenix E retroviral packaging cells, described in Swift, S. et al. Current Protocols in Immunology, John Wiley and Sons, Inc., New York, Vol. 10.17C, pg 1-17, 1999, were carried in 10% fetal bovine serum with 1% penicillin-streptomycin and Dulbecco's modified Eagle media (Mediatech Cellgro, Herndon, Va.). Jurkat E cells stably expressing the ecotropic receptor (Jurkat E) were carried in 10% fetal calf serum with 1% penicillin-streptomycin in RPMI 1630 media (JRH Bioscience, Williamsburg, Va.). Calcium phosphate transfection of Phoenix E cells and infection of Jurket E cells and infection of Jurket E cells was carried out as described in Swift et al.

Gel Filtration

Gel filtration was carried out on a 1×30 cm Pharmacia Superdex 75 column, equilibrated in phosphate buffered saline and eluted at 0.3 ml/min. at 22° C. The column was on a Hewlett-Packard 1100 HPLC system equipped with a standard fluorescence detector with an 8 μl flow cell. GFP peaks were detected by absorption at 489 nm or by fluorescence emission at 512 nm. Fluorescence excitation spectra were recorded with a fixed emission wavelength at 549 nm, and emission spectra were recorded at a fixed excitation wavelength of 450 nm.

FACS and Microscopy

Flow-cytometry analysis and cell sorting of GFP expressing cells were performed on a FACScan (Beckton-Dickson, San Jose, Calif.) or MoFlo (Cytomation, Fort Collins, Colo.) instrument, and data analyzed using FloJo software (Treestar Software, San Carlos, Calif.). Live cells were gated by scatter and propidium iodide staining during data analysis. GFP fluorescence intensity measurements (Geometric mean) were of GFP positive cells only. Cells expressing GFP were visualized using Nikon Ellipse TE300 fluorescence microscope.

Immunoprecipitation and Western Analysis (a2)

For preparation of whole-cell lysates, cells were counted, collected, washed in PBS, and lysed by freeze-thaw/vortexing in lysis buffer (50 mM HEPES pH 7.4, 150 mM NaCl, 5 mM EDTA, 5 mM EGTA, 1% Triton X-100) with added complete protease inhibitor cocktail (Boehringer Mannheim, Chicago, Ill.). Lysate cleared by centrifugation was resolved on 4-12% NuPage SDS polyacrylamide gels (Novex, San Diego, Calif.) as per the manufacturer's recommendations. For immunoprecipitations, antibody conjugated agarose beads were added to the cell lysate and incubated for 4 h. The beads were washed in lysis buffer and samples separated by SDS PAGE as above. Samples transferred to PVDF membranes were blocked overnight at 4° C. using PBS buffer containing 10% Milk, 0.10% Tween20. Primary antibodies (polyclonal flag-probe, Santa Cruz Biotechnology, Santa Cruz, Calif.) were used at a 1:2000 dilution while secondary antibodies were used at a 1:5000 dilution. Membranes were developed using ECL plus enhanced chemiluminescence kit (Amersham Pharmacia, Piscataway, N.J.) and Hyperfilm ECL film (Amersham Life Sciences, Buckinghamshire, UK). For comparative Western blot analysis, GFPs containing a C-terminal flag were used. Exposed film was scanned with a Hewlett Packard (Palo Alto, Calif.) ScanJet 4C scanner and band intensities were integrated using the program NIH Image (available on-line at rsb.info.nih.gov/nih-image/about.html).

GFP Purification from *E. coli*

All components used for purification of the GFP gene products were from Pharmacia Biotech (Piscataway, N.J.) except as noted. The human codon-optimized gene for each protein was expressed in BL21 TIL codon plus (DE3) *E. coli* (Strategene, San Diego, Calif.) as a fusion protein with glutathione S-transferase from pGEX6p-1 derived vectors. Each protein was purified using Glutathione Sepharose 4B beads as per the manufacturer's directions, and the mature GFP was removed from the protein with Precision Protease. The purified proteins ran as single bands by SDS-PAGE and appeared as single peaks of the expected molecular mass by MALDI-TOF mass spectometry on a Bruker Reflex III instrument (Bruker Daltonics, Billerica, Mass.). Due to the cloning strategy, purified *R. muelleri* GFP has the amino acids PLGSEF- and *Ptilosarcus* GFP the residues GPLGS-fused to their N-termini. Purified recombinant EGFP was from Clontech (Palo Alto, Calif.).

CD Studies

CD spectra were recorded as described in Gururaja, T. L. et al. (2000) Chem Biol 7: 515-27. CD spectra were recorded on an AVIV 62A DS CD spectrophotometer (Lakewood, N.J.) equipped with a Peltier temperature control unit. The temperature of the instrument was maintained constantly below 20° C. using a Neslab CFT-33 refrigerated recirculator water bath. The device was periodically calibrated with the ammonium salt of (+)-10-camphorsulfuric acid according to manufacturers' recommendations. Spectra were recorded between 200 and 250 nm at 0.2 nm intervals with a time constant of 1 s at 25° C. in 10 mM phosphate buffer containing 100 mM KF at pH 7.5. A cylindrical quartz cell of path length 0.1 cm was used for the spectral range with the sample concentration of 5 to 10 µM as determined by Lowry, O. et al. (1951) J. Biol. Chem. 193: 265-275. Mean residual ellipticity (MRE) is expressed in deg.cm$^2$/dmol. The thermal denaturation was measured at 218 nm over a range of 4-98° C. with a temperature step of 2° C., a 2 minute equilibration time, and a 60 s signal averaging time. The $T_m$ datas were fitted to a logistic sigmoid equation using the Levenberg-Marquardt algorithm in Ultrafit (Biosoft, Cambridge, UK). CD spectra were deconvoluted with the program CDNN (CD neural network) downloaded from the Internet at bioinformatik.biochemtech.uni-halle.de/cdnn/index.html.

Example 2

Expression of *Renilla* GFP Codon Optimized for Expression in Human Cells

*Renilla muelleri* and *Ptilosarcus* GFP genes were constructed with a glycine following the initial methionine to optimize translations (see Experiment 1). The sequences were codon optimized for efficient expression in human cells. These GFPs were introduced into Jurkat-E cells by retroviral delivery using the protocol of Swift et al., supra. Based on FACS analysis of scatter and propidium iodide staining of cell populations from 13 hours to 8 days post infection, there was no observed toxicity of either *Ptilosarcus* or *Renilla* GFP. By 2 days post infection, the accumulation of intracellular GFP slowed to a steady state level. Based on FL1 channel fluorescence, the rate for reaching the steady state level occurred more rapidly for *Ptilosarcus* and *Renilla* GFPs than for EGFP. The excitation and emission spectra were 501 and 511 nm; 498 and 509 nm; and 489 and 510 nm for *Ptilosarcus* GFP, *Renilla* GFP, and *Aequoria* GFP, respectively.

The relative levels of wild type and codon optimized *Renilla* GFP and EGFP were analyzed by FACS at 4 days post infection. Based on geometric mean fluorescence values in the FL1 channel, codon optimized. *Renilla* GFP was expressed greater than 28 fold higher than wild-type cDNA sequence, and was 1.4 fold brighter than EGFP.

*Ptilosarcus* GFP, *Renilla* GFP and EGFP fused at their carboxy termini to a linker-flag tag sequence, EEAAKA-DYKDDDDK (SEQ ID NO: 104), were expressed in Jurkat-E, and their fluorescence levels compared by FACS. The *Ptilosarcus* and *Renilla* GFPs were on average 1.4 fold and 1.2 fold more fluorescent than EGFP, respectively. Lysates from 2.8×104 Jurkat-E cells, sorted 8 days after infection for GFP fluorescence, were compared by Western blot using ant-flag antibody. All GFPs gave only a single band. EGFP migrated at a slightly higher molecular mass than the other two flag-tagged antibodies. The integrated intensity values derived using NIH Image were 3200, 3206, and 2314 for each band, and had ratios of 1.4:1.4:1.0 for *Ptilosarcus* GFP, *Renilla* GFP and EGFP, respectively. Thus, both *Renilla* and *Ptilosarcus* are expressed at slightly higher levels that EGFP in these cells, making these codon optimized construct efficient reporter proteins.

Example 3

Epitope Tag Insertion for Loop Suitable for Presentation of Peptides

To test for the location of potential surface loops in *Renilla* GFP, the peptide sequence GQGGGYPYDVPD-YASLGQAGGG (SEQ ID NO: 105) containing the influenza hemagglutinin epitope tag flanked by two flexible linker sequences was inserted into candidate sites corresponding to putative loops of *Renilla* GFP (see Experiment 1). Following retroviral delivery into human cells, the fluorescence of the modified GFPs were examined. Six different insertion sites, A-F were tested in codon optimized GFP. FIG. 7 shows the fluorescence of the different modified *Renilla* GFPs retrovirally expressed in Jurkat-E cells and analyzed by FACS 4 days post infection. The geometric mean fluorescence values for the populations indicated by the gates are shown in the upper right corner for each FACS plot. Comparisons of these values are for samples that have populations present within the same dynamic range. All modified *Renilla* GFPs, except that with insertion into position A, were expressed and fluorescent. The rank order of fluorescence intensities was D>F>>B>E=C. Relative to the unaltered *Renilla* GFP, the average expression levels of *Renilla* GFP with the HA peptide positions D and F were ca. 49% and 47%, and B, C, and E less than 1%. Thus, *Renilla* GFP with HA tags inserted into positions D and F best tolerate insertion of the 22 mer peptide. *Renilla* with the position D insertion was on average 2.3 fold more fluorescent than *Aequoria* EGFP with the identical 22 mer present in its most fluorescent loop (Peelle et al. (2001) Chem. Biol. 8: 521-534). Comparison of insertions of tag peptides between *Aequoria* and *Renilla* shows the most significant difference in position F. In EGFP, this analogous site is a loop between two twisted beta strands with a distance across the top of the loop of ca 11 Å. An 8mer peptide inserted into *Aequoria* GFP at the equivalent position F is only 0.6% as fluorescent as the parent GFP when expressed in yeast (Abedi, et al (1998), whereas insertion of a 22 mer HA tag into position F of *Renilla* GFP retains 32% of the parent fluorescence. Thus, the *Renilla* structure appears to be significantly more tolerant that *Aequoria* GFP to insertion of peptides into this particular site. Although the position F site is likely to be surface exposed in both GFPs, its structure or significance in the folding pathway of *Renilla* GFP may differ from *Aequoria* GFP.

Example 4

Intracellular Presentation of a Peptide on a *Renilla* GFP Scaffold

To examine *Renilla* GFP as a peptide display scaffold, the SV40 derived nuclear localization signal (NLS) -PP-KKKRKV- (SEQ ID NO: 106) flanked by glycine linkers used in the epitope tag scan was inserted into sites D and F. This NLS peptide interacts with karyopherins in the nuclear pore complex for transport into the nucleus (Radu, et al. (1995) Cell 81: 215-22; Rexach and Blobel (1995) Cell 83: 683-92; Moroianu, et al. (1995) Proc. Natl. Acad. Sci. USA 92: 2008-11). About $10^6$ A549 cells with retrovirally expressed *Renilla* site D or F inserted peptide were grown for 14 days and then observed by fluorescence microscopy. The HA epitope tag flanked by 4 glycines, G4YPYDVPDYASLG4- (SEQ ID NO: 107) was inserted along with the linker residues as a control for each experiment. GFP with this tag inserted in both site D and F fluoresced throughout the cell, while the NLS containing insert showed only nuclear fluorescence, with some preferential localization to intra-nuclear structures for the loop D insert. The inserted peptide is thus solvent exposed and can functionally interact with its target in the cell. Thus, the use of *Renilla* GFP as a scaffold allows use of additional GFP peptide display sites, with possibly a different structural bias for phenotypic screening of peptide libraries.

We claim:

1. An isolated polynucleotide consisting of the sequence of SEQ ID NO: 1, which is a humanized polynucleotide encoding *Renilla mulleri* green fluorescent protein.

2. A recombinant vector comprising a polynucleotide of claim 1.

3. A cell containing a recombinant vector of claim 2.

* * * * *

SEQUENCE LISTING

<160> NUMBER OF SEQ ID NOS: 107

<210> SEQ ID NO 1
<211> LENGTH: 717
<212> TYPE: DNA
<213> ORGANISM: Renilla muelleri

<400> SEQUENCE: 1

```
atgggcagca agcagatcct gaagaacacc tgcctgcagg aggtgatgag ctacaaggtg      60
aacctggagg gcatcgttaa caaccacgtg ttcaccatgg agggctgcgg caagggcaac     120
atcctgttcg gcaaccaatt ggtgcagatc cgcgtgacca agggcgcccc cctgcccttc     180
gccttcgaca tcgtgagccc cgccttccag tacggcaacc gtacgttcac caagtacccc     240
aacgacatca gcgactactt catccagagc ttccccgccg gcttcatgta cgagcgcacc     300
ctgcgctacg aggacggcgg cctggtggag atccgcagcg acatcaacct gatcgaggac     360
aagttcgtgt accgcgtgga gtacaagggc agcaacttcc ccgacgacgg gcccgtgatg     420
cagaagacca tcctgggcat cgagcccagc ttcgaggcca tgtacatgaa caacggcgtg     480
ctggtgggcg aggtgatcct ggtgtacaag cttaacagcg gcaagtacta cagctgccac     540
atgaagaccc tgatgaagag caagggcgtg gtgaaggagt tccccagcta ccacttcatc     600
cagcaccgcc tcgagaagac ctacgtggag gacggcggct tcgtggagca gcacgagacc     660
gccatcgccc agatgaccag catcggcaag cccctgggat ccctgcacga gtgggtg       717
```

<210> SEQ ID NO 2
<211> LENGTH: 717
<212> TYPE: DNA
<213> ORGANISM: Ptilosarcus gurneyi

<400> SEQUENCE: 2

```
atgggcaacc gcaacgtgct gaagaacacc ggcctgaagg agatcatgag cgccaaggcc      60
agcgtggagg gcatcgtgaa caaccacgtg ttcagcatgg agggcttcgg caagggcaac     120
gtgctgttcg gcaaccagct gatgcagatc cgcgtgacca agggcggccc cctgcccttc     180
gccttcgaca tcgtgagcat cgccttccag tacggcaacc gcaccttcac caagtacccc     240
gacgacatcg ccgactactt cgtgcagagc ttccccgccg gcttcttcta cgagcgcaac     300
```

```
ctgcgcttcg aggacggcgc catcgtggac atccgcagcg acatcagcct ggaggacgac      360
aagttccact acaaggtgga gtaccgcggc aacggcttcc ccagcaacgg ccccgtgatg      420
cagaaggcca tcctgggcat ggagcccagc ttcgaggtgg tgtacatgaa cagcggcgtg      480
ctggtgggcg aggtggacct ggtgtacaag ctggagagcg gcaactacta cagctgccac      540
atgaagacct tctaccgcag caagggcggc gtgaaggagt tccccgagta ccacttcatc      600
caccaccgcc tggagaagac ctacgtggag gagggcagct tcgtggagca gcacgagacc      660
gccatcgccc agctgaccac catcggcaag cccctgggca gcctgcacga gtgggtg          717
```

<210> SEQ ID NO 3
<211> LENGTH: 231
<212> TYPE: PRT
<213> ORGANISM: Zoanthus sp.

<400> SEQUENCE: 3

```
Met Ala Gln Ser Lys His Gly Leu Thr Lys Glu Met Thr Met Lys Tyr
1               5                  10                  15

Arg Met Glu Gly Cys Val Asp Gly His Lys Phe Val Ile Thr Gly Glu
            20                  25                  30

Gly Ile Gly Tyr Pro Phe Lys Gly Lys Gln Ala Ile Asn Leu Cys Val
        35                  40                  45

Val Glu Gly Gly Pro Leu Pro Phe Ala Glu Asp Ile Leu Ser Ala Ala
    50                  55                  60

Phe Asn Tyr Gly Asn Arg Val Phe Thr Glu Tyr Pro Gln Asp Ile Val
65                  70                  75                  80

Asp Tyr Phe Lys Asn Ser Cys Pro Ala Gly Tyr Thr Trp Asp Arg Ser
                85                  90                  95

Phe Leu Phe Glu Asp Gly Ala Val Cys Ile Cys Asn Ala Asp Ile Thr
            100                 105                 110

Val Ser Val Glu Glu Asn Cys Met Tyr His Glu Ser Lys Phe Tyr Gly
        115                 120                 125

Val Asn Phe Pro Ala Asp Gly Pro Val Met Lys Lys Met Thr Asp Asn
    130                 135                 140

Trp Glu Pro Ser Cys Glu Lys Ile Ile Pro Val Pro Lys Gln Gly Ile
145                 150                 155                 160

Leu Lys Gly Asp Val Ser Met Tyr Leu Leu Leu Lys Asp Gly Gly Arg
                165                 170                 175

Leu Arg Cys Gln Phe Asp Thr Val Tyr Lys Ala Lys Ser Val Pro Arg
            180                 185                 190

Lys Met Pro Asp Trp His Phe Ile Gln His Lys Leu Thr Arg Glu Asp
        195                 200                 205

Arg Ser Asp Ala Lys Asn Gln Lys Trp His Leu Thr Glu His Ala Ile
    210                 215                 220

Ala Ser Gly Ser Ala Leu Pro
225                 230
```

<210> SEQ ID NO 4
<211> LENGTH: 229
<212> TYPE: PRT
<213> ORGANISM: Anemonia majano

<400> SEQUENCE: 4

```
Met Ala Leu Ser Asn Lys Phe Ile Gly Asp Asp Met Lys Met Thr Tyr
1               5                  10                  15
```

His Met Asp Gly Cys Val Asn Gly His Tyr Phe Thr Val Lys Gly Glu
        20                  25                  30

Gly Asn Gly Lys Pro Tyr Glu Gly Thr Gln Thr Ser Thr Phe Lys Val
        35                  40                  45

Thr Met Ala Asn Gly Gly Pro Leu Ala Phe Ser Phe Asp Ile Leu Ser
50                  55                  60

Thr Val Phe Lys Tyr Gly Asn Arg Cys Phe Thr Ala Tyr Pro Thr Ser
65                  70                  75                  80

Met Pro Asp Tyr Phe Lys Gln Ala Phe Pro Asp Gly Met Ser Tyr Glu
                85                  90                  95

Arg Thr Phe Thr Tyr Glu Asp Gly Gly Val Ala Thr Ala Ser Trp Glu
                100                 105                 110

Ile Ser Leu Lys Gly Asn Cys Phe Glu His Lys Ser Thr Phe His Gly
                115                 120                 125

Val Asn Phe Pro Ala Asp Gly Pro Val Met Ala Lys Lys Thr Thr Gly
130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Gly Asn Tyr Arg
                165                 170                 175

Cys Gln Phe His Thr Ser Tyr Lys Thr Lys Lys Pro Val Thr Met Pro
                180                 185                 190

Pro Asn His Val Val Glu His Arg Ile Ala Arg Thr Asp Leu Asp Lys
                195                 200                 205

Gly Gly Asn Ser Val Gln Leu Thr Glu His Ala Val Ala His Ile Thr
210                 215                 220

Ser Val Val Pro Phe
225

<210> SEQ ID NO 5
<211> LENGTH: 232
<212> TYPE: PRT
<213> ORGANISM: Discosoma striata

<400> SEQUENCE: 5

Met Ser Cys Ser Lys Ser Val Ile Lys Glu Glu Met Leu Ile Asp Leu
1               5                   10                  15

His Leu Glu Gly Thr Phe Asn Gly His Tyr Phe Glu Ile Lys Gly Lys
                20                  25                  30

Gly Lys Gly Gln Pro Asn Glu Gly Thr Asn Thr Val Thr Leu Glu Val
        35                  40                  45

Thr Lys Gly Gly Pro Leu Pro Phe Gly Trp His Ile Leu Cys Pro Gln
50                  55                  60

Phe Gln Tyr Gly Asn Lys Ala Phe Val His His Pro Asp Asn Ile His
65                  70                  75                  80

Asp Tyr Leu Lys Leu Ser Phe Pro Glu Gly Tyr Thr Trp Glu Arg Ser
                85                  90                  95

Met His Phe Glu Asp Gly Gly Leu Cys Cys Ile Thr Asn Asp Ile Ser
                100                 105                 110

Leu Thr Gly Asn Cys Phe Tyr Tyr Asp Ile Lys Phe Thr Gly Leu Asn
                115                 120                 125

Phe Pro Pro Asn Gly Pro Val Val Gln Lys Lys Thr Thr Gly Trp Glu
130                 135                 140

Pro Ser Thr Glu Arg Leu Tyr Pro Arg Asp Gly Val Leu Ile Gly Asp
145                 150                 155                 160

```
Ile His His Ala Leu Thr Val Glu Gly Gly His Tyr Ala Cys Asp
            165                 170                 175

Ile Lys Thr Val Tyr Arg Ala Lys Ala Ala Leu Lys Met Pro Gly
            180                 185                 190

Tyr His Tyr Val Asp Thr Lys Leu Val Ile Trp Asn Asn Asp Lys Glu
            195                 200                 205

Phe Met Lys Val Glu Glu His Glu Ile Ala Val Ala Arg His His Pro
            210                 215                 220

Phe Tyr Glu Pro Lys Lys Asp Lys
225                 230

<210> SEQ ID NO 6
<211> LENGTH: 231
<212> TYPE: PRT
<213> ORGANISM: Clavularia sp.

<400> SEQUENCE: 6

Ile Pro Lys Ala Leu Thr Thr Met Gly Val Ile Lys Pro Asp Met Lys
1               5                   10                  15

Ile Lys Leu Lys Met Glu Gly Asn Val Asn Gly His Ala Phe Val Ile
            20                  25                  30

Glu Gly Glu Gly Glu Gly Lys Pro Tyr Asp Gly Thr His Thr Leu Asn
        35                  40                  45

Leu Glu Val Lys Glu Gly Ala Pro Leu Pro Phe Ser Tyr Asp Ile Leu
    50                  55                  60

Ser Asn Ala Phe Gln Tyr Gly Asn Arg Ala Leu Thr Lys Tyr Pro Asp
65                  70                  75                  80

Asp Ile Ala Asp Tyr Phe Lys Gln Ser Phe Pro Glu Gly Tyr Ser Trp
                85                  90                  95

Glu Arg Thr Met Thr Phe Glu Asp Lys Gly Ile Val Lys Val Lys Ser
            100                 105                 110

Asp Ile Ser Met Glu Glu Asp Ser Phe Ile Tyr Glu Ile Arg Phe Asp
        115                 120                 125

Gly Met Asn Phe Pro Pro Asn Gly Pro Val Met Gln Lys Lys Thr Leu
130                 135                 140

Lys Trp Glu Pro Ser Thr Glu Ile Met Tyr Val Arg Asp Gly Val Leu
145                 150                 155                 160

Val Gly Asp Ile Ser His Ser Leu Leu Leu Glu Gly Gly Gly His Tyr
                165                 170                 175

Arg Cys Asp Phe Lys Ser Ile Tyr Lys Ala Lys Lys Val Val Lys Leu
            180                 185                 190

Pro Asp Tyr His Phe Val Asp His Arg Ile Glu Ile Leu Asn His Asp
        195                 200                 205

Lys Asp Tyr Asn Lys Val Thr Leu Tyr Glu Asn Ala Val Ala Arg Tyr
    210                 215                 220

Ser Leu Leu Pro Ser Gln Ala
225                 230

<210> SEQ ID NO 7
<211> LENGTH: 238
<212> TYPE: PRT
<213> ORGANISM: Ptilosarcus gurneyi

<400> SEQUENCE: 7

Met Asn Arg Asn Val Leu Lys Asn Thr Gly Leu Lys Glu Ile Met Ser
1               5                   10                  15
```

```
Ala Lys Ala Ser Val Glu Gly Ile Val Asn Asn His Val Phe Ser Met
            20                  25                  30

Glu Gly Phe Gly Lys Gly Asn Val Leu Phe Gly Asn Gln Leu Met Gln
        35                  40                  45

Ile Arg Val Thr Lys Gly Gly Pro Leu Pro Phe Ala Phe Asp Ile Val
    50                  55                  60

Ser Ile Ala Phe Gln Tyr Gly Asn Arg Thr Phe Thr Lys Tyr Pro Asp
65                  70                  75                  80

Asp Ile Ala Asp Tyr Phe Val Gln Ser Phe Pro Ala Gly Phe Tyr
                85                  90                  95

Glu Arg Asn Leu Arg Phe Glu Asp Gly Ala Ile Val Asp Ile Arg Ser
            100                 105                 110

Asp Ile Ser Leu Glu Asp Asp Lys Phe His Tyr Lys Val Glu Tyr Arg
        115                 120                 125

Gly Asn Gly Phe Pro Ser Asn Gly Pro Val Met Gln Lys Ala Ile Leu
    130                 135                 140

Gly Met Glu Pro Ser Phe Glu Val Val Tyr Met Asn Ser Gly Val Leu
145                 150                 155                 160

Val Gly Glu Val Asp Leu Val Tyr Lys Leu Glu Ser Gly Asn Tyr Tyr
                165                 170                 175

Ser Cys His Met Lys Thr Phe Tyr Arg Ser Lys Gly Gly Val Lys Glu
            180                 185                 190

Phe Pro Glu Tyr His Phe Ile His His Arg Leu Glu Lys Thr Tyr Val
        195                 200                 205

Glu Glu Gly Ser Phe Val Glu Gln His Glu Thr Ala Ile Ala Gln Leu
    210                 215                 220

Thr Thr Ile Gly Lys Pro Leu Gly Ser Leu His Glu Trp Val
225                 230                 235

<210> SEQ ID NO 8
<211> LENGTH: 238
<212> TYPE: PRT
<213> ORGANISM: Renilla muelleri

<400> SEQUENCE: 8

Met Ser Lys Gln Ile Leu Lys Asn Thr Cys Leu Gln Glu Val Met Ser
1               5                   10                  15

Tyr Lys Val Asn Leu Glu Gly Ile Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Val
    50                  55                  60

Ser Pro Ala Phe Gln Tyr Gly Asn Arg Thr Phe Thr Lys Tyr Pro Asn
65                  70                  75                  80

Asp Ile Ser Asp Tyr Phe Ile Gln Ser Phe Pro Ala Gly Phe Met Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Asp Lys Phe Val Tyr Arg Val Glu Tyr Lys
        115                 120                 125

Gly Ser Asn Phe Pro Asp Asp Gly Pro Val Met Gln Lys Thr Ile Leu
    130                 135                 140

Gly Ile Glu Pro Ser Phe Glu Ala Met Tyr Met Asn Asn Gly Val Leu
```

```
                145                 150                 155                 160
Val Gly Glu Val Ile Leu Val Tyr Lys Leu Asn Ser Gly Lys Tyr Tyr
                    165                 170                 175

Ser Cys His Met Lys Thr Leu Met Lys Ser Lys Gly Val Val Lys Glu
                180                 185                 190

Phe Pro Ser Tyr His Phe Ile Gln His Arg Leu Glu Lys Thr Tyr Val
            195                 200                 205

Glu Asp Gly Gly Phe Val Glu Gln His Glu Thr Ala Ile Ala Gln Met
        210                 215                 220

Thr Ser Ile Gly Lys Pro Leu Gly Ser Leu His Glu Trp Val
225                 230                 235

<210> SEQ ID NO 9
<211> LENGTH: 238
<212> TYPE: PRT
<213> ORGANISM: Aequorea victoria

<400> SEQUENCE: 9

Met Ser Lys Gly Glu Glu Leu Phe Thr Gly Val Val Pro Ile Leu Val
1               5                   10                  15

Glu Leu Asp Gly Asp Val Asn Gly Gln Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Tyr Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Met Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
                180                 185                 190

Val Leu Leu Pro Asp Asn His Tyr Leu Ser Thr Gln Ser Ala Leu Ser
            195                 200                 205

Lys Asp Pro Asn Glu Lys Arg Asp His Met Ile Leu Leu Glu Phe Val
        210                 215                 220

Thr Ala Ala Gly Ile Thr His Gly Met Asp Glu Leu Tyr Lys
225                 230                 235

<210> SEQ ID NO 10
<211> LENGTH: 714
<212> TYPE: DNA
<213> ORGANISM: Renilla muelleri

<400> SEQUENCE: 10
atgagtaaac aaatattgaa gaacactgt ttacaagaag taatgtcgta taaagtaaat     60
```

```
ctggaaggaa ttgtaaacaa ccatgttttt acaatggagg gttgcggcaa agggaatatt      120
ttattcggca atcaactggt tcagattcgt gtcacgaaag gggcccccact gcctttttgca    180 tttgatattg tgtcaccagc ttttcaatat ggcaaccgta ctttcacgaa atatccgaat      240
gatatatcag attattttat acaatcattt ccagcaggat ttatgtatga cgaacatta      300 cgttacgaag atggcggact tgttgaaatt cgttcagata taaatttaat agaagacaag      360
ttcgtctaca gagtggaata caaaggtagt aacttcccag atgatggtcc cgtcatgcag      420
aagactatct taggaataga gccttcattt gaagccatgt acatgaataa tggcgtcttg      480
gtcggcgaag taattcttgt ctataaacta aactctggga atattattc atgtcacatg       540 aaaacattaa tgaagtcgaa aggtgtagta aaggagtttc cttcgtatca ttttattcaa      600
catcgtttgg aaaagactta cgtagaagac gggggggttcg ttgaacagca tgagactgct     660
attgctcaaa tgcatctat aggaaaacca ctaggatcct tacacgaatg ggtt             714

<210> SEQ ID NO 11
<211> LENGTH: 714
<212> TYPE: DNA
<213> ORGANISM: Ptilosarcus gurneyi

<400> SEQUENCE: 11
atgaaccgca acgtattaaa gaacactgga ctgaaagaga ttatgtcggc aaaagctagc       60
gttgaaggaa tcgtgaacaa tcacgttttt tccatggaag gatttggaaa aggcaatgta     120
ttatttggaa accaattgat gcaaatccgg gttacaaagg gaggtccgtt gccattcgct      180
ttcgacattg tttccatagc tttccaatac gggaatcgca ctttcacgaa atacccagac      240
gacattgcgg actactttgt tcaatcattt ccggctggat ttttctacga agaaatctca      300
cgctttgaag atggcgccat tgttgacatt cgttcagata taagtttaga agatgataag      360
ttccactaca aagtggagta tagaggcaac ggtttcccta gtaacggacc cgtgatgcaa      420
aaagccatcc tcggcatgga gccatcgttt gaggtggtct acatgaacag cggcgttctg     480
gtgggcgaag tagatctcgt ttacaaactc gagtcaggga actattactc gtgccacatg      540
aaaacgtttt acagatccaa aggtggagtg aaagaattcc cggaatatca ctttatccat      600
catcgtctgg agaaaaccta cgtggaagaa ggaagcttcg tggaacaaca cgagacggcc      660
attgcacaac tgaccacaat tggaaaacct ctgggctccc ttcatgaatg ggtg            714

<210> SEQ ID NO 12
<211> LENGTH: 21
<212> TYPE: PRT
<213> ORGANISM: Encephalomyocarditis virus

<400> SEQUENCE: 12

Ala His Tyr Ala Gly Tyr Phe Ala Asp Leu Leu Ile His Asp Ile Glu
1               5                   10                  15

Thr Asn Pro Gly Pro
            20

<210> SEQ ID NO 13
<211> LENGTH: 21
<212> TYPE: PRT
<213> ORGANISM: Encephalomyocarditis virus

<400> SEQUENCE: 13

Ala His Tyr Ala Gly Tyr Phe Ala Ser Leu Leu Ile His Asp Val Glu
1               5                   10                  15
```

-continued

Thr Asn Pro Gly Pro
            20

<210> SEQ ID NO 14
<211> LENGTH: 21
<212> TYPE: PRT
<213> ORGANISM: Theiler's murine encephalitis virus

<400> SEQUENCE: 14

Gly Tyr His Ala Asp Tyr Tyr Arg Gln Arg Leu Ile His Asp Val Glu
1               5                   10                  15

Thr Asn Pro Gly Pro
            20

<210> SEQ ID NO 15
<211> LENGTH: 21
<212> TYPE: PRT
<213> ORGANISM: Theiler's murine encephalitis virus

<400> SEQUENCE: 15

Ala Tyr His Ala Asp Tyr Tyr Lys Gln Arg Leu Ile His Asp Val Glu
1               5                   10                  15

Met Asn Pro Gly Pro
            20

<210> SEQ ID NO 16
<211> LENGTH: 21
<212> TYPE: PRT
<213> ORGANISM: Theiler's murine encephalitis virus

<400> SEQUENCE: 16

Gly Tyr His Ala Asp Tyr Tyr Lys Gln Arg Leu Ile His Asp Val Glu
1               5                   10                  15

Met Asn Pro Gly Pro
            20

<210> SEQ ID NO 17
<211> LENGTH: 21
<212> TYPE: PRT
<213> ORGANISM: Foot-and-mouth disease virus

<400> SEQUENCE: 17

Lys Gln Thr Leu Asn Phe Asp Leu Leu Lys Leu Ala Gly Asp Val Glu
1               5                   10                  15

Ser Asn Pro Gly Pro
            20

<210> SEQ ID NO 18
<211> LENGTH: 21
<212> TYPE: PRT
<213> ORGANISM: Foot-and-mouth disease virus

<400> SEQUENCE: 18

Lys Gln Leu Leu Asn Phe Asp Leu Leu Lys Leu Ala Gly Asp Val Glu
1               5                   10                  15

Ser Asn Pro Gly Pro
            20

<210> SEQ ID NO 19
<211> LENGTH: 21
<212> TYPE: PRT
<213> ORGANISM: Foot-and-mouth disease virus

```
<400> SEQUENCE: 19

Lys Gln Met Cys Asn Phe Asp Leu Leu Lys Leu Ala Gly Asp Val Glu
1               5                   10                  15

Ser Asn Pro Gly Pro
            20

<210> SEQ ID NO 20
<211> LENGTH: 21
<212> TYPE: PRT
<213> ORGANISM: Equine Rhinovirus type 1

<400> SEQUENCE: 20

Lys Gln Cys Thr Asn Phe Ser Leu Leu Lys Leu Ala Gly Asp Val Glu
1               5                   10                  15

Ser Asn Pro Gly Pro
            20

<210> SEQ ID NO 21
<211> LENGTH: 21
<212> TYPE: PRT
<213> ORGANISM: Equine Rhinovirus type 1

<400> SEQUENCE: 21

Lys Gln Cys Thr Asn Phe Ser Ala Leu Lys Leu Ala Gly Asp Val Glu
1               5                   10                  15

Ser Asn Pro Gly Pro
            20

<210> SEQ ID NO 22
<211> LENGTH: 21
<212> TYPE: PRT
<213> ORGANISM: Equine Rhinovirus type 2

<400> SEQUENCE: 22

Glu Gly Ala Thr Asn Phe Ser Leu Leu Lys Leu Ala Gly Asp Val Glu
1               5                   10                  15

Leu Asn Pro Gly Pro
            20

<210> SEQ ID NO 23
<211> LENGTH: 21
<212> TYPE: PRT
<213> ORGANISM: Artificial sequence
<220> FEATURE:
<223> OTHER INFORMATION: 2A-like seqeunce motif
<220> FEATURE:
<221> NAME/KEY: MISC_FEATURE
<222> LOCATION: (1)..(17)
<223> OTHER INFORMATION: "Xaa" at positions 1-10, 12-13, 15, and 17 can
      be any amino acid

<400> SEQUENCE: 23

Xaa Xaa Xaa Xaa Xaa Xaa Xaa Xaa Xaa Xaa Leu Xaa Xaa Asp Xaa Glu
1               5                   10                  15

Xaa Asn Pro Gly Pro
            20

<210> SEQ ID NO 24
<211> LENGTH: 61
<212> TYPE: PRT
<213> ORGANISM: Artificial sequence
<220> FEATURE:
<223> OTHER INFORMATION: coiled-coil presentation structure
```

```
<400> SEQUENCE: 24

Met Gly Cys Ala Ala Leu Glu Ser Glu Val Ser Ala Leu Glu Ser Glu
1               5                   10                  15

Val Ala Ser Leu Glu Ser Glu Val Ala Ala Leu Gly Arg Gly Asp Met
            20                  25                  30

Pro Leu Ala Ala Val Lys Ser Lys Leu Ser Ala Val Lys Ser Lys Leu
        35                  40                  45

Ala Ser Val Lys Ser Lys Leu Ala Ala Cys Gly Pro Pro
    50                  55                  60

<210> SEQ ID NO 25
<211> LENGTH: 69
<212> TYPE: PRT
<213> ORGANISM: Artificial sequence
<220> FEATURE:
<223> OTHER INFORMATION: minibody presentation structure

<400> SEQUENCE: 25

Met Gly Arg Asn Ser Gln Ala Thr Ser Gly Phe Thr Phe Ser His Phe
1               5                   10                  15

Tyr Met Glu Trp Val Arg Gly Gly Glu Tyr Ile Ala Ala Ser Arg His
            20                  25                  30

Lys His Asn Lys Tyr Thr Thr Glu Tyr Ser Ala Ser Val Lys Gly Arg
        35                  40                  45

Tyr Ile Val Ser Arg Asp Thr Ser Gln Ser Ile Leu Tyr Leu Gln Lys
    50                  55                  60

Lys Lys Gly Pro Pro
65

<210> SEQ ID NO 26
<211> LENGTH: 32
<212> TYPE: PRT
<213> ORGANISM: Artificial sequence
<220> FEATURE:
<223> OTHER INFORMATION: zinc finger consensus sequence
<220> FEATURE:
<221> NAME/KEY: MISC_FEATURE
<222> LOCATION: (1)..(32)
<223> OTHER INFORMATION: "Xaa" at positions 1-5, 7-9, 11-22, 24-26, and
      28-32 can be any amino acid

<400> SEQUENCE: 26

Xaa Xaa Xaa Xaa Xaa Cys Xaa Xaa Xaa Cys Xaa Xaa Xaa Xaa Xaa Xaa
1               5                   10                  15

Xaa Xaa Xaa Xaa Xaa Xaa His Xaa Xaa Xaa His Xaa Xaa Xaa Xaa Xaa
            20                  25                  30

<210> SEQ ID NO 27
<211> LENGTH: 33
<212> TYPE: PRT
<213> ORGANISM: Artificial sequence
<220> FEATURE:
<223> OTHER INFORMATION: C2H2 zinc finger consensus sequence
<220> FEATURE:
<221> NAME/KEY: MISC_FEATURE
<222> LOCATION: (7)..(26)
<223> OTHER INFORMATION: "Xaa" at positions 7 to 26 can be any 3 to 20
      amino acids

<400> SEQUENCE: 27

Phe Gln Cys Glu Glu Cys Xaa Xaa Xaa Xaa Xaa Xaa Xaa Xaa Xaa Xaa
1               5                   10                  15
```

```
Xaa Xaa Xaa Xaa Xaa Xaa Xaa Xaa Xaa Xaa His Ile Arg Ser His Thr
            20                  25                  30

Gly

<210> SEQ ID NO 28
<211> LENGTH: 30
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (2)..(29)
<223> OTHER INFORMATION: "Xaa" at positions 2-3, 5-24, and 26-29 can be
      any amino acid

<400> SEQUENCE: 28

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa His Xaa Xaa Xaa Xaa Cys
            20                  25                  30

<210> SEQ ID NO 29
<211> LENGTH: 33
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (7)..(26)
<223> OTHER INFORMATION: "Xaa" at positions 7 to 26 can be any 4 to 20
      random amino acids

<400> SEQUENCE: 29

Val Lys Cys Phe Asn Cys Xaa Xaa Xaa Xaa Xaa Xaa Xaa Xaa Xaa
1               5                   10                  15

Xaa Xaa Xaa Xaa Xaa Xaa Xaa Xaa Xaa His Thr Ala Arg Asn Cys
            20                  25                  30

Arg

<210> SEQ ID NO 30
<211> LENGTH: 34
<212> TYPE: PRT
<213> ORGANISM: Artificial sequence
<220> FEATURE:
<223> OTHER INFORMATION: CCHC box consensus sequence
<220> FEATURE:
<221> NAME/KEY: MISC_FEATURE
<222> LOCATION: (10)..(29)
<223> OTHER INFORMATION: "Xaa" at positions 10 to 29 can be any 4 to 20
      random amino acids

<400> SEQUENCE: 30

Met Asn Pro Asn Cys Ala Arg Cys Gly Xaa Xaa Xaa Xaa Xaa Xaa
1               5                   10                  15

Xaa Xaa Xaa Xaa Xaa Xaa Xaa Xaa Xaa Xaa Xaa Xaa Xaa His Lys Ala
            20                  25                  30

Cys Phe

<210> SEQ ID NO 31
<211> LENGTH: 7
<212> TYPE: PRT
<213> ORGANISM: Artificial sequence
<220> FEATURE:
<223> OTHER INFORMATION: dimerization sequence
```

```
<400> SEQUENCE: 31

Glu Phe Leu Ile Val Lys Ser
1               5

<210> SEQ ID NO 32
<211> LENGTH: 9
<212> TYPE: PRT
<213> ORGANISM: Artificial sequence
<220> FEATURE:
<223> OTHER INFORMATION: dimerization sequence

<400> SEQUENCE: 32

Glu Glu Phe Leu Ile Val Lys Lys Ser
1               5

<210> SEQ ID NO 33
<211> LENGTH: 7
<212> TYPE: PRT
<213> ORGANISM: Artificial sequence
<220> FEATURE:
<223> OTHER INFORMATION: dimerization sequence

<400> SEQUENCE: 33

Phe Glu Ser Ile Lys Leu Val
1               5

<210> SEQ ID NO 34
<211> LENGTH: 7
<212> TYPE: PRT
<213> ORGANISM: Artificial sequence
<220> FEATURE:
<223> OTHER INFORMATION: dimerization sequence

<400> SEQUENCE: 34

Val Ser Ile Lys Phe Glu Leu
1               5

<210> SEQ ID NO 35
<211> LENGTH: 10
<212> TYPE: PRT
<213> ORGANISM: Artificial sequence
<220> FEATURE:
<223> OTHER INFORMATION: dimerization sequence

<400> SEQUENCE: 35

Glu Glu Glu Phe Leu Ile Val Glu Glu Glu
1               5                   10

<210> SEQ ID NO 36
<211> LENGTH: 10
<212> TYPE: PRT
<213> ORGANISM: Artificial sequence
<220> FEATURE:
<223> OTHER INFORMATION: dimerization sequence

<400> SEQUENCE: 36

Lys Lys Lys Phe Leu Ile Val Lys Lys Lys
1               5                   10

<210> SEQ ID NO 37
<211> LENGTH: 7
<212> TYPE: PRT
<213> ORGANISM: Simian virus 40

<400> SEQUENCE: 37
```

```
Pro Lys Lys Lys Arg Lys Val
1               5
```

<210> SEQ ID NO 38
<211> LENGTH: 6
<212> TYPE: PRT
<213> ORGANISM: Homo sapiens

<400> SEQUENCE: 38

```
Ala Arg Arg Arg Arg Pro
1               5
```

<210> SEQ ID NO 39
<211> LENGTH: 10
<212> TYPE: PRT
<213> ORGANISM: Mus musculus

<400> SEQUENCE: 39

```
Glu Glu Val Gln Arg Lys Arg Gln Lys Leu
1               5                   10
```

<210> SEQ ID NO 40
<211> LENGTH: 9
<212> TYPE: PRT
<213> ORGANISM: Mus musculus

<400> SEQUENCE: 40

```
Glu Glu Lys Arg Lys Arg Thr Tyr Glu
1               5
```

<210> SEQ ID NO 41
<211> LENGTH: 20
<212> TYPE: PRT
<213> ORGANISM: Xenopus laevis

<400> SEQUENCE: 41

```
Ala Val Lys Arg Pro Ala Ala Thr Lys Lys Ala Gly Gln Ala Lys Lys
1               5                   10                  15

Lys Lys Leu Asp
            20
```

<210> SEQ ID NO 42
<211> LENGTH: 31
<212> TYPE: PRT
<213> ORGANISM: Mus musculus

<400> SEQUENCE: 42

```
Met Ala Ser Pro Leu Thr Arg Phe Leu Ser Leu Asn Leu Leu Leu Leu
1               5                   10                  15

Gly Glu Ser Ile Leu Gly Ser Gly Glu Ala Lys Pro Gln Ala Pro
            20                  25                  30
```

<210> SEQ ID NO 43
<211> LENGTH: 21
<212> TYPE: PRT
<213> ORGANISM: Homo sapiens

<400> SEQUENCE: 43

```
Met Ser Ser Phe Gly Tyr Arg Thr Leu Thr Val Ala Leu Phe Thr Leu
1               5                   10                  15

Ile Cys Cys Pro Gly
            20
```

```
<210> SEQ ID NO 44
<211> LENGTH: 51
<212> TYPE: PRT
<213> ORGANISM: Mus musculus

<400> SEQUENCE: 44

Pro Gln Arg Pro Glu Asp Cys Arg Pro Arg Gly Ser Val Lys Gly Thr
1               5                   10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
        35                  40                  45

His Ser Arg
    50

<210> SEQ ID NO 45
<211> LENGTH: 33
<212> TYPE: PRT
<213> ORGANISM: Homo sapiens

<400> SEQUENCE: 45

Met Val Ile Ile Val Thr Val Val Ser Val Leu Leu Ser Leu Phe Val
1               5                   10                  15

Thr Ser Val Leu Leu Cys Phe Ile Phe Gly Gln His Leu Arg Gln Gln
            20                  25                  30

Arg

<210> SEQ ID NO 46
<211> LENGTH: 37
<212> TYPE: PRT
<213> ORGANISM: Rattus sp.

<400> SEQUENCE: 46

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 47
<211> LENGTH: 14
<212> TYPE: PRT
<213> ORGANISM: Gallus gallus

<400> SEQUENCE: 47

Met Gly Ser Ser Lys Ser Lys Pro Lys Asp Pro Ser Gln Arg
1               5                   10

<210> SEQ ID NO 48
<211> LENGTH: 11
<212> TYPE: PRT
<213> ORGANISM: Rous sarcoma virus

<400> SEQUENCE: 48

Met Gly Gln Ser Leu Thr Thr Pro Leu Ser Leu
1               5                   10

<210> SEQ ID NO 49
<211> LENGTH: 18
<212> TYPE: PRT
<213> ORGANISM: Homo sapiens
```

```
<400> SEQUENCE: 49

Ser Lys Asp Gly Lys Lys Lys Lys Lys Ser Lys Thr Lys Cys Val
1               5                   10                  15

Ile Met

<210> SEQ ID NO 50
<211> LENGTH: 11
<212> TYPE: PRT
<213> ORGANISM: Rattus sp.

<400> SEQUENCE: 50

Met Val Cys Cys Met Arg Arg Thr Lys Gln Val
1               5                   10

<210> SEQ ID NO 51
<211> LENGTH: 14
<212> TYPE: PRT
<213> ORGANISM: Mus musculus

<400> SEQUENCE: 51

Cys Met Ser Cys Lys Cys Val Leu Lys Lys Lys Lys Lys
1               5                   10

<210> SEQ ID NO 52
<211> LENGTH: 26
<212> TYPE: PRT
<213> ORGANISM: Homo sapiens

<400> SEQUENCE: 52

Leu Leu Gln Arg Leu Phe Ser Arg Gln Asp Cys Cys Gly Asn Cys Ser
1               5                   10                  15

Asp Ser Glu Glu Glu Leu Pro Thr Arg Leu
            20                  25

<210> SEQ ID NO 53
<211> LENGTH: 20
<212> TYPE: PRT
<213> ORGANISM: Rattus norvegicus

<400> SEQUENCE: 53

Lys Gln Phe Arg Asn Cys Met Leu Thr Ser Leu Cys Cys Gly Lys Asn
1               5                   10                  15

Pro Leu Gly Asp
            20

<210> SEQ ID NO 54
<211> LENGTH: 19
<212> TYPE: PRT
<213> ORGANISM: Homo sapiens

<400> SEQUENCE: 54

Leu Asn Pro Pro Asp Glu Ser Gly Pro Gly Cys Met Ser Cys Lys Cys
1               5                   10                  15

Val Leu Ser

<210> SEQ ID NO 55
<211> LENGTH: 19
<212> TYPE: PRT
<213> ORGANISM: Mus musculus
<220> FEATURE:
<221> NAME/KEY: MOD_RES
<222> LOCATION: (11)..(11)
```

```
<223> OTHER INFORMATION: Cys at position 11 is modified by a palmitoyl
      group
<220> FEATURE:
<221> NAME/KEY: MOD_RES
<222> LOCATION: (14)..(14)
<223> OTHER INFORMATION: Cys at position 14 is modified by a palmitoyl
      group
<220> FEATURE:
<221> NAME/KEY: MOD_RES
<222> LOCATION: (16)..(16)
<223> OTHER INFORMATION: Cys at position 16 is modified by a farnesyl
      group

<400> SEQUENCE: 55

Leu Asn Pro Pro Asp Glu Ser Gly Pro Gly Cys Met Ser Cys Lys Cys
1               5                   10                  15

Val Leu Ser

<210> SEQ ID NO 56
<211> LENGTH: 5
<212> TYPE: PRT
<213> ORGANISM: Artificial sequence
<220> FEATURE:
<223> OTHER INFORMATION: lysosomal degradation sequence

<400> SEQUENCE: 56

Lys Phe Glu Arg Gln
1               5

<210> SEQ ID NO 57
<211> LENGTH: 36
<212> TYPE: PRT
<213> ORGANISM: Cricetulus griseus

<400> SEQUENCE: 57

Met Leu Ile Pro Ile Ala Gly Phe Phe Ala Leu Ala Gly Leu Val Leu
1               5                   10                  15

Ile Val Leu Ile Ala Tyr Leu Ile Gly Arg Lys Arg Ser His Ala Gly
            20                  25                  30

Tyr Gln Thr Ile
        35

<210> SEQ ID NO 58
<211> LENGTH: 35
<212> TYPE: PRT
<213> ORGANISM: Homo sapiens

<400> SEQUENCE: 58

Leu Val Pro Ile Ala Val Gly Ala Ala Leu Ala Gly Val Leu Ile Leu
1               5                   10                  15

Val Leu Leu Ala Tyr Phe Ile Gly Leu Lys His His His Ala Gly Tyr
            20                  25                  30

Glu Gln Phe
        35

<210> SEQ ID NO 59
<211> LENGTH: 27
<212> TYPE: PRT
<213> ORGANISM: Saccharomyces cerevisiae

<400> SEQUENCE: 59

Met Leu Arg Thr Ser Ser Leu Phe Thr Arg Arg Val Gln Pro Ser Leu
1               5                   10                  15

Phe Ser Arg Asn Ile Leu Arg Leu Gln Ser Thr
```

<210> SEQ ID NO 60
<211> LENGTH: 25
<212> TYPE: PRT
<213> ORGANISM: Saccharomyces cerevisiae

<400> SEQUENCE: 60

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 61
<211> LENGTH: 64
<212> TYPE: PRT
<213> ORGANISM: Saccharomyces cerevisiae

<400> SEQUENCE: 61

Met Phe Ser Met Leu Ser Lys Arg Trp Ala Gln Arg Thr Leu Ser Lys
1               5                   10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60

<210> SEQ ID NO 62
<211> LENGTH: 41
<212> TYPE: PRT
<213> ORGANISM: Saccharomyces cerevisiae

<400> SEQUENCE: 62

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40

<210> SEQ ID NO 63
<211> LENGTH: 4
<212> TYPE: PRT
<213> ORGANISM: Homo sapiens

<400> SEQUENCE: 63

Lys Asp Glu Leu
1

<210> SEQ ID NO 64
<211> LENGTH: 15
<212> TYPE: PRT
<213> ORGANISM: unidentified adenovirus

<400> SEQUENCE: 64

Leu Tyr Leu Ser Arg Arg Ser Phe Ile Asp Glu Lys Lys Met Pro
1               5                   10                  15

<210> SEQ ID NO 65
<211> LENGTH: 9
<212> TYPE: PRT

```
<213> ORGANISM: Unknown
<220> FEATURE:
<223> OTHER INFORMATION: cyclin B1 destruction box

<400> SEQUENCE: 65

Arg Thr Ala Leu Gly Asp Ile Gly Asn
1               5

<210> SEQ ID NO 66
<211> LENGTH: 20
<212> TYPE: PRT
<213> ORGANISM: Unknown
<220> FEATURE:
<223> OTHER INFORMATION: signal sequence from Interleukin-2

<400> SEQUENCE: 66

Met Tyr Arg Met Gln Leu Leu Ser Cys Ile Ala Leu Ser Leu Ala Leu
1               5                   10                  15

Val Thr Asn Ser
            20

<210> SEQ ID NO 67
<211> LENGTH: 29
<212> TYPE: PRT
<213> ORGANISM: Homo sapiens

<400> SEQUENCE: 67

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr
            20                  25

<210> SEQ ID NO 68
<211> LENGTH: 27
<212> TYPE: PRT
<213> ORGANISM: Homo sapiens

<400> SEQUENCE: 68

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn
            20                  25

<210> SEQ ID NO 69
<211> LENGTH: 18
<212> TYPE: PRT
<213> ORGANISM: Influenza virus

<400> SEQUENCE: 69

Met Lys Ala Lys Leu Leu Val Leu Leu Tyr Ala Phe Val Ala Gly Asp
1               5                   10                  15

Gln Ile

<210> SEQ ID NO 70
<211> LENGTH: 24
<212> TYPE: PRT
<213> ORGANISM: Unknown
<220> FEATURE:
<223> OTHER INFORMATION: signal sequence from Interleukin-4

<400> SEQUENCE: 70

Met Gly Leu Thr Ser Gln Leu Leu Pro Pro Leu Phe Phe Leu Leu Ala
1               5                   10                  15
```

Cys Ala Gly Asn Phe Val His Gly
            20

<210> SEQ ID NO 71
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3 to 6 can be any amino acid

<400> SEQUENCE: 71

Met Gly Xaa Xaa Xaa Xaa Gly Gly Pro Pro
1               5                   10

<210> SEQ ID NO 72
<211> LENGTH: 5
<212> TYPE: PRT
<213> ORGANISM: Artificial sequence
<220> FEATURE:
<223> OTHER INFORMATION: linker consensus sequence

<400> SEQUENCE: 72

Gly Ser Gly Gly Ser
1               5

<210> SEQ ID NO 73
<211> LENGTH: 4
<212> TYPE: PRT
<213> ORGANISM: Artificial sequence
<220> FEATURE:
<223> OTHER INFORMATION: linker consensus sequence

<400> SEQUENCE: 73

Gly Gly Gly Ser
1

<210> SEQ ID NO 74
<211> LENGTH: 21
<212> TYPE: PRT
<213> ORGANISM: Apis mellifera

<400> SEQUENCE: 74

Met Lys Phe Leu Val Asp Val Ala Leu Val Phe Met Val Val Tyr Ile
1               5                   10                  15

Ser Tyr Ile Tyr Ala
            20

<210> SEQ ID NO 75
<211> LENGTH: 9
<212> TYPE: PRT
<213> ORGANISM: Unknown
<220> FEATURE:
<223> OTHER INFORMATION: cyclin A destruction box

<400> SEQUENCE: 75

Arg Thr Val Leu Gly Val Ile Gly Asp
1               5

<210> SEQ ID NO 76
<211> LENGTH: 27
<212> TYPE: PRT
<213> ORGANISM: Rattus sp.

```
<400> SEQUENCE: 76

Tyr Met Thr Val Ser Ile Ile Asp Arg Phe Met Gln Asp Ser Cys Val
1               5                   10                  15

Pro Lys Lys Met Leu Gln Leu Val Gly Val Thr
            20                  25

<210> SEQ ID NO 77
<211> LENGTH: 28
<212> TYPE: PRT
<213> ORGANISM: Mus sp.

<400> SEQUENCE: 77

Lys Phe Arg Leu Leu Gln Glu Thr Met Tyr Met Thr Val Ser Ile Ile
1               5                   10                  15

Asp Arg Phe Met Gln Asn Ser Cys Val Pro Lys Lys
            20                  25

<210> SEQ ID NO 78
<211> LENGTH: 27
<212> TYPE: PRT
<213> ORGANISM: Mus sp.

<400> SEQUENCE: 78

Arg Ala Ile Leu Ile Asp Trp Leu Ile Gln Val Gln Met Lys Phe Arg
1               5                   10                  15

Leu Leu Gln Glu Thr Met Tyr Met Thr Val Ser
            20                  25

<210> SEQ ID NO 79
<211> LENGTH: 27
<212> TYPE: PRT
<213> ORGANISM: Mus sp.

<400> SEQUENCE: 79

Asp Arg Phe Leu Gln Ala Gln Leu Val Cys Arg Lys Lys Leu Gln Val
1               5                   10                  15

Val Gly Ile Thr Ala Leu Leu Leu Ala Ser Lys
            20                  25

<210> SEQ ID NO 80
<211> LENGTH: 18
<212> TYPE: PRT
<213> ORGANISM: Mus sp.

<400> SEQUENCE: 80

Met Ser Val Leu Arg Gly Lys Leu Gln Leu Val Gly Thr Ala Ala Met
1               5                   10                  15

Leu Leu

<210> SEQ ID NO 81
<211> LENGTH: 6
<212> TYPE: PRT
<213> ORGANISM: Artificial sequence
<220> FEATURE:
<223> OTHER INFORMATION: linker sequence

<400> SEQUENCE: 81

Glu Glu Ala Ala Lys Ala
1               5

<210> SEQ ID NO 82
<211> LENGTH: 55
```

```
<212> TYPE: DNA
<213> ORGANISM: Artificial sequence
<220> FEATURE:
<223> OTHER INFORMATION: primer

<400> SEQUENCE: 82
gatcatagaa ttcgccacca tgggcagcaa gcagatcctg aagaacacct gcctg      55

<210> SEQ ID NO 83
<211> LENGTH: 55
<212> TYPE: DNA
<213> ORGANISM: Artificial sequence
<220> FEATURE:
<223> OTHER INFORMATION: primer

<400> SEQUENCE: 83
gatcatagaa ttcgccacca tgggcaaccg caacgtgctg aagaacaccg gcctg      55

<210> SEQ ID NO 84
<211> LENGTH: 53
<212> TYPE: DNA
<213> ORGANISM: Artificial sequence
<220> FEATURE:
<223> OTHER INFORMATION: primer

<400> SEQUENCE: 84
atgatcgcgg ccgctacacc cactcgtgca gggatcccag gggcttgccg atg        53

<210> SEQ ID NO 85
<211> LENGTH: 83
<212> TYPE: DNA
<213> ORGANISM: Artificial sequence
<220> FEATURE:
<223> OTHER INFORMATION: primer

<400> SEQUENCE: 85
gatccctgca cgagtgggtg gaggaggccg ccaaggccga ctacaaggac gacgacgaca  60
agtaggcccg tgaggccctaagc                                           83

<210> SEQ ID NO 86
<211> LENGTH: 80
<212> TYPE: DNA
<213> ORGANISM: Artificial sequence
<220> FEATURE:
<223> OTHER INFORMATION: primer

<400> SEQUENCE: 86
ggccgcttag ggcctcacgg gcctacttgt cgtcgtcctt gtagtcggcc ttggcggcct  60
cctccaccca ctcgtgcagg                                              80

<210> SEQ ID NO 87
<211> LENGTH: 42
<212> TYPE: DNA
<213> ORGANISM: Artificial sequence
<220> FEATURE:
<223> OTHER INFORMATION: primer

<400> SEQUENCE: 87
gatcatgaat tcgccatgag taaacaaata ttgaagaaca ct                     42

<210> SEQ ID NO 88
<211> LENGTH: 44
<212> TYPE: DNA
<213> ORGANISM: Artificial sequence
<220> FEATURE:
```

<223> OTHER INFORMATION: primer

<400> SEQUENCE: 88
tagatcgcgg ccgcttaaac ccattcgtgt aaggatccta gtgg    44

<210> SEQ ID NO 89
<211> LENGTH: 69
<212> TYPE: DNA
<213> ORGANISM: Artificial sequence
<220> FEATURE:
<223> OTHER INFORMATION: synthetic

<400> SEQUENCE: 89
ctggcgtagt cgggcacgtc gtaggggtag ccaccgccct ggccctcgta gcgcagggtg    60
cgctcgtac    69

<210> SEQ ID NO 90
<211> LENGTH: 69
<212> TYPE: DNA
<213> ORGANISM: Artificial sequence
<220> FEATURE:
<223> OTHER INFORMATION: synthetic

<400> SEQUENCE: 90
ctggcgtagt cgggcacgtc gtaggggtag ccaccgccct ggccctcgat caggttgatg    60
tcgctgcgg    69

<210> SEQ ID NO 91
<211> LENGTH: 69
<212> TYPE: DNA
<213> ORGANISM: Artificial sequence
<220> FEATURE:
<223> OTHER INFORMATION: synthetic

<400> SEQUENCE: 91
ctggcgtagt cgggcacgtc gtaggggtag ccaccgccct ggccgttcat gtacatggcc    60
tcgaagctg    69

<210> SEQ ID NO 92
<211> LENGTH: 68
<212> TYPE: DNA
<213> ORGANISM: Artificial sequence
<220> FEATURE:
<223> OTHER INFORMATION: synthetic

<400> SEQUENCE: 92
ctggcgtagt cgggcacgtc gtaggggtag ccaccgccct ggccgttaag cttgtacaca    60
ggatcacc    68

<210> SEQ ID NO 93
<211> LENGTH: 68
<212> TYPE: DNA
<213> ORGANISM: Artificial sequence
<220> FEATURE:
<223> OTHER INFORMATION: synthetic

<400> SEQUENCE: 93
ctggcgtagt cgggacgtcg tagggtagc caccgaaatg aagaaattg ctcttcatca    60 gggtcttc    68

<210> SEQ ID NO 94
<211> LENGTH: 69

<210> SEQ ID NO 94
<211> LENGTH: 69
<212> TYPE: DNA
<213> ORGANISM: Artificial sequence
<220> FEATURE:
<223> OTHER INFORMATION: synthetic

<400> SEQUENCE: 94
ctggcgtagt cgggcacgtc gtaggggtag ccaccgccct ggccgccgcc gtcctccacg    60
taggtcttc                                                           69

<210> SEQ ID NO 95
<211> LENGTH: 71
<212> TYPE: DNA
<213> ORGANISM: Artificial sequence
<220> FEATURE:
<223> OTHER INFORMATION: synthetic

<400> SEQUENCE: 95
cctacgacgt gcccgactac gccagcctgg gccagcaggt ggaggcgacg gcggcctggt    60
ggagatccgc a                                                        71

<210> SEQ ID NO 96
<211> LENGTH: 71
<212> TYPE: DNA
<213> ORGANISM: Artificial sequence
<220> FEATURE:
<223> OTHER INFORMATION: synthetic

<400> SEQUENCE: 96
cctacgacgt gcccgactag ccagcctggg ccaagcaggt ggaggcgaca agttcgtgta    60
ccgcgtggag t                                                        71

<210> SEQ ID NO 97
<211> LENGTH: 72
<212> TYPE: DNA
<213> ORGANISM: Artificial sequence
<220> FEATURE:
<223> OTHER INFORMATION: synthetic

<400> SEQUENCE: 97
cctacgacgt gcccgactac gccagcctgg gccaagcagg tggaggcaac ggcgtgctgg    60
tgggcgaggt ga                                                       72

<210> SEQ ID NO 98
<211> LENGTH: 72
<212> TYPE: DNA
<213> ORGANISM: Artificial sequence
<220> FEATURE:
<223> OTHER INFORMATION: synthetic

<400> SEQUENCE: 98
cctacgacgt gcccgactac gccagcctgg gccaagcagg tggaggcagc ggcaagtact    60
acagctgcca ca                                                       72

<210> SEQ ID NO 99
<211> LENGTH: 72
<212> TYPE: DNA
<213> ORGANISM: Artificial sequence
<220> FEATURE:
<223> OTHER INFORMATION: synthetic

<400> SEQUENCE: 99
cctacgacgt gcccgactac gccagcctgg gccaagcagg tggaggcgtg gtgaaggagt    60

-continued

```
tccccagcta cc                                                            72

<210> SEQ ID NO 100
<211> LENGTH: 72
<212> TYPE: DNA
<213> ORGANISM: Artificial sequence
<220> FEATURE:
<223> OTHER INFORMATION: synthetic

<400> SEQUENCE: 100
cctacgacgt gcccgactac gccagcctgg gccaagcagg tggaggcttc gtggagcagc        60
acgagaccgc ca                                                            72

<210> SEQ ID NO 101
<211> LENGTH: 49
<212> TYPE: DNA
<213> ORGANISM: Artificial sequence
<220> FEATURE:
<223> OTHER INFORMATION: primer

<400> SEQUENCE: 101
agatcataga tctatgggca accgcaacgt gctgaagaac accggcctg                    49

<210> SEQ ID NO 102
<211> LENGTH: 88
<212> TYPE: DNA
<213> ORGANISM: Artificial sequence
<220> FEATURE:
<223> OTHER INFORMATION: primer

<400> SEQUENCE: 102
agatcataga tctgaattca tgggcagcaa gcagatcctg aagaacaccg gcctgcagga        60
ggtgatgagc tacaaggtga cctggagg                                           88

<210> SEQ ID NO 103
<211> LENGTH: 89
<212> TYPE: DNA
<213> ORGANISM: Artificial sequence
<220> FEATURE:
<223> OTHER INFORMATION: primer

<400> SEQUENCE: 103
gccaacagga tgttgccctt gccctcgccc tccatggtga cacgtggtt gttaacgatg         60 ccctccaggt tcaccttgta gctcatcac                                          89

<210> SEQ ID NO 104
<211> LENGTH: 14
<212> TYPE: PRT
<213> ORGANISM: Artificial sequence
<220> FEATURE:
<223> OTHER INFORMATION: linker-flag tag sequence

<400> SEQUENCE: 104

Glu Glu Ala Ala Lys Ala Asp Tyr Lys Asp Asp Asp Asp Lys
1               5                   10

<210> SEQ ID NO 105
<211> LENGTH: 22
<212> TYPE: PRT
<213> ORGANISM: Artificial sequence
<220> FEATURE:
<223> OTHER INFORMATION: influenza hemagglutinin epitope tag flanked by
      linker sequences

<400> SEQUENCE: 105
```

```
Gly Gln Gly Gly Gly Tyr Pro Tyr Asp Val Pro Asp Tyr Ala Ser Leu
1               5                   10                  15

Gly Gln Ala Gly Gly Gly
            20

<210> SEQ ID NO 106
<211> LENGTH: 8
<212> TYPE: PRT
<213> ORGANISM: Simian virus 40

<400> SEQUENCE: 106

Pro Pro Lys Lys Lys Arg Lys Val
1               5

<210> SEQ ID NO 107
<211> LENGTH: 19
<212> TYPE: PRT
<213> ORGANISM: Artificial sequence
<220> FEATURE:
<223> OTHER INFORMATION: HA epitope tag flanked by glycines

<400> SEQUENCE: 107

Gly Gly Gly Gly Tyr Pro Tyr Asp Val Pro Asp Tyr Ala Ser Leu Gly
1               5                   10                  15

Gly Gly Gly
```